(12) United States Patent
Wu et al.

(10) Patent No.: US 7,659,374 B2
(45) Date of Patent: Feb. 9, 2010

(54) EPH RECEPTOR FC VARIANTS WITH ENHANCED ANTIBODY DEPENDENT CELL-MEDIATED CYTOTOXICITY ACTIVITY

(75) Inventors: Herren Wu, Boyds, MD (US); Changshou Gao, Potomac, MD (US)

(73) Assignee: MedImmune, LLC, Gaithersburg, MD (US)

( * ) Notice: Subject to any disclaimer, the term of this patent is extended or adjusted under 35 U.S.C. 154(b) by 264 days.

(21) Appl. No.: 11/203,251

(22) Filed: Aug. 15, 2005

(65) Prior Publication Data

US 2006/0039904 A1  Feb. 23, 2006

Related U.S. Application Data

(60) Provisional application No. 60/608,852, filed on Sep. 13, 2004, provisional application No. 60/601,634, filed on Aug. 16, 2004.

(51) Int. Cl.
*C07K 16/00* (2006.01)
*C12P 21/08* (2006.01)
*C07K 17/00* (2006.01)

(52) U.S. Cl. .............. 530/387.1; 530/387.3; 530/387.7; 530/388.1; 530/388.22; 530/391.1

(58) Field of Classification Search ........................ None
See application file for complete search history.

(56) References Cited

U.S. PATENT DOCUMENTS

| | | | |
|---|---|---|---|
| 5,624,821 A | 4/1997 | Winter et al. | |
| 5,635,177 A | 6/1997 | Bennett et al. | |
| 5,770,195 A | 6/1998 | Hudziak et al. | |
| 5,869,046 A | 2/1999 | Presta et al. | |
| 5,885,573 A | 3/1999 | Bluestone et al. | |
| 6,165,745 A | 12/2000 | Ward et al. | |
| 6,194,551 B1 | 2/2001 | Idusogie et al. | |
| 6,277,375 B1 | 8/2001 | Ward et al. | |
| 6,737,056 B1 | 5/2004 | Presta et al. | |
| 6,927,203 B1 | 8/2005 | Kinch et al. | |
| 7,101,976 B1 | 9/2006 | Kinch et al. | |
| 7,192,698 B1 | 3/2007 | Kinch et al. | |
| 2001/0036459 A1 | 11/2001 | Ravetch | |
| 2002/0147311 A1 | 10/2002 | Gillies et al. | |
| 2003/0157108 A1 | 8/2003 | Presta | |
| 2003/0190311 A1 | 10/2003 | Dall'Acqua et al. | |
| 2004/0002587 A1 | 1/2004 | Watkins et al. | |
| 2004/0028685 A1 | 2/2004 | Kinch et al. | |
| 2004/0091486 A1 | 5/2004 | Kinch et al. | |
| 2004/0106132 A1 | 6/2004 | Huang et al. | |
| 2004/0132101 A1 | 7/2004 | Lazar et al. | |
| 2004/0234520 A1 | 11/2004 | Aguet | |
| 2005/0032114 A1 | 2/2005 | Hinton | |
| 2005/0037000 A1 | 2/2005 | Stavenhagen | |
| 2005/0049176 A1 | 3/2005 | Kiener et al. | |
| 2005/0054832 A1 | 3/2005 | Lazar et al. | |
| 2005/0059592 A1 | 3/2005 | Kiener et al. | |
| 2005/0147593 A1 | 7/2005 | Kinch | |
| 2005/0152899 A1 | 7/2005 | Kinch et al. | |
| 2005/0153923 A1 | 7/2005 | Kinch | |
| 2005/0215768 A1 | 9/2005 | Armour | |
| 2005/0244403 A1 | 11/2005 | Lazar et al. | |
| 2006/0040325 A1 | 2/2006 | Wu et al. | |
| 2006/0121043 A1 | 6/2006 | Kinch et al. | |
| 2006/0122138 A1 | 6/2006 | Kinch et al. | |
| 2006/0235208 A1* | 10/2006 | Lazar et al. ............ | 530/388.22 |

FOREIGN PATENT DOCUMENTS

| | | |
|---|---|---|
| EP | 1135153 B1 | 4/2005 |
| WO | WO-94-29351 | 12/1994 |
| WO | WO-95-27061 | 10/1995 |
| WO | WO-98-23289 | 6/1998 |
| WO | WO-99-58572 | 11/1999 |
| WO | WO-00-30673 | 6/2000 |
| WO | WO 00/42072 A | 7/2000 |
| WO | WO-01-12172 | 2/2001 |
| WO | WO-01-12840 | 2/2001 |
| WO | WO-03-074679 | 9/2003 |
| WO | WO-03-094859 | 11/2003 |
| WO | WO-03-099313 | 12/2003 |
| WO | WO-2004-014292 | 2/2004 |
| WO | WO 2004/029207 A | 4/2004 |

(Continued)

OTHER PUBLICATIONS

Alegre, M. L., et al. "A Non-Activating "Humanized" Anti-CD3 Monoclonal Antibody Retains Immunosuppressive Properties in Vivo." *Transplantation* (1994) 57: 1537-43.

(Continued)

*Primary Examiner*—Maher M Haddad
*Assistant Examiner*—Chun Dahle

(57) ABSTRACT

The present invention relates to novel Fc variants that immuno-specifically bind to an Eph receptor. The Fc variants comprise a binding region that immunospecifically binds to an Eph receptor and an Fc region that further comprises at least one novel amino acid residue which may provide for enhanced effector function. More specifically, this invention provides Fc variants that have modified binding affinity to one or more Fc ligand (e.g., FcγR, C1q). Additionally, the Fc variants have altered antibody-dependent cell-mediated cytotoxicity (ADCC) and/or complement dependent cytotoxicity (CDC) activity. The invention further provides methods and protocols for the application of said Fc variants that immunospecifically bind to an Eph receptor, particularly for therapeutic purposes.

14 Claims, 22 Drawing Sheets

FOREIGN PATENT DOCUMENTS

Figure 4:
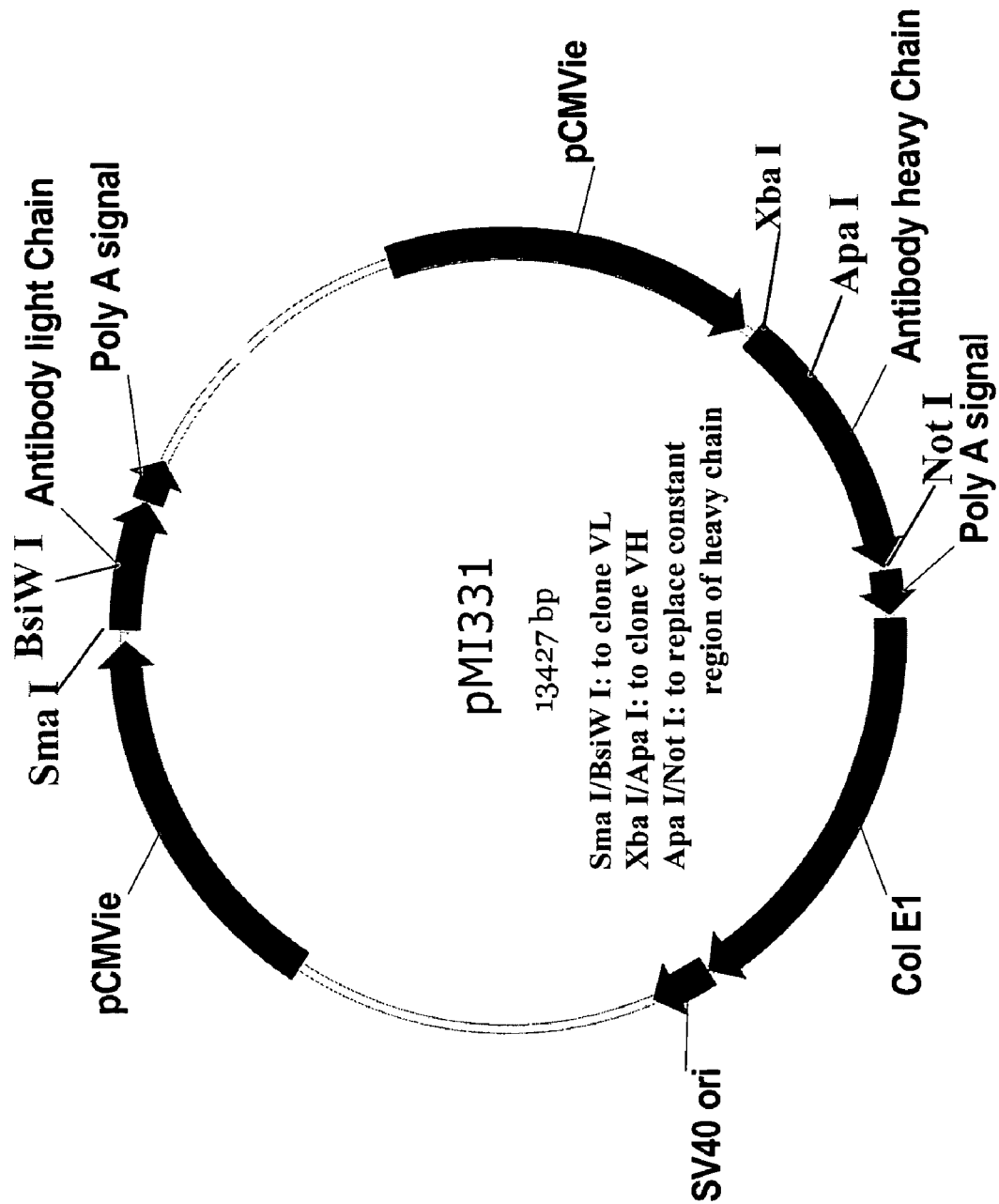

| WO | WO-2005-047327    | 5/2005 |
|----|-------------------|--------|
| WO | WO2005051307      | 6/2005 |
| WO | WO-2005-070963    | 8/2005 |
| WO | WO-2006-023403 A3 | 3/2006 |
| WO | WO 2006/023420 A2 | 3/2006 |
| WO | WO-2007-075706 A2 | 7/2007 |

OTHER PUBLICATIONS

Armour, K. L., et al. "Recombinant Human IgG Molecules Lacking Fcgamma Receptor I Binding and Monocyte Triggering Activities." Eur.J.Immunol. (1999) 29: 2613-24.

Bruggemann, M., et al. "Comparison of the Effector Functions of Human Immunoglobulins using a Matched Set of Chimeric Antibodies." J.Exp.Med. (1987) 166: 1351-61.

Clynes, R., et al. "Fc Receptors are Required in Passive and Active Immunity to Melanoma." Proc.Natl.Acad.Sci.U.S.A. (1998) 95: 652-6.

Dall'Acqua, W. F., et al. "Modulation of the Effector Functions of a Human IgG1 through Engineering of its Hinge Region." J.Immunol. (2006) 177: 1129-38.

Duncan, A. R., et al. "Localization of the Binding Site for the Human High-Affinity Fc Receptor on IgG." Nature (1988) 332: 563-4.

Ghetie, V., et al. "Increasing the Serum Persistence of an IgG Fragment by Random Mutagenesis." Nat.Biotechnol. (1997) 15: 637-40.

Hutchins, J. T., et al. "Improved Biodistribution, Tumor Targeting, and Reduced Immunogenicity in Mice with a Gamma 4 Variant of Campath-1H." Proc.Natl.Acad.Sci.U.S.A. (1995) 92: 11980-4.

Idusogie, E. E., et al. "Engineered Antibodies with Increased Activity to Recruit Complement." J.Immunol. (2001) 166: 2571-5.

Idusogie, E. E., et al. "Mapping of the C1q Binding Site on Rituxan, a Chimeric Antibody with a Human IgG1 Fc." J.Immunol. (2000) 164: 4178-84.

Jefferis, R., et al. "Interaction Sites on Human IgG-Fc for FcgammaR: Current Models." Immunol.Lett. (2002) 82: 57-65.

Jefferis, R., et al. "Modulation of Fc(Gamma)R and Human Complement Activation by IgG3-Core Oligosaccharide Interactions." Immunol.Lett. (1996) 54: 101-4.

Jefferis, R., et al. "Recognition Sites on Human IgG for Fc Gamma Receptors: The Role of Glycosylation." Immunol.Lett. (1995) 44: 111-7.

Lund, J., et al. "Multiple Interactions of IgG with its Core Oligosaccharide can Modulate Recognition by Complement and Human Fc Gamma Receptor I and Influence the Synthesis of its Oligosaccharide Chains." J.Immunol. (1996) 157: 4963-9.

Lund, J., et al. "Oligosaccharide-Protein Interactions in IgG can Modulate Recognition by Fc Gamma Receptors." FASEB J. (1995) 9: 115-9.

Lund, J., et al. "Multiple Binding Sites on the CH2 Domain of IgG for Mouse Fc Gamma R11." Mol.Immunol. (1992) 29: 53-9.

Lund, J., et al. "Human Fc Gamma RI and Fc Gamma RII Interact with Distinct but Overlapping Sites on Human IgG." J.Immunol. (1991) 147: 2657-62.

MedImmune Inc. "International Preliminary Report on Patentability and Written Opinion of the International Searching Authority for PCT/US2005/028839." : 1-6.

Patel, A. K., et al. "An Improved Assay for Antibody Dependent Cellular Cytotoxicity Based on Time Resolved Fluorometry." J.Immunol.Methods (1995) 184: 29-38.

Presta, L. G., et al. "Engineering Therapeutic Antibodies for Improved Function." Biochem.Soc.Trans. (2002) 30: 487-90.

Reddy, M. P., et al. "Elimination of Fc Receptor-Dependent Effector Functions of a Modified IgG4 Monoclonal Antibody to Human CD4." J.Immunol. (2000) 164: 1925-33.

Shields, R. L., et al. "Lack of Fucose on Human IgG1 N-Linked Oligosaccharide Improves Binding to Human Fcgamma RIII and Antibody-Dependent Cellular Toxicity." J.Biol.Chem. (2002) 277: 26733-40.

Shields, R. L., et al. "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R." J.Biol.Chem. (2001) 276: 6591-604.

Wilkinson, R. W., et al. "Antibody-Dependent Cell-Mediated Cytotoxicity: A Flow Cytometry-Based Assay using Fluorophores." J.Immunol.Methods (2001) 258: 183-91.

Wisecarver, J., et al. "A Method for Determination of Antibody-Dependent Cellular Cytotoxicity (ADCC) of Human Peripheral Mononuclear Cells." J.Immunol.Methods (1985) 79: 277-82.

Xu, D., et al. "In Vitro Characterization of Five Humanized OKT3 Effector Function Variant Antibodies." Cell.Immunol. (2000) 200: 16-26.

Alves, P. M., et al. "EphA2 as Target of Anticancer Immunotherapy: Identification of HLA-A*0201-Restricted Epitopes." Cancer research 63.23 (2003): 8476-80.

Cai, W., et al. "Quantitative radioimmunoPET Imaging of EphA2 in Tumor-Bearing Mice." Eur.J.Nucl.Med.Mol.Imaging (2007), 34: 2024-2036.

Carles-Kinch, K., et al. "Antibody Targeting of the EphA2 Tyrosine Kinase Inhibits Malignant Cell Behavior." Cancer research 62.10 (2002): 2840-7.

Cheng, N., et al. "The Ephrins and Eph Receptors in Angiogenesis." Cytokine & growth factor reviews 13.1 (2002): 75-85.

Cheng, N., et al. "Blockade of EphA Receptor Tyrosine Kinase Activation Inhibits Vascular Endothelial Cell Growth Factor-Induced Angiogenesis." Mol.Cancer.Res. 1.1(2002): 2-11.

Coffman, K. T., et al. "Differential EphA2 Epitope Display on Normal Versus Malignant Cells." Cancer research 63.22 (2003): 7907-12.

Hu, et al. "Antibody Targeting of the EphA2 Receptor Tyrosine Kinase on Breast Cancer Cells." Proceedings of the annual meeting of the AACR 44 (2003): 6178.

Kiewlich, D., et al. "Anti-EphA2 Antibodies Decrease EphA2 Protein Levels in Murine CT26 Colorectal and Human MDA-231 Breast Tumors but do Not Inhibit Tumor Growth." Neoplasia (New York, N.Y.) 8.1 (2006): 18-30.

Kinch, et al. "Epitope Targeting of EphA2: New Opportunities for Selective Killing of Tumor Cells." Proceedings of the annual meeting of the AACR 44 (2003): 5616.

Landen, C. N.,Jr, et al. "Efficacy and Antivascular Effects of EphA2 Reduction with an Agonistic Antibody in Ovarian Cancer." Journal of the National Cancer Institute 98.21 (2006): 1558-70.

Miao, H., et al. "Activation of EphA2 Kinase Suppresses Integrin Function and Causes Focal-Adhesion-Kinase Dephosphorylation." Nature cell biology 2.2 (2000): 62-9.

Pratt, R. L., et al. "Activation of the EphA2 Tyrosine Kinase Stimulates the MAP/ERK Kinase Signaling Cascade." Oncogene 21.50(2002): 7690-9.

Walker-Daniels, et al. "The Mechanism of EphA2 Protein Degradation: Implications of Increased EphA2 Protein Levels in Metastatic Cancer Cells." Proceedings of the American Association for Cancer Research Annual Meeting 42 (2001): 840.

European Search Report mailed Feb. 16, 2009 in connection with copending European Application No. 05788101.3, pp. 1-7.

International Search Report published Jun. 19, 2006 in connection with copending application No. WO 2006/023420, pp. 1-2.

* cited by examiner

A

| | | |
|---|---|---|
| CAG GTG CAG CTG GTG GAG TCT GGG GGA GGC GTT GTG CAG CCT GGA AGG | 48 | |
| Gln Val Gln Leu Val Glu Ser Gly Gly Gly Val Val Gln Pro Gly Arg | 16 | |
| TCC CTG AGA CTC TCC TGT GCA GCC TCT GGA TTC ACC TTC AGT AGC TAT | 96 | |
| Ser Leu Arg Leu Ser Cys Ala Ala Ser Gly Phe Thr Phe Ser Ser Tyr | 32 | |
| GAC ATG TCT TGG GTT CGC CAG GCT CCG GGC AAG GGT CTG GAG TGG GTC | 144 | |
| Asp Met Ser Trp Val Arg Gln Ala Pro Gly Lys Gly Leu Glu Trp Val | 48 | |
| GCA AAA GTT AGT AGT GGT GGT GGT AGC ACC TAC TAT TTA GAC ACT GTG | 192 | |
| Ala Lys Val Ser Ser Gly Gly Gly Ser Thr Tyr Tyr Leu Asp Thr Val | 64 | |
| CAG GGC CGA TTC ACC ATC TCC AGA GAC AAT AGT AAG AAC ACC CTA TAC | 240 | |
| Gln Gly Arg Phe Thr Ile Ser Arg Asp Asn Ser Lys Asn Thr Leu Tyr | 80 | |
| CTG CAA ATG AAC TCT CTG AGA GCC GAG GAC ACA GCC GTG TAT TAC TGT | 288 | |
| Leu Gln Met Asn Ser Leu Arg Ala Glu Asp Thr Ala Val Tyr Tyr Cys | 96 | |
| GCA AGA CAT CTG CAT GGC AGT TTT GCT TCT TGG GGC CAA GGG ACT ACA | 336 | |
| Ala Arg His Leu His Gly Ser Phe Ala Ser Trp Gly Gln Gly Thr Thr | 112 | |
| GTG ACT GTT TCT AGT | 351 | |
| Val Thr Val Ser Ser | 117 | |

B

| | | |
|---|---|---|
| GAG ATT GTG CTA ACT CAG TCT CCA GCC ACC CTG TCT CTC AGC CCA GGA | 48 | |
| Glu Ile Val Leu Thr Gln Ser Pro Ala Thr Leu Ser Leu Ser Pro Gly | 16 | |
| GAA AGG GCG ACT CTT TCC TGC CAG GCC AGC CAA AGT ATT AGC AAC TTC | 96 | |
| Glu Arg Ala Thr Leu Ser Cys Gln Ala Ser Gln Ser Ile Ser Asn Phe | 32 | |
| CTA CAC TGG TAT CAA CAA AGG CCT GGT CAA GCC CCA AGG CTT CTC ATC | 144 | |
| Leu His Trp Tyr Gln Gln Arg Pro Gly Gln Ala Pro Arg Leu Leu Ile | 48 | |
| CGC TAT CGT TCC CAG TCC ATC TCT GGG ATC CCC GCC AGG TTC AGT GGC | 192 | |
| Arg Tyr Arg Ser Gln Ser Ile Ser Gly Ile Pro Ala Arg Phe Ser Gly | 62 | |
| AGT GGA TCA GGG ACA GAT TTC ACC CTC ACT ATC TCC AGT CTG GAG CCT | 240 | |
| Ser Gly Ser Gly Thr Asp Phe Thr Leu Thr Ile Ser Ser Leu Glu Pro | 80 | |
| GAA GAT TTT GCA GTC TAT TAC TGT CAA CAG AGT GGC AGC TGG CCT CTG | 288 | |
| Glu Asp Phe Ala Val Tyr Tyr Cys Gln Gln Ser Gly Ser Trp Pro Leu | 96 | |
| ACG TTC GGA GGG GGG ACC AAG GTG GAA ATT AAG | 321 | |
| Thr Phe Gly Gly Gly Thr Lys Val Glu Ile Lys | 107 | |

FIG. 1

A

CAAATGCAGCTGGTGCAGTCTGGGCCTGAGGTGAAGAAGCCTGGGACCTCAGTGAAGGTC 60
Gln Met Gln Leu Val Gln Ser Gly Pro Glu Val Lys Lys Pro Gly Thr Ser Val Lys Val

TCCTGCAAGGCTTCTGGATTCACCTTTGACGATTACTCCATGAACTGGGTGCGACAGGCT 120
Ser Cys Lys Ala Ser Gly Phe Thr Phe Asp Asp Tyr Ser Met Asn Trp Val Arg Gln Ala

CGTGGACAACGCCTTGAGTGGATAGGATTTATTAGAAACAAAGCTAATGACTACACAACA 180
Arg Gly Gln Arg Leu Glu Trp Ile Gly Phe Ile Arg Asn Lys Ala Asn Asp Tyr Thr Thr

GAGTACGCTGACTCTGTGAAGGGTAGAGTCACCATTACCAGGGACATGTCCACGAGCACA 240
Glu Tyr Ala Asp Ser Val Lys Gly Arg Val Thr Ile Thr Arg Asp Met Ser Thr Ser Thr

GCCTACATGGAGCTGAGCAGCCTGAGATCCGAGGACACGGCCGTGTATTACTGTGCGAGA 300
Ala Tyr Met Glu Leu Ser Ser Leu Arg Ser Glu Asp Thr Ala Val Tyr Tyr Cys Ala Arg

TACCCTAGGCATCATGCTATGGACTCCTGGGGCCAAGGAACCTCGGTCACCGTCTCCTCA 360
Tyr Pro Arg His His Ala Met Asp Ser Trp Gly Gln Gly Thr Ser Val Thr Val Ser Ser

B

GACATCCAGATGACCCAGTCTCCATCCTCCCTGTCTGCATCTGTAGGAGACAGAGTCACC 60
Asp Ile Gln Met Thr Gln Ser Pro Ser Ser Leu Ser Ala Ser Val Gly Asp Arg Val Thr

ATCACTTGCAGGGCCAGCCAAAGTATTAGCAACAACCTACACTGGTATCAGCAGAAACCA 120
Ile Thr Cys Arg Ala Ser Gln Ser Ile Ser Asn Asn Leu His Trp Tyr Gln Gln Lys Pro

GGGAAAGCCCCTAAGCTCCTGATCAAGTATGCCTTCCAGTCCATCTCTGGGGTCCCATCA 180
Gly Lys Ala Pro Lys Leu Leu Ile Lys Tyr Ala Phe Gln Ser Ile Ser Gly Val Pro Ser

AGGTTCAGTGGAAGTGGATCTGGGACAGATTTTACTTTCACCATCAGCAGCCTGCAGCCT 240
Arg Phe Ser Gly Ser Gly Ser Gly Thr Asp Phe Thr Phe Thr Ile Ser Ser Leu Gln Pro

GAAGATTTTGCAACATATTACTGTCAACAGGCCAACAGCTGGCCGCTCACGTTCGGCGGA 300
Glu Asp Phe Ala Thr Tyr Tyr Cys Gln Gln Ala Asn Ser Trp Pro Leu Thr Phe Gly Gly

GGGACCAAGGTGGAGATCAAA 321
Gly Thr Lys Val Glu Ile Lys

FIG. 2

A

| | | | | | | | | | | | | | | | | |
|---|---|---|---|---|---|---|---|---|---|---|---|---|---|---|---|---|
| GAG | GTG | CAG | CTG | GTG | GAG | TCT | GGG | GGA | GGT | GTG | GTA | CGG | CCT | GGG | GGG | 48 |
| Glu | Val | Gln | Leu | Val | Glu | Ser | Gly | Gly | Gly | Val | Val | Arg | Pro | Gly | Gly | 16 |
| TCC | CTG | AGA | CTC | TCC | TGT | GCA | GCC | TCT | GGG | TTC | ACC | GTC | AGT | GAT | TAC | 96 |
| Ser | Leu | Arg | Leu | Ser | Cys | Ala | Ala | Ser | Gly | Phe | Thr | Val | Ser | Asp | Tyr | 32 |
| TCC | ATG | AAC | TGG | GTC | CGC | CAG | GCT | CCA | GGG | AAG | GGC | CTG | GAG | TGG | ATT | 144 |
| Ser | Met | Asn | Trp | Val | Arg | Gln | Ala | Pro | Gly | Lys | Gly | Leu | Glu | Trp | Ile | 48 |
| GGG | TTT | ATT | AGA | AAC | AAA | GCT | AAT | GCC | TAC | ACA | ACA | GAG | TAC | AGT | GCA | 192 |
| Gly | Phe | Ile | Arg | Asn | Lys | Ala | Asn | Ala | Tyr | Thr | Thr | Glu | Tyr | Ser | Ala | 64 |
| TCT | GTG | AAG | GGT | AGA | TTC | ACC | ATC | TCA | AGA | GAT | GAT | TCA | AAA | AAC | ACG | 240 |
| Ser | Val | Lys | Gly | Arg | Phe | Thr | Ile | Ser | Arg | Asp | Asp | Ser | Lys | Asn | Thr | 80 |
| CTG | TAT | CTG | CAA | ATG | AAC | AGC | CTG | AAA | ACC | GAG | GAC | ACA | GCC | GTG | TAT | 288 |
| Leu | Tyr | Leu | Gln | Met | Asn | Ser | Leu | Lys | Thr | Glu | Asp | Thr | Ala | Val | Tyr | 96 |
| TAC | TGT | ACC | ACA | TAC | CCT | AGG | TAT | CAT | GCT | ATG | GAC | TCC | TGG | GGC | CAG | 336 |
| Tyr | Cys | Thr | Thr | Tyr | Pro | Arg | Tyr | His | Ala | Met | Asp | Ser | Trp | Gly | Gln | 112 |
| GGC | ACC | ATG | GTC | ACC | GTC | TCC | TCA | | | | | | | | | 360 |
| Gly | Thr | Met | Val | Thr | Val | Ser | Ser | | | | | | | | | 120 |

B

| | | | | | | | | | | | | | | | | |
|---|---|---|---|---|---|---|---|---|---|---|---|---|---|---|---|---|
| GCC | ATC | CAG | TTG | ACT | CAG | TCT | CCA | TCC | TCC | CTG | TCT | GCA | TCT | GTA | GGA | 48 |
| Ala | Ile | Gln | Leu | Thr | Gln | Ser | Pro | Ser | Ser | Leu | Ser | Ala | Ser | Val | Gly | 16 |
| GAC | AGA | GTC | ACC | ATC | ACT | TGC | AGG | GCC | AGC | CAA | AGT | ATT | AGC | AAC | AAC | 96 |
| Asp | Arg | Val | Thr | Ile | Thr | Cys | Arg | Ala | Ser | Gln | Ser | Ile | Ser | Asn | Asn | 32 |
| CTA | CAC | TGG | TAC | CTG | CAG | AAG | CCA | GGG | CAG | TCT | CCA | CAG | CTC | CTG | ATC | 144 |
| Leu | His | Trp | Tyr | Leu | Gln | Lys | Pro | Gly | Gln | Ser | Pro | Gln | Leu | Leu | Ile | 48 |
| TAT | TAT | GGC | TTC | CAG | TCC | ATC | TCT | GGG | GTC | CCA | TCA | AGG | TTC | AGT | GGC | 192 |
| Tyr | Tyr | Gly | Phe | Gln | Ser | Ile | Ser | Gly | Val | Pro | Ser | Arg | Phe | Ser | Gly | 64 |
| AGT | GGA | TCT | GGG | ACA | GAT | TTC | ACT | CTC | ACC | ATC | AGC | AGT | CTG | CAA | CCT | 240 |
| Ser | Gly | Ser | Gly | Thr | Asp | Phe | Thr | Leu | Thr | Ile | Ser | Ser | Leu | Gln | Pro | 80 |
| GAA | GAT | TTT | GCA | ACT | TAC | TAC | TGT | CAA | CAG | GCC | AAC | AGC | TGG | CCG | CTC | 288 |
| Glu | Asp | Phe | Ala | Thr | Tyr | Tyr | Cys | Gln | Gln | Ala | Asn | Ser | Trp | Pro | Leu | 96 |
| ACG | TTC | GGC | GGA | GGG | ACC | AAG | CTG | GAG | ATC | AAA | | | | | | 321 |
| Thr | Phe | Gly | Gly | Gly | Thr | Lys | Leu | Glu | Ile | Lys | | | | | | 107 |

FIG. 3

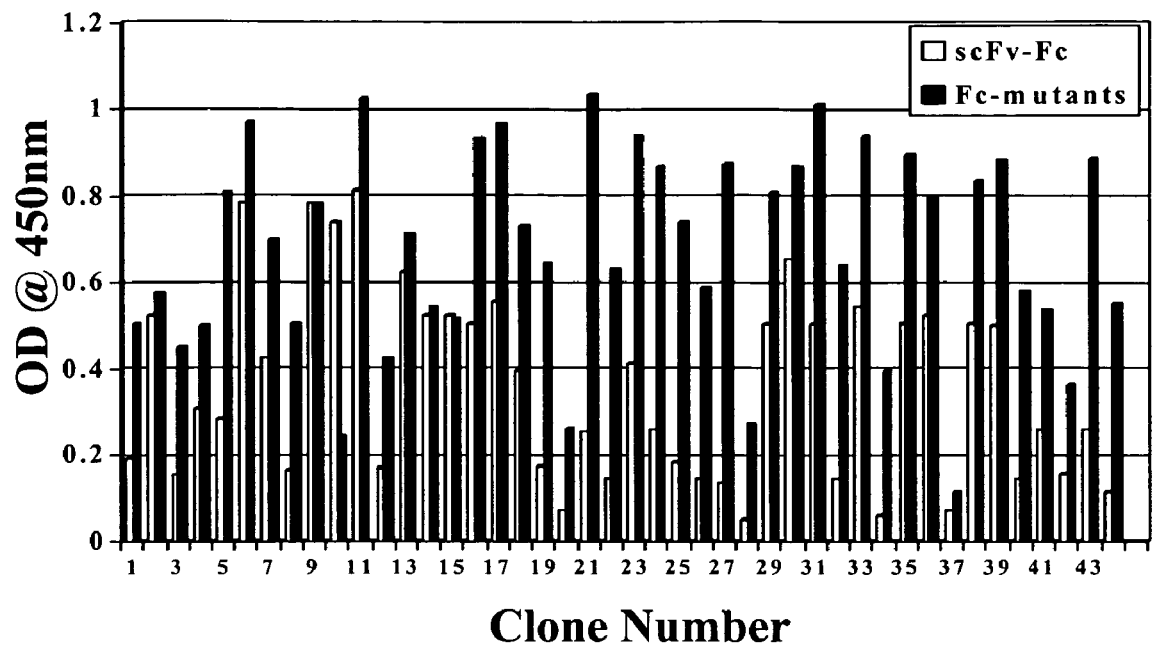

Clone 1: RI-1 (L234E)
Clone 2: RI-2 (L235R)
Clone 3: RI-13 (L235A)
Clone 4: RI-16 (L235W)
Clone 5: RI-61 (L235P)
Clone 6: RI-63 (L235P)
Clone 7: RI-69 (L235V)
Clone 8: RI-83 (G236E)
Clone 9: RI-102 (L235Y)
Clone 10: RII-III-19 (D265L)
Clone 11: RII-III-81 (S298I)
Clone 12: RII-III-121 (S298T)
Clone 13: RII-III-123 (S298F)
Clone 14: RII-III-145 (E269S)
Clone 15: RII-III-20-4-F5 (E269G)
Clone 16: RIV-2 (P329Q)
Clone 17: RIV-3 (I332E)
Clone 18: RIV-21(L328S)
Clone 19: RIV-22 (A330K)
Clone 20: RIV-23 (I332E)
Clone 21: RIV-43 (A327W)
Clone 22: RIV-47 (I332H)

Clone 23: RIV-49 (I332E)
Clone 24: RIV-50 (A330V)
Clone 25: RIV-59 (A330G)
Clone 26: RIV-65 (A330Y)
Clone 27: RIV-84 (I332S)
Clone 28: RIV-90 (A330G)
Clone 29: RIV-100 (P329H)
Clone 30: RIV-112 (I332W)
Clone 31: RIV-116 (L328V)
Clone 32: RIV-122 (A330T)
Clone 33: RIV-125 (I332F)
Clone 34: RIV-135 (I332Y)
Clone 35: RIV-141(A330L)
Clone 36: RIV-150 (A327N)
Clone 37: RIV-151 (A330I)
Clone 38: RIV-159 (I332Y)
Clone 39: RIV-161 (I332Y)
Clone 40: RIV-165 (A327G)
Clone 41: RIV-168 (L328V)
Clone 42: RIV-173 (L328S)
Clone 43: RIV-189 (A330R)
Clone 44: RIV-203 (A330C)

FIG. 5

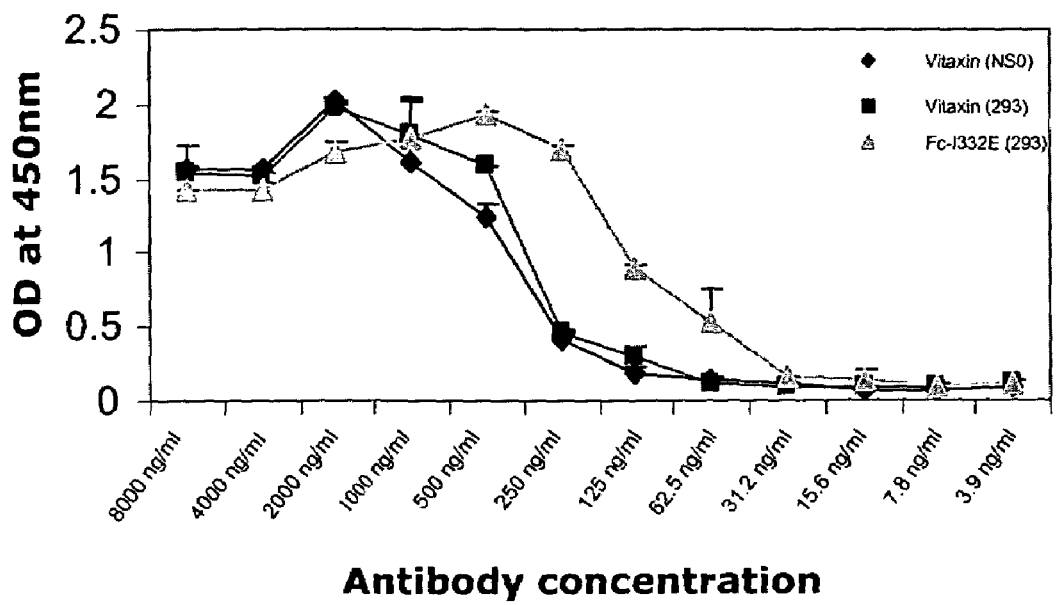
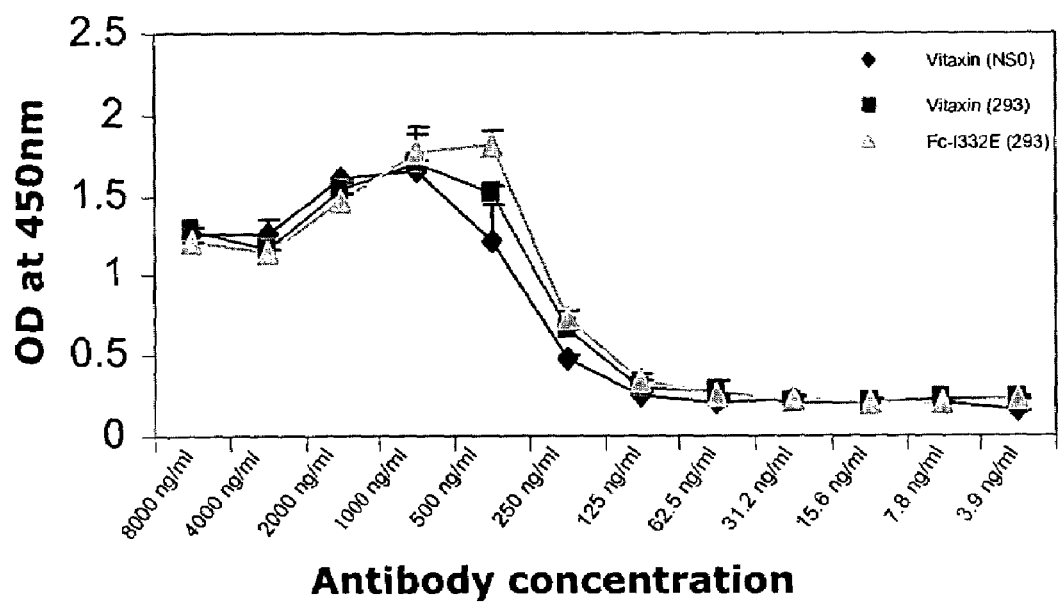
FIG. 8

A
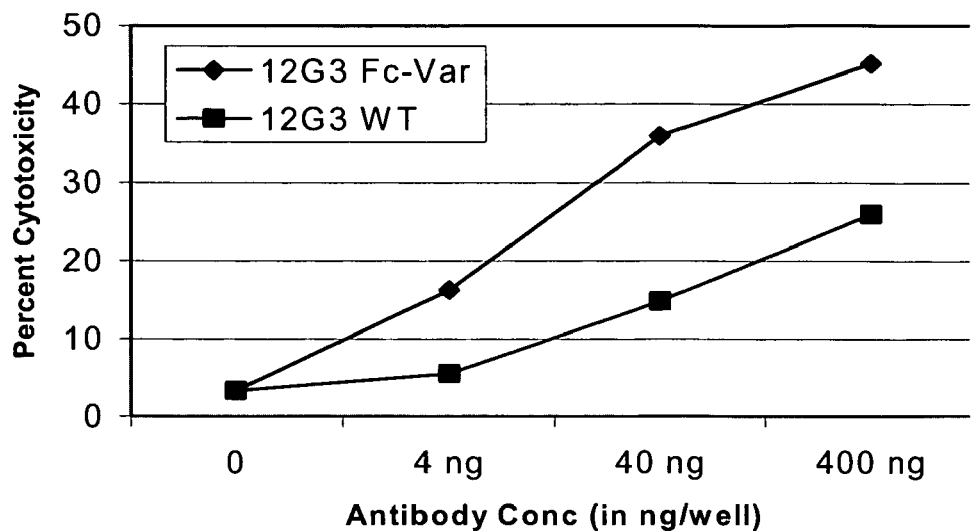
B
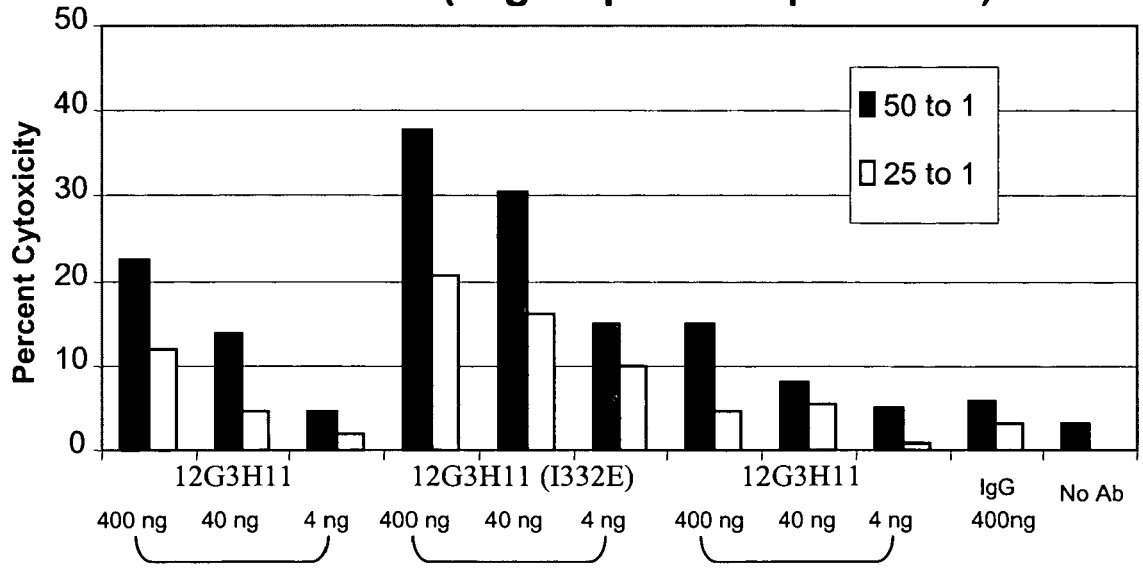
FIG. 14

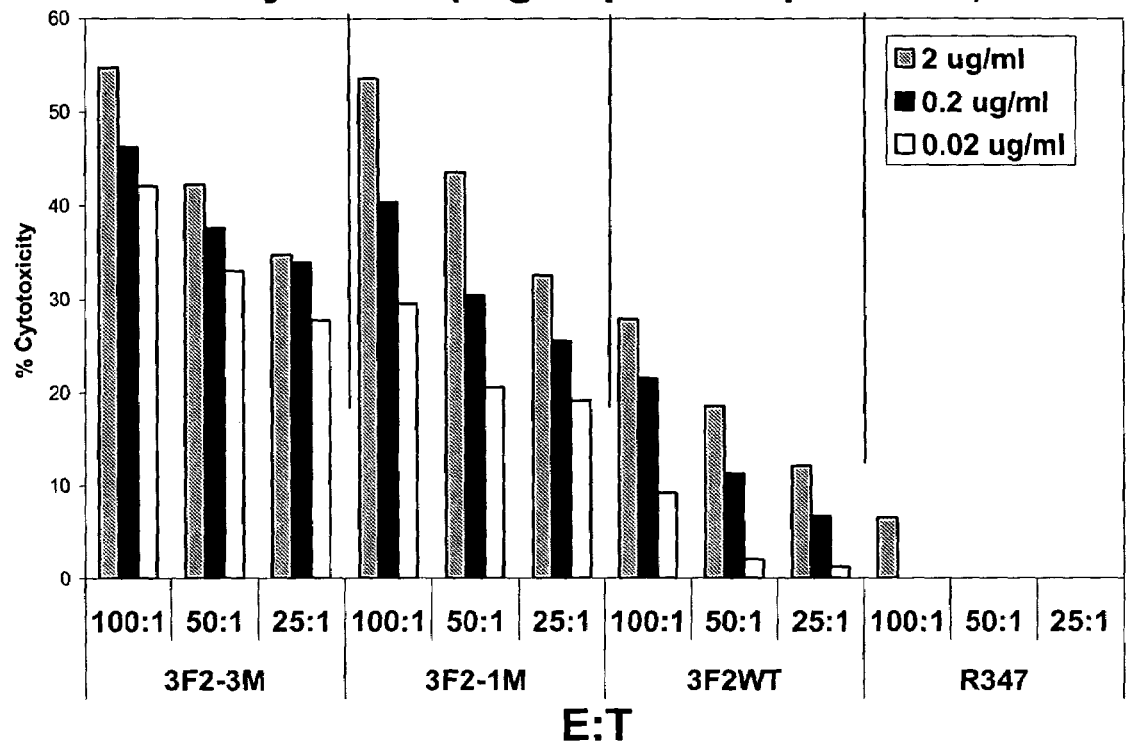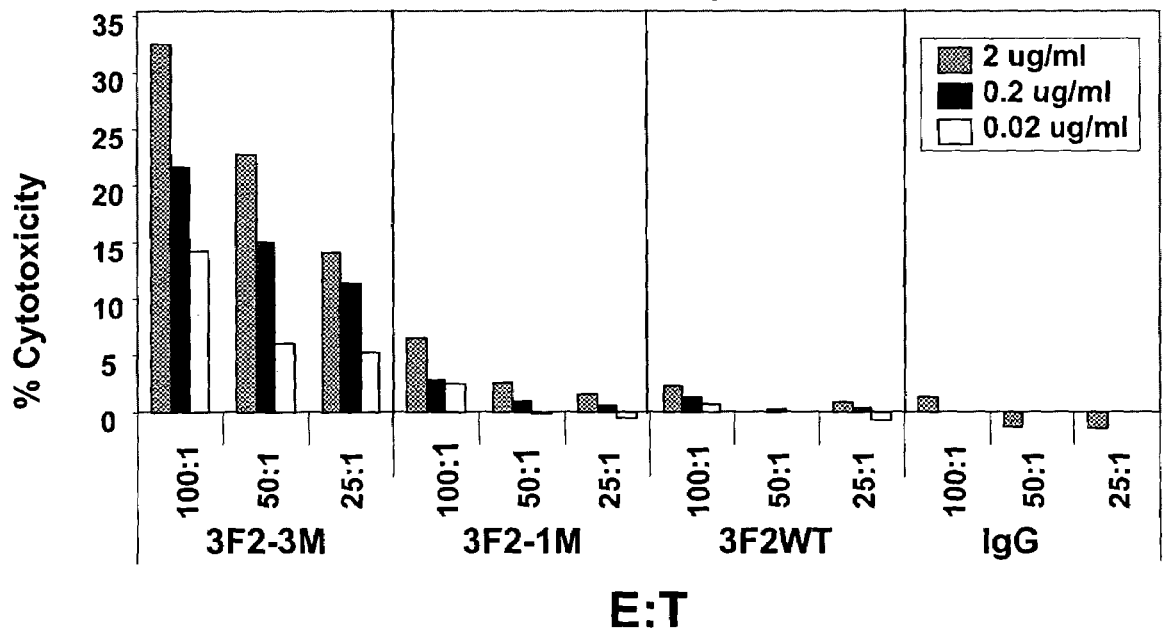
FIG. 16

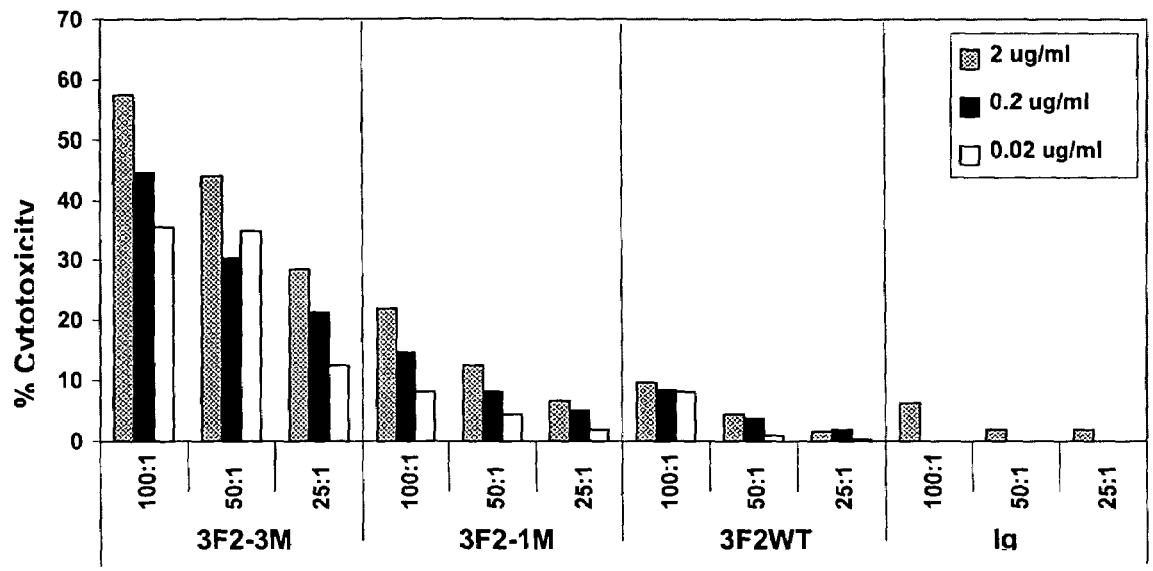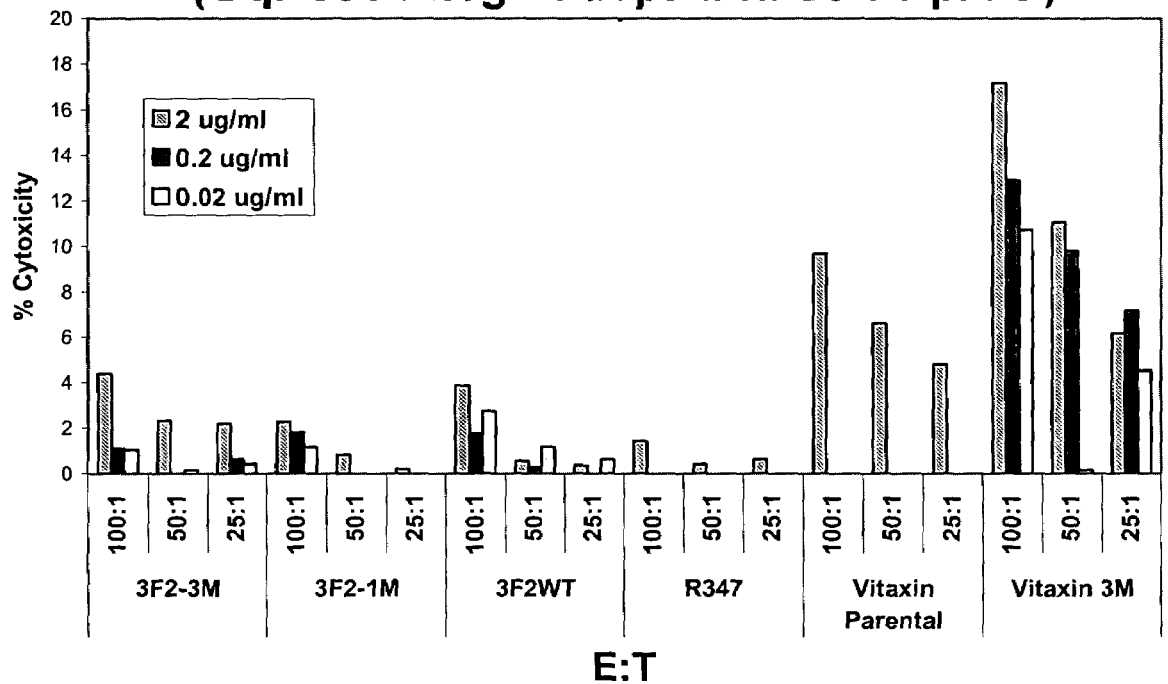
FIG. 17

SEQUENCE LISTING

```
<160> NUMBER OF SEQ ID NOS: 101

<210> SEQ ID NO 1
<211> LENGTH: 351
<212> TYPE: DNA
<213> ORGANISM: Artificial
<220> FEATURE:
<223> OTHER INFORMATION: recombinant antibody variable region

<400> SEQUENCE: 1
caggtgcagc tggtggagtc tgggggaggc gttgtgcagc ctggaaggtc cctgagactc        60
```

```
tcctgtgcag cctctggatt caccttcagt agctatgaca tgtcttgggt tcgccaggct    120
ccgggcaagg gtctggagtg ggtcgcaaaa gttagtagtg gtggtggtag cacctactat    180
ttagacactg tgcagggccg attcaccatc tccagagaca atagtaagaa caccctatac    240
ctgcaaatga actctctgag agccgaggac acagccgtgt attactgtgc aagacatctg    300
catggcagtt tgcttcttg gggccaaggg actacagtga ctgtttctag t              351

<210> SEQ ID NO 2
<211> LENGTH: 321
<212> TYPE: DNA
<213> ORGANISM: Artificial
<220> FEATURE:
<223> OTHER INFORMATION: recombinant antibody variable region

<400> SEQUENCE: 2
gagattgtgc taactcagtc tccagccacc ctgtctctca gcccaggaga aagggcgact     60
ctttcctgcc aggccagcca agtattagc aacttcctac actggtatca acaaaggcct    120
ggtcaagccc caaggcttct catccgctat cgttcccagt ccatctctgg gatccccgcc    180
aggttcagtg gcagtggatc agggacagat ttcaccctca ctatctccag tctggagcct    240
gaagattttg cagtctatta ctgtcaacag agtggcagct ggcctctgac gttcggaggg    300
gggaccaagg tggaaattaa g                                              321

<210> SEQ ID NO 3
<211> LENGTH: 117
<212> TYPE: PRT
<213> ORGANISM: Artificial
<220> FEATURE:
<223> OTHER INFORMATION: recombinant antibody variable region

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Lys Val Ser Ser Gly Gly Gly Ser Thr Tyr Tyr Leu Asp Thr Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Leu His Gly Ser Phe Ala Ser Trp Gly Gln Gly Thr Thr
            100                 105                 110

Val Thr Val Ser Ser
        115

<210> SEQ ID NO 4
<211> LENGTH: 107
<212> TYPE: PRT
<213> ORGANISM: Artificial
<220> FEATURE:
<223> OTHER INFORMATION: recombinant antibody variable region

<400> SEQUENCE: 4

Glu Ile Val Leu Thr Gln Ser Pro Ala Thr Leu Ser Leu Ser Pro Gly
1               5                   10                  15
```

```
Glu Arg Ala Thr Leu Ser Cys Gln Ala Ser Gln Ser Ile Ser Asn Phe
            20                  25                  30

Leu His Trp Tyr Gln Gln Arg Pro Gly Gln Ala Pro Arg Leu Leu Ile
        35                  40                  45

Arg Tyr Arg Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Gly Ser Trp Pro Leu
                85                  90                  95

Thr Phe Gly Gly Gly Thr Lys Val Glu Ile Lys
            100                 105

<210> SEQ ID NO 5
<211> LENGTH: 5
<212> TYPE: PRT
<213> ORGANISM: Artificial
<220> FEATURE:
<223> OTHER INFORMATION: recombinant antibody CDR

<400> SEQUENCE: 5

Asp Tyr Ser Met Asn
1               5

<210> SEQ ID NO 6
<211> LENGTH: 19
<212> TYPE: PRT
<213> ORGANISM: Artificial
<220> FEATURE:
<223> OTHER INFORMATION: recombinant antibody CDR

<400> SEQUENCE: 6

Phe Ile Arg Asn Lys Ala Asn Asp Tyr Thr Thr Glu Tyr Ala Asp Ser
1               5                   10                  15

Val Lys Gly

<210> SEQ ID NO 7
<211> LENGTH: 9
<212> TYPE: PRT
<213> ORGANISM: Artificial
<220> FEATURE:
<223> OTHER INFORMATION: recombinant antibody CDR

<400> SEQUENCE: 7

Tyr Pro Arg His His Ala Met Asp Ser
1               5

<210> SEQ ID NO 8
<211> LENGTH: 11
<212> TYPE: PRT
<213> ORGANISM: Artificial
<220> FEATURE:
<223> OTHER INFORMATION: recombinant antibody CDR

<400> SEQUENCE: 8

Arg Ala Ser Gln Ser Ile Ser Asn Asn Leu His
1               5                   10

<210> SEQ ID NO 9
<211> LENGTH: 7
<212> TYPE: PRT
<213> ORGANISM: Artificial
<220> FEATURE:
```

<223> OTHER INFORMATION: recombinant antibody CDR

<400> SEQUENCE: 9

Tyr Ala Phe Gln Ser Ile Ser
1               5

<210> SEQ ID NO 10
<211> LENGTH: 9
<212> TYPE: PRT
<213> ORGANISM: Artificial
<220> FEATURE:
<223> OTHER INFORMATION: recombinant antibody CDR

<400> SEQUENCE: 10

Gln Gln Ala Asn Ser Trp Pro Leu Thr
1               5

<210> SEQ ID NO 11
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 11
ccgtgcccag cacctgaann kctgggggga ccgtcagtc                                  39

<210> SEQ ID NO 12
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 12
ccgtgcccag cacctgaact cnnkggggga ccgtcagtct tc                              42

<210> SEQ ID NO 13
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (25)..(26)
<223> OTHER INFORMATION: n is a, c, g, or t

<400> SEQUENCE: 13
ccgtgcccag cacctgaact cctgnnkgga ccgtcagtct tcctc                           45

<210> SEQ ID NO 14
<211> LENGTH: 48
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (28)..(29)
<223> OTHER INFORMATION: n is a, c, g, or t

<400> SEQUENCE: 14
ccgtgcccag cacctgaact cctggggnnk ccgtcagtct tcctcttc    48

<210> SEQ ID NO 15
<211> LENGTH: 51
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (31)..(32)
<223> OTHER INFORMATION: n is a, c, g, or t

<400> SEQUENCE: 15
ccgtgcccag cacctgaact cctgggggga nnktcagtct tcctcttccc c    51

<210> SEQ ID NO 16
<211> LENGTH: 54
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (34)..(35)
<223> OTHER INFORMATION: n is a, c, g, or t

<400> SEQUENCE: 16
ccgtgcccag cacctgaact cctgggggga ccgnnkgtct tcctcttccc ccca    54

<210> SEQ ID NO 17
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 17
gtcacatgcg tggtggtgnn kgtgagccac gaagaccct    39

<210> SEQ ID NO 18
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (25)..(26)
<223> OTHER INFORMATION: n is a, c, g, or t

<400> SEQUENCE: 18
gtcacatgcg tggtggtgga cgtgnnkcac gaagaccctg aggtc    45

<210> SEQ ID NO 19
<211> LENGTH: 51
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (31)..(32)

<223> OTHER INFORMATION: n is a, c, g, or t

<400> SEQUENCE: 19
gtcacatgcg tggtggtgga cgtgagccac nnkgaccctg aggtcaagtt c    51

<210> SEQ ID NO 20
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 20
cgggaggagc agtacaacnn kacgtaccgt gtggtcagc    39

<210> SEQ ID NO 21
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 21
tgcaaggtct ccaacaaann kctcccagcc cccatcgag    39

<210> SEQ ID NO 22
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 22
tgcaaggtct ccaacaaagc cnnkccagcc cccatcgaga aa    42

<210> SEQ ID NO 23
<211> LENGTH: 45
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (25)..(26)
<223> OTHER INFORMATION: n is a, c, g, or t

<400> SEQUENCE: 23
tgcaaggtct ccaacaaagc cctcnnkgcc cccatcgaga aaacc    45

<210> SEQ ID NO 24
<211> LENGTH: 48
<212> TYPE: DNA
<213> ORGANISM: Artificial
<220> FEATURE:
<223> OTHER INFORMATION: synthetic primer
<220> FEATURE:
<221> NAME/KEY: misc_feature

```
<222> LOCATION: (28)..(29)
<223> OTHER INFORMATION: n is a, c, g, or t

<400> SEQUENCE: 24
tgcaaggtct ccaacaaagc cctcccannk cccatcgaga aaaccatc            48

<210> SEQ ID NO 25
<211> LENGTH: 54
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (34)..(35)
<223> OTHER INFORMATION: n is a, c, g, or t

<400> SEQUENCE: 25
tgcaaggtct ccaacaaagc cctcccagcc cccnnkgaga aaaccatctc caaa     54

<210> SEQ ID NO 26
<211> LENGTH: 33
<212> TYPE: DNA
<213> ORGANISM: Artificial
<220> FEATURE:
<223> OTHER INFORMATION: synthetic primer

<400> SEQUENCE: 26
actcacacat gtccaccgtg cccagcacct gaa                            33

<210> SEQ ID NO 27
<211> LENGTH: 18
<212> TYPE: DNA
<213> ORGANISM: Artificial
<220> FEATURE:
<223> OTHER INFORMATION: synthetic primer

<400> SEQUENCE: 27
caccaccacg catgtgac                                             18

<210> SEQ ID NO 28
<211> LENGTH: 18
<212> TYPE: DNA
<213> ORGANISM: Artificial
<220> FEATURE:
<223> OTHER INFORMATION: synthetic primer

<400> SEQUENCE: 28
gttgtactgc tcctcccg                                             18

<210> SEQ ID NO 29
<211> LENGTH: 18
<212> TYPE: DNA
<213> ORGANISM: Artificial
<220> FEATURE:
<223> OTHER INFORMATION: synthetic primer

<400> SEQUENCE: 29
tttgttggag accttgca                                             18

<210> SEQ ID NO 30
<211> LENGTH: 24
<212> TYPE: DNA
<213> ORGANISM: Artificial
<220> FEATURE:
<223> OTHER INFORMATION: synthetic primer
```

<400> SEQUENCE: 30
aacctctaca aatgtggtat ggct                                          24

<210> SEQ ID NO 31
<211> LENGTH: 42
<212> TYPE: DNA
<213> ORGANISM: Artificial
<220> FEATURE:
<223> OTHER INFORMATION: synthetic primer

<400> SEQUENCE: 31
aagcttcggt ccgccaccat ggcaactgaa gatctcccaa ag                      42

<210> SEQ ID NO 32
<211> LENGTH: 39
<212> TYPE: DNA
<213> ORGANISM: Artificial
<220> FEATURE:
<223> OTHER INFORMATION: synthetic primer

<400> SEQUENCE: 32
gtctgccgaa ccgctgcctg ccaaaccttg agtgatggt                          39

<210> SEQ ID NO 33
<211> LENGTH: 48
<212> TYPE: DNA
<213> ORGANISM: Artificial
<220> FEATURE:
<223> OTHER INFORMATION: synthetic primer

<400> SEQUENCE: 33
agcttcggtc cgccaccatg gctgtgctat tcctggcagc tcccccaa                48

<210> SEQ ID NO 34
<211> LENGTH: 42
<212> TYPE: DNA
<213> ORGANISM: Artificial
<220> FEATURE:
<223> OTHER INFORMATION: synthetic primer

<400> SEQUENCE: 34
gtctgccgaa ccgctgcccc ccatcggtga agagctggga gc                      42

<210> SEQ ID NO 35
<211> LENGTH: 30
<212> TYPE: DNA
<213> ORGANISM: Artificial
<220> FEATURE:
<223> OTHER INFORMATION: synthetic primer

<400> SEQUENCE: 35
ggcagcggtt cggcagaccc ctccaaggac                                    30

<210> SEQ ID NO 36
<211> LENGTH: 35
<212> TYPE: DNA
<213> ORGANISM: Artificial
<220> FEATURE:
<223> OTHER INFORMATION: synthetic primer

<400> SEQUENCE: 36
cagggcgtag cttactgctg aacggcgtcg agcgg                              35

<210> SEQ ID NO 37
<211> LENGTH: 39

```
<212> TYPE: DNA
<213> ORGANISM: Artificial
<220> FEATURE:
<223> OTHER INFORMATION: synthetic primer

<400> SEQUENCE: 37
tccacaggtg tccactcccg gactgaagat ctcccaaag                              39

<210> SEQ ID NO 38
<211> LENGTH: 91
<212> TYPE: DNA
<213> ORGANISM: Artificial
<220> FEATURE:
<223> OTHER INFORMATION: synthetic primer

<400> SEQUENCE: 38
gggagaattc cgcggccgct tatttgtcat cgtcatcttt gtagtcatgg tgatggtgat       60
ggtgtgcgcc tgccaaacct tgagtgatgg t                                     91

<210> SEQ ID NO 39
<211> LENGTH: 48
<212> TYPE: DNA
<213> ORGANISM: Artificial
<220> FEATURE:
<223> OTHER INFORMATION: synthetic primer

<400> SEQUENCE: 39
tccacaggtg tccactccgc tgtgctattc ctggcagctc ccccaaag                   48

<210> SEQ ID NO 40
<211> LENGTH: 94
<212> TYPE: DNA
<213> ORGANISM: Artificial
<220> FEATURE:
<223> OTHER INFORMATION: synthetic primer

<400> SEQUENCE: 40
gggagaattc cgcggccgct tatttgtcat cgtcatcttt gtagtcatgg tgatggtgat       60
ggtgtgcgcc ccccatcggt gaagagctgg gagc                                  94

<210> SEQ ID NO 41
<211> LENGTH: 33
<212> TYPE: DNA
<213> ORGANISM: Artificial
<220> FEATURE:
<223> OTHER INFORMATION: synthetic primer

<400> SEQUENCE: 41
gccctcccag cccccgagga gaaaaccatc tcc                                   33

<210> SEQ ID NO 42
<211> LENGTH: 33
<212> TYPE: DNA
<213> ORGANISM: Artificial
<220> FEATURE:
<223> OTHER INFORMATION: synthetic primer

<400> SEQUENCE: 42
gccctcccag cccccccagga gaaaaccatc tcc                                  33

<210> SEQ ID NO 43
<211> LENGTH: 33
<212> TYPE: DNA
<213> ORGANISM: Artificial
<220> FEATURE:
```

<223> OTHER INFORMATION: synthetic primer

<400> SEQUENCE: 43
gccctcccag cccccggcga gaaaaccatc tcc    33

<210> SEQ ID NO 44
<211> LENGTH: 33
<212> TYPE: DNA
<213> ORGANISM: Artificial
<220> FEATURE:
<223> OTHER INFORMATION: synthetic primer

<400> SEQUENCE: 44
gccctcccag ccccccgccga gaaaaccatc tcc   33

<210> SEQ ID NO 45
<211> LENGTH: 33
<212> TYPE: DNA
<213> ORGANISM: Artificial
<220> FEATURE:
<223> OTHER INFORMATION: synthetic primer

<400> SEQUENCE: 45
gccctcccag cccccctacga gaaaaccatc tcc   33

<210> SEQ ID NO 46
<211> LENGTH: 33
<212> TYPE: DNA
<213> ORGANISM: Artificial
<220> FEATURE:
<223> OTHER INFORMATION: synthetic primer

<400> SEQUENCE: 46
gccctcccag cccccgacga gaaaaccatc tcc    33

<210> SEQ ID NO 47
<211> LENGTH: 33
<212> TYPE: DNA
<213> ORGANISM: Artificial
<220> FEATURE:
<223> OTHER INFORMATION: synthetic primer

<400> SEQUENCE: 47
gccctcccag cccccaacga gaaaaccatc tcc    33

<210> SEQ ID NO 48
<211> LENGTH: 33
<212> TYPE: DNA
<213> ORGANISM: Artificial
<220> FEATURE:
<223> OTHER INFORMATION: synthetic primer

<400> SEQUENCE: 48
gccctcccag cccccgtgga gaaaaccatc tcc    33

<210> SEQ ID NO 49
<211> LENGTH: 33
<212> TYPE: DNA
<213> ORGANISM: Artificial
<220> FEATURE:
<223> OTHER INFORMATION: synthetic primer

<400> SEQUENCE: 49
gccctcccag cccctggga gaaaaccatc tcc     33

```
<210> SEQ ID NO 50
<211> LENGTH: 33
<212> TYPE: DNA
<213> ORGANISM: Artificial
<220> FEATURE:
<223> OTHER INFORMATION: synthetic primer

<400> SEQUENCE: 50
gccctcccag cccccgcga gaaaaccatc tcc                                  33

<210> SEQ ID NO 51
<211> LENGTH: 33
<212> TYPE: DNA
<213> ORGANISM: Artificial
<220> FEATURE:
<223> OTHER INFORMATION: synthetic primer

<400> SEQUENCE: 51
gccctcccag ccccagcga gaaaaccatc tcc                                  33

<210> SEQ ID NO 52
<211> LENGTH: 33
<212> TYPE: DNA
<213> ORGANISM: Artificial
<220> FEATURE:
<223> OTHER INFORMATION: synthetic primer

<400> SEQUENCE: 52
gccctcccag ccccaagga gaaaaccatc tcc                                  33

<210> SEQ ID NO 53
<211> LENGTH: 33
<212> TYPE: DNA
<213> ORGANISM: Artificial
<220> FEATURE:
<223> OTHER INFORMATION: synthetic primer

<400> SEQUENCE: 53
gccctcccag ccccatgga gaaaaccatc tcc                                  33

<210> SEQ ID NO 54
<211> LENGTH: 33
<212> TYPE: DNA
<213> ORGANISM: Artificial
<220> FEATURE:
<223> OTHER INFORMATION: synthetic primer

<400> SEQUENCE: 54
gccctcccag ccccaccga gaaaaccatc tcc                                  33

<210> SEQ ID NO 55
<211> LENGTH: 33
<212> TYPE: DNA
<213> ORGANISM: Artificial
<220> FEATURE:
<223> OTHER INFORMATION: synthetic primer

<400> SEQUENCE: 55
gccctcccag ccccctgcga gaaaaccatc tcc                                 33

<210> SEQ ID NO 56
<211> LENGTH: 33
<212> TYPE: DNA
<213> ORGANISM: Artificial
<220> FEATURE:
<223> OTHER INFORMATION: synthetic primer
```

```
<400> SEQUENCE: 56
gccctcccag cccccctgga gaaaaccatc tcc                                    33

<210> SEQ ID NO 57
<211> LENGTH: 33
<212> TYPE: DNA
<213> ORGANISM: Artificial
<220> FEATURE:
<223> OTHER INFORMATION: synthetic primer

<400> SEQUENCE: 57
gccctcccag cccccttcga gaaaaccatc tcc                                    33

<210> SEQ ID NO 58
<211> LENGTH: 33
<212> TYPE: DNA
<213> ORGANISM: Artificial
<220> FEATURE:
<223> OTHER INFORMATION: synthetic primer

<400> SEQUENCE: 58
gccctcccag cccccacga gaaaaccatc tcc                                     33

<210> SEQ ID NO 59
<211> LENGTH: 33
<212> TYPE: DNA
<213> ORGANISM: Artificial
<220> FEATURE:
<223> OTHER INFORMATION: synthetic primer

<400> SEQUENCE: 59
gccctcccag ccccccctga gaaaaccatc tcc                                    33

<210> SEQ ID NO 60
<211> LENGTH: 27
<212> TYPE: DNA
<213> ORGANISM: Artificial
<220> FEATURE:
<223> OTHER INFORMATION: synthetic primer

<400> SEQUENCE: 60 ctgggggac cggacgtctt cctcttc                                            27

<210> SEQ ID NO 61
<211> LENGTH: 27
<212> TYPE: DNA
<213> ORGANISM: Artificial
<220> FEATURE:
<223> OTHER INFORMATION: synthetic primer

<400> SEQUENCE: 61
aaagccctcc cactgcccga ggagaaa                                           27

<210> SEQ ID NO 62
<211> LENGTH: 360
<212> TYPE: DNA
<213> ORGANISM: Artificial
<220> FEATURE:
<223> OTHER INFORMATION: recombinant antibody variable region

<400> SEQUENCE: 62
caaatgcagc tggtgcagtc tgggcctgag gtgaagaagc ctgggacctc agtgaaggtc       60
tcctgcaagg cttctggatt caccttttgac gattactcca tgaactgggt gcgacaggct    120
cgtggacaac gccttgagtg gataggattt attagaaaca agctaatga ctacacaaca      180
```

```
gagtacgctg actctgtgaa gggtagagtc accattacca gggacatgtc cacgagcaca    240
gcctacatgg agctgagcag cctgagatcc gaggacacgg ccgtgtatta ctgtgcgaga    300
taccctaggc atcatgctat ggactcctgg ggccaaggaa cctcggtcac cgtctcctca    360
```

<210> SEQ ID NO 63
<211> LENGTH: 321
<212> TYPE: DNA
<213> ORGANISM: Artificial
<220> FEATURE:
<223> OTHER INFORMATION: recombinant antibody variable region

<400> SEQUENCE: 63

```
gacatccaga tgacccagtc tccatcctcc ctgtctgcat ctgtaggaga cagagtcacc     60
atcacttgca gggccagcca agtattagc aacaacctac actggtatca gcagaaacca    120
gggaaagccc ctaagctcct gatcaagtat gccttccagt ccatctctgg gtcccatca    180 aggttcagtg gaagtggatc tgggacagat tttactttca ccatcagcag cctgcagcct    240
gaagattttg caacatatta ctgtcaacag gccaacagct ggccgctcac gttcggcgga    300
gggaccaagg tggagatcaa a                                              321
```

<210> SEQ ID NO 64
<211> LENGTH: 120
<212> TYPE: PRT
<213> ORGANISM: Artificial
<220> FEATURE:
<223> OTHER INFORMATION: recombinant antibody variable region

<400> SEQUENCE: 64

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Asp Asp Tyr
            20                  25                  30

Ser Met Asn Trp Val Arg Gln Ala Arg Gly Gln Arg Leu Glu Trp Ile
        35                  40                  45

Gly Phe Ile Arg Asn Lys Ala Asn Asp Tyr Thr Thr Glu Tyr Ala Asp
    50                  55                  60

Ser Val Lys Gly Arg Val Thr Ile Thr Arg Asp Met Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Tyr Pro Arg His His Ala Met Asp Ser Trp Gly Gln
            100                 105                 110

Gly Thr Ser Val Thr Val Ser Ser
        115                 120

<210> SEQ ID NO 65
<211> LENGTH: 107
<212> TYPE: PRT
<213> ORGANISM: Artificial
<220> FEATURE:
<223> OTHER INFORMATION: recombinant antibody variable region

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

```
Leu His Trp Tyr Gln Gln Lys Pro Gly Lys Ala Pro Lys Leu Leu Ile
         35                  40                  45

Lys Tyr Ala Phe Gln Ser Ile Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Gln Gln Ala Asn Ser Trp Pro Leu
                 85                  90                  95

Thr Phe Gly Gly Gly Thr Lys Val Glu Ile Lys
                100                 105

<210> SEQ ID NO 66
<211> LENGTH: 361
<212> TYPE: DNA
<213> ORGANISM: Artificial
<220> FEATURE:
<223> OTHER INFORMATION: recombinant antibody variable region

<400> SEQUENCE: 66
gaggtgcagc tggtggagtc tgggggaggt gtggtacggc ctgggggtc cctgagactc        60 tcctgtgcag cctctgggtt caccgtcagt gattactcca tgaactgggt ccgccaggct      120
ccagggaagg gcctggagtg gattgggttt attagaaaca agctaatgc ctacacaaca       180 gagtacagtg catctgtgaa gggtagattc accatctcaa gagatgattc aaaaaacacg      240
ctgtatctgc aaatgaacag cctgaaaacc gaggacacag ccgtgtatta ctgtaccaca      300
taccctaggt atcatgctat ggactcctgg ggccagggca ccatggtcac cgtctcctca      360
g                                                                     361

<210> SEQ ID NO 67
<211> LENGTH: 321
<212> TYPE: DNA
<213> ORGANISM: Artificial
<220> FEATURE:
<223> OTHER INFORMATION: recombinant antibody variable region

<400> SEQUENCE: 67
gccatccagt tgactcagtc tccatcctcc ctgtctgcat ctgtaggaga cagagtcacc        60
atcacttgca gggccagcca agtattagc acaacctac actggtacct gcagaagcca        120
gggcagtctc cacagctcct gatctattat ggcttccagt ccatctctgg ggtcccatca      180
aggttcagtg gcagtggatc tgggacagat ttcactctca ccatcagcag tctgcaacct      240
gaagattttg caacttacta ctgtcaacag gccaacagct ggccgctcac gttcggcgga      300
gggaccaagc tggagatcaa a                                               321

<210> SEQ ID NO 68
<211> LENGTH: 120
<212> TYPE: PRT
<213> ORGANISM: Artificial
<220> FEATURE:
<223> OTHER INFORMATION: recombinant antibody variable region

<400> SEQUENCE: 68

Glu Val Gln Leu Val Glu Ser Gly Gly Gly Val Val Arg Pro Gly Gly
  1               5                  10                  15

Ser Leu Arg Leu Ser Cys Ala Ala Ser Gly Phe Thr Val Ser Asp Tyr
                 20                  25                  30

Ser Met Asn Trp Val Arg Gln Ala Pro Gly Lys Gly Leu Glu Trp Ile
             35                  40                  45
```

Gly Phe Ile Arg Asn Lys Ala Asn Ala Tyr Thr Thr Glu Tyr Ser Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Tyr Pro Arg Tyr His Ala Met Asp Ser Trp Gly Gln
            100                 105                 110

Gly Thr Met Val Thr Val Ser Ser
        115                 120

<210> SEQ ID NO 69
<211> LENGTH: 107
<212> TYPE: PRT
<213> ORGANISM: Artificial
<220> FEATURE:
<223> OTHER INFORMATION: recombinant antibody variable region

<400> SEQUENCE: 69

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
                20                  25                  30

Leu His Trp Tyr Leu Gln Lys Pro Gly Gln Ser Pro Gln Leu Leu Ile
            35                  40                  45

Tyr Tyr Gly Phe Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Trp Pro Leu
                85                  90                  95

Thr Phe Gly Gly Gly Thr Lys Leu Glu Ile Lys
            100                 105

<210> SEQ ID NO 70
<211> LENGTH: 5
<212> TYPE: PRT
<213> ORGANISM: Artificial
<220> FEATURE:
<223> OTHER INFORMATION: recombinant antibody CDR

<400> SEQUENCE: 70

Asp Tyr Ser Met Asn
1               5

<210> SEQ ID NO 71
<211> LENGTH: 19
<212> TYPE: PRT
<213> ORGANISM: Artificial
<220> FEATURE:
<223> OTHER INFORMATION: recombinant antibody CDR

<400> SEQUENCE: 71

Phe Ile Arg Asn Lys Ala Asn Ala Tyr Thr Thr Glu Tyr Ser Ala Ser
1               5                   10                  15

Val Lys Gly

<210> SEQ ID NO 72
<211> LENGTH: 9
<212> TYPE: PRT

-continued

<213> ORGANISM: Artificial
<220> FEATURE:
<223> OTHER INFORMATION: recombinant antibody CDR

<400> SEQUENCE: 72

Tyr Pro Arg Tyr His Ala Met Asp Ser
1               5

<210> SEQ ID NO 73
<211> LENGTH: 11
<212> TYPE: PRT
<213> ORGANISM: Artificial
<220> FEATURE:
<223> OTHER INFORMATION: recombinant antibody CDR

<400> SEQUENCE: 73

Arg Ala Ser Gln Ser Ile Ser Asn Asn Leu His
1               5                   10

<210> SEQ ID NO 74
<211> LENGTH: 7
<212> TYPE: PRT
<213> ORGANISM: Artificial
<220> FEATURE:
<223> OTHER INFORMATION: recombinant antibody CDR

<400> SEQUENCE: 74

Tyr Gly Phe Gln Ser Ile Ser
1               5

<210> SEQ ID NO 75
<211> LENGTH: 9
<212> TYPE: PRT
<213> ORGANISM: Artificial
<220> FEATURE:
<223> OTHER INFORMATION: recombinant antibody CDR

<400> SEQUENCE: 75

Gln Gln Ala Asn Ser Trp Pro Leu Thr
1               5

<210> SEQ ID NO 76
<211> LENGTH: 976
<212> TYPE: PRT
<213> ORGANISM: Homo sapiens

<400> SEQUENCE: 76

Met Glu Arg Arg Trp Pro Leu Gly Leu Gly Leu Val Leu Leu Leu Cys
1               5                   10                  15

Ala Pro Leu Pro Pro Gly Ala Arg Ala Lys Glu Val Thr Leu Met Asp
                20                  25                  30

Thr Ser Lys Ala Gln Gly Glu Leu Gly Trp Leu Leu Asp Pro Pro Lys
            35                  40                  45

Asp Gly Trp Ser Glu Gln Gln Ile Leu Asn Gly Thr Pro Leu Tyr
        50                  55                  60

Met Tyr Gln Asp Cys Pro Met Gln Gly Arg Arg Asp Thr Asp His Trp
65                  70                  75                  80

Leu Arg Ser Asn Trp Ile Tyr Arg Gly Glu Glu Ala Ser Arg Val His
                85                  90                  95

Val Glu Leu Gln Phe Thr Val Arg Asp Cys Lys Ser Phe Pro Gly Gly
                100                 105                 110

Ala Gly Pro Leu Gly Cys Lys Glu Thr Phe Asn Leu Leu Tyr Met Glu
            115                 120                 125

-continued

```
Ser Asp Gln Asp Val Gly Ile Gln Leu Arg Arg Pro Leu Phe Gln Lys
130                 135                 140

Val Thr Thr Val Ala Ala Asp Gln Ser Phe Thr Ile Arg Asp Leu Ala
145                 150                 155                 160

Ser Gly Ser Val Lys Leu Asn Val Glu Arg Cys Ser Leu Gly Arg Leu
                165                 170                 175

Thr Arg Arg Gly Leu Tyr Leu Ala Phe His Asn Pro Gly Ala Cys Val
            180                 185                 190

Ala Leu Val Ser Val Arg Val Phe Tyr Gln Arg Cys Pro Glu Thr Leu
        195                 200                 205

Asn Gly Leu Ala Gln Phe Pro Asp Thr Leu Pro Gly Pro Ala Gly Leu
    210                 215                 220

Val Glu Val Ala Gly Thr Cys Leu Pro His Ala Arg Ala Ser Pro Arg
225                 230                 235                 240

Pro Ser Gly Ala Pro Arg Met His Cys Ser Pro Asp Gly Glu Trp Leu
                245                 250                 255

Val Pro Val Gly Arg Cys His Cys Glu Pro Gly Tyr Glu Glu Gly Gly
            260                 265                 270

Ser Gly Glu Ala Cys Val Ala Cys Pro Ser Gly Ser Tyr Arg Met Asp
        275                 280                 285

Met Asp Thr Pro His Cys Leu Thr Cys Pro Gln Gln Ser Thr Ala Glu
    290                 295                 300

Ser Glu Gly Ala Thr Ile Cys Thr Cys Glu Ser Gly His Tyr Arg Ala
305                 310                 315                 320

Pro Gly Glu Gly Pro Gln Val Ala Cys Thr Gly Pro Pro Ser Ala Pro
                325                 330                 335

Arg Asn Leu Ser Phe Ser Ala Ser Gly Thr Gln Leu Ser Leu Arg Trp
            340                 345                 350

Glu Pro Pro Ala Asp Thr Gly Gly Arg Gln Asp Val Arg Tyr Ser Val
        355                 360                 365

Arg Cys Ser Gln Cys Gln Gly Thr Ala Gln Asp Gly Gly Pro Cys Gln
    370                 375                 380

Pro Cys Gly Val Gly Val His Phe Ser Pro Gly Ala Arg Ala Leu Thr
385                 390                 395                 400

Thr Pro Ala Val His Val Asn Gly Leu Glu Pro Tyr Ala Asn Tyr Thr
                405                 410                 415

Phe Asn Val Glu Ala Gln Asn Gly Val Ser Gly Leu Gly Ser Ser Gly
            420                 425                 430

His Ala Ser Thr Ser Val Ser Ile Ser Met Gly His Ala Glu Ser Leu
        435                 440                 445

Ser Gly Leu Ser Leu Arg Leu Val Lys Lys Glu Pro Arg Gln Leu Glu
    450                 455                 460

Leu Thr Trp Ala Gly Ser Arg Pro Arg Ser Pro Gly Ala Asn Leu Thr
465                 470                 475                 480

Tyr Glu Leu His Val Leu Asn Gln Asp Glu Glu Arg Tyr Gln Met Val
                485                 490                 495

Leu Glu Pro Arg Val Leu Leu Thr Glu Leu Gln Pro Asp Thr Thr Tyr
            500                 505                 510

Ile Val Arg Val Arg Met Leu Thr Pro Leu Gly Pro Gly Pro Phe Ser
        515                 520                 525

Pro Asp His Glu Phe Arg Thr Ser Pro Pro Val Ser Arg Gly Leu Thr
    530                 535                 540
```

-continued

```
Gly Gly Glu Ile Val Ala Val Ile Phe Gly Leu Leu Gly Ala Ala
545                 550                 555                 560

Leu Leu Leu Gly Ile Leu Val Phe Arg Ser Arg Ala Gln Arg Gln
                565                 570                 575

Arg Gln Gln Arg Gln Arg Asp Arg Ala Thr Asp Val Asp Arg Glu Asp
            580                 585                 590

Lys Leu Trp Leu Lys Pro Tyr Val Asp Leu Gln Ala Tyr Glu Asp Pro
            595                 600                 605

Ala Gln Gly Ala Leu Asp Phe Thr Arg Glu Leu Asp Pro Ala Trp Leu
    610                 615                 620

Met Val Asp Thr Val Ile Gly Glu Gly Glu Phe Gly Glu Val Tyr Arg
625                 630                 635                 640

Gly Thr Leu Arg Leu Pro Ser Gln Asp Cys Lys Thr Val Ala Ile Lys
                645                 650                 655

Thr Leu Lys Asp Thr Ser Pro Gly Gly Gln Trp Trp Asn Phe Leu Arg
            660                 665                 670

Glu Ala Thr Ile Met Gly Gln Phe Ser His Pro His Ile Leu His Leu
            675                 680                 685

Glu Gly Val Val Thr Lys Arg Lys Pro Ile Met Ile Ile Thr Glu Phe
    690                 695                 700

Met Glu Asn Gly Ala Leu Asp Ala Phe Leu Arg Glu Arg Glu Asp Gln
705                 710                 715                 720

Leu Val Pro Gly Gln Leu Val Ala Met Leu Gln Gly Ile Ala Ser Gly
                725                 730                 735

Met Asn Tyr Leu Ser Asn His Asn Tyr Val His Arg Asp Leu Ala Ala
            740                 745                 750

Arg Asn Ile Leu Val Asn Gln Asn Leu Cys Cys Lys Val Ser Asp Phe
            755                 760                 765

Gly Leu Thr Arg Leu Leu Asp Asp Phe Asp Gly Thr Tyr Glu Thr Gln
    770                 775                 780

Gly Gly Lys Ile Pro Ile Arg Trp Thr Ala Pro Glu Ala Ile Ala His
785                 790                 795                 800

Arg Ile Phe Thr Thr Ala Ser Asp Val Trp Ser Phe Gly Ile Val Met
                805                 810                 815

Trp Glu Val Leu Ser Phe Gly Asp Lys Pro Tyr Gly Glu Met Ser Asn
            820                 825                 830

Gln Glu Val Met Lys Ser Ile Glu Asp Gly Tyr Arg Leu Pro Pro Pro
            835                 840                 845

Val Asp Cys Pro Ala Pro Leu Tyr Glu Leu Met Lys Asn Cys Trp Ala
850                 855                 860

Tyr Asp Arg Ala Arg Arg Pro His Phe Gln Lys Leu Gln Ala His Leu
865                 870                 875                 880

Glu Gln Leu Leu Ala Asn Pro His Ser Leu Arg Thr Ile Ala Asn Phe
                885                 890                 895

Asp Pro Arg Val Thr Leu Arg Leu Pro Ser Leu Ser Gly Ser Asp Gly
            900                 905                 910

Ile Pro Tyr Arg Thr Val Ser Glu Trp Leu Glu Ser Ile Arg Met Lys
            915                 920                 925

Arg Tyr Ile Leu His Phe His Ser Ala Gly Leu Asp Thr Met Glu Cys
    930                 935                 940

Val Leu Glu Leu Thr Ala Glu Asp Leu Thr Gln Met Gly Ile Thr Leu
945                 950                 955                 960

Pro Gly His Gln Lys Arg Ile Leu Cys Ser Ile Gln Gly Phe Lys Asp
```

-continued

```
                        965                 970                 975

<210> SEQ ID NO 77
<211> LENGTH: 976
<212> TYPE: PRT
<213> ORGANISM: Homo sapiens

<400> SEQUENCE: 77

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Gly Gly Glu Leu Gly Trp Leu Thr His Pro Tyr
            35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365
```

-continued

```
Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Val Ala Val Gly
    530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
        675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
    770                 775                 780

Ala Pro Glu Ala Ile Ser Tyr Arg Lys Phe Thr Ser Ala Ser Asp Val
```

```
            785                 790                 795                 800
Trp Ser Phe Gly Ile Val Met Trp Glu Val Met Thr Tyr Gly Glu Arg
                805                 810                 815
Pro Tyr Trp Glu Leu Ser Asn His Glu Val Met Lys Ala Ile Asn Asp
            820                 825                 830
Gly Phe Arg Leu Pro Thr Pro Met Asp Cys Pro Ser Ala Ile Tyr Gln
        835                 840                 845
Leu Met Met Gln Cys Trp Gln Gln Glu Arg Ala Arg Arg Pro Lys Phe
    850                 855                 860
Ala Asp Ile Val Ser Ile Leu Asp Lys Leu Ile Arg Ala Pro Asp Ser
865                 870                 875                 880
Leu Lys Thr Leu Ala Asp Phe Asp Pro Arg Val Ser Ile Arg Leu Pro
                885                 890                 895
Ser Thr Ser Gly Ser Glu Gly Val Pro Phe Arg Thr Val Ser Glu Trp
            900                 905                 910
Leu Glu Ser Ile Lys Met Gln Gln Tyr Thr Glu His Phe Met Ala Ala
        915                 920                 925
Gly Tyr Thr Ala Ile Glu Lys Val Val Gln Met Thr Asn Asp Asp Ile
    930                 935                 940
Lys Arg Ile Gly Val Arg Leu Pro Gly His Gln Lys Arg Ile Ala Tyr
945                 950                 955                 960
Ser Leu Leu Gly Leu Lys Asp Gln Val Asn Thr Val Gly Ile Pro Ile
                965                 970                 975

<210> SEQ ID NO 78
<211> LENGTH: 983
<212> TYPE: PRT
<213> ORGANISM: Homo sapiens

<400> SEQUENCE: 78

Met Asp Cys Gln Leu Ser Ile Leu Leu Leu Ser Cys Ser Val Leu
1               5                   10                  15
Asp Ser Phe Gly Glu Leu Ile Pro Gln Pro Ser Asn Glu Val Asn Leu
                20                  25                  30
Leu Asp Ser Lys Thr Ile Gln Gly Glu Leu Gly Trp Ile Ser Tyr Pro
            35                  40                  45
Ser His Gly Trp Glu Glu Ile Ser Gly Val Asp Glu His Tyr Thr Pro
        50                  55                  60
Ile Arg Thr Tyr Gln Val Cys Asn Val Met Asp His Ser Gln Asn Asn
65                  70                  75                  80
Trp Leu Arg Thr Asn Trp Val Pro Arg Asn Ser Ala Gln Lys Ile Tyr
                85                  90                  95
Val Glu Leu Lys Phe Thr Leu Arg Asp Cys Asn Ser Ile Pro Leu Val
                100                 105                 110
Leu Gly Thr Cys Lys Glu Thr Phe Asn Leu Tyr Tyr Met Glu Ser Asp
            115                 120                 125
Asp Asp His Gly Val Lys Phe Arg Glu His Gln Phe Thr Lys Ile Asp
        130                 135                 140
Thr Ile Ala Ala Asp Glu Ser Phe Thr Gln Met Asp Leu Gly Asp Arg
145                 150                 155                 160
Ile Leu Lys Leu Asn Thr Glu Ile Arg Glu Val Gly Pro Val Asn Lys
                165                 170                 175
Lys Gly Phe Tyr Leu Ala Phe Gln Asp Val Gly Ala Cys Val Ala Leu
            180                 185                 190
```

-continued

```
Val Ser Val Arg Val Tyr Phe Lys Lys Cys Pro Phe Thr Val Lys Asn
        195                 200                 205

Leu Ala Met Phe Pro Asp Thr Val Pro Met Asp Ser Gln Ser Leu Val
210                 215                 220

Glu Val Arg Gly Ser Cys Val Asn Asn Ser Lys Glu Glu Asp Pro Pro
225                 230                 235                 240

Arg Met Tyr Cys Ser Thr Glu Gly Glu Trp Leu Val Pro Ile Gly Lys
                245                 250                 255

Cys Ser Cys Asn Ala Gly Tyr Glu Glu Arg Gly Phe Met Cys Gln Ala
            260                 265                 270

Cys Arg Pro Gly Phe Tyr Lys Ala Leu Asp Gly Asn Met Lys Cys Ala
        275                 280                 285

Lys Cys Pro Pro His Ser Ser Thr Gln Glu Asp Gly Ser Met Asn Cys
290                 295                 300

Arg Cys Glu Asn Asn Tyr Phe Arg Ala Asp Lys Asp Pro Pro Ser Met
305                 310                 315                 320

Ala Cys Thr Arg Pro Pro Ser Ser Pro Arg Asn Val Ile Ser Asn Ile
                325                 330                 335

Asn Glu Thr Ser Val Ile Leu Asp Trp Ser Trp Pro Leu Asp Thr Gly
            340                 345                 350

Gly Arg Lys Asp Val Thr Phe Asn Ile Ile Cys Lys Lys Cys Gly Trp
        355                 360                 365

Asn Ile Lys Gln Cys Glu Pro Cys Ser Pro Asn Val Arg Phe Leu Pro
370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
                405                 410                 415

Glu Leu Ser Ser Pro Pro Arg Gln Phe Ala Ala Val Ser Ile Thr Thr
            420                 425                 430

Asn Gln Ala Ala Pro Ser Pro Val Leu Thr Ile Lys Lys Asp Arg Thr
        435                 440                 445

Ser Arg Asn Ser Ile Ser Leu Ser Trp Gln Glu Pro Glu His Pro Asn
450                 455                 460

Gly Ile Ile Leu Asp Tyr Glu Val Lys Tyr Tyr Glu Lys Gln Glu Gln
465                 470                 475                 480

Glu Thr Ser Tyr Thr Ile Leu Arg Ala Arg Gly Thr Asn Val Thr Ile
                485                 490                 495

Ser Ser Leu Lys Pro Asp Thr Ile Tyr Val Phe Gln Ile Arg Ala Arg
            500                 505                 510

Thr Ala Ala Gly Tyr Gly Thr Asn Ser Arg Lys Phe Glu Phe Glu Thr
        515                 520                 525

Ser Pro Asp Ser Phe Ser Ile Ser Gly Glu Ser Ser Gln Val Val Met
530                 535                 540

Ile Ala Ile Ser Ala Ala Val Ala Ile Ile Leu Leu Thr Val Val Ile
545                 550                 555                 560

Tyr Val Leu Ile Gly Arg Phe Cys Gly Tyr Lys Ser Lys His Gly Ala
                565                 570                 575

Asp Glu Lys Arg Leu His Phe Gly Asn Gly His Leu Lys Leu Pro Gly
            580                 585                 590

Leu Arg Thr Tyr Val Asp Pro His Thr Tyr Glu Asp Pro Thr Gln Ala
        595                 600                 605

Val His Glu Phe Ala Lys Glu Leu Asp Ala Thr Asn Ile Ser Ile Asp
```

```
                610                 615                 620
Lys Val Val Gly Ala Gly Glu Phe Gly Glu Val Cys Ser Gly Arg Leu
625                 630                 635                 640

Lys Leu Pro Ser Lys Lys Glu Ile Ser Val Ala Ile Lys Thr Leu Lys
                645                 650                 655

Val Gly Tyr Thr Glu Lys Gln Arg Arg Asp Phe Leu Gly Glu Ala Ser
            660                 665                 670

Ile Met Gly Gln Phe Asp His Pro Asn Ile Ile Arg Leu Glu Gly Val
            675                 680                 685

Val Thr Lys Ser Lys Pro Val Met Ile Val Thr Glu Tyr Met Glu Asn
690                 695                 700

Gly Ser Leu Asp Ser Phe Leu Arg Lys His Asp Ala Gln Phe Thr Val
705                 710                 715                 720

Ile Gln Leu Val Gly Met Leu Arg Gly Ile Ala Ser Gly Met Lys Tyr
                725                 730                 735

Leu Ser Asp Met Gly Tyr Val His Arg Asp Leu Ala Ala Arg Asn Ile
            740                 745                 750

Leu Ile Asn Ser Asn Leu Val Cys Lys Val Ser Asp Phe Gly Leu Ser
            755                 760                 765

Arg Val Leu Glu Asp Asp Pro Glu Ala Ala Tyr Thr Thr Arg Gly Gly
770                 775                 780

Lys Ile Pro Ile Arg Trp Thr Ser Pro Glu Ala Ile Ala Tyr Arg Lys
785                 790                 795                 800

Phe Thr Ser Ala Ser Asp Val Trp Ser Tyr Gly Ile Val Leu Trp Glu
                805                 810                 815

Val Met Ser Tyr Gly Glu Arg Pro Tyr Trp Glu Met Ser Asn Gln Asp
            820                 825                 830

Val Ile Lys Ala Val Asp Glu Gly Tyr Arg Leu Pro Pro Pro Met Asp
            835                 840                 845

Cys Pro Ala Ala Leu Tyr Gln Leu Met Leu Asp Cys Trp Gln Lys Asp
850                 855                 860

Arg Asn Asn Arg Pro Lys Phe Glu Gln Ile Val Ser Ile Leu Asp Lys
865                 870                 875                 880

Leu Ile Arg Asn Pro Gly Ser Leu Lys Ile Ile Thr Ser Ala Ala Ala
                885                 890                 895

Arg Pro Ser Asn Leu Leu Leu Asp Gln Ser Asn Val Asp Ile Thr Thr
            900                 905                 910

Phe Arg Thr Thr Gly Asp Trp Leu Asn Gly Val Trp Thr Ala His Cys
            915                 920                 925

Lys Glu Ile Phe Thr Gly Val Glu Tyr Ser Ser Cys Asp Thr Ile Ala
            930                 935                 940

Lys Ile Ser Thr Asp Asp Met Lys Lys Val Gly Val Thr Val Val Gly
945                 950                 955                 960

Pro Gln Lys Lys Ile Ile Ser Ser Ile Lys Ala Leu Glu Thr Gln Ser
                965                 970                 975

Lys Asn Gly Pro Val Pro Val
            980

<210> SEQ ID NO 79
<211> LENGTH: 539
<212> TYPE: PRT
<213> ORGANISM: Homo sapiens

<400> SEQUENCE: 79
```

-continued

```
Met Asp Cys Gln Leu Ser Ile Leu Leu Leu Ser Cys Ser Val Leu
1               5                   10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
            35                  40                  45

Ser His Gly Trp Glu Glu Ile Ser Gly Val Asp Glu His Tyr Thr Pro
50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
                100                 105                 110

Leu Gly Thr Cys Lys Glu Thr Phe Asn Leu Tyr Tyr Met Glu Ser Asp
            115                 120                 125

Asp Asp His Gly Val Lys Phe Arg Glu His Gln Phe Thr Lys Ile Asp
            130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
            180                 185                 190

Val Ser Val Arg Val Tyr Phe Lys Lys Cys Pro Phe Thr Val Lys Asn
            195                 200                 205

Leu Ala Met Phe Pro Asp Thr Val Pro Met Asp Ser Gln Ser Leu Val
210                 215                 220

Glu Val Arg Gly Ser Cys Val Asn Asn Ser Lys Glu Glu Asp Pro Pro
225                 230                 235                 240

Arg Met Tyr Cys Ser Thr Glu Gly Glu Trp Leu Val Pro Ile Gly Lys
                245                 250                 255

Cys Ser Cys Asn Ala Gly Tyr Glu Glu Arg Gly Phe Met Cys Gln Ala
            260                 265                 270

Cys Arg Pro Gly Phe Tyr Lys Ala Leu Asp Gly Asn Met Lys Cys Ala
            275                 280                 285

Lys Cys Pro Pro His Ser Ser Thr Gln Glu Asp Gly Ser Met Asn Cys
            290                 295                 300

Arg Cys Glu Asn Asn Tyr Phe Arg Ala Asp Lys Asp Pro Pro Ser Met
305                 310                 315                 320

Ala Cys Thr Arg Pro Pro Ser Ser Pro Arg Asn Val Ile Ser Asn Ile
                325                 330                 335

Asn Glu Thr Ser Val Ile Leu Asp Trp Ser Trp Pro Leu Asp Thr Gly
            340                 345                 350

Gly Arg Lys Asp Val Thr Phe Asn Ile Ile Cys Lys Lys Cys Gly Trp
            355                 360                 365

Asn Ile Lys Gln Cys Glu Pro Cys Ser Pro Asn Val Arg Phe Leu Pro
            370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
                405                 410                 415

Glu Leu Ser Ser Pro Pro Arg Gln Phe Ala Ala Val Ser Ile Thr Thr
```

-continued

```
                   420                 425                 430
Asn Gln Ala Ala Pro Ser Pro Val Leu Thr Ile Lys Lys Asp Arg Thr
                435                 440                 445
Ser Arg Asn Ser Ile Ser Leu Ser Trp Gln Glu Pro Glu His Pro Asn
            450                 455                 460
Gly Ile Ile Leu Asp Tyr Glu Val Lys Tyr Glu Lys Gln Glu Gln
465                 470                 475                 480
Glu Thr Ser Tyr Thr Ile Leu Arg Ala Arg Gly Thr Asn Val Thr Ile
                485                 490                 495
Ser Ser Leu Lys Pro Asp Thr Ile Tyr Val Phe Gln Ile Arg Ala Arg
                500                 505                 510
Thr Ala Ala Gly Tyr Gly Thr Asn Ser Arg Lys Phe Glu Phe Glu Thr
                515                 520                 525
Ser Pro Asp Cys Met Tyr Tyr Phe Asn Ala Val
                530                 535

<210> SEQ ID NO 80
<211> LENGTH: 986
<212> TYPE: PRT
<213> ORGANISM: Homo sapiens

<400> SEQUENCE: 80

Met Ala Gly Ile Phe Tyr Phe Ala Leu Phe Ser Cys Leu Phe Gly Ile
1               5                   10                  15
Cys Asp Ala Val Thr Gly Ser Arg Val Tyr Pro Ala Asn Glu Val Thr
                20                  25                  30
Leu Leu Asp Ser Arg Ser Val Gln Gly Glu Leu Gly Trp Ile Ala Ser
            35                  40                  45
Pro Leu Glu Gly Gly Trp Glu Val Ser Ile Met Asp Glu Lys Asn
        50                  55                  60
Thr Pro Ile Arg Thr Tyr Gln Val Cys Asn Val Met Glu Pro Ser Gln
65                  70                  75                  80
Asn Asn Trp Leu Arg Thr Asp Trp Ile Thr Arg Glu Gly Ala Gln Arg
                85                  90                  95
Val Tyr Ile Glu Ile Lys Phe Thr Leu Arg Asp Cys Asn Ser Leu Pro
                100                 105                 110
Gly Val Met Gly Thr Cys Lys Glu Thr Phe Asn Leu Tyr Tyr Tyr Glu
                115                 120                 125
Ser Asp Asn Asp Lys Glu Arg Phe Ile Arg Glu Asn Gln Phe Val Lys
            130                 135                 140
Ile Asp Thr Ile Ala Ala Asp Glu Ser Phe Thr Gln Val Asp Ile Gly
145                 150                 155                 160
Asp Arg Ile Met Lys Leu Asn Thr Glu Ile Arg Asp Val Gly Pro Leu
                165                 170                 175
Ser Lys Lys Gly Phe Tyr Leu Ala Phe Gln Asp Val Gly Ala Cys Ile
                180                 185                 190
Ala Leu Val Ser Val Arg Val Phe Tyr Lys Lys Cys Pro Leu Thr Val
                195                 200                 205
Arg Asn Leu Ala Gln Phe Pro Asp Thr Ile Thr Gly Ala Asp Thr Ser
            210                 215                 220
Ser Leu Val Glu Val Arg Gly Ser Cys Val Asn Asn Ser Glu Glu Lys
225                 230                 235                 240
Asp Val Pro Lys Met Tyr Cys Gly Ala Asp Gly Glu Trp Leu Val Pro
                245                 250                 255
```

```
Ile Gly Asn Cys Leu Cys Asn Ala Gly His Glu Glu Arg Ser Gly Glu
            260                 265                 270
Cys Gln Ala Cys Lys Ile Gly Tyr Tyr Lys Ala Leu Ser Thr Asp Ala
            275                 280                 285
Thr Cys Ala Lys Cys Pro Pro His Ser Tyr Ser Val Trp Glu Gly Ala
290                 295                 300
Thr Ser Cys Thr Cys Asp Arg Gly Phe Phe Arg Ala Asp Asn Asp Ala
305                 310                 315                 320
Ala Ser Met Pro Cys Thr Arg Pro Ser Ala Pro Leu Asn Leu Ile
            325                 330                 335
Ser Asn Val Asn Glu Thr Ser Val Asn Leu Glu Trp Ser Ser Pro Gln
            340                 345                 350
Asn Thr Gly Gly Arg Gln Asp Ile Ser Tyr Asn Val Val Cys Lys Lys
            355                 360                 365
Cys Gly Ala Gly Asp Pro Ser Lys Cys Arg Pro Cys Gly Ser Gly Val
            370                 375                 380
His Tyr Thr Pro Gln Gln Asn Gly Leu Lys Thr Thr Lys Val Ser Ile
385                 390                 395                 400
Thr Asp Leu Leu Ala His Thr Asn Tyr Thr Phe Glu Ile Trp Ala Val
            405                 410                 415
Asn Gly Val Ser Lys Tyr Asn Pro Asn Pro Asp Gln Ser Val Ser Val
            420                 425                 430
Thr Val Thr Thr Asn Gln Ala Ala Pro Ser Ser Ile Ala Leu Val Gln
            435                 440                 445
Ala Lys Glu Val Thr Arg Tyr Ser Val Ala Leu Ala Trp Leu Glu Pro
450                 455                 460
Asp Arg Pro Asn Gly Val Ile Leu Glu Tyr Glu Val Lys Tyr Tyr Glu
465                 470                 475                 480
Lys Asp Gln Asn Glu Arg Ser Tyr Arg Ile Val Arg Thr Ala Ala Arg
            485                 490                 495
Asn Thr Asp Ile Lys Gly Leu Asn Pro Leu Thr Ser Tyr Val Phe His
            500                 505                 510
Val Arg Ala Arg Thr Ala Ala Gly Tyr Gly Asp Phe Ser Glu Pro Leu
            515                 520                 525
Glu Val Thr Thr Asn Thr Val Pro Ser Arg Ile Ile Gly Asp Gly Ala
            530                 535                 540
Asn Ser Thr Val Leu Leu Val Ser Val Ser Gly Ser Val Val Leu Val
545                 550                 555                 560
Val Ile Leu Ile Ala Ala Phe Val Ile Ser Arg Arg Arg Ser Lys Tyr
            565                 570                 575
Ser Lys Ala Lys Gln Glu Ala Asp Glu Glu Lys His Leu Asn Gln Gly
            580                 585                 590
Val Arg Thr Tyr Val Asp Pro Phe Thr Tyr Glu Asp Pro Asn Gln Ala
            595                 600                 605
Val Arg Glu Phe Ala Lys Glu Ile Asp Ala Ser Cys Ile Lys Ile Glu
            610                 615                 620
Lys Val Ile Gly Val Gly Glu Phe Gly Glu Val Cys Ser Gly Arg Leu
625                 630                 635                 640
Lys Val Pro Gly Lys Arg Glu Ile Cys Val Ala Ile Lys Thr Leu Lys
            645                 650                 655
Ala Gly Tyr Thr Asp Lys Gln Arg Arg Asp Phe Leu Ser Glu Ala Ser
            660                 665                 670
Ile Met Gly Gln Phe Asp His Pro Asn Ile Ile His Leu Glu Gly Val
```

```
                    675                 680                 685

Val Thr Lys Cys Lys Pro Val Met Ile Ile Thr Glu Tyr Met Glu Asn
690                 695                 700

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735

Leu Ser Asp Met Ser Tyr Val His Arg Asp Leu Ala Ala Arg Asn Ile
            740                 745                 750

Leu Val Asn Ser Asn Leu Val Cys Lys Val Ser Asp Phe Gly Met Ser
                755                 760                 765

Arg Val Leu Glu Asp Asp Pro Glu Ala Ala Tyr Thr Thr Arg Gly Gly
        770                 775                 780

Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                805                 810                 815

Val Met Ser Tyr Gly Glu Arg Pro Tyr Trp Asp Met Ser Asn Gln Asp
            820                 825                 830

Val Ile Lys Ala Ile Glu Glu Gly Tyr Arg Leu Pro Pro Pro Met Asp
        835                 840                 845

Cys Pro Ile Ala Leu His Gln Leu Met Leu Asp Cys Trp Gln Lys Glu
850                 855                 860

Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Thr Glu Ser Ser
                885                 890                 895

Arg Pro Asn Thr Ala Leu Leu Asp Pro Ser Ser Pro Glu Phe Ser Ala
            900                 905                 910

Val Val Ser Val Gly Asp Trp Leu Gln Ala Ile Lys Met Asp Arg Tyr
        915                 920                 925

Lys Asp Asn Phe Thr Ala Ala Gly Tyr Thr Thr Leu Glu Ala Val Val
930                 935                 940

His Val Asn Gln Glu Asp Leu Ala Arg Ile Gly Ile Thr Ala Ile Thr
945                 950                 955                 960

His Gln Asn Lys Ile Leu Ser Ser Val Gln Ala Met Arg Thr Gln Met
                965                 970                 975

Gln Gln Met His Gly Arg Met Val Pro Val
            980                 985

<210> SEQ ID NO 81
<211> LENGTH: 1037
<212> TYPE: PRT
<213> ORGANISM: Homo sapiens

<400> SEQUENCE: 81

Met Arg Gly Ser Gly Pro Arg Gly Ala Gly His Arg Arg Pro Pro Ser
1               5                   10                  15

Gly Gly Gly Asp Thr Pro Ile Thr Pro Ala Ser Leu Ala Gly Cys Tyr
            20                  25                  30

Ser Ala Pro Arg Arg Ala Pro Leu Trp Thr Cys Leu Leu Leu Cys Ala
        35                  40                  45

Ala Leu Arg Thr Leu Leu Ala Ser Pro Ser Asn Glu Val Asn Leu Leu
    50                  55                  60
```

-continued

```
Asp Ser Arg Thr Val Met Gly Asp Leu Gly Trp Ile Ala Phe Pro Lys
 65                  70                  75                  80

Asn Gly Trp Glu Glu Ile Gly Glu Val Asp Glu Asn Tyr Ala Pro Ile
                 85                  90                  95

His Thr Tyr Gln Val Cys Lys Val Met Glu Gln Asn Gln Asn Asn Trp
            100                 105                 110

Leu Leu Thr Ser Trp Ile Ser Asn Glu Gly Ala Ser Arg Ile Phe Ile
        115                 120                 125

Glu Leu Lys Phe Thr Leu Arg Asp Cys Asn Ser Leu Pro Gly Gly Leu
130                 135                 140

Gly Thr Cys Lys Glu Thr Phe Asn Met Tyr Tyr Phe Glu Ser Asp Asp
145                 150                 155                 160

Gln Asn Gly Arg Asn Ile Lys Glu Asn Gln Tyr Ile Lys Ile Asp Thr
                165                 170                 175

Ile Ala Ala Asp Glu Ser Phe Thr Glu Leu Asp Leu Gly Asp Arg Val
            180                 185                 190

Met Lys Leu Asn Thr Glu Val Arg Asp Val Gly Pro Leu Ser Lys Lys
        195                 200                 205

Gly Phe Tyr Leu Ala Phe Gln Asp Val Gly Ala Cys Ile Ala Leu Val
210                 215                 220

Ser Val Arg Val Tyr Tyr Lys Glu Cys Pro Ser Val Val Arg His Leu
225                 230                 235                 240

Ala Val Phe Pro Asp Thr Ile Thr Gly Ala Asp Ser Ser Gln Leu Leu
                245                 250                 255

Glu Val Ser Gly Ser Cys Val Asn His Ser Val Thr Asp Glu Pro Pro
            260                 265                 270

Lys Met His Cys Ser Ala Glu Gly Glu Trp Leu Val Pro Ile Gly Lys
        275                 280                 285

Cys Met Cys Lys Ala Gly Tyr Glu Glu Lys Asn Gly Thr Cys Gln Val
290                 295                 300

Cys Arg Pro Gly Phe Phe Lys Ala Ser Pro His Ile Gln Ser Cys Gly
305                 310                 315                 320

Lys Cys Pro Pro His Ser Tyr Thr His Glu Glu Ala Ser Thr Ser Cys
                325                 330                 335

Val Cys Glu Lys Asp Tyr Phe Arg Arg Glu Ser Asp Pro Pro Thr Met
            340                 345                 350

Ala Cys Thr Arg Pro Pro Ser Ala Pro Arg Asn Ala Ile Ser Asn Val
        355                 360                 365

Asn Glu Thr Ser Val Phe Leu Glu Trp Ile Pro Pro Ala Asp Thr Gly
370                 375                 380

Gly Arg Lys Asp Val Ser Tyr Tyr Ile Ala Cys Lys Lys Cys Asn Ser
385                 390                 395                 400

His Ala Gly Val Cys Glu Glu Cys Gly Gly His Val Arg Tyr Leu Pro
                405                 410                 415

Arg Gln Ser Gly Leu Lys Asn Thr Ser Val Met Met Val Asp Leu Leu
            420                 425                 430

Ala His Thr Asn Tyr Thr Phe Glu Ile Glu Ala Val Asn Gly Val Ser
        435                 440                 445

Asp Leu Ser Pro Gly Ala Arg Gln Tyr Val Ser Val Asn Val Thr Thr
450                 455                 460

Asn Gln Ala Ala Pro Ser Pro Val Thr Asn Val Lys Lys Gly Lys Ile
465                 470                 475                 480

Ala Lys Asn Ser Ile Ser Leu Ser Trp Gln Glu Pro Asp Arg Pro Asn
```

```
                485                 490                 495
Gly Ile Ile Leu Glu Tyr Glu Ile Lys Tyr Phe Glu Lys Asp Gln Glu
            500                 505                 510

Thr Ser Tyr Thr Ile Ile Lys Ser Lys Glu Thr Thr Ile Thr Ala Glu
            515                 520                 525

Gly Leu Lys Pro Ala Ser Val Tyr Val Phe Gln Ile Arg Ala Arg Thr
            530                 535                 540

Ala Ala Gly Tyr Gly Val Phe Ser Arg Arg Phe Glu Phe Glu Thr Thr
545                 550                 555                 560

Pro Val Phe Ala Ala Ser Ser Asp Gln Ser Gln Ile Pro Val Ile Ala
                565                 570                 575

Val Ser Val Thr Val Gly Val Ile Leu Leu Ala Val Val Ile Gly Val
            580                 585                 590

Leu Leu Ser Gly Ser Cys Cys Glu Cys Gly Cys Gly Arg Ala Ser Ser
            595                 600                 605

Leu Cys Ala Val Ala His Pro Ser Leu Ile Trp Arg Cys Gly Tyr Ser
            610                 615                 620

Lys Ala Lys Gln Asp Pro Glu Glu Lys Met His Phe His Asn Gly
625                 630                 635                 640

His Ile Lys Leu Pro Gly Val Arg Thr Tyr Ile Asp Pro His Thr Tyr
                645                 650                 655

Glu Asp Pro Asn Gln Ala Val His Glu Phe Ala Lys Glu Ile Glu Ala
                660                 665                 670

Ser Cys Ile Thr Ile Glu Arg Val Ile Gly Ala Gly Glu Phe Gly Glu
            675                 680                 685

Val Cys Ser Gly Arg Leu Lys Leu Pro Gly Lys Arg Glu Leu Pro Val
            690                 695                 700

Ala Ile Lys Thr Leu Lys Val Gly Tyr Thr Glu Lys Gln Arg Arg Asp
705                 710                 715                 720

Phe Leu Gly Glu Ala Ser Ile Met Gly Gln Phe Asp His Pro Asn Ile
                725                 730                 735

Ile His Leu Glu Gly Val Val Thr Lys Ser Lys Pro Val Met Ile Val
            740                 745                 750

Thr Glu Tyr Met Glu Asn Gly Ser Leu Asp Thr Phe Leu Lys Lys Asn
            755                 760                 765

Asp Gly Gln Phe Thr Val Ile Gln Leu Val Gly Met Leu Arg Gly Ile
            770                 775                 780

Ser Ala Gly Met Lys Tyr Leu Ser Asp Met Gly Tyr Val His Arg Asp
785                 790                 795                 800

Leu Ala Ala Arg Asn Ile Leu Ile Asn Ser Asn Leu Val Cys Lys Val
                805                 810                 815

Ser Asp Phe Gly Leu Ser Arg Val Leu Glu Asp Asp Pro Glu Ala Ala
                820                 825                 830

Tyr Thr Thr Arg Gly Gly Lys Ile Pro Ile Arg Trp Thr Ala Pro Glu
            835                 840                 845

Ala Ile Ala Phe Arg Lys Phe Thr Ser Ala Ser Asp Val Trp Ser Tyr
            850                 855                 860

Gly Ile Val Met Trp Glu Val Ser Tyr Gly Glu Arg Pro Tyr Trp
865                 870                 875                 880

Glu Met Thr Asn Gln Asp Val Ile Lys Ala Val Glu Glu Gly Tyr Arg
                885                 890                 895

Leu Pro Ser Pro Met Asp Cys Pro Ala Ala Leu Tyr Gln Leu Met Leu
            900                 905                 910
```

```
Asp Cys Trp Gln Lys Glu Arg Asn Ser Arg Pro Lys Phe Asp Glu Ile
            915                 920                 925

Val Asn Met Leu Asp Lys Leu Ile Arg Asn Pro Ser Ser Leu Lys Thr
        930                 935                 940

Leu Val Asn Ala Ser Cys Arg Val Ser Asn Leu Leu Ala Glu His Ser
945                 950                 955                 960

Pro Leu Gly Ser Gly Ala Tyr Arg Ser Val Gly Glu Trp Leu Glu Ala
            965                 970                 975

Ile Lys Met Gly Arg Tyr Thr Glu Ile Phe Met Glu Asn Gly Tyr Ser
            980                 985                 990

Ser Met Asp Ala Val Ala Gln Val Thr Leu Glu Asp Leu Arg Arg Leu
            995                 1000                1005

Gly Val Thr Leu Val Gly His Gln Lys Lys Ile Met Asn Ser Leu
            1010                1015                1020

Gln Glu Met Lys Val Gln Leu Val Asn Gly Met Val Pro Leu
            1025                1030                1035

<210> SEQ ID NO 82
<211> LENGTH: 1015
<212> TYPE: PRT
<213> ORGANISM: Homo sapiens

<400> SEQUENCE: 82

Met Arg Gly Ser Gly Pro Arg Gly Ala Gly His Arg Arg Pro Pro Ser
1               5                   10                  15

Gly Gly Gly Asp Thr Pro Ile Thr Pro Ala Ser Leu Ala Gly Cys Tyr
            20                  25                  30

Ser Ala Pro Arg Arg Ala Pro Leu Trp Thr Cys Leu Leu Leu Cys Ala
        35                  40                  45

Ala Leu Arg Thr Leu Leu Ala Ser Pro Ser Asn Glu Val Asn Leu Leu
    50                  55                  60

Asp Ser Arg Thr Val Met Gly Asp Leu Gly Trp Ile Ala Phe Pro Lys
65                  70                  75                  80

Asn Gly Trp Glu Glu Ile Gly Glu Val Asp Glu Asn Tyr Ala Pro Ile
                85                  90                  95

His Thr Tyr Gln Val Cys Lys Val Met Glu Gln Asn Gln Asn Asn Trp
            100                 105                 110

Leu Leu Thr Ser Trp Ile Ser Asn Glu Gly Ala Ser Arg Ile Phe Ile
        115                 120                 125

Glu Leu Lys Phe Thr Leu Arg Asp Cys Asn Ser Leu Pro Gly Gly Leu
    130                 135                 140

Gly Thr Cys Lys Glu Thr Phe Asn Met Tyr Tyr Phe Glu Ser Asp Asp
145                 150                 155                 160

Gln Asn Gly Arg Asn Ile Lys Glu Asn Gln Tyr Ile Lys Ile Asp Thr
                165                 170                 175

Ile Ala Ala Asp Glu Ser Phe Thr Glu Leu Asp Leu Gly Asp Arg Val
            180                 185                 190

Met Lys Leu Asn Thr Glu Val Arg Asp Val Gly Pro Leu Ser Lys Lys
        195                 200                 205

Gly Phe Tyr Leu Ala Phe Gln Asp Val Gly Ala Cys Ile Ala Leu Val
    210                 215                 220

Ser Val Arg Val Tyr Tyr Lys Glu Cys Pro Ser Val Val Arg His Leu
225                 230                 235                 240

Ala Val Phe Pro Asp Thr Ile Thr Gly Ala Asp Ser Ser Gln Leu Leu
```

-continued

```
                245                 250                 255
Glu Val Ser Gly Ser Cys Val Asn His Ser Val Thr Asp Pro Pro
            260                 265                 270
Lys Met His Cys Ser Ala Glu Gly Glu Trp Leu Val Pro Ile Gly Lys
            275                 280                 285
Cys Met Cys Lys Ala Gly Tyr Glu Glu Lys Asn Gly Thr Cys Gln Val
            290                 295                 300
Cys Arg Pro Gly Phe Phe Lys Ala Ser Pro His Ile Gln Ser Cys Gly
305                     310                 315                 320
Lys Cys Pro Pro His Ser Tyr Thr His Glu Glu Ala Ser Thr Ser Cys
                325                 330                 335
Val Cys Glu Lys Asp Tyr Phe Arg Arg Glu Ser Asp Pro Thr Met
            340                 345                 350
Ala Cys Thr Arg Pro Pro Ser Ala Pro Arg Asn Ala Ile Ser Asn Val
            355                 360                 365
Asn Glu Thr Ser Val Phe Leu Glu Trp Ile Pro Pro Ala Asp Thr Gly
            370                 375                 380
Gly Arg Lys Asp Val Ser Tyr Tyr Ile Ala Cys Lys Lys Cys Asn Ser
385                     390                 395                 400
His Ala Gly Val Cys Glu Cys Gly Gly His Val Arg Tyr Leu Pro
                405                 410                 415
Arg Gln Ser Gly Leu Lys Asn Thr Ser Val Met Met Val Asp Leu Leu
            420                 425                 430
Ala His Thr Asn Tyr Thr Phe Glu Ile Glu Ala Val Asn Gly Val Ser
            435                 440                 445
Asp Leu Ser Pro Gly Ala Arg Gln Tyr Val Ser Val Asn Val Thr Thr
            450                 455                 460
Asn Gln Ala Ala Pro Ser Pro Val Thr Asn Val Lys Lys Gly Lys Ile
465                     470                 475                 480
Ala Lys Asn Ser Ile Ser Leu Ser Trp Gln Glu Pro Asp Arg Pro Asn
                485                 490                 495
Gly Ile Ile Leu Glu Tyr Glu Ile Lys Tyr Phe Glu Lys Asp Gln Glu
            500                 505                 510
Thr Ser Tyr Thr Ile Ile Lys Ser Lys Glu Thr Thr Ile Thr Ala Glu
            515                 520                 525
Gly Leu Lys Pro Ala Ser Val Tyr Val Phe Gln Ile Arg Ala Arg Thr
            530                 535                 540
Ala Ala Gly Tyr Gly Val Phe Ser Arg Arg Phe Glu Phe Glu Thr Thr
545                     550                 555                 560
Pro Val Phe Ala Ala Ser Ser Asp Gln Ser Gln Ile Pro Val Ile Ala
                565                 570                 575
Val Ser Val Thr Val Gly Val Ile Leu Leu Ala Val Val Ile Gly Val
            580                 585                 590
Leu Leu Ser Gly Arg Arg Cys Gly Tyr Ser Lys Ala Lys Gln Asp Pro
            595                 600                 605
Glu Glu Glu Lys Met His Phe His Asn Gly His Ile Lys Leu Pro Gly
            610                 615                 620
Val Arg Thr Tyr Ile Asp Pro His Thr Tyr Glu Asp Pro Asn Gln Ala
625                     630                 635                 640
Val His Glu Phe Ala Lys Glu Ile Glu Ala Ser Cys Ile Thr Ile Glu
                645                 650                 655
Arg Val Ile Gly Ala Gly Glu Phe Gly Glu Val Cys Ser Gly Arg Leu
            660                 665                 670
```

```
Lys Leu Pro Gly Lys Arg Glu Leu Pro Val Ala Ile Lys Thr Leu Lys
            675                 680                 685

Val Gly Tyr Thr Glu Lys Gln Arg Arg Asp Phe Leu Gly Glu Ala Ser
        690                 695                 700

Ile Met Gly Gln Phe Asp His Pro Asn Ile Ile His Leu Glu Gly Val
705                 710                 715                 720

Val Thr Lys Ser Lys Pro Val Met Ile Val Thr Glu Tyr Met Glu Asn
                725                 730                 735

Gly Ser Leu Asp Thr Phe Leu Lys Lys Asn Asp Gly Gln Phe Thr Val
            740                 745                 750

Ile Gln Leu Val Gly Met Leu Arg Gly Ile Ser Ala Gly Met Lys Tyr
        755                 760                 765

Leu Ser Asp Met Gly Tyr Val His Arg Asp Leu Ala Ala Arg Asn Ile
    770                 775                 780

Leu Ile Asn Ser Asn Leu Val Cys Lys Val Ser Asp Phe Gly Leu Ser
785                 790                 795                 800

Arg Val Leu Glu Asp Asp Pro Glu Ala Ala Tyr Thr Thr Arg Gly Gly
                805                 810                 815

Lys Ile Pro Ile Arg Trp Thr Ala Pro Glu Ala Ile Ala Phe Arg Lys
            820                 825                 830

Phe Thr Ser Ala Ser Asp Val Trp Ser Tyr Gly Ile Val Met Trp Glu
        835                 840                 845

Val Val Ser Tyr Gly Glu Arg Pro Tyr Trp Glu Met Thr Asn Gln Asp
    850                 855                 860

Val Ile Lys Ala Val Glu Glu Gly Tyr Arg Leu Pro Ser Pro Met Asp
865                 870                 875                 880

Cys Pro Ala Ala Leu Tyr Gln Leu Met Leu Asp Cys Trp Gln Lys Glu
                885                 890                 895

Arg Asn Ser Arg Pro Lys Phe Asp Glu Ile Val Asn Met Leu Asp Lys
            900                 905                 910

Leu Ile Arg Asn Pro Ser Ser Leu Lys Thr Leu Val Asn Ala Ser Cys
        915                 920                 925

Arg Val Ser Asn Leu Leu Ala Glu His Ser Pro Leu Gly Ser Gly Ala
    930                 935                 940

Tyr Arg Ser Val Gly Glu Trp Leu Glu Ala Ile Lys Met Gly Arg Tyr
945                 950                 955                 960

Thr Glu Ile Phe Met Glu Asn Gly Tyr Ser Ser Met Asp Ala Val Ala
                965                 970                 975

Gln Val Thr Leu Glu Asp Leu Arg Arg Leu Gly Val Thr Leu Val Gly
            980                 985                 990

His Gln Lys Lys Ile Met Asn Ser  Leu Gln Glu Met Lys  Val Gln Leu
            995                 1000                1005

Val Asn  Gly Met Val Pro Leu
    1010                1015

<210> SEQ ID NO 83
<211> LENGTH: 998
<212> TYPE: PRT
<213> ORGANISM: Homo sapiens

<400> SEQUENCE: 83

Met Val Phe Gln Thr Arg Tyr Pro Ser Trp Ile Ile Leu Cys Tyr Ile
1               5                   10                  15

Trp Leu Leu Arg Phe Ala His Thr Gly Glu Ala Gln Ala Ala Lys Glu
```

-continued

```
                20                  25                  30
Val Leu Leu Leu Asp Ser Lys Ala Gln Gln Thr Glu Leu Glu Trp Ile
            35                  40                  45
Ser Ser Pro Pro Asn Gly Trp Glu Glu Ile Ser Gly Leu Asp Glu Asn
        50                  55                  60
Tyr Thr Pro Ile Arg Thr Tyr Gln Val Cys Gln Val Met Glu Pro Asn
65                  70                  75                  80
Gln Asn Asn Trp Leu Arg Thr Asn Trp Ile Ser Lys Gly Asn Ala Gln
                85                  90                  95
Arg Ile Phe Val Glu Leu Lys Phe Thr Leu Arg Asp Cys Asn Ser Leu
            100                 105                 110
Pro Gly Val Leu Gly Thr Cys Lys Glu Thr Phe Asn Leu Tyr Tyr Tyr
        115                 120                 125
Glu Thr Asp Tyr Asp Thr Gly Arg Asn Ile Arg Glu Asn Leu Tyr Val
    130                 135                 140
Lys Ile Asp Thr Ile Ala Ala Asp Glu Ser Phe Thr Gln Gly Asp Leu
145                 150                 155                 160
Gly Glu Arg Lys Met Lys Leu Asn Thr Glu Val Arg Glu Ile Gly Pro
                165                 170                 175
Leu Ser Lys Lys Gly Phe Tyr Leu Ala Phe Gln Asp Val Gly Ala Cys
            180                 185                 190
Ile Ala Leu Val Ser Val Lys Val Tyr Tyr Lys Lys Cys Trp Ser Ile
        195                 200                 205
Ile Glu Asn Leu Ala Ile Phe Pro Asp Thr Val Thr Gly Ser Glu Phe
    210                 215                 220
Ser Ser Leu Val Glu Val Arg Gly Thr Cys Val Ser Ser Ala Glu Glu
225                 230                 235                 240
Glu Ala Glu Asn Ala Pro Arg Met His Cys Ser Ala Glu Gly Glu Trp
                245                 250                 255
Leu Val Pro Ile Gly Lys Cys Ile Cys Lys Ala Gly Tyr Gln Gln Lys
            260                 265                 270
Gly Asp Thr Cys Glu Pro Cys Gly Arg Gly Phe Tyr Lys Ser Ser Ser
        275                 280                 285
Gln Asp Leu Gln Cys Ser Arg Cys Pro Thr His Ser Phe Ser Asp Lys
    290                 295                 300
Glu Gly Ser Ser Arg Cys Glu Cys Glu Asp Gly Tyr Tyr Arg Ala Pro
305                 310                 315                 320
Ser Asp Pro Pro Tyr Val Ala Cys Thr Arg Pro Pro Ser Ala Pro Gln
                325                 330                 335
Asn Leu Ile Phe Asn Ile Asn Gln Thr Thr Val Ser Leu Glu Trp Ser
            340                 345                 350
Pro Pro Ala Asp Asn Gly Gly Arg Asn Asp Val Thr Tyr Arg Ile Leu
        355                 360                 365
Cys Lys Arg Cys Ser Trp Glu Gln Gly Glu Cys Val Pro Cys Gly Ser
    370                 375                 380
Asn Ile Gly Tyr Met Pro Gln Gln Thr Gly Leu Glu Asp Asn Tyr Val
385                 390                 395                 400
Thr Val Met Asp Leu Leu Ala His Ala Asn Tyr Thr Phe Glu Val Glu
                405                 410                 415
Ala Val Asn Gly Val Ser Asp Leu Ser Arg Ser Gln Arg Leu Phe Ala
            420                 425                 430
Ala Val Ser Ile Thr Thr Gly Gln Ala Ala Pro Ser Gln Val Ser Gly
        435                 440                 445
```

-continued

```
Val Met Lys Glu Arg Val Leu Gln Arg Ser Val Glu Leu Ser Trp Gln
450                 455                 460
Glu Pro Glu His Pro Asn Gly Val Ile Thr Glu Tyr Glu Ile Lys Tyr
465                 470                 475                 480
Tyr Glu Lys Asp Gln Arg Glu Arg Thr Tyr Ser Thr Val Lys Thr Lys
                485                 490                 495
Ser Thr Ser Ala Ser Ile Asn Asn Leu Lys Pro Gly Thr Val Tyr Val
            500                 505                 510
Phe Gln Ile Arg Ala Phe Thr Ala Ala Gly Tyr Gly Asn Tyr Ser Pro
        515                 520                 525
Arg Leu Asp Val Ala Thr Leu Glu Glu Ala Thr Gly Lys Met Phe Glu
530                 535                 540
Ala Thr Ala Val Ser Ser Glu Gln Asn Pro Val Ile Ile Ala Val
545                 550                 555                 560
Val Ala Val Ala Gly Thr Ile Ile Leu Val Phe Met Val Phe Gly Phe
                565                 570                 575
Ile Ile Gly Arg Arg His Cys Gly Tyr Ser Lys Ala Asp Gln Glu Gly
            580                 585                 590
Asp Glu Glu Leu Tyr Phe His Phe Lys Phe Pro Gly Thr Lys Thr Tyr
        595                 600                 605
Ile Asp Pro Glu Thr Tyr Glu Asp Pro Asn Arg Ala Val His Gln Phe
610                 615                 620
Ala Lys Glu Leu Asp Ala Ser Cys Ile Lys Ile Glu Arg Val Ile Gly
625                 630                 635                 640
Ala Gly Glu Phe Gly Glu Val Cys Ser Gly Arg Leu Lys Leu Pro Gly
                645                 650                 655
Lys Arg Asp Val Ala Val Ala Ile Lys Thr Leu Lys Val Gly Tyr Thr
            660                 665                 670
Glu Lys Gln Arg Arg Asp Phe Leu Cys Glu Ala Ser Ile Met Gly Gln
        675                 680                 685
Phe Asp His Pro Asn Val Val His Leu Glu Gly Val Val Thr Arg Gly
690                 695                 700
Lys Pro Val Met Ile Val Ile Glu Phe Met Glu Asn Gly Ala Leu Asp
705                 710                 715                 720
Ala Phe Leu Arg Lys His Asp Gly Gln Phe Thr Val Ile Gln Leu Val
                725                 730                 735
Gly Met Leu Arg Gly Ile Ala Ala Gly Met Arg Tyr Leu Ala Asp Met
            740                 745                 750
Gly Tyr Val His Arg Asp Leu Ala Ala Arg Asn Ile Leu Val Asn Ser
        755                 760                 765
Asn Leu Val Cys Lys Val Ser Asp Phe Gly Leu Ser Arg Val Ile Glu
770                 775                 780
Asp Asp Pro Glu Ala Val Tyr Thr Thr Gly Gly Lys Ile Pro Val
785                 790                 795                 800
Arg Trp Thr Ala Pro Glu Ala Ile Gln Tyr Arg Lys Phe Thr Ser Ala
                805                 810                 815
Ser Asp Val Trp Ser Tyr Gly Ile Val Met Trp Glu Val Met Ser Tyr
            820                 825                 830
Gly Glu Arg Pro Tyr Trp Asp Met Ser Asn Gln Asp Val Ile Lys Ala
        835                 840                 845
Ile Glu Glu Gly Tyr Arg Leu Pro Ala Pro Met Asp Cys Pro Ala Gly
850                 855                 860
```

```
Leu His Gln Leu Met Leu Asp Cys Trp Gln Lys Glu Arg Ala Glu Arg
865                 870                 875                 880

Pro Lys Phe Glu Gln Ile Val Gly Ile Leu Asp Lys Met Ile Arg Asn
                885                 890                 895

Pro Asn Ser Leu Lys Thr Pro Leu Gly Thr Cys Ser Arg Pro Ile Ser
                900                 905                 910

Pro Leu Leu Asp Gln Asn Thr Pro Asp Phe Thr Thr Phe Cys Ser Val
                915                 920                 925

Gly Glu Trp Leu Gln Ala Ile Lys Met Glu Arg Tyr Lys Asp Asn Phe
            930                 935                 940

Thr Ala Ala Gly Tyr Asn Ser Leu Glu Ser Val Ala Arg Met Thr Ile
945                 950                 955                 960

Glu Asp Val Met Ser Leu Gly Ile Thr Leu Val Gly His Gln Lys Lys
                965                 970                 975

Ile Met Ser Ser Ile Gln Thr Met Arg Ala Gln Met Leu His Leu His
                980                 985                 990

Gly Thr Gly Ile Gln Val
            995

<210> SEQ ID NO 84
<211> LENGTH: 1005
<212> TYPE: PRT
<213> ORGANISM: Homo sapiens

<400> SEQUENCE: 84

Met Ala Pro Ala Arg Gly Arg Leu Pro Pro Ala Leu Trp Val Val Thr
1               5                   10                  15

Ala Ala Ala Ala Ala Thr Cys Val Ser Ala Ala Arg Gly Glu Val
                20                  25                  30

Asn Leu Leu Asp Thr Ser Thr Ile His Gly Asp Trp Gly Trp Leu Thr
                35                  40                  45

Tyr Pro Ala His Gly Trp Asp Ser Ile Asn Glu Val Asp Glu Ser Phe
            50                  55                  60

Gln Pro Ile His Thr Tyr Gln Val Cys Asn Val Met Ser Pro Asn Gln
65                  70                  75                  80

Asn Asn Trp Leu Arg Thr Ser Trp Val Pro Arg Asp Gly Ala Arg Arg
                85                  90                  95

Val Tyr Ala Glu Ile Lys Phe Thr Leu Arg Asp Cys Asn Ser Met Pro
                100                 105                 110

Gly Val Leu Gly Thr Cys Lys Glu Thr Phe Asn Leu Tyr Tyr Leu Glu
                115                 120                 125

Ser Asp Arg Asp Leu Gly Ala Ser Thr Gln Glu Ser Gln Phe Leu Lys
            130                 135                 140

Ile Asp Thr Ile Ala Ala Asp Glu Ser Phe Thr Gly Ala Asp Leu Gly
145                 150                 155                 160

Val Arg Arg Leu Lys Leu Asn Thr Glu Val Arg Ser Val Gly Pro Leu
                165                 170                 175

Ser Lys Arg Gly Phe Tyr Leu Ala Phe Gln Asp Ile Gly Ala Cys Leu
                180                 185                 190

Ala Ile Leu Ser Leu Arg Ile Tyr Tyr Lys Lys Cys Pro Ala Met Val
                195                 200                 205

Arg Asn Leu Ala Ala Phe Ser Glu Ala Val Thr Gly Ala Asp Ser Ser
            210                 215                 220

Ser Leu Val Glu Val Arg Gly Gln Cys Val Arg His Ser Glu Glu Arg
225                 230                 235                 240
```

-continued

```
Asp Thr Pro Lys Met Tyr Cys Ser Ala Glu Gly Glu Trp Leu Val Pro
            245                 250                 255

Ile Gly Lys Cys Val Cys Ser Ala Gly Tyr Glu Glu Arg Arg Asp Ala
        260                 265                 270

Cys Val Ala Cys Glu Leu Gly Phe Tyr Lys Ser Ala Pro Gly Asp Gln
    275                 280                 285

Leu Cys Ala Arg Cys Pro Pro His Ser His Ser Ala Ala Pro Ala Ala
        290                 295                 300

Gln Ala Cys His Cys Asp Leu Ser Tyr Tyr Arg Ala Ala Leu Asp Pro
305                 310                 315                 320

Pro Ser Ser Ala Cys Thr Arg Pro Pro Ser Ala Pro Val Asn Leu Ile
                325                 330                 335

Ser Ser Val Asn Gly Thr Ser Val Thr Leu Glu Trp Ala Pro Pro Leu
            340                 345                 350

Asp Pro Gly Gly Arg Ser Asp Ile Thr Tyr Asn Ala Val Cys Arg Arg
        355                 360                 365

Cys Pro Trp Ala Leu Ser Arg Cys Glu Ala Cys Gly Ser Gly Thr Arg
    370                 375                 380

Phe Val Pro Gln Gln Thr Ser Leu Val Gln Ala Ser Leu Leu Val Ala
385                 390                 395                 400

Asn Leu Leu Ala His Met Asn Tyr Ser Phe Trp Ile Glu Ala Val Asn
                405                 410                 415

Gly Val Ser Asp Leu Ser Pro Glu Pro Arg Arg Ala Ala Val Val Asn
            420                 425                 430

Ile Thr Thr Asn Gln Ala Ala Pro Ser Gln Val Val Ile Arg Gln
        435                 440                 445

Glu Arg Ala Gly Gln Thr Ser Val Ser Leu Leu Trp Gln Glu Pro Glu
    450                 455                 460

Gln Pro Asn Gly Ile Ile Leu Glu Tyr Glu Ile Lys Tyr Tyr Glu Lys
465                 470                 475                 480

Asp Lys Glu Met Gln Ser Tyr Ser Thr Leu Lys Ala Val Thr Thr Arg
                485                 490                 495

Ala Thr Val Ser Gly Leu Lys Pro Gly Thr Arg Tyr Val Phe Gln Val
            500                 505                 510

Arg Ala Arg Thr Ser Ala Gly Cys Gly Arg Phe Ser Gln Ala Met Glu
        515                 520                 525

Val Glu Thr Gly Lys Pro Arg Pro Arg Tyr Asp Thr Arg Thr Ile Val
    530                 535                 540

Trp Ile Cys Leu Thr Leu Ile Thr Gly Leu Val Val Leu Leu Leu Leu
545                 550                 555                 560

Leu Ile Cys Lys Lys Arg His Cys Gly Tyr Ser Lys Ala Phe Gln Asp
                565                 570                 575

Ser Asp Glu Glu Lys Met His Tyr Gln Asn Gly Gln Ala Pro Pro Pro
            580                 585                 590

Val Phe Leu Pro Leu His His Pro Gly Lys Leu Pro Glu Pro Gln
        595                 600                 605

Phe Tyr Ala Glu Pro His Thr Tyr Glu Glu Pro Gly Arg Ala Gly Arg
    610                 615                 620

Ser Phe Thr Arg Glu Ile Glu Ala Ser Arg Ile His Ile Glu Lys Ile
625                 630                 635                 640

Ile Gly Ser Gly Asp Ser Gly Glu Val Cys Tyr Gly Arg Leu Arg Val
                645                 650                 655
```

```
Pro Gly Gln Arg Asp Val Pro Val Ala Ile Lys Ala Leu Lys Ala Gly
            660                 665                 670

Tyr Thr Glu Arg Gln Arg Arg Asp Phe Leu Ser Glu Ala Ser Ile Met
        675                 680                 685

Gly Gln Phe Asp His Pro Asn Ile Ile Arg Leu Glu Gly Val Val Thr
    690                 695                 700

Arg Gly Arg Leu Ala Met Ile Val Thr Glu Tyr Met Glu Asn Gly Ser
705                 710                 715                 720

Leu Asp Thr Phe Leu Arg Thr His Asp Gly Gln Phe Thr Ile Met Gln
                725                 730                 735

Leu Val Gly Met Leu Arg Gly Val Gly Ala Gly Met Arg Tyr Leu Ser
            740                 745                 750

Asp Leu Gly Tyr Val His Arg Asp Leu Ala Ala Arg Asn Val Leu Val
        755                 760                 765

Asp Ser Asn Leu Val Cys Lys Val Ser Asp Phe Gly Leu Ser Arg Val
    770                 775                 780

Leu Glu Asp Asp Pro Asp Ala Ala Tyr Thr Thr Thr Gly Gly Lys Ile
785                 790                 795                 800

Pro Ile Arg Trp Thr Ala Pro Glu Ala Ile Ala Phe Arg Thr Phe Ser
                805                 810                 815

Ser Ala Ser Asp Val Trp Ser Phe Gly Val Val Met Trp Glu Val Leu
            820                 825                 830

Ala Tyr Gly Glu Arg Pro Tyr Trp Asn Met Thr Asn Arg Asp Val Ile
        835                 840                 845

Ser Ser Val Glu Glu Gly Tyr Arg Leu Pro Ala Pro Met Gly Cys Pro
    850                 855                 860

His Ala Leu His Gln Leu Met Leu Asp Cys Trp His Lys Asp Arg Ala
865                 870                 875                 880

Gln Arg Pro Arg Phe Ser Gln Ile Val Ser Val Leu Asp Ala Leu Ile
                885                 890                 895

Arg Ser Pro Glu Ser Leu Arg Ala Thr Ala Thr Val Ser Arg Cys Pro
            900                 905                 910

Pro Pro Ala Phe Val Arg Ser Cys Phe Asp Leu Arg Gly Gly Ser Gly
        915                 920                 925

Gly Gly Gly Gly Leu Thr Val Gly Asp Trp Leu Asp Ser Ile Arg Met
    930                 935                 940

Gly Arg Tyr Arg Asp His Phe Ala Ala Gly Gly Tyr Ser Ser Leu Gly
945                 950                 955                 960

Met Val Leu Arg Met Asn Ala Gln Asp Val Arg Ala Leu Gly Ile Thr
                965                 970                 975

Leu Met Gly His Gln Lys Lys Ile Leu Gly Ser Ile Gln Thr Met Arg
            980                 985                 990

Ala Gln Leu Thr Ser Thr Gln Gly  Pro Arg Arg His Leu
        995                1000                1005

<210> SEQ ID NO 85
<211> LENGTH: 984
<212> TYPE: PRT
<213> ORGANISM: Homo sapiens

<400> SEQUENCE: 85

Met Ala Leu Asp Tyr Leu Leu Leu Leu Leu Ala Ser Ala Val Ala
1               5                   10                  15

Ala Met Glu Glu Thr Leu Met Asp Thr Arg Thr Ala Thr Ala Glu Leu
                20                  25                  30
```

-continued

```
Gly Trp Thr Ala Asn Pro Ala Ser Gly Trp Glu Glu Val Ser Gly Tyr
             35                  40                  45
Asp Glu Asn Leu Asn Thr Ile Arg Thr Tyr Gln Val Cys Asn Val Phe
 50                  55                  60
Glu Pro Asn Gln Asn Asn Trp Leu Leu Thr Thr Phe Ile Asn Arg Arg
 65                  70                  75                  80
Gly Ala His Arg Ile Tyr Thr Glu Met Arg Phe Thr Val Arg Asp Cys
                 85                  90                  95
Ser Ser Leu Pro Asn Val Pro Gly Ser Cys Lys Glu Thr Phe Asn Leu
                100                 105                 110
Tyr Tyr Tyr Glu Thr Asp Ser Val Ile Ala Thr Lys Lys Ser Ala Phe
            115                 120                 125
Trp Ser Glu Ala Pro Tyr Leu Lys Val Asp Thr Ile Ala Ala Asp Glu
        130                 135                 140
Ser Phe Ser Gln Val Asp Phe Gly Gly Arg Leu Met Lys Val Asn Thr
145                 150                 155                 160
Glu Val Arg Ser Phe Gly Pro Leu Thr Arg Asn Gly Phe Tyr Leu Ala
                165                 170                 175
Phe Gln Asp Tyr Gly Ala Cys Met Ser Leu Leu Ser Val Arg Val Phe
            180                 185                 190
Phe Lys Lys Cys Pro Ser Ile Val Gln Asn Phe Ala Val Phe Pro Glu
        195                 200                 205
Thr Met Thr Gly Ala Glu Ser Thr Ser Leu Val Ile Ala Arg Gly Thr
    210                 215                 220
Cys Ile Pro Asn Ala Glu Glu Val Asp Val Pro Ile Lys Leu Tyr Cys
225                 230                 235                 240
Asn Gly Asp Gly Glu Trp Met Val Pro Ile Gly Arg Cys Thr Cys Lys
                245                 250                 255
Pro Gly Tyr Glu Pro Glu Asn Ser Val Ala Cys Lys Ala Cys Pro Ala
            260                 265                 270
Gly Thr Phe Lys Ala Ser Gln Glu Ala Glu Gly Cys Ser His Cys Pro
        275                 280                 285
Ser Asn Ser Arg Ser Pro Ala Glu Ala Ser Pro Ile Cys Thr Cys Arg
290                 295                 300
Thr Gly Tyr Tyr Arg Ala Asp Phe Asp Pro Pro Glu Val Ala Cys Thr
305                 310                 315                 320
Ser Val Pro Ser Gly Pro Arg Asn Val Ile Ser Ile Val Asn Glu Thr
                325                 330                 335
Ser Ile Ile Leu Glu Trp His Pro Pro Arg Glu Thr Gly Gly Arg Asp
            340                 345                 350
Asp Val Thr Tyr Asn Ile Ile Cys Lys Lys Cys Arg Ala Asp Arg Arg
        355                 360                 365
Ser Cys Ser Arg Cys Asp Asp Asn Val Glu Phe Val Pro Arg Gln Leu
370                 375                 380
Gly Leu Thr Glu Cys Arg Val Ser Ile Ser Ser Leu Trp Ala His Thr
385                 390                 395                 400
Pro Tyr Thr Phe Asp Ile Gln Ala Ile Asn Gly Val Ser Ser Lys Ser
                405                 410                 415
Pro Phe Pro Pro Gln His Val Ser Val Asn Ile Thr Thr Asn Gln Ala
            420                 425                 430
Ala Pro Ser Thr Val Pro Ile Met His Gln Val Ser Ala Thr Met Arg
        435                 440                 445
```

```
Ser Ile Thr Leu Ser Trp Pro Gln Pro Glu Gln Pro Asn Gly Ile Ile
    450                 455                 460

Leu Asp Tyr Glu Ile Arg Tyr Tyr Glu Lys Glu His Asn Glu Phe Asn
465                     470                 475                 480

Ser Ser Met Ala Arg Ser Gln Thr Asn Thr Ala Arg Ile Asp Gly Leu
            485                 490                 495

Arg Pro Gly Met Val Tyr Val Gln Val Arg Ala Arg Thr Val Ala
                500                 505                 510

Gly Tyr Gly Lys Phe Ser Gly Lys Met Cys Phe Gln Thr Leu Thr Asp
        515                 520                 525

Asp Tyr Lys Ser Glu Leu Arg Glu Gln Leu Pro Leu Ile Ala Gly
    530                 535                 540

Ser Ala Ala Gly Val Val Phe Val Val Ser Leu Val Ala Ile Ser
545                 550                 555                 560

Ile Val Cys Ser Arg Lys Arg Ala Tyr Ser Lys Glu Ala Val Tyr Ser
                565                 570                 575

Asp Lys Leu Gln His Tyr Ser Thr Gly Arg Gly Ser Pro Gly Met Lys
            580                 585                 590

Ile Tyr Ile Asp Pro Phe Thr Tyr Glu Asp Pro Asn Glu Ala Val Arg
    595                 600                 605

Glu Phe Ala Lys Glu Ile Asp Val Ser Phe Val Lys Ile Glu Glu Val
    610                 615                 620

Ile Gly Ala Gly Glu Phe Gly Glu Val Tyr Lys Gly Arg Leu Lys Leu
625                 630                 635                 640

Pro Gly Lys Arg Glu Ile Tyr Val Ala Ile Lys Thr Leu Lys Ala Gly
                645                 650                 655

Tyr Ser Glu Lys Gln Arg Arg Asp Phe Leu Ser Glu Ala Ser Ile Met
            660                 665                 670

Gly Gln Phe Asp His Pro Asn Ile Ile Arg Leu Glu Gly Val Val Thr
        675                 680                 685

Lys Ser Arg Pro Val Met Ile Ile Thr Glu Phe Met Glu Asn Gly Ala
690                 695                 700

Leu Asp Ser Phe Leu Arg Gln Asn Asp Gly Gln Phe Thr Val Ile Gln
705                 710                 715                 720

Leu Val Gly Met Leu Arg Gly Ile Ala Ala Gly Met Lys Tyr Leu Ala
                725                 730                 735

Glu Met Asn Tyr Val His Arg Asp Leu Ala Ala Arg Asn Ile Leu Val
            740                 745                 750

Asn Ser Asn Leu Val Cys Lys Val Ser Asp Phe Gly Leu Ser Arg Tyr
        755                 760                 765

Leu Gln Asp Asp Thr Ser Asp Pro Thr Tyr Thr Ser Ser Leu Gly Gly
    770                 775                 780

Lys Ile Pro Val Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                805                 810                 815

Val Met Ser Phe Gly Glu Arg Pro Tyr Trp Asp Met Ser Asn Gln Asp
            820                 825                 830

Val Ile Asn Ala Ile Glu Gln Asp Tyr Arg Leu Pro Pro Met Asp
    835                 840                 845

Cys Pro Ala Ala Leu His Gln Leu Met Leu Asp Cys Trp Gln Lys Asp
850                 855                 860

Arg Asn Ser Arg Pro Arg Phe Ala Glu Ile Val Asn Thr Leu Asp Lys
```

```
                865                 870                 875                 880
Met Ile Arg Asn Pro Ala Ser Leu Lys Thr Val Ala Thr Ile Thr Ala
                    885                 890                 895

Val Pro Ser Gln Pro Leu Leu Asp Arg Ser Ile Pro Asp Phe Thr Ala
                900                 905                 910

Phe Thr Thr Val Asp Asp Trp Leu Ser Ala Ile Lys Met Val Gln Tyr
            915                 920                 925

Arg Asp Ser Phe Leu Thr Ala Gly Phe Thr Ser Leu Gln Leu Val Thr
    930                 935                 940

Gln Met Thr Ser Glu Asp Leu Leu Arg Ile Gly Ile Thr Leu Ala Gly
945                 950                 955                 960

His Gln Lys Lys Ile Leu Asn Ser Ile His Ser Met Arg Val Gln Ile
                965                 970                 975

Ser Gln Ser Pro Thr Ala Met Ala
                980

<210> SEQ ID NO 86
<211> LENGTH: 1055
<212> TYPE: PRT
<213> ORGANISM: Homo sapiens

<400> SEQUENCE: 86

Met Ala Leu Arg Arg Leu Gly Ala Ala Leu Leu Leu Leu Pro Leu Leu
1               5                   10                  15

Ala Ala Val Glu Glu Thr Leu Met Asp Ser Thr Thr Ala Thr Ala Glu
                20                  25                  30

Leu Gly Trp Met Val His Pro Pro Ser Gly Trp Glu Glu Val Ser Gly
            35                  40                  45

Tyr Asp Glu Asn Met Asn Thr Ile Arg Thr Tyr Gln Val Cys Asn Val
    50                  55                  60

Phe Glu Ser Ser Gln Asn Asn Trp Leu Arg Thr Lys Phe Ile Arg Arg
65                  70                  75                  80

Arg Gly Ala His Arg Ile His Val Glu Met Lys Phe Ser Val Arg Asp
                85                  90                  95

Cys Ser Ser Ile Pro Ser Val Pro Gly Ser Cys Lys Glu Thr Phe Asn
                100                 105                 110

Leu Tyr Tyr Tyr Glu Ala Asp Phe Asp Ser Ala Thr Lys Thr Phe Pro
            115                 120                 125

Asn Trp Met Glu Asn Pro Trp Val Lys Val Asp Thr Ile Ala Ala Asp
    130                 135                 140

Glu Ser Phe Ser Gln Val Asp Leu Gly Gly Arg Val Met Lys Ile Asn
145                 150                 155                 160

Thr Glu Val Arg Ser Phe Gly Pro Val Ser Arg Ser Gly Phe Tyr Leu
                165                 170                 175

Ala Phe Gln Asp Tyr Gly Gly Cys Met Ser Leu Ile Ala Val Arg Val
            180                 185                 190

Phe Tyr Arg Lys Cys Pro Arg Ile Ile Gln Asn Gly Ala Ile Phe Gln
    195                 200                 205

Glu Thr Leu Ser Gly Ala Glu Ser Thr Ser Leu Val Ala Ala Arg Gly
210                 215                 220

Ser Cys Ile Ala Asn Ala Glu Glu Val Asp Val Pro Ile Lys Leu Tyr
225                 230                 235                 240

Cys Asn Gly Asp Gly Glu Trp Leu Val Pro Ile Gly Arg Cys Met Cys
                245                 250                 255
```

```
Lys Ala Gly Phe Glu Ala Val Glu Asn Gly Thr Val Cys Arg Gly Cys
            260                 265                 270

Pro Ser Gly Thr Phe Lys Ala Asn Gln Gly Asp Glu Ala Cys Thr His
            275                 280                 285

Cys Pro Ile Asn Ser Arg Thr Ser Glu Gly Ala Thr Asn Cys Val
            290                 295                 300

Cys Arg Asn Gly Tyr Tyr Arg Ala Asp Leu Asp Pro Leu Asp Met Pro
305                 310                 315                 320

Cys Thr Thr Ile Pro Ser Ala Pro Gln Ala Val Ile Ser Ser Val Asn
                325                 330                 335

Glu Thr Ser Leu Met Leu Glu Trp Thr Pro Pro Arg Asp Ser Gly Gly
            340                 345                 350

Arg Glu Asp Leu Val Tyr Asn Ile Ile Cys Lys Ser Cys Gly Ser Gly
            355                 360                 365

Arg Gly Ala Cys Thr Arg Cys Gly Asp Asn Val Gln Tyr Ala Pro Arg
            370                 375                 380

Gln Leu Gly Leu Thr Glu Pro Arg Ile Tyr Ile Ser Asp Leu Leu Ala
385                 390                 395                 400

His Thr Gln Tyr Thr Phe Glu Ile Gln Ala Val Asn Gly Val Thr Asp
                405                 410                 415

Gln Ser Pro Phe Ser Pro Gln Phe Ala Ser Val Asn Ile Thr Thr Asn
            420                 425                 430

Gln Ala Ala Pro Ser Ala Val Ser Ile Met His Gln Val Ser Arg Thr
            435                 440                 445

Val Asp Ser Ile Thr Leu Ser Trp Ser Gln Pro Asp Gln Pro Asn Gly
            450                 455                 460

Val Ile Leu Asp Tyr Glu Leu Gln Tyr Glu Lys Glu Leu Ser Glu
465                 470                 475                 480

Tyr Asn Ala Thr Ala Ile Lys Ser Pro Thr Asn Thr Val Thr Val Gln
                485                 490                 495

Gly Leu Lys Ala Gly Ala Ile Tyr Val Phe Gln Val Arg Ala Arg Thr
            500                 505                 510

Val Ala Gly Tyr Gly Arg Tyr Ser Gly Lys Met Tyr Phe Gln Thr Met
            515                 520                 525

Thr Glu Ala Glu Tyr Gln Thr Ser Ile Gln Glu Lys Leu Pro Leu Ile
            530                 535                 540

Ile Gly Ser Ser Ala Ala Gly Leu Val Phe Leu Ile Ala Val Val Val
545                 550                 555                 560

Ile Ala Ile Val Cys Asn Arg Arg Gly Phe Glu Arg Ala Asp Ser Glu
                565                 570                 575

Tyr Thr Asp Lys Leu Gln His Tyr Thr Ser Gly His Met Thr Pro Gly
            580                 585                 590

Met Lys Ile Tyr Ile Asp Pro Phe Thr Tyr Glu Asp Pro Asn Glu Ala
            595                 600                 605

Val Arg Glu Phe Ala Lys Glu Ile Asp Ile Ser Cys Val Lys Ile Glu
            610                 615                 620

Gln Val Ile Gly Ala Gly Glu Phe Gly Glu Val Cys Ser Gly His Leu
625                 630                 635                 640

Lys Leu Pro Gly Lys Arg Glu Ile Phe Val Ala Ile Lys Thr Leu Lys
                645                 650                 655

Ser Gly Tyr Thr Glu Lys Gln Arg Arg Asp Phe Leu Ser Glu Ala Ser
            660                 665                 670

Ile Met Gly Gln Phe Asp His Pro Asn Val Ile His Leu Glu Gly Val
```

```
                675                 680                 685
Val Thr Lys Ser Thr Pro Val Met Ile Ile Thr Glu Phe Met Glu Asn
        690                 695                 700

Gly Ser Leu Asp Ser Phe Leu Arg Gln Asn Asp Gly Gln Phe Thr Val
705                 710                 715                 720

Ile Gln Leu Val Gly Met Leu Arg Gly Ile Ala Ala Gly Met Lys Tyr
                725                 730                 735

Leu Ala Asp Met Asn Tyr Val His Arg Asp Leu Ala Ala Arg Asn Ile
            740                 745                 750

Leu Val Asn Ser Asn Leu Val Cys Lys Val Ser Asp Phe Gly Leu Ser
        755                 760                 765

Arg Phe Leu Glu Asp Asp Thr Ser Asp Pro Thr Tyr Thr Ser Ala Leu
770                 775                 780

Gly Gly Lys Ile Pro Ile Arg Trp Thr Ala Pro Glu Ala Ile Gln Tyr
785                 790                 795                 800

Arg Lys Phe Thr Ser Ala Ser Asp Val Trp Ser Tyr Gly Ile Val Met
                805                 810                 815

Trp Glu Val Met Ser Tyr Gly Glu Arg Pro Tyr Trp Asp Met Thr Asn
            820                 825                 830

Gln Asp Val Ile Asn Ala Ile Glu Gln Asp Tyr Arg Leu Pro Pro Pro
        835                 840                 845

Met Asp Cys Pro Ser Ala Leu His Gln Leu Met Leu Asp Cys Trp Gln
850                 855                 860

Lys Asp Arg Asn His Arg Pro Lys Phe Gly Gln Ile Val Asn Thr Leu
865                 870                 875                 880

Asp Lys Met Ile Arg Asn Pro Asn Ser Leu Lys Ala Met Ala Pro Leu
                885                 890                 895

Ser Ser Gly Ile Asn Leu Pro Leu Leu Asp Arg Thr Ile Pro Asp Tyr
            900                 905                 910

Thr Ser Phe Asn Thr Val Asp Glu Trp Leu Glu Ala Ile Lys Met Gly
        915                 920                 925

Gln Tyr Lys Glu Ser Phe Ala Asn Ala Gly Phe Thr Ser Phe Asp Val
930                 935                 940

Val Ser Gln Met Met Met Glu Asp Ile Leu Arg Val Gly Val Thr Leu
945                 950                 955                 960

Ala Gly His Gln Lys Lys Ile Leu Asn Ser Ile Gln Val Met Arg Ala
                965                 970                 975

Gln Met Asn Gln Ile Gln Ser Val Glu Gly Gln Pro Leu Ala Arg Arg
            980                 985                 990

Pro Arg Ala Thr Gly Arg Thr Lys Arg Cys Gln Pro Arg Asp Val Thr
        995                 1000                1005

Lys Lys Thr Cys Asn Ser Asn Asp Gly Lys Lys Lys Gly Met Gly
        1010                1015                1020

Lys Lys Lys Thr Asp Pro Gly Arg Gly Arg Glu Ile Gln Gly Ile
        1025                1030                1035

Phe Phe Lys Glu Asp Ser His Lys Glu Ser Asn Asp Cys Ser Cys
        1040                1045                1050

Gly Gly
    1055

<210> SEQ ID NO 87
<211> LENGTH: 987
<212> TYPE: PRT
<213> ORGANISM: Homo sapiens
```

```
<400> SEQUENCE: 87

Met Ala Leu Arg Arg Leu Gly Ala Ala Leu Leu Leu Pro Leu Leu
1               5                   10                  15

Ala Ala Val Glu Glu Thr Leu Met Asp Ser Thr Thr Ala Thr Ala Glu
            20                  25                  30

Leu Gly Trp Met Val His Pro Pro Ser Gly Trp Glu Glu Val Ser Gly
        35                  40                  45

Tyr Asp Glu Asn Met Asn Thr Ile Arg Thr Tyr Gln Val Cys Asn Val
    50                  55                  60

Phe Glu Ser Ser Gln Asn Asn Trp Leu Arg Thr Lys Phe Ile Arg Arg
65                  70                  75                  80

Arg Gly Ala His Arg Ile His Val Glu Met Lys Phe Ser Val Arg Asp
                85                  90                  95

Cys Ser Ser Ile Pro Ser Val Pro Gly Ser Cys Lys Glu Thr Phe Asn
            100                 105                 110

Leu Tyr Tyr Tyr Glu Ala Asp Phe Asp Ser Ala Thr Lys Thr Phe Pro
        115                 120                 125

Asn Trp Met Glu Asn Pro Trp Val Lys Val Asp Thr Ile Ala Ala Asp
    130                 135                 140

Glu Ser Phe Ser Gln Val Asp Leu Gly Gly Arg Val Met Lys Ile Asn
145                 150                 155                 160

Thr Glu Val Arg Ser Phe Gly Pro Val Ser Arg Ser Gly Phe Tyr Leu
                165                 170                 175

Ala Phe Gln Asp Tyr Gly Gly Cys Met Ser Leu Ile Ala Val Arg Val
            180                 185                 190

Phe Tyr Arg Lys Cys Pro Arg Ile Ile Gln Asn Gly Ala Ile Phe Gln
        195                 200                 205

Glu Thr Leu Ser Gly Ala Glu Ser Thr Ser Leu Val Ala Ala Arg Gly
    210                 215                 220

Ser Cys Ile Ala Asn Ala Glu Val Asp Val Pro Ile Lys Leu Tyr
225                 230                 235                 240

Cys Asn Gly Asp Gly Glu Trp Leu Val Pro Ile Gly Arg Cys Met Cys
                245                 250                 255

Lys Ala Gly Phe Glu Ala Val Glu Asn Gly Thr Val Cys Arg Gly Cys
            260                 265                 270

Pro Ser Gly Thr Phe Lys Ala Asn Gln Gly Asp Glu Ala Cys Thr His
        275                 280                 285

Cys Pro Ile Asn Ser Arg Thr Thr Ser Glu Gly Ala Thr Asn Cys Val
    290                 295                 300

Cys Arg Asn Gly Tyr Tyr Arg Ala Asp Leu Asp Pro Leu Asp Met Pro
305                 310                 315                 320

Cys Thr Thr Ile Pro Ser Ala Pro Gln Ala Val Ile Ser Ser Val Asn
                325                 330                 335

Glu Thr Ser Leu Met Leu Glu Trp Thr Pro Pro Arg Asp Ser Gly Gly
            340                 345                 350

Arg Glu Asp Leu Val Tyr Asn Ile Ile Cys Lys Ser Cys Gly Ser Gly
        355                 360                 365

Arg Gly Ala Cys Thr Arg Cys Gly Asp Asn Val Gln Tyr Ala Pro Arg
    370                 375                 380

Gln Leu Gly Leu Thr Glu Pro Arg Ile Tyr Ile Ser Asp Leu Leu Ala
385                 390                 395                 400

His Thr Gln Tyr Thr Phe Glu Ile Gln Ala Val Asn Gly Val Thr Asp
```

```
                    405                 410                 415
Gln Ser Pro Phe Ser Pro Gln Phe Ala Ser Val Asn Ile Thr Thr Asn
            420                 425                 430
Gln Ala Ala Pro Ser Ala Val Ser Ile Met His Gln Val Ser Arg Thr
            435                 440                 445
Val Asp Ser Ile Thr Leu Ser Trp Ser Gln Pro Asp Gln Pro Asn Gly
            450                 455                 460
Val Ile Leu Asp Tyr Glu Leu Gln Tyr Tyr Glu Lys Glu Leu Ser Glu
465                 470                 475                 480
Tyr Asn Ala Thr Ala Ile Lys Ser Pro Thr Asn Thr Val Thr Val Gln
            485                 490                 495
Gly Leu Lys Ala Gly Ala Ile Tyr Val Phe Gln Val Arg Ala Arg Thr
            500                 505                 510
Val Ala Gly Tyr Gly Arg Tyr Ser Gly Lys Met Tyr Phe Gln Thr Met
            515                 520                 525
Thr Glu Ala Glu Tyr Gln Thr Ser Ile Gln Glu Lys Leu Pro Leu Ile
            530                 535                 540
Ile Gly Ser Ser Ala Ala Gly Leu Val Phe Leu Ile Ala Val Val Val
545                 550                 555                 560
Ile Ala Ile Val Cys Asn Arg Arg Gly Phe Glu Arg Ala Asp Ser
            565                 570                 575
Glu Tyr Thr Asp Lys Leu Gln His Tyr Thr Ser Gly His Met Thr Pro
            580                 585                 590
Gly Met Lys Ile Tyr Ile Asp Pro Phe Thr Tyr Glu Asp Pro Asn Glu
            595                 600                 605
Ala Val Arg Glu Phe Ala Lys Glu Ile Asp Ile Ser Cys Val Lys Ile
            610                 615                 620
Glu Gln Val Ile Gly Ala Gly Glu Phe Gly Glu Val Cys Ser Gly His
625                 630                 635                 640
Leu Lys Leu Pro Gly Lys Arg Glu Ile Phe Val Ala Ile Lys Thr Leu
            645                 650                 655
Lys Ser Gly Tyr Thr Glu Lys Gln Arg Arg Asp Phe Leu Ser Glu Ala
            660                 665                 670
Ser Ile Met Gly Gln Phe Asp His Pro Asn Val Ile His Leu Glu Gly
            675                 680                 685
Val Val Thr Lys Ser Thr Pro Val Met Ile Ile Thr Glu Phe Met Glu
            690                 695                 700
Asn Gly Ser Leu Asp Ser Phe Leu Arg Gln Asn Asp Gly Gln Phe Thr
705                 710                 715                 720
Val Ile Gln Leu Val Gly Met Leu Arg Gly Ile Ala Ala Gly Met Lys
            725                 730                 735
Tyr Leu Ala Asp Met Asn Tyr Val His Arg Asp Leu Ala Ala Arg Asn
            740                 745                 750
Ile Leu Val Asn Ser Asn Leu Val Cys Lys Val Ser Asp Phe Gly Leu
            755                 760                 765
Ser Arg Phe Leu Glu Asp Asp Thr Ser Asp Pro Thr Tyr Thr Ser Ala
            770                 775                 780
Leu Gly Gly Lys Ile Pro Ile Arg Trp Thr Ala Pro Glu Ala Ile Gln
785                 790                 795                 800
Tyr Arg Lys Phe Thr Ser Ala Ser Asp Val Trp Ser Tyr Gly Ile Val
            805                 810                 815
Met Trp Glu Val Met Ser Tyr Gly Glu Arg Pro Tyr Trp Asp Met Thr
            820                 825                 830
```

```
Asn Gln Asp Val Ile Asn Ala Ile Glu Gln Asp Tyr Arg Leu Pro Pro
                835                 840                 845

Pro Met Asp Cys Pro Ser Ala Leu His Gln Leu Met Leu Asp Cys Trp
    850                 855                 860

Gln Lys Asp Arg Asn His Arg Pro Lys Phe Gly Gln Ile Val Asn Thr
865                 870                 875                 880

Leu Asp Lys Met Ile Arg Asn Pro Asn Ser Leu Lys Ala Met Ala Pro
                885                 890                 895

Leu Ser Ser Gly Ile Asn Leu Pro Leu Leu Asp Arg Thr Ile Pro Asp
                900                 905                 910

Tyr Thr Ser Phe Asn Thr Val Asp Glu Trp Leu Glu Ala Ile Lys Met
                915                 920                 925

Gly Gln Tyr Lys Glu Ser Phe Ala Asn Ala Gly Phe Thr Ser Phe Asp
                930                 935                 940

Val Val Ser Gln Met Met Met Glu Asp Ile Leu Arg Val Gly Val Thr
945                 950                 955                 960

Leu Ala Gly His Gln Lys Lys Ile Leu Asn Ser Ile Gln Val Met Arg
                965                 970                 975

Ala Gln Met Asn Gln Ile Gln Ser Val Glu Val
                980                 985
```

<210> SEQ ID NO 88
<211> LENGTH: 998
<212> TYPE: PRT
<213> ORGANISM: Homo sapiens
<400> SEQUENCE: 88

```
Met Ala Arg Ala Arg Pro Pro Pro Pro Ser Pro Pro Pro Gly Leu
1               5                   10                  15

Leu Pro Leu Leu Pro Pro Leu Leu Leu Pro Leu Leu Leu Leu Pro
                20                  25                  30

Ala Gly Cys Arg Ala Leu Glu Glu Thr Leu Met Asp Thr Lys Trp Val
                35                  40                  45

Thr Ser Glu Leu Ala Trp Thr Ser His Pro Glu Ser Gly Trp Glu Glu
50                  55                  60

Val Ser Gly Tyr Asp Glu Ala Met Asn Pro Ile Arg Thr Tyr Gln Val
65                  70                  75                  80

Cys Asn Val Arg Glu Ser Ser Gln Asn Asn Trp Leu Arg Thr Gly Phe
                85                  90                  95

Ile Trp Arg Arg Asp Val Gln Arg Val Tyr Val Glu Leu Lys Phe Thr
                100                 105                 110

Val Arg Asp Cys Asn Ser Ile Pro Asn Ile Pro Gly Ser Cys Lys Glu
                115                 120                 125

Thr Phe Asn Leu Phe Tyr Tyr Glu Ala Asp Ser Asp Val Ala Ser Ala
                130                 135                 140

Ser Ser Pro Phe Trp Met Glu Asn Pro Tyr Val Lys Val Asp Thr Ile
145                 150                 155                 160

Ala Pro Asp Glu Ser Phe Ser Arg Leu Asp Ala Gly Arg Val Asn Thr
                165                 170                 175

Lys Val Arg Ser Phe Gly Pro Leu Ser Lys Ala Gly Phe Tyr Leu Ala
                180                 185                 190

Phe Gln Asp Gln Gly Ala Cys Met Ser Leu Ile Ser Val Arg Ala Phe
                195                 200                 205

Tyr Lys Lys Cys Ala Ser Thr Thr Ala Gly Phe Ala Leu Phe Pro Glu
```

```
                 210                 215                 220
Thr Leu Thr Gly Ala Glu Pro Thr Ser Leu Val Ile Ala Pro Gly Thr
225                 230                 235                 240

Cys Ile Pro Asn Ala Val Glu Val Ser Val Pro Leu Lys Leu Tyr Cys
                245                 250                 255

Asn Gly Asp Gly Glu Trp Met Val Pro Val Gly Ala Cys Thr Cys Ala
                260                 265                 270

Thr Gly His Glu Pro Ala Ala Lys Glu Ser Gln Cys Arg Pro Cys Pro
                275                 280                 285

Pro Gly Ser Tyr Lys Ala Lys Gln Gly Glu Gly Pro Cys Leu Pro Cys
290                 295                 300

Pro Pro Asn Ser Arg Thr Thr Ser Pro Ala Ala Ser Ile Cys Thr Cys
305                 310                 315                 320

His Asn Asn Phe Tyr Arg Ala Asp Ser Asp Ser Ala Asp Ser Ala Cys
                325                 330                 335

Thr Thr Val Pro Ser Pro Pro Arg Gly Val Ile Ser Asn Val Asn Glu
                340                 345                 350

Thr Ser Leu Ile Leu Glu Trp Ser Glu Pro Arg Asp Leu Gly Gly Arg
                355                 360                 365

Asp Asp Leu Leu Tyr Asn Val Ile Cys Lys Lys Cys His Gly Ala Gly
                370                 375                 380

Gly Ala Ser Ala Cys Ser Arg Cys Asp Asp Asn Val Glu Phe Val Pro
385                 390                 395                 400

Arg Gln Leu Gly Leu Thr Glu Arg Arg Val His Ile Ser His Leu Leu
                405                 410                 415

Ala His Thr Arg Tyr Thr Phe Glu Val Gln Ala Val Asn Gly Val Ser
                420                 425                 430

Gly Lys Ser Pro Leu Pro Pro Arg Tyr Ala Ala Val Asn Ile Thr Thr
                435                 440                 445

Asn Gln Ala Ala Pro Ser Glu Val Pro Thr Leu Arg Leu His Ser Ser
                450                 455                 460

Ser Gly Ser Ser Leu Thr Leu Ser Trp Ala Pro Pro Glu Arg Pro Asn
465                 470                 475                 480

Gly Val Ile Leu Asp Tyr Glu Met Lys Tyr Phe Glu Lys Ser Glu Gly
                485                 490                 495

Ile Ala Ser Thr Val Thr Ser Gln Met Asn Ser Val Gln Leu Asp Gly
                500                 505                 510

Leu Arg Pro Asp Ala Arg Tyr Val Val Gln Val Arg Ala Arg Thr Val
                515                 520                 525

Ala Gly Tyr Gly Gln Tyr Ser Arg Pro Ala Glu Phe Glu Thr Thr Ser
                530                 535                 540

Glu Arg Gly Ser Gly Ala Gln Gln Leu Gln Glu Gln Leu Pro Leu Ile
545                 550                 555                 560

Val Gly Ser Ala Thr Ala Gly Leu Val Phe Val Ala Val Val Val Val
                565                 570                 575

Ile Ala Ile Val Cys Leu Arg Lys Gln Arg His Gly Ser Asp Ser Glu
                580                 585                 590

Tyr Thr Glu Lys Leu Gln Gln Tyr Ile Ala Pro Gly Met Lys Val Tyr
                595                 600                 605

Ile Asp Pro Phe Thr Tyr Glu Asp Pro Asn Glu Ala Val Arg Glu Phe
                610                 615                 620

Ala Lys Glu Ile Asp Val Ser Cys Val Lys Ile Glu Glu Val Ile Gly
625                 630                 635                 640
```

Ala Gly Glu Phe Gly Glu Val Cys Arg Gly Arg Leu Lys Gln Pro Gly
            645                 650                 655

Arg Arg Glu Val Phe Ala Ile Lys Thr Leu Lys Val Gly Tyr Thr
        660                 665                 670

Glu Arg Gln Arg Arg Asp Phe Leu Ser Glu Ala Ser Ile Met Gly Gln
    675                 680                 685

Phe Asp His Pro Asn Ile Ile Arg Leu Glu Gly Val Val Thr Lys Ser
    690                 695                 700

Arg Pro Val Met Ile Leu Thr Glu Phe Met Glu Asn Cys Ala Leu Asp
705                 710                 715                 720

Ser Phe Leu Arg Leu Asn Asp Gly Gln Phe Thr Val Ile Gln Leu Val
            725                 730                 735

Gly Met Leu Arg Gly Ile Ala Ala Gly Met Lys Tyr Leu Ser Glu Met
            740                 745                 750

Asn Tyr Val His Arg Asp Leu Ala Ala Arg Asn Ile Leu Val Asn Ser
        755                 760                 765

Asn Leu Val Cys Lys Val Ser Asp Phe Gly Leu Ser Arg Phe Leu Glu
    770                 775                 780

Asp Asp Pro Ser Asp Pro Thr Tyr Thr Ser Ser Leu Gly Gly Lys Ile
785                 790                 795                 800

Pro Ile Arg Trp Thr Ala Pro Glu Ala Ile Ala Tyr Arg Lys Phe Thr
            805                 810                 815

Ser Ala Ser Asp Val Trp Ser Tyr Gly Ile Val Met Trp Glu Val Met
            820                 825                 830

Ser Tyr Gly Glu Arg Pro Tyr Trp Asp Met Ser Asn Gln Asp Val Ile
    835                 840                 845

Asn Ala Val Glu Gln Asp Tyr Arg Leu Pro Pro Met Asp Cys Pro
    850                 855                 860

Thr Ala Leu His Gln Leu Met Leu Asp Cys Trp Val Arg Asp Arg Asn
865                 870                 875                 880

Leu Arg Pro Lys Phe Ser Gln Ile Val Asn Thr Leu Asp Lys Leu Ile
            885                 890                 895

Arg Asn Ala Ala Ser Leu Lys Val Ile Ala Ser Ala Gln Ser Gly Met
            900                 905                 910

Ser Gln Pro Leu Leu Asp Arg Thr Val Pro Asp Tyr Thr Thr Phe Thr
    915                 920                 925

Thr Val Gly Asp Trp Leu Asp Ala Ile Lys Met Gly Arg Tyr Lys Glu
    930                 935                 940

Ser Phe Val Ser Ala Gly Phe Ala Ser Phe Asp Leu Val Ala Gln Met
945                 950                 955                 960

Thr Ala Glu Asp Leu Leu Arg Ile Gly Val Thr Leu Ala Gly His Gln
            965                 970                 975

Lys Lys Ile Leu Ser Ser Ile Gln Asp Met Arg Leu Gln Met Asn Gln
            980                 985                 990

Thr Leu Pro Val Gln Val
        995

<210> SEQ ID NO 89
<211> LENGTH: 987
<212> TYPE: PRT
<213> ORGANISM: Homo sapiens

<400> SEQUENCE: 89

Met Glu Leu Arg Val Leu Leu Cys Trp Ala Ser Leu Ala Ala Ala Leu

```
1               5                   10                  15
Glu Glu Thr Leu Leu Asn Thr Lys Leu Glu Thr Ala Asp Leu Lys Trp
                20                  25                  30
Val Thr Phe Pro Gln Val Asp Gly Gln Trp Glu Glu Leu Ser Gly Leu
                35                  40                  45
Asp Glu Glu Gln His Ser Val Arg Thr Tyr Glu Val Cys Asp Val Gln
            50                  55                  60
Arg Ala Pro Gly Gln Ala His Trp Leu Arg Thr Gly Trp Val Pro Arg
65                  70                  75                  80
Arg Gly Ala Val His Val Tyr Ala Thr Leu Arg Phe Thr Met Leu Glu
                85                  90                  95
Cys Leu Ser Leu Pro Arg Ala Gly Arg Ser Cys Lys Glu Thr Phe Thr
                100                 105                 110
Val Phe Tyr Tyr Glu Ser Asp Ala Asp Thr Ala Thr Ala Leu Thr Pro
                115                 120                 125
Ala Trp Met Glu Asn Pro Tyr Ile Lys Val Asp Thr Val Ala Ala Glu
        130                 135                 140
His Leu Thr Arg Lys Arg Pro Gly Ala Glu Ala Thr Gly Lys Val Asn
145                 150                 155                 160
Val Lys Thr Leu Arg Leu Gly Pro Leu Ser Lys Ala Gly Phe Tyr Leu
                165                 170                 175
Ala Phe Gln Asp Gln Gly Ala Cys Met Ala Leu Leu Ser Leu His Leu
            180                 185                 190
Phe Tyr Lys Lys Cys Ala Gln Leu Thr Val Asn Leu Thr Arg Phe Pro
            195                 200                 205
Glu Thr Val Pro Arg Glu Leu Val Val Pro Val Ala Gly Ser Cys Val
        210                 215                 220
Val Asp Ala Val Pro Ala Pro Gly Pro Ser Pro Ser Leu Tyr Cys Arg
225                 230                 235                 240
Glu Asp Gly Gln Trp Ala Glu Gln Pro Val Thr Gly Cys Ser Cys Ala
                245                 250                 255
Pro Gly Phe Glu Ala Ala Glu Gly Asn Thr Lys Cys Arg Ala Cys Ala
                260                 265                 270
Gln Gly Thr Phe Lys Pro Leu Ser Gly Glu Gly Ser Cys Gln Pro Cys
            275                 280                 285
Pro Ala Asn Ser His Ser Asn Thr Ile Gly Ser Ala Val Cys Gln Cys
        290                 295                 300
Arg Val Gly Tyr Phe Arg Ala Arg Thr Asp Pro Arg Gly Ala Pro Cys
305                 310                 315                 320
Thr Thr Pro Pro Ser Ala Pro Arg Ser Val Val Ser Arg Leu Asn Gly
                325                 330                 335
Ser Ser Leu His Leu Glu Trp Ser Ala Pro Leu Glu Ser Gly Gly Arg
            340                 345                 350
Glu Asp Leu Thr Tyr Ala Leu Arg Cys Arg Glu Cys Arg Pro Gly Gly
            355                 360                 365
Ser Cys Ala Pro Cys Gly Gly Asp Leu Thr Phe Asp Pro Gly Pro Arg
        370                 375                 380
Asp Leu Val Glu Pro Trp Val Val Arg Gly Leu Arg Pro Asp Phe
385                 390                 395                 400
Thr Tyr Thr Phe Glu Val Thr Ala Leu Asn Gly Val Ser Ser Leu Ala
                405                 410                 415
Thr Gly Pro Val Pro Phe Glu Pro Val Asn Val Thr Thr Asp Arg Glu
            420                 425                 430
```

```
Val Pro Pro Ala Val Ser Asp Ile Arg Val Thr Arg Ser Ser Pro Ser
            435                 440                 445

Ser Leu Ser Leu Ala Trp Ala Val Pro Arg Ala Pro Ser Gly Ala Val
        450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
                500                 505                 510

Ala Gly Tyr Gly Pro Phe Gly Gln Glu His His Ser Gln Thr Gln Leu
                515                 520                 525

Asp Glu Ser Glu Gly Trp Arg Glu Gln Leu Ala Leu Ile Ala Gly Thr
            530                 535                 540

Ala Val Val Gly Val Val Leu Val Leu Val Val Ile Val Val Ala Val
545                 550                 555                 560

Leu Cys Leu Arg Lys Gln Ser Asn Gly Arg Glu Ala Glu Tyr Ser Asp
                565                 570                 575

Lys His Gly Gln Tyr Leu Ile Gly His Gly Thr Lys Val Tyr Ile Asp
                580                 585                 590

Pro Phe Thr Tyr Glu Asp Pro Asn Glu Ala Val Arg Glu Phe Ala Lys
            595                 600                 605

Glu Ile Asp Val Ser Tyr Val Lys Ile Glu Glu Val Ile Gly Ala Gly
            610                 615                 620

Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
                645                 650                 655

Gln Arg Arg Glu Phe Leu Ser Glu Ala Ser Ile Met Gly Gln Phe Glu
                660                 665                 670

His Pro Asn Ile Ile Arg Leu Glu Gly Val Val Thr Asn Ser Met Pro
            675                 680                 685

Val Met Ile Leu Thr Glu Phe Met Glu Asn Gly Ala Leu Asp Ser Phe
            690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
                725                 730                 735

Val His Arg Asp Leu Ala Ala Arg Asn Ile Leu Val Asn Ser Asn Leu
            740                 745                 750

Val Cys Lys Val Ser Asp Phe Gly Leu Ser Arg Phe Leu Glu Glu Asn
            755                 760                 765

Ser Ser Asp Pro Thr Tyr Thr Ser Ser Leu Gly Gly Lys Ile Pro Ile
770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
                805                 810                 815

Gly Glu Arg Pro Tyr Trp Asp Met Ser Asn Gln Asp Val Ile Asn Ala
            820                 825                 830

Ile Glu Gln Asp Tyr Arg Leu Pro Pro Pro Asp Cys Pro Thr Ser
            835                 840                 845
```

```
Leu His Gln Leu Met Leu Asp Cys Trp Gln Lys Asp Arg Asn Ala Arg
        850                 855                 860

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
                885                 890                 895

Pro Leu Leu Asp Gln Arg Gln Pro His Tyr Ser Ala Phe Gly Ser Val
            900                 905                 910

Gly Glu Trp Leu Arg Ala Ile Lys Met Gly Arg Tyr Glu Glu Ser Phe
        915                 920                 925

Ala Ala Ala Gly Phe Gly Ser Phe Glu Leu Val Ser Gln Ile Ser Ala
    930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Thr
                965                 970                 975

Pro Gly Gly Thr Gly Gly Pro Ala Pro Gln Tyr
            980                 985

<210> SEQ ID NO 90
<211> LENGTH: 1006
<212> TYPE: PRT
<213> ORGANISM: Homo sapiens

<400> SEQUENCE: 90

Met Val Cys Ser Leu Trp Val Leu Leu Val Ser Ser Val Leu Ala
1               5                   10                  15

Leu Glu Glu Val Leu Leu Asp Thr Thr Gly Glu Thr Ser Glu Ile Gly
            20                  25                  30

Trp Leu Thr Tyr Pro Pro Gly Gly Trp Asp Glu Val Ser Val Leu Asp
        35                  40                  45

Asp Gln Arg Arg Leu Thr Arg Thr Phe Glu Ala Cys His Val Ala Gly
    50                  55                  60

Ala Pro Pro Gly Thr Gly Gln Asp Asn Trp Leu Gln Thr His Phe Val
65                  70                  75                  80

Glu Arg Arg Gly Ala Gln Arg Ala His Ile Arg Leu His Phe Ser Val
                85                  90                  95

Arg Ala Cys Ser Ser Leu Gly Val Ser Gly Gly Thr Cys Arg Glu Thr
                100                 105                 110

Phe Thr Leu Tyr Tyr Arg Gln Ala Glu Glu Pro Asp Ser Pro Asp Ser
            115                 120                 125

Val Ser Ser Trp His Leu Lys Arg Trp Thr Lys Val Asp Thr Ile Ala
    130                 135                 140

Ala Asp Glu Ser Phe Pro Ser Ser Ser Ser Ser Ser Ser Ser Ser Ser
145                 150                 155                 160

Ser Ala Ala Trp Ala Val Gly Pro His Gly Ala Gly Gln Arg Ala Gly
                165                 170                 175

Leu Gln Leu Asn Val Lys Glu Arg Ser Phe Gly Pro Leu Thr Gln Arg
            180                 185                 190

Gly Phe Tyr Val Ala Phe Gln Asp Thr Gly Ala Cys Leu Ala Leu Val
        195                 200                 205

Ala Val Arg Leu Phe Ser Tyr Thr Cys Pro Ala Val Leu Arg Ser Phe
    210                 215                 220

Ala Ser Phe Pro Glu Thr Gln Ala Ser Gly Ala Gly Gly Ala Ser Leu
225                 230                 235                 240
```

-continued

```
Val Ala Ala Val Gly Thr Cys Val Ala His Ala Glu Pro Glu Glu Asp
                245                 250                 255

Gly Val Gly Gly Gln Ala Gly Gly Ser Pro Pro Arg Leu His Cys Asn
            260                 265                 270

Gly Glu Gly Lys Trp Met Val Ala Val Gly Gly Cys Arg Cys Gln Pro
        275                 280                 285

Gly Tyr Gln Pro Ala Arg Gly Asp Lys Ala Cys Gln Ala Cys Pro Arg
    290                 295                 300

Gly Leu Tyr Lys Ser Ser Ala Gly Asn Ala Pro Cys Ser Pro Cys Pro
305                 310                 315                 320

Ala Arg Ser His Ala Pro Asn Pro Ala Ala Pro Val Cys Pro Cys Leu
                325                 330                 335

Glu Gly Phe Tyr Arg Ala Ser Ser Asp Pro Pro Glu Ala Pro Cys Thr
            340                 345                 350

Gly Pro Pro Ser Ala Pro Gln Glu Leu Trp Phe Glu Val Gln Gly Ser
        355                 360                 365

Ala Leu Met Leu His Trp Arg Leu Pro Arg Glu Leu Gly Gly Arg Gly
    370                 375                 380

Asp Leu Leu Phe Asn Val Val Cys Lys Glu Cys Glu Gly Arg Gln Glu
385                 390                 395                 400

Pro Ala Ser Gly Gly Gly Gly Thr Cys His Arg Cys Arg Asp Glu Val
                405                 410                 415

His Phe Asp Pro Arg Gln Arg Gly Leu Thr Glu Ser Arg Val Leu Val
            420                 425                 430

Gly Gly Leu Arg Ala His Val Pro Tyr Ile Leu Glu Val Gln Ala Val
        435                 440                 445

Asn Gly Val Ser Glu Leu Ser Pro Asp Pro Pro Gln Ala Ala Ala Ile
    450                 455                 460

Asn Val Ser Thr Ser His Glu Val Pro Ser Ala Val Pro Val Val His
465                 470                 475                 480

Gln Val Ser Arg Ala Ser Asn Ser Ile Thr Val Ser Trp Pro Gln Pro
                485                 490                 495

Asp Gln Thr Asn Gly Asn Ile Leu Asp Tyr Gln Leu Arg Tyr Tyr Asp
            500                 505                 510

Gln Ala Glu Asp Glu Ser His Ser Phe Thr Leu Thr Ser Glu Thr Asn
        515                 520                 525

Thr Ala Thr Val Thr Gln Leu Ser Pro Gly His Ile Tyr Gly Phe Gln
    530                 535                 540

Val Arg Ala Arg Thr Ala Ala Gly His Gly Pro Tyr Gly Gly Lys Val
545                 550                 555                 560

Tyr Phe Gln Thr Leu Pro Gln Gly Glu Leu Ser Ser Gln Leu Pro Glu
                565                 570                 575

Arg Leu Ser Leu Val Ile Gly Ser Ile Leu Gly Ala Leu Ala Phe Leu
            580                 585                 590

Leu Leu Ala Ala Ile Thr Val Leu Ala Val Phe Gln Arg Lys Arg
    595                 600                 605

Arg Gly Thr Gly Tyr Thr Glu Gln Leu Gln Gln Tyr Ser Ser Pro Gly
    610                 615                 620

Leu Gly Val Lys Tyr Tyr Ile Asp Pro Ser Thr Tyr Glu Asp Pro Cys
625                 630                 635                 640

Gln Ala Ile Arg Glu Leu Ala Arg Glu Val Asp Pro Ala Tyr Ile Lys
                645                 650                 655
```

```
Ile Glu Glu Val Ile Gly Thr Gly Ser Phe Gly Glu Val Arg Gln Gly
        660                 665                 670

Arg Leu Gln Pro Arg Gly Arg Glu Gln Thr Val Ala Ile Gln Ala
        675                 680                 685

Leu Trp Ala Gly Ala Glu Ser Leu Gln Met Thr Phe Leu Gly Arg
        690                 695                 700

Ala Ala Val Leu Gly Gln Phe Gln His Pro Asn Ile Leu Arg Leu Glu
705                 710                 715                 720

Gly Val Val Thr Lys Ser Arg Pro Leu Met Val Leu Thr Glu Phe Met
                725                 730                 735

Glu Leu Gly Pro Leu Asp Ser Phe Leu Arg Gln Arg Glu Gly Gln Phe
                740                 745                 750

Ser Ser Leu Gln Leu Val Ala Met Gln Arg Gly Val Ala Ala Ala Met
                755                 760                 765

Gln Tyr Leu Ser Ser Phe Ala Phe Val His Arg Ser Leu Ser Ala His
        770                 775                 780

Ser Val Leu Val Asn Ser His Leu Val Cys Lys Val Ala Arg Leu Gly
785                 790                 795                 800

His Ser Pro Gln Gly Pro Ser Cys Leu Leu Arg Trp Ala Ala Pro Glu
                805                 810                 815

Val Ile Ala His Gly Lys His Thr Thr Ser Ser Asp Val Trp Ser Phe
        820                 825                 830

Gly Ile Leu Met Trp Glu Val Met Ser Tyr Gly Glu Arg Pro Tyr Trp
                835                 840                 845

Asp Met Ser Glu Gln Glu Val Leu Asn Ala Ile Glu Gln Glu Phe Arg
        850                 855                 860

Leu Pro Pro Pro Gly Cys Pro Pro Gly Leu His Leu Leu Met Leu
865                 870                 875                 880

Asp Thr Trp Gln Lys Asp Arg Ala Arg Arg Pro His Phe Asp Gln Leu
                885                 890                 895

Val Ala Ala Phe Asp Lys Met Ile Arg Lys Pro Asp Thr Leu Gln Ala
                900                 905                 910

Gly Gly Asp Pro Gly Glu Arg Pro Ser Gln Ala Leu Leu Thr Pro Val
        915                 920                 925

Ala Leu Asp Phe Pro Cys Leu Asp Ser Pro Gln Ala Trp Leu Ser Ala
930                 935                 940

Ile Gly Leu Glu Cys Tyr Gln Asp Asn Phe Ser Lys Phe Gly Leu Cys
945                 950                 955                 960

Thr Phe Ser Asp Val Ala Gln Leu Ser Leu Glu Asp Leu Pro Ala Leu
                965                 970                 975

Gly Ile Thr Leu Ala Gly His Gln Lys Lys Leu Leu His Ile Gln
        980                 985                 990

Leu Leu Gln Gln His Leu Arg Gln   Gln Gly Ser Val Glu   Val
        995                 1000                1005

<210> SEQ ID NO 91
<211> LENGTH: 205
<212> TYPE: PRT
<213> ORGANISM: Homo sapiens

<400> SEQUENCE: 91

Met Glu Phe Leu Trp Ala Pro Leu Leu Gly Leu Cys Cys Ser Leu Ala
1               5                   10                  15

Ala Ala Asp Arg His Thr Val Phe Trp Asn Ser Ser Asn Pro Lys Phe
                20                  25                  30
```

-continued

```
Arg Asn Glu Asp Tyr Thr Ile His Val Gln Leu Asn Asp Tyr Val Asp
             35                  40                  45

Ile Ile Cys Pro His Tyr Glu Asp His Ser Val Ala Asp Ala Ala Met
 50                  55                  60

Glu Gln Tyr Ile Leu Tyr Leu Val Glu His Glu Glu Tyr Gln Leu Cys
 65                  70                  75                  80

Gln Pro Gln Ser Lys Asp Gln Val Arg Trp Gln Cys Asn Arg Pro Ser
                 85                  90                  95

Ala Lys His Gly Pro Glu Lys Leu Ser Glu Lys Phe Gln Arg Phe Thr
                100                 105                 110

Pro Phe Thr Leu Gly Lys Glu Phe Lys Glu Gly His Ser Tyr Tyr Tyr
            115                 120                 125

Ile Ser Lys Pro Ile His Gln His Glu Asp Arg Cys Leu Arg Leu Lys
        130                 135                 140

Val Thr Val Ser Gly Lys Ile Thr His Ser Pro Gln Ala His Asp Asn
145                 150                 155                 160

Pro Gln Glu Lys Arg Leu Ala Ala Asp Asp Pro Glu Val Arg Val Leu
                165                 170                 175

His Ser Ile Gly His Ser Ala Ala Pro Arg Leu Phe Pro Leu Ala Trp
                180                 185                 190

Thr Val Leu Leu Leu Pro Leu Leu Leu Gln Thr Pro
            195                 200                 205

<210> SEQ ID NO 92
<211> LENGTH: 183
<212> TYPE: PRT
<213> ORGANISM: Homo sapiens

<400> SEQUENCE: 92

Met Glu Phe Leu Trp Ala Pro Leu Leu Gly Leu Cys Cys Ser Leu Ala
  1               5                  10                  15

Ala Ala Asp Arg His Thr Val Phe Trp Asn Ser Ser Asn Pro Lys Phe
                 20                  25                  30

Arg Asn Glu Asp Tyr Thr Ile His Val Gln Leu Asn Asp Tyr Val Asp
             35                  40                  45

Ile Ile Cys Pro His Tyr Glu Asp His Ser Val Ala Asp Ala Ala Met
 50                  55                  60

Glu Gln Tyr Ile Leu Tyr Leu Val Glu His Glu Glu Tyr Gln Leu Cys
 65                  70                  75                  80

Gln Pro Gln Ser Lys Asp Gln Val Arg Trp Gln Cys Asn Arg Pro Ser
                 85                  90                  95

Ala Lys His Gly Pro Glu Lys Leu Ser Glu Lys Phe Gln Arg Phe Thr
                100                 105                 110

Pro Phe Thr Leu Gly Lys Glu Phe Lys Glu Gly His Ser Tyr Tyr Tyr
            115                 120                 125

Ile Ser His Ser Pro Gln Ala His Asp Asn Pro Gln Glu Lys Arg Leu
        130                 135                 140

Ala Ala Asp Asp Pro Glu Val Arg Val Leu His Ser Ile Gly His Ser
145                 150                 155                 160

Ala Ala Pro Arg Leu Phe Pro Leu Ala Trp Thr Val Leu Leu Leu Pro
                165                 170                 175

Leu Leu Leu Leu Gln Thr Pro
            180
```

<210> SEQ ID NO 93
<211> LENGTH: 213
<212> TYPE: PRT
<213> ORGANISM: Homo sapiens

<400> SEQUENCE: 93

Met Ala Pro Ala Gln Arg Pro Leu Leu Pro Leu Leu Leu Leu Leu Leu
1               5                   10                  15

Pro Leu Pro Pro Pro Phe Ala Arg Ala Glu Asp Ala Ala Arg Ala
            20                  25                  30

Asn Ser Asp Arg Tyr Ala Val Tyr Trp Asn Arg Ser Asn Pro Arg Phe
        35                  40                  45

His Ala Gly Ala Gly Asp Asp Gly Gly Tyr Thr Val Glu Val Ser
    50                  55                  60

Ile Asn Asp Tyr Leu Asp Ile Tyr Cys Pro His Tyr Gly Ala Pro Leu
65                  70                  75                  80

Pro Pro Ala Glu Arg Met Glu His Tyr Val Leu Tyr Met Val Asn Gly
                85                  90                  95

Glu Gly His Ala Ser Cys Asp His Arg Gln Arg Gly Phe Lys Arg Trp
            100                 105                 110

Glu Cys Asn Arg Pro Ala Ala Pro Gly Gly Pro Leu Lys Phe Ser Glu
        115                 120                 125

Lys Phe Gln Leu Phe Thr Pro Phe Ser Leu Gly Phe Glu Phe Arg Pro
    130                 135                 140

Gly His Glu Tyr Tyr Ile Ser Ala Thr Pro Pro Asn Ala Val Asp
145                 150                 155                 160

Arg Pro Cys Leu Arg Leu Lys Val Tyr Val Arg Pro Thr Asn Glu Thr
                165                 170                 175

Leu Tyr Glu Ala Pro Glu Pro Ile Phe Thr Ser Asn Asn Ser Cys Ser
            180                 185                 190

Ser Pro Gly Gly Cys Arg Leu Phe Leu Ser Thr Ile Pro Val Leu Trp
        195                 200                 205

Thr Leu Leu Gly Ser
    210

<210> SEQ ID NO 94
<211> LENGTH: 238
<212> TYPE: PRT
<213> ORGANISM: Homo sapiens

<400> SEQUENCE: 94

Met Ala Ala Ala Pro Leu Leu Leu Leu Leu Val Pro Val Pro
1               5                   10                  15

Leu Leu Pro Leu Leu Ala Gln Gly Pro Gly Gly Ala Leu Gly Asn Arg
            20                  25                  30

His Ala Val Tyr Trp Asn Ser Ser Asn Gln His Leu Arg Arg Glu Gly
        35                  40                  45

Tyr Thr Val Gln Val Asn Val Asn Asp Tyr Leu Asp Ile Tyr Cys Pro
    50                  55                  60

His Tyr Asn Ser Ser Gly Val Gly Pro Gly Ala Gly Pro Gly Pro Gly
65                  70                  75                  80

Gly Gly Ala Glu Gln Tyr Val Leu Tyr Met Val Ser Arg Asn Gly Tyr
                85                  90                  95

Arg Thr Cys Asn Ala Ser Gln Gly Phe Lys Arg Trp Glu Cys Asn Arg
            100                 105                 110

Pro His Ala Pro His Ser Pro Ile Lys Phe Ser Glu Lys Phe Gln Arg

-continued

```
                115                 120                 125

Tyr Ser Ala Phe Ser Leu Gly Tyr Glu Phe His Ala Gly His Glu Tyr
    130                 135                 140

Tyr Tyr Ile Ser Thr Pro Thr His Asn Leu His Trp Lys Cys Leu Arg
145                 150                 155                 160

Met Lys Val Phe Val Cys Ala Ser Thr Ser His Ser Gly Glu Lys
                165                 170                 175

Pro Val Pro Thr Leu Pro Gln Phe Thr Met Gly Pro Asn Val Lys Ile
                180                 185                 190

Asn Val Leu Glu Asp Phe Glu Gly Glu Asn Pro Gln Val Pro Lys Leu
                195                 200                 205

Glu Lys Ser Ile Ser Gly Thr Ser Pro Lys Arg Glu His Leu Pro Leu
            210                 215                 220

Ala Val Gly Ile Ala Phe Phe Leu Met Thr Phe Leu Ala Ser
225                 230                 235

<210> SEQ ID NO 95
<211> LENGTH: 201
<212> TYPE: PRT
<213> ORGANISM: Homo sapiens

<400> SEQUENCE: 95

Met Arg Leu Leu Pro Leu Leu Arg Thr Val Leu Trp Ala Ala Phe Leu
1               5                   10                  15

Gly Ser Pro Leu Arg Gly Gly Ser Ser Leu Arg His Val Val Tyr Trp
                20                  25                  30

Asn Ser Ser Asn Pro Arg Leu Leu Arg Gly Asp Ala Val Val Glu Leu
            35                  40                  45

Gly Leu Asn Asp Tyr Leu Asp Ile Val Cys Pro His Tyr Glu Gly Pro
        50                  55                  60

Gly Pro Pro Glu Gly Pro Glu Thr Phe Ala Leu Tyr Met Val Asp Trp
65                  70                  75                  80

Pro Gly Tyr Glu Ser Cys Gln Ala Glu Gly Pro Arg Ala Tyr Lys Arg
                85                  90                  95

Trp Val Cys Ser Leu Pro Phe Gly His Val Gln Phe Ser Glu Lys Ile
                100                 105                 110

Gln Arg Phe Thr Pro Phe Ser Leu Gly Phe Glu Phe Leu Pro Gly Glu
            115                 120                 125

Thr Tyr Tyr Tyr Ile Ser Val Pro Thr Pro Glu Ser Ser Gly Gln Cys
        130                 135                 140

Leu Arg Leu Gln Val Ser Val Cys Cys Lys Glu Arg Lys Ser Glu Ser
145                 150                 155                 160

Ala His Pro Val Gly Ser Pro Gly Glu Ser Gly Thr Ser Gly Trp Arg
                165                 170                 175

Gly Gly Asp Thr Pro Ser Pro Leu Cys Leu Leu Leu Leu Leu Leu Leu
                180                 185                 190

Leu Ile Leu Arg Leu Leu Arg Ile Leu
            195                 200

<210> SEQ ID NO 96
<211> LENGTH: 207
<212> TYPE: PRT
<213> ORGANISM: Homo sapiens

<400> SEQUENCE: 96

Met Arg Leu Leu Pro Leu Leu Arg Thr Val Leu Trp Ala Ala Phe Leu
```

-continued

```
                 1               5                   10                  15
Gly Ser Pro Leu Arg Gly Gly Ser Ser Leu Arg His Val Val Tyr Trp
                20                  25                  30

Asn Ser Ser Asn Pro Arg Leu Leu Arg Gly Asp Ala Val Val Glu Leu
                35                  40                  45

Gly Leu Asn Asp Tyr Leu Asp Ile Val Cys Pro His Tyr Glu Gly Pro
                50                  55                  60

Gly Pro Pro Glu Gly Pro Glu Thr Phe Ala Leu Tyr Met Val Asp Trp
65                  70                  75                  80

Pro Gly Tyr Glu Ser Cys Gln Ala Glu Gly Pro Arg Ala Tyr Lys Arg
                85                  90                  95

Trp Val Cys Ser Leu Pro Phe Gly His Val Gln Phe Ser Glu Lys Ile
                100                 105                 110

Gln Arg Phe Thr Pro Phe Ser Leu Gly Phe Glu Phe Leu Pro Gly Glu
                115                 120                 125

Thr Tyr Tyr Tyr Ile Ser Val Pro Thr Pro Glu Ser Ser Gly Gln Cys
                130                 135                 140

Leu Arg Leu Gln Val Ser Val Cys Cys Lys Glu Arg Arg Ala Arg Val
145                 150                 155                 160

Leu Pro Arg Ser Pro Gly Gly Gly Ile Pro Ala Ala Cys Thr Gly
                165                 170                 175

Gly Ala Asn Ser Asp Arg Gln Asp Gly Ala Leu Met Gly Glu Ile Arg
                180                 185                 190

Gly Ser Glu Val Thr Leu Ala Gly Ala Cys Pro Leu Ile Thr Gly
                195                 200                 205
```

<210> SEQ ID NO 97
<211> LENGTH: 214
<212> TYPE: PRT
<213> ORGANISM: Homo sapiens

<400> SEQUENCE: 97

```
Met Arg Leu Leu Pro Leu Leu Arg Thr Val Leu Trp Ala Ala Phe Leu
1               5                   10                  15

Gly Ser Pro Leu Arg Gly Gly Ser Ser Leu Arg His Val Val Tyr Trp
                20                  25                  30

Asn Ser Ser Asn Pro Arg Leu Leu Arg Gly Asp Ala Val Val Glu Leu
                35                  40                  45

Gly Leu Asn Asp Tyr Leu Asp Ile Val Cys Pro His Tyr Glu Gly Pro
                50                  55                  60

Gly Pro Pro Glu Gly Pro Glu Thr Phe Ala Leu Tyr Met Val Asp Trp
65                  70                  75                  80

Pro Gly Tyr Glu Ser Cys Gln Ala Glu Gly Pro Arg Ala Tyr Lys Arg
                85                  90                  95

Trp Val Cys Ser Leu Pro Phe Gly His Val Gln Phe Ser Glu Lys Ile
                100                 105                 110

Gln Arg Phe Thr Pro Phe Ser Leu Gly Phe Glu Phe Leu Pro Gly Glu
                115                 120                 125

Thr Tyr Tyr Tyr Ile Ser Val Pro Thr Pro Glu Ser Ser Gly Gln Cys
                130                 135                 140

Leu Arg Leu Gln Val Ser Val Cys Cys Lys Glu Arg Pro Ser Leu
145                 150                 155                 160

Ser Ser Gln Gly Ala Arg Val Leu Pro Arg Ser Pro Gly Gly Gly Gly
                165                 170                 175
```

```
Ile Pro Ala Ala Cys Thr Gly Gly Ala Asn Ser Asp Arg Gln Asp Gly
            180                 185                 190

Ala Leu Met Gly Glu Ile Arg Gly Ser Glu Val Thr Leu Ala Gly Ala
            195                 200                 205

Cys Pro Leu Ile Thr Gly
    210
```

<210> SEQ ID NO 98
<211> LENGTH: 228
<212> TYPE: PRT
<213> ORGANISM: Homo sapiens

<400> SEQUENCE: 98

```
Met Leu His Val Glu Met Leu Thr Leu Val Phe Leu Val Leu Trp Met
1               5                   10                  15

Cys Val Phe Ser Gln Asp Pro Gly Ser Lys Ala Val Ala Asp Arg Tyr
            20                  25                  30

Ala Val Tyr Trp Asn Ser Ser Asn Pro Arg Phe Gln Arg Gly Asp Tyr
        35                  40                  45

His Ile Asp Val Cys Ile Asn Asp Tyr Leu Asp Val Phe Cys Pro His
    50                  55                  60

Tyr Glu Asp Ser Val Pro Glu Asp Lys Thr Glu Arg Tyr Val Leu Tyr
65                  70                  75                  80

Met Val Asn Phe Asp Gly Tyr Ser Ala Cys Asp His Thr Ser Lys Gly
                85                  90                  95

Phe Lys Arg Trp Glu Cys Asn Arg Pro His Ser Pro Asn Gly Pro Leu
            100                 105                 110

Lys Phe Ser Glu Lys Phe Gln Leu Phe Thr Pro Phe Ser Leu Gly Phe
        115                 120                 125

Glu Phe Arg Pro Gly Arg Glu Tyr Phe Tyr Ile Ser Ser Ala Ile Pro
    130                 135                 140

Asp Asn Gly Arg Arg Ser Cys Leu Lys Leu Lys Val Phe Val Arg Pro
145                 150                 155                 160

Thr Asn Ser Cys Met Lys Thr Ile Gly Val His Asp Arg Val Phe Asp
                165                 170                 175

Val Asn Asp Lys Val Glu Asn Ser Leu Glu Pro Ala Asp Asp Thr Val
            180                 185                 190

His Glu Ser Ala Glu Pro Ser Arg Gly Glu Asn Ala Ala Gln Thr Pro
        195                 200                 205

Arg Ile Pro Ser Arg Leu Leu Ala Ile Leu Leu Phe Leu Leu Ala Met
    210                 215                 220

Leu Leu Thr Leu
225
```

<210> SEQ ID NO 99
<211> LENGTH: 346
<212> TYPE: PRT
<213> ORGANISM: Homo sapiens

<400> SEQUENCE: 99

```
Met Ala Arg Pro Gly Gln Arg Trp Leu Gly Lys Trp Leu Val Ala Met
1               5                   10                  15

Val Val Trp Ala Leu Cys Arg Leu Ala Thr Pro Leu Ala Lys Asn Leu
            20                  25                  30

Glu Pro Val Ser Trp Ser Ser Leu Asn Pro Lys Phe Leu Ser Gly Lys
        35                  40                  45
```

```
Gly Leu Val Ile Tyr Pro Lys Ile Gly Asp Lys Leu Asp Ile Ile Cys
         50                  55                  60
Pro Arg Ala Glu Ala Gly Arg Pro Tyr Glu Tyr Tyr Lys Leu Tyr Leu
 65                  70                  75                  80
Val Arg Pro Glu Gln Ala Ala Cys Ser Thr Val Leu Asp Pro Asn
             85                  90                  95
Val Leu Val Thr Cys Asn Arg Pro Glu Gln Glu Ile Arg Phe Thr Ile
                100                 105                 110
Lys Phe Gln Glu Phe Ser Pro Asn Tyr Met Gly Leu Glu Phe Lys Lys
            115                 120                 125
His His Asp Tyr Tyr Ile Thr Ser Thr Ser Asn Gly Ser Leu Glu Gly
        130                 135                 140
Leu Glu Asn Arg Glu Gly Gly Val Cys Arg Thr Arg Thr Met Lys Ile
145                 150                 155                 160
Ile Met Lys Val Gly Gln Asp Pro Asn Ala Val Thr Pro Glu Gln Leu
                165                 170                 175
Thr Thr Ser Arg Pro Ser Lys Glu Ala Asp Asn Thr Val Lys Met Ala
            180                 185                 190
Thr Gln Ala Pro Gly Ser Arg Gly Ser Leu Gly Asp Ser Asp Gly Lys
        195                 200                 205
His Glu Thr Val Asn Gln Glu Glu Lys Ser Gly Pro Gly Ala Ser Gly
    210                 215                 220
Gly Ser Ser Gly Asp Pro Asp Gly Phe Phe Asn Ser Lys Val Ala Leu
225                 230                 235                 240
Phe Ala Ala Val Gly Ala Gly Cys Val Ile Phe Leu Leu Ile Ile Ile
                245                 250                 255
Phe Leu Thr Val Leu Leu Leu Lys Leu Arg Lys Arg His Arg Lys His
            260                 265                 270
Thr Gln Gln Arg Ala Ala Ala Leu Ser Leu Ser Thr Leu Ala Ser Pro
        275                 280                 285
Lys Gly Gly Ser Gly Thr Ala Gly Thr Glu Pro Ser Asp Ile Ile Ile
    290                 295                 300
Pro Leu Arg Thr Thr Glu Asn Asn Tyr Cys Pro His Tyr Glu Lys Val
305                 310                 315                 320
Ser Gly Asp Tyr Gly His Pro Val Tyr Ile Val Gln Glu Met Pro Pro
                325                 330                 335
Gln Ser Pro Ala Asn Ile Tyr Tyr Lys Val
            340                 345

<210> SEQ ID NO 100
<211> LENGTH: 333
<212> TYPE: PRT
<213> ORGANISM: Homo sapiens

<400> SEQUENCE: 100

Met Ala Val Arg Arg Asp Ser Val Trp Lys Tyr Cys Trp Gly Val Leu
  1               5                  10                  15
Met Val Leu Cys Arg Thr Ala Ile Ser Lys Ser Ile Val Leu Glu Pro
                 20                  25                  30
Ile Tyr Trp Asn Ser Ser Asn Ser Lys Phe Leu Pro Gly Gln Gly Leu
             35                  40                  45
Val Leu Tyr Pro Gln Ile Gly Asp Lys Leu Asp Ile Ile Cys Pro Lys
         50                  55                  60
Val Asp Ser Lys Thr Val Gly Gln Tyr Glu Tyr Tyr Lys Val Tyr Met
 65                  70                  75                  80
```

```
Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
    130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
    210                 215                 220

Val Ala Leu Phe Ala Gly Ile Ala Ser Gly Cys Ile Ile Phe Ile Val
225                 230                 235                 240

Ile Ile Ile Thr Leu Val Val Leu Leu Lys Tyr Arg Arg Arg His
                245                 250                 255

Arg Lys His Ser Pro Gln His Thr Thr Thr Leu Ser Leu Ser Thr Leu
                260                 265                 270

Ala Thr Pro Lys Arg Ser Gly Asn Asn Asn Gly Ser Glu Pro Ser Asp
            275                 280                 285

Ile Ile Ile Pro Leu Arg Thr Ala Asp Ser Val Phe Cys Pro His Tyr
        290                 295                 300

Glu Lys Val Ser Gly Asp Tyr Gly His Pro Val Tyr Ile Val Gln Glu
305                 310                 315                 320

Met Pro Pro Gln Ser Pro Ala Asn Ile Tyr Tyr Lys Val
                325                 330

<210> SEQ ID NO 101
<211> LENGTH: 340
<212> TYPE: PRT
<213> ORGANISM: Homo sapiens

<400> SEQUENCE: 101

Met Gly Pro Pro His Ser Gly Pro Gly Gly Val Arg Val Gly Ala Leu
1               5                   10                  15

Leu Leu Leu Gly Val Leu Gly Leu Val Ser Gly Leu Ser Leu Glu Pro
                20                  25                  30

Val Tyr Trp Asn Ser Ala Asn Lys Arg Phe Gln Ala Glu Gly Gly Tyr
            35                  40                  45

Val Leu Tyr Pro Gln Ile Gly Asp Arg Leu Asp Leu Leu Cys Pro Arg
        50                  55                  60

Ala Arg Pro Pro Gly Pro His Ser Ser Pro Asn Tyr Glu Phe Tyr Lys
65                  70                  75                  80

Leu Tyr Leu Val Gly Gly Ala Gln Gly Arg Arg Cys Glu Ala Pro Pro
                85                  90                  95

Ala Pro Asn Leu Leu Leu Thr Cys Asp Arg Pro Asp Leu Asp Leu Arg
            100                 105                 110

Phe Thr Ile Lys Phe Gln Glu Tyr Ser Pro Asn Leu Trp Gly His Glu
```

-continued

```
                115                 120                 125
    Phe Arg Ser His His Asp Tyr Tyr Ile Ile Ala Thr Ser Asp Gly Thr
        130                 135                 140

Arg Glu Gly Leu Glu Ser Leu Gln Gly Gly Val Cys Leu Thr Arg Gly
    145                 150                 155                 160

Met Lys Val Leu Leu Arg Val Gly Gln Ser Pro Arg Gly Gly Ala Val
                    165                 170                 175

Pro Arg Lys Pro Val Ser Glu Met Pro Met Glu Arg Asp Arg Gly Ala
                    180                 185                 190

Ala His Ser Leu Glu Pro Gly Lys Glu Asn Leu Pro Gly Asp Pro Thr
                195                 200                 205

Ser Asn Ala Thr Ser Arg Gly Ala Glu Gly Pro Leu Pro Pro Pro Ser
        210                 215                 220

Met Pro Ala Val Ala Gly Ala Ala Gly Gly Leu Ala Leu Leu Leu Leu
    225                 230                 235                 240

Gly Val Ala Gly Ala Gly Gly Ala Met Cys Trp Arg Arg Arg Arg Ala
                    245                 250                 255

Lys Pro Ser Glu Ser Arg His Pro Gly Pro Gly Ser Phe Gly Arg Gly
                260                 265                 270

Gly Ser Leu Gly Leu Gly Gly Gly Gly Met Gly Pro Arg Glu Ala
                275                 280                 285

Glu Pro Gly Glu Leu Gly Ile Ala Leu Arg Gly Gly Gly Ala Ala Asp
        290                 295                 300

Pro Pro Phe Cys Pro His Tyr Glu Lys Val Ser Gly Asp Tyr Gly His
    305                 310                 315                 320

Pro Val Tyr Ile Val Gln Asp Gly Pro Pro Gln Ser Pro Pro Asn Ile
                    325                 330                 335

Tyr Tyr Lys Val
                340
```

EPH RECEPTOR FC VARIANTS WITH ENHANCED ANTIBODY DEPENDENT CELL-MEDIATED CYTOTOXICITY ACTIVITY

1. CROSS REFERENCE TO RELATED APPLICATIONS

This application claims the benefit under 35 U.S.C. § 119(e) of the following U.S. Provisional Application Nos. 60/601,634, filed, Aug. 16, 2004 and 60/608,852, filed, Sep. 13, 2004. The priority applications are hereby incorporated by reference herein in their entirety for all purposes.

2. FIELD OF THE INVENTION

The present invention provides novel antibodies comprising at least one antigen binding region and an Fc region that further comprises at least one novel amino acid residue of the invention. The present invention also relates to novel antibodies comprising a variable region, or fragment thereof, that immunospecifically binds to at least one Eph receptor and an Fc region that further comprises at least one high effector function amino acid residue. The present invention further relates to novel variants of antibodies that immunospecifically bind to at least one Eph receptor which contain one or more substitutions in their Fc regions. Collectively, these novel antibodies are referred to herein as "Fc variants of the invention" or "Fc variants." In one embodiment, the Fc variants of the invention have enhanced effector function. In another embodiment the Fc variants of the invention have altered binding affinity to one or more Fc ligands. In another embodiment, the Fc variants of the invention have enhanced binding to FcγRIIIA and increased ability to mediate antibody dependent cell-mediated cytotoxicity (ADCC). In another embodiment, the Fc variants have reduced binding to FcγRIIIA and decreased ability to mediate ADCC (referred to herein as "ADCC activity"). In still another embodiment, the Fc variants have enhanced binding to the C1q and increased ability to mediate complement dependent cytotoxicity (CDC). In yet another embodiment, the Fc variants have reduced binding to C1q and decreased ability to mediate CDC. In particular, the present invention relates to Fc variants that can bind to one or more Eph receptors. In addition, the present invention provides methods and protocols for the application or use of Fc variants, particularly for therapeutic purposes. Specifically, the methods and protocols involve the administration of a prophylactically or therapeutically effective amount of one or more Fc variants alone or in combination with the administration of one or more other therapies useful for the treatment and/or prevention of Eph receptor-mediated (and/or Ephrin-mediated) and/or associated diseases and disorders or one or more symptoms thereof, including but not limited to cancer, inflammatory and autoimmune diseases. The Fc variants utilized for therapeutic purposes may or may not be conjugated or fused to a moiety (e.g., a therapeutic agent or drug). The methods of the invention are particularly useful for the prevention, management, treatment or amelioration numerous forms of cancer. The invention also provides methods for screening for an antibody that immunospecifically binds to at least one Eph receptor as well as methods to manipulate the Fc region and thereby modulate the ability of said Fc region to mediate ADCC and/or CDC activity and/or the binding affinity for one or more Fc ligands. The invention also provides methods for generating Fc variant fusions that immunospecifically bind to at least one Eph receptor. Further, the invention provides pharmaceutical formulations and kits for use in preventing, managing, treating or ameliorating Eph receptor-mediated (and/or Ephrin-mediated) and/or associated diseases and disorders or one or more symptoms thereof, including but not limited to cancer, inflammatory and autoimmune diseases.

3. BACKGROUND OF THE INVENTION

3.1 Cancer

A neoplasm, or tumor, is a neoplastic mass resulting from abnormal uncontrolled cell growth, which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, Basic Pathology, 2d Ed., W.B. Saunders Co., Philadelphia, pp. 68-122). Cancer can arise in many sites of the body and behave differently depending upon its origin. Cancerous cells destroy the part of the body in which they originate and then spread to other part(s) of the body where they start new growth and cause more destruction.

More than 1.2 million Americans develop cancer each year. Cancer is the second leading case of death in the United States and if current trends continue, cancer is expected to be the leading cause of the death by the year 2010. Lung and prostate cancer are the top cancer killers for men in the United States. Lung and breast cancer are the top cancer killers for women in the United States. One in two men in the United States will be diagnosed with cancer at some time during his lifetime. One in three women in the United States will be diagnosed with cancer at some time during her lifetime.

A reliable cure for cancer has yet to be found. Current treatment options, such as surgery, chemotherapy and radiation treatment, are oftentimes either ineffective or present serious side effects.

3.2 Metastasis

The most life-threatening forms of cancer often arise when a population of tumor cells gains the ability to colonize distant and foreign sites in the body. These metastatic cells survive by overriding restrictions that normally constrain cell colonization into dissimilar tissues. For example, typical mammary epithelial cells will generally not grow or survive if transplanted to the lung, yet lung metastases are a major cause of breast cancer morbidity and mortality. Recent evidence suggests that dissemination of metastatic cells through the body can occur long before clinical presentation of the primary tumor. These micrometastatic cells may remain dormant for many months or years following the detection and removal of the primary tumor. Thus, a better understanding of the mechanisms that allow for the growth and survival of metastatic cells in a foreign microenvironment is critical for the improvement of therapeutics designed to fight metastatic cancer and diagnostics for the early detection and localization of metastases.

3.3 Cancer Cell Signaling

Cancer is a disease of aberrant signal transduction. Aberrant cell signaling overrides anchorage-dependent constraints on cell growth and survival (Rhim, et al., Critical Reviews in Oncogenesis 8:305, 1997; Patarca, Critical Reviews in Oncogenesis 7:343, 1996; Malik, et al., Biochimica et Biophysica Acta 1287:73, 1996; Cance, et al., Breast Cancer Res Treat 35:105, 1995). Tyrosine kinase activity is induced by ECM anchorage and indeed, the expression or function of tyrosine kinases is usually increased in malignant cells (Rhim, et al., Critical Reviews in Oncogenesis 8:305, 1997; Cance, et al., Breast Cancer Res Treat 35:105, 1995; Hunter, Cell 88:333, 1997). Based on evidence that tyrosine kinase activity is necessary for malignant cell growth, tyrosine kinases have been targeted with new therapeutics (Levitzki, et al., Science 267:1782, 1995; Kondapaka, et al., Molecular & Cellular Endocrinology 117:53, 1996; Fry, et al., Current Opinion in BioTechnology 6: 662, 1995). Unfortunately, obstacles associated with specific targeting to tumor cells often limit the application of these drugs. In particular, tyrosine kinase activity is often vital for the function and survival of benign tissues (Levitzki, et al., Science 267:1782, 1995). To minimize collateral toxicity, it is critical to identify and then target tyrosine kinases that are selectively overexpressed in tumor cells.

3.4 Eph Family of Receptor Tyrosine Kinases

The Eph family of receptors are the largest family of receptor tyrosine kinases (RTKs). The Eph receptors, and their membrane bound ephrin ligands are important mediators of cell-cell communication regulating cell attachment, shape, and mobility. Eph RTK signaling events control multiple aspects of embryonic development, particularly in the nervous system (reviewed in Kullander et al., 2002, Nat. Rev. Mol. Cell Biol. 3:473 and Mamling et al., 2002, Trends Biochem Sci 27:514-520. Receptors in the EPH subfamily typically have a single kinase domain and an extracellular region containing a Cys-rich domain and 2 fibronectin type III repeats (see FIG. 18). The ephrin receptors are divided into 2 groups based on the similarity of their extracellular domain sequences and their affinities for binding ephrin-A and ephrin-B ligands. Many members of the Eph receptors have been identified as important markers and/or regulators of the development and progression of cancer (see for example Thaker et al., 2004, Clin. Cancer Res. 10:5145; Fox B P et al., 2004, Biochem. Biophys. Res. Commun. 318:882; Nakada et al., 2004, Cancer Res. 64:3179; Coffman et al., 2003, Cancer Res. 63:7907; also reviewed in Dodelet et al., 2000, Oncogene 19:5614). Of the Eph receptors known to be involved in cancer the role and expression patterns of EphA2 and EphA4 are among the best characterized.

EphA2 is expressed in adult epithelia, where it is found at low levels and is enriched within sites of cell-cell adhesion (Zantek, et al, 1999, Cell Growth & Diff 10:629; Lindberg, et al., 1990, Mol & Cell Biol 10: 6316). This subcellular localization is important because EphA2 binds EphrinsA1 to A5 that are anchored to the cell membrane (Eph Nomenclature Committee, 1997, Cell 90:403; Gale, et al., 1997, Cell & Tissue Res 290: 227). The primary consequence of ligand binding is EphA2 autophosphorylation (Lindberg, et al., 1990, supra). However, unlike other receptor tyrosine kinases, EphA2 retains enzymatic activity in the absence of ligand binding or phosphotyrosine content (Zantek, et al., 1999, supra). EphA2 and ephrin-A1 are upregulated in the transformed cells of a wide variety of tumors including breast, prostate, colon, skin, and esophageal cancers (Ogawa, et al., 2000, Oncogene 19:6043; Zelinski, et al., 2001, Cancer Res 61:2301; Walker-Daniels, et al., 1999, Prostate 41:275; Easty, et al., 1995, Int J Cancer 60: 129; Nemoto, et al., 1997, Pathobiology 65:195).

EphA4 is expressed in brain, heart, lung, muscle, kidney, placenta, pancreas (Fox, et al, 1995, Oncogene 10:897) and melanocytes (Easty, et al., 1997, Int. J. Cancer 71:1061). EphA4 binds Ephrins A1, A2, A3, A4, A5, B2, and B3, (Pasquale, 1997, Curr. Opin. in Cell Biology 9:608) also ligands B61, AL1/RAGS, LERK4, Htk-L, and Elk-L3, (Martone, et al., 1997, Brain Research 771:238). Ligand binding leads to EphA4 autophosphorylation on tyrosine residues (Ellis, et al., 1996, Oncogene 12:1727). EphA4 tyrosine phosphorylation creates a binding region for proteins with Src Homology 2/3 (SH2/SH3) domains, such as the cytoplasmic tyrosine kinase p59fyn (Ellis, et al., supra; Cheng, et al., Cytokine and Growth Factor Reviews 13:75, 2002). Activation of EphA4 in Xenopus embryos leads to loss of cadherin-dependent cell adhesion (Winning, et al., Differentiation 70:46, 2002; Cheng, et al., supra), suggesting a role for EphA4 in tumor angiogenesis; however, the role of EphA4 in cancer progression is unclear. EphA4 appears to be upregulated in breast cancer, esophageal cancer, and pancreatic cancer (Kuang, et al., Nucleic Acids Res. 26:1116, 1998; Meric, et al, Clinical Cancer Res. 8:361, 2002; Nemoto, et al., Pathobiology 65:195, 1997; Logsdon, et al., Cancer Res. 63:2649, 2003), yet it is downregulated in melanoma tissue (Easty, et al., supra).

EphB2 and EphB4 receptors are also overexpressed in certain tumor tissues. EphB4 overexpression is mainly found in infiltrating ductal breast carcinomas with high grade malignancy-2 (Berclaz et al., 1996, Biochem Biophys Res Commun 226:869) while EphB2 is overexpressed in a majority of gastric tumors (Kiynokawa et al., 1994, Cancer Res 54:3645). Both receptors are overexpressed in many tumor cell lines as well (Berclaz et al., supra; Kiynokawa et al., supra; Bennett et al., 1995, PNAS USA 92:1866). Both EphB2 and EphB4 are also upregulated in colon carcinoma tissue (Liu et al., 2002, Cancer 94:934; Stephenson et al., 2001, BMC Mol Biol 2:15). In addition, EphB2 and EphB4 are also important for vascular development in the embryo and possibly in tumors (Wang et al., 1998, Cell 93:741; Gerety, S. S. et al. 1999 Mol Cell 4:403).

3.5 Cancer Therapy

One barrier to the development of anti-metastasis agents has been the assay systems that are used to design and evaluate these drugs. Most conventional cancer therapies target rapidly growing cells. However, cancer cells do not necessarily grow more rapidly but instead survive and grow under conditions that are non-permissive to normal cells (Lawrence and Steeg, 1996, World J. Urol. 14:124-130). These fundamental differences between the behaviors of normal and malignant cells provide opportunities for therapeutic targeting. The paradigm that micrometastatic tumors have already disseminated throughout the body emphasizes the need to evaluate potential chemotherapeutic drugs in the context of a foreign and three-dimensional microenvironment. Many standard cancer drug assays measure tumor cell growth or survival under typical cell culture conditions (i.e., monolayer growth). However, cell behavior in two-dimensional assays often does not reliably predict tumor cell behavior in vivo.

Currently, cancer therapy may involve surgery, chemotherapy, hormonal therapy and/or radiation treatment to eradicate neoplastic cells in a patient (see, for example, Stockdale, 1998, "Principles of Cancer Patient Management", in Scientific American: Medicine, vol. 3, Rubenstein and Federman, eds., Chapter 12, Section IV). All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although can be effective, is often used to prevent or delay recurrence of cancer after other treatments have removed the majority of the cancer cells.

With respect to chemotherapy, there are a variety of chemotherapeutic agents available for treatment of cancer. A significant majority of cancer chemotherapeutics act by inhibiting DNA synthesis (see, for example, Gilman et al., Goodman and Gilman's: The Pharmacological Basis of Therapeutics, Eighth Ed. (Pergamom Press, New York, 1990)). As such, chemotherapy agents are inherently nonspecific. In addition almost all chemotherapeutic agents are toxic, and chemotherapy causes significant, and often dangerous, side effects, including severe nausea, bone marrow depression, immunosuppression, etc. (see, for example, Stockdale, 1998, "Principles Of Cancer Patient Management" in Scientific American Medicine, vol. 3, Rubenstein and Federman, eds., ch. 12, sect. 10). Furthermore, even with administration of combinations of chemotherapeutic agents, many tumor cells are resistant or develop resistance to the chemotherapeutic agents.

Recently, cancer therapy could also involve biological therapy or immunotherapy. Biological therapies/immunotherapies are limited in number and although more specific then chemotherapeutic agents many still target both health and cancerous cells. In addition, such therapies may produce side effects such as rashes or swellings, flu-like symptoms, including fever, chills and fatigue, digestive tract problems or allergic reactions.

Thus, there is a significant need for alternative cancer treatments, particularly for treatments that more specifically target cancer cells. The identification of members of the Eph receptor family as markers for tumor cells makes them powerful targets for therapeutics. Thus, a cancer treatment that would specifically target and destroy tumor cells aberrantly expressing one or more members of the Eph receptor family would be a powerful tool for the treatment and prevention of cancers.

3.6 Antibodies for the Treatment of Cancer

Antibodies are immunological proteins that bind a specific antigen. In most mammals, including humans and mice, antibodies are constructed from paired heavy and light polypeptide chains. Each chain is made up of two distinct regions, referred to as the variable (Fv) and constant (Fc) regions. The light and heavy chain Fv regions contain the antigen binding determinants of the molecule and are responsible for binding the target antigen. The Fc regions define the class (or isotype) of antibody (IgG for example) and are responsible for binding a number of natural proteins to elicit important biochemical events.

The Fc region of an antibody interacts with a number of ligands including Fc receptors and other ligands, imparting an array of important functional capabilities referred to as effector functions. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CID64), including isoforms FcγRIA, FcγRIB, and FcγRIC; FcγRII (CD32), including isoforms FcγRIIA, FcγRIIB, and FcγRIIC; and FcγRIII (CID16), including isoforms FcγRIIIA and FcγRIIIB (Jefferis et al., 2002, Immunol Lett 82:57-65). These receptors typically have an extracellular domain that mediates binding to Fc, a membrane spanning region, and an intracellular domain that may mediate some signaling event within the cell. These different FcγR subtypes are expressed on different cell types (reviewed in Ravetch et al., 1991, Annu Rev Immunol 9:457-492). For example, in humans, FcγRIIIB is found only on neutrophils, whereas FcγRIIIA is found on macrophages, monocytes, natural killer (NK) cells, and a subpopulation of T-cells.

Formation of the Fc/FcγR complex recruits effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). Notably, the primary cells for mediating ADCC, NK cells, express only FcγRIIIA, whereas monocytes express FcγRI, FcγRII and FcγRIII (Ravetch et al., 1991, supra).

Another important Fc ligand is the complement protein C1q. Fc binding to C1q mediates a process called complement dependent cytotoxicity (CDC) (reviewed in Ward et al., 1995, Ther Immunol 2:77-94). C1q is capable of binding six antibodies, although binding to two IgGs is sufficient to activate the complement cascade. C1q forms a complex with the C1r and C1s serine proteases to form the C1 complex of the complement pathway.

Several key features of antibodies including but not limited to, specificity for target, ability to mediate immune effector mechanisms, and long half-life in serum, make antibodies and related immunoglobulin molecules powerful therapeutics. Numerous monoclonal antibodies are currently in development or are being used therapeutically for the treatment of a variety of conditions including cancer. Examples of these include Vitaxin® (MedImmune), a humanized Integrin αvβ3 antibody (e.g., PCT publication WO 2003/075957), Herceptin® (Genentech), a humanized anti-Her2/neu antibody approved to treat breast cancer (e.g., U.S. Pat. No. 5,677,171), CNTO 95 (Centocor), a human Integrin αv antibody (PCT publication WO 02/12501), Rituxan® (IDEC/Genentech/Roche), a chimeric anti-CD20 antibody approved to treat Non-Hodgkin's lymphoma (e.g., U.S. Pat. No. 5,736,137) and Erbitux® (ImClone), a chimeric anti-EGFR antibody (e.g., U.S. Pat. No. 4,943,533).

There are a number of possible mechanisms by which antibodies destroy tumor cells, including anti-proliferation via blockage of needed growth pathways, intracellular signaling leading to apoptosis, enhanced down regulation and/or turnover of receptors, ADCC, CDC, and promotion of an adaptive immune response (Cragg et al., 1999, Curr Opin Immunol 11:541-547; Glennie et al., 2000, Immunol Today 21:403-410). However, despite widespread use, antibodies are not yet optimized for clinical use and many have suboptimal anticancer potency. Thus, there is a significant need to enhance the capacity of antibodies to destroy targeted cancer cells. Methods for enhancing the anti-tumor-potency of antibodies via enhancement of their ability to mediate cytotoxic effector functions such as ADCC and CDC are particularly promising. The importance of FcγR-mediated effector functions for the anti-cancer activity of antibodies has been demonstrated in mice (Clynes et al., 1998, Proc Natl Acad Sci U.S.A. 95:652-656; Clynes et al., 2000, Nat Med 6:443-446), and the affinity of the interaction between Fc and certain FcγRs correlates with targeted cytotoxicity in cell-based assays (Shields et al., 2001, J Biol Chem 276:6591-6604; Presta et al., 2002, Biochem Soc Trans 30:487-490; Shields et al., 2002, J Biol Chem 277:26733-26740). Together these data suggest that manipulating the binding ability of the Fc region of an IgG1 antibody to certain FcγRs may enhance effector functions resulting in more effective destruction of cancer cells in patients. Furthermore, because FcγRs can mediate antigen uptake and processing by antigen presenting cells, enhanced Fc/FcγR affinity may also improve the capacity of antibody therapeutics to elicit an adaptive immune response.

While enhancing effector function can increase the capacity of antibodies to destroy target cells, for some antibody therapies reduced or eliminated effector function may be more desirable. This is particularly true for those antibodies designed to deliver a drug (e.g., toxins and isotopes) to the target cell where the Fc/FcγR mediated effector functions bring healthy immune cells into the proximity of the deadly payload, resulting in depletion of normal lymphoid tissue along with the target cells (Hutchins et al., 1995, PNAS USA 92:11980-11984; White et al., 2001, Annu Rev Med 52:125-145). In these cases the use of Fc variants that poorly recruit complement or effector cells would be of tremendous benefit (see for example, Wu et al., 2000, Cell Immunol 200:16-26; Shields et al., 2001, J. Biol Chem 276:6591-6604; U.S. Pat. No. 6,194,551; U.S. Pat. No. 5,885,573 and PCT publication WO 04/029207).

All FcγRs bind the same region on the Fc of the IgG subclass, but with different affinities (e.g., FcγRI is a high affinity while FcγRII and FcγRIII are low affinity binders. Other differences between the FcγRs are mechanistic. For example, FcγRI, FcγRIIA/C, and FcγRIIIA are positive regulators of immune complex triggered activation, characterized by having an immunoreceptor tyrosine-based activation motif (ITAM) while FcγRIIB has an immunoreceptor tyrosine-based inhibition motif (ITIM) and is therefore inhibitory. Thus, the balance between activating and inhibiting receptors is an important consideration. For example, enhancing Fc binding to the positive regulators (e.g., FcγRIIIA) while leaving unchanged or even reducing Fc binding to the negative regulator FcγRIIB could result in optimized effector function such as enhanced ADCC mediated destruction of tumor cells. Another critical consideration is that Fc variants should be engineered such that the binding to FcγRs and/or C1q is modulated in the desired manner but so that they maintain their stability, solubility, structural integrity as well as their ability to interact with other important Fc ligands such as FcRn and proteins A and G.

Numerous mutagenesis studies have been carried out on the Fc domain (See for example, Duncan et al., 1988, Nature 332:563-564; Lund et al., 1995, Faseb J 9:115-119; Lund et al., 1996, J Immunol 157:4963-4969; Armour et al., 1999, Eur J Immunol 29:2613-2624; Shields et al., 2001, J Biol Chem 276:6591-6604; Jefferis et al., 2002, Immunol Lett 82:57-65; Presta et al., 2002, Biochem Soc Trans 30:487-490; U.S. Pat. Nos. 5,624,821, 5,885,573 and PCT publication Nos. WO 00/42072, WO 99/58572 and WO 04/029207). While the vast majority of substitutions reduce or ablate Fc binding with FcγRs some have resulted in higher FcγR affinity. However, most of the methods disclosed resulted in only modest improvements in FcRγIIIA binding and ADCC activity. The present invention provides for the first time a modified Fc of antibody that immunospecifically binds to one or more Eph receptor that has increased binding to FcRγIIIA binding, significant enhancement in ADCC and does not show an increase in FcRγIIB binding.

Citation or discussion of a reference herein shall not be construed as an admission that such is prior art to the present invention.

4. SUMMARY OF THE INVENTION

The present invention provides novel antibodies comprising immunologically active fragments of immunoglobulin molecules and an Fc region that further comprises at least one novel amino acid residue of the invention (also referred to herein as "high effector function amino acid residue(s))". Said novel antibodies are referred to herein as "Fc variants of the invention" or "Fc variants" or alternatively, a "modified antibody." Fc binding interactions are essential for a variety of effector functions and downstream signaling events including, but not limited to, antibody dependent cell-mediated cytotoxicity (ADCC) and complement dependent cytotoxicity (CDC). Accordingly, the invention provides Fc variants that exhibit altered binding affinity for at least one or more Fc ligands (e.g., FcγRs, C1q) relative to an antibody having the same amino acid sequence as the molecule of the invention but not comprising the novel amino acids residues of the invention (referred to herein as a "comparable molecule") such as, for example, an antibody comprising an unmodified Fc region containing naturally occurring amino acid residues at the corresponding position in the Fc domain. In addition, the present invention provides novel Fc variants comprising a variable region, or fragment thereof, that immunospecifically binds to one or more Eph receptor and at least one high effector function amino acid residue.

The present invention further provides Fc variants of antibodies that immunospecifically bind to one or more Eph receptor, said Fc variants comprising an Fc region in which at least one amino acid residue has been substituted. It is specifically contemplated that said Fc variants may be generated by methods well known to one skilled in the art. Briefly, such methods include but are not limited to, combining a variable region with the desired specificity (e.g., a variable region isolated from a phage display or expression library or derived from a human or non-human antibody) with an Fc region containing at least one high effector function amino acid residue. Alternatively, one skilled in the art may generate an Fc variant by substituting at least one amino acid residue in the Fc region of an antibody.

The present invention also provides Fc variants that have altered binding affinity for one or more Fc ligands (e.g., FcγRs, C1q) relative to a comparable molecule (e.g., an antibody having an original unmodified Fc region). In one embodiment, the Fc variants have higher binding affinity to activating FcγRs (e.g., FcγRIIIA) and/or unchanged or lower binding affinity to inhibitory FcγRs (e.g., FcγRIIB) relative to a comparable molecule (e.g., an antibody having an original unmodified Fc region). The present invention further provides Fc variants with enhanced ADCC function relative to a comparable molecule (e.g., an antibody having an original unmodified Fc region). In another embodiment, the Fc variants of the invention have enhanced ability to mediate ADCC ("referred to herein as ADCC activity") in addition to the above changes in FcγR affinities relative to a comparable molecule (e.g., an antibody having an original unmodified Fc region). In a further embodiment, the Fc variants of the invention are variants of an antibody that immunospecifically binds to one or more Eph receptor (e.g., EphA2 and EphA4). In another embodiment, the Fc variants of the invention do not have significantly altered antigen binding specificity.

The present invention also provides Fc variants have lower binding affinity to activating FcγRs (e.g., FcγRIIIA) and/or increased binding affinity to inhibitory FcγRs (e.g., FcγRIIB) relative to a comparable molecule (e.g., an antibody having an original unmodified Fc region). The present invention further provides Fc variants with decreased ADCC activity relative to a comparable molecule (e.g., an antibody having an original unmodified Fc region) original antibodies. In one embodiment, the Fc variants of the invention exhibit decreased ADCC activity in addition to the above changes in FcγR affinities relative to a comparable molecule (e.g., an antibody having an original unmodified Fc region). In another embodiment, the Fc variants of the invention are variants of an antibody that immunospecifically binds to one or more Eph receptor. In a further embodiment, the Fc variants of the invention do not have significantly altered antigen binding specificity.

The present invention additionally provides Fc variants that have altered binding affinity to the complement protein C1q relative to a comparable molecule (e.g., an antibody having an original unmodified Fc region). In one embodiment, the Fc variants have enhanced binding affinity to C1q and enhanced ability to mediate CDC (referred to herein as "CDC activity"). In another embodiment, the Fc variants have reduced binding affinity to C1q and reduced CDC activity relative to a comparable molecule (e.g., an antibody having an original unmodified Fc region). In a further embodiment, the Fc variants of the invention are variants of an antibody that immunospecifically binds to one or more Eph receptor.

In a specific embodiment, Fc variants of the invention comprise an Fc region comprising at least one high effector function amino acid residue selected from the group consisting of: 234E, 235R, 235A, 235W, 235P, 235V, 235Y, 236E, 239D, 265L, 269S, 269G, 298I, 298T, 298F, 327N, 327G, 327W, 328S, 328V, 329H, 329Q, 330K, 330V, 330G, 330Y, 330T, 330L, 330I, 330R, 330C, 332E, 332H, 332S, 332W, 332F, 332D, and 332Y, wherein the numbering system is that of the EU index as set forth in Kabat et al. (1991, NIH Publication 91-3242, National Technical Information Service, Springfield, Va.).

In another specific embodiment, Fc variants of the invention comprise an Fc region comprising at least one high effector function amino acid residue selected from the group consisting of: 239D, 330K, 330V, 330G, 330Y, 330T, 330L, 330I, 330R, 330C, 332E, 332H, 332S, 332W, 332F, 332D, and 332Y wherein the numbering system is that of the EU index as set forth in Kabat.

In still another specific embodiment, Fc variants of the invention comprise an Fc region comprising at least one high effector function amino acid residue selected from the group consisting of: 239D, 330L and 332E. In one embodiment, Fc variants of the invention comprise an Fc region comprising at least the high effector function amino acid residue 332E. In a specific embodiment, Fc variants of the invention comprise an Fc region comprising the high effector function amino acid residues 239D, 330L and 332E.

In a one embodiment, the Fc variants comprise at least one amino acid substitution at a position selected from the group consisting of: 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 239, 242, 246, 250, 251, 257, 259, 260, 261, 265, 269, 273, 274, 275, 277, 281, 282, 284, 287, 291, 298, 300, 302, 304, 306, 308, 310, 314, 316, 318, 319, 321, 323, 327, 328, 329, 330, 332 and 336, wherein the numbering of the residues in the Fc region is that of the EU index as set forth in Kabat.

In a specific embodiment, the Fc variants comprise at least one substitution selected from the group consisting of: L234E, L235R, L235A, L235W, L235P, L235V, L235Y, G236E, S239D, D265L, E269S, E269G, S298I, S298T, S298F, A327N, A327G, A327W, L328S, L328V, P329H, P329Q, A330K, A330V, A330Q, A330Y, A330T, A330L, A330I, A330R, A330C, I332E, I332H, I332S, I332W, I332F, I332D, and I332Y, wherein the numbering system is that of the EU index as set forth in Kabat. In one embodiment, the Fc variants comprise at least one substitution selected from the group consisting of S239D, A330L and I332E. In another embodiment, the Fc variants comprise at least each of the following substitutions, S239D, A330L and I332E. In a further embodiment, the Fc variants have at least the amino acid substitution I332E.

It is an object of the present invention to provide Fc variants that bind with greater affinity to one or more Fc ligand (e.g., FcγRs, C1q). In one embodiment, said variants have an affinity for one or more Fc ligand (e.g., FcγRs, C1q) that is at least 2 fold greater than that of a comparable molecule (e.g., an antibody prior to Fc modification). In a further embodiment, the Fc variants of the invention have affinity for an Fc ligand (e.g., FcγR, C1q that is between 2 fold and 500 fold greater than that of a comparable molecule (e.g., an antibody prior to Fc modification). In one specific embodiment, an Fc variant of the invention has a greater affinity for FcγRIIIA. In another specific embodiment, an Fc variant of the invention has a greater affinity for FcγRIIB. In yet another specific embodiment, an Fc variant of the invention has a greater affinity for C1q.

It is a further object of the present invention to provide a Fc variants that bind with reduced affinity to one or more Fc ligand (e.g., FcγRs, C1q). In one embodiment, the Fc variants of the invention have affinity for one or more Fc ligand (e.g., FcγRs, C1q) that is between about 2 fold and about 500 fold lower than that of a comparable molecule (e.g., an antibody prior to Fc modification). In another embodiment, the Fc variants of the invention have affinity for one or more Fc ligand (e.g., FcγRs, C1q) that is between 2 fold and 500 fold lower than that of a comparable molecule (e.g., an antibody prior to Fc modification). In a specific embodiment, the Fc variants of the invention have an affinity for FcγRIIB that is either unchanged, or more preferably reduced. In another specific embodiment, the Fc variants of the invention have an affinity for FcγRIIIA that is reduced. In yet another embodiment, the Fc variants of the invention have an affinity for C1q that is reduced.

It is a further object of the present invention to provide Fc variants that have enhanced ADCC and/or CDC activity. In one embodiment, Fc variants of the invention have ADCC and/or CDC activity that is at least about 2 fold greater then that of a comparable molecule (e.g., an antibody prior to Fc modification). In another embodiment, the Fc variants of the invention have ADCC and/or CDC activity that is between about 2 fold and about 100 fold greater than that of a comparable molecule. In a further embodiment, Fc variants of the invention have ADCC and/or CDC activity that is at least 2 fold greater then that of a comparable molecule (e.g., an antibody prior to Fc modification). In yet a further embodiment, the Fc variants of the invention have ADCC and/or CDC activity that is between 2 fold and 100 fold greater than that of a comparable molecule.

It is a further object of the present invention to provide Fc variants that have reduced ADCC and/or CDC activity. In one embodiment, Fc variants of the invention have ADCC and/or CDC activity that is at least 2 fold lower than that of a comparable molecule (e.g., an antibody prior to Fc modification). In another embodiment, the Fc variants of the invention have ADCC and/or CDC activity that is between 2 fold and 100 fold lower than that of a comparable molecule. In a further embodiment, Fc variants of the invention have ADCC and/or CDC activity that is at least about 2 fold lower than that of a comparable molecule (e.g., an antibody prior to Fc modification). In another embodiment, the Fc variants of the invention have ADCC and/or CDC activity that is between about 2 fold and about 100 fold lower than that of a comparable molecule.

In one specific embodiment, an Fc variant of the invention has an increased affinity for FcγRIIIA and an affinity for FcγRIIB that is unchanged or preferably reduced and enhanced ADCC activity. In another specific embodiment, an Fc variant of the invention has an equilibrium dissociation constant ($K_D$) that is decreased between about 2 fold and about 10 fold, or between about 5 fold and about 50 fold, or between about 25 fold and about 250 fold, or between about 100 fold and about 500 fold, relative to a comparable molecule. In a further specific embodiment, an Fc variant of the invention has an equilibrium dissociation constant ($K_D$) that is decreased between 2 fold and 10 fold, or between 5 fold and 50 fold, or between 25 fold and 250 fold, or between 100 fold and 500 fold, relative to a comparable molecule. In another specific embodiment, an Fc variant of the invention has a ratio of FcγRIIIA/FcγRIIB equilibrium dissociation constants ($K_D$) that is decreased and enhanced ADCC activity relative to a comparable molecule.

In one embodiment, an Fc variant of the invention has an increased affinity for FcγRIIIA and an affinity for FcγRIIB that is unchanged or preferably reduced, an affinity for C1q that is reduced and enhanced ADCC activity relative to a comparable molecule (e.g., an antibody prior to Fc modification).

In another embodiment, an Fc variant of the invention has a decreased affinity for FcγRIIIA and an affinity for FcγRIIB that is increased and reduced ADCC activity relative to a comparable molecule (e.g., an antibody prior to Fc modification). In still another embodiment, an Fc variant of the invention has a ratio of FcγRIIIA/FcγRIIB equilibrium dissociation constants ($K_D$) that is increased and reduced ADCC activity relative to a comparable molecule.

The binding properties of a receptor for its ligand, may be determined by a variety of methods well-known in the art, including but not limited to, equilibrium methods (e.g., enzyme-linked immunoabsorbent assay (ELISA) or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other well-known methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4$^{th}$ Ed., Lippincott-Raven, Philadelphia (1999), which focuses on antibody-immunogen interactions.

The Fc variants of the present invention may be combined with other Fc modifications (e.g., other amino acid substitutions, altered glycosylation, etc.), including but not limited to modifications that alter Fc ligand binding and/or effector function. The invention encompasses combining an Fc variant of the invention with other Fc modifications to provide additive, synergistic, or novel properties in antibodies or Fc fusions. Preferably, the other Fc modifications enhance the phenotype of the Fc variants of the present invention (e.g., Fc variant comprising at least one high effector function amino acid) with which they are combined. For example, if an Fc variant (i.e., incorporating a hinge modification of the invention) is combined with a mutant known to bind FcγRIIIA with a higher affinity than a comparable molecule comprising a wild type Fc region, the combination results in a greater fold enhancement in FcγRIIIA affinity.

The invention encompasses molecules that comprise homodimers or heterodimers of Fc regions wherein at least one Fc region incorporates at least one high effector function amino acid of the invention. Heterodimers comprising Fc regions refer to molecules where the two Fc chains have different sequences. In some embodiments, in the heterodimeric molecules comprising an Fc region incorporating at least one high effector function amino acid and/or other Fc modification, each chain has one or more different modifications from the other chain. In other embodiments, in the heterodimeric molecules comprising an Fc region incorporating a hinge modification, one chain contains the wild-type Fc region and the other chains comprises one or more modifications. Methods of engineering heterodimeric Fc containing molecules are known in the art and encompassed within the invention.

In one embodiment, the Fc variants of the invention with modified binding affinity to one or more Fc ligand (e.g., FcγRs, C1q) and altered ADCC and/or CDC activity immunospecifically bind to one or more Eph receptor. In another embodiment, said Fc variants are antagonists of one or more Eph receptor. An antagonist of one or more Eph receptor is any molecule that blocks, inhibits, reduces or neutralizes the function, activity and/or expression of one or more Eph receptor. Antagonists may act by interfering with the binding of a receptor to a ligand and vice versa, by incapacitating or killing cells which have been activated by a ligand, and/or by interfering with receptor or ligand activation (e.g., tyrosine kinase activation) or signal transduction after ligand binding to a cellular receptor. The antagonist may completely block receptor-ligand interactions or may substantially reduce such interactions. Thus, an antagonist of an Eph receptor can block Eph receptor signaling.

In yet another embodiment, the Fc variants of the invention are agonists of one or more Eph receptor. An agonist of an Eph receptor is any molecule that can increase the activity, activation or function of an Eph receptor. Agonists may, for example, act by activating a target molecule and/or mediating signal transduction. In a preferred embodiment, said Fc variant is a variant of an antibody that immunospecifically binds one or more Eph receptor, such as those described herein. Additional Eph receptor specific antibodies have been described in PCT Publication Nos. WO 04/014292, WO 03/094859 and U.S. patent application Ser. No. 10/863,729 all of which are incorporated by reference herein in their entireties.

In one embodiment, an Fc variant of the invention with modified binding affinity to one or more Fc ligand (e.g., FcγRs, C1q) and altered ADCC and/or CDC activity preferentially binds one or more Eph receptor (e.g., EphA1, A2, A3a, A3b, A4, A5a, A5b, A6, A7, A8, B1, B2a, B2b, B3, B4 and B6) versus other receptor tyrosine kinases. In one embodiment, Eph receptors of the invention include but are not limited to those described in section 6.1 entitled "Fc Variants that Immunospecifically Bind to an Eph Receptor", infra, and those shown in FIG. 18. In another embodiment, said Fc variant of the invention preferentially binds EphA2 over other Eph receptors. In another embodiment, the Fc variant of the invention do not bind Eph A2. In another embodiment, the Fc variant of the invention preferentially binds EphA4 over other Eph receptors. In yet another embodiment, an Fc variant of the invention does not bind EphA4. In still another embodiment, the Fc variant of the invention immunoreacts with more then one Eph receptor. In one embodiment, the Fc variant of the invention binds both EphA4 and Epha2. In yet another embodiment, the Fc variant of the invention binds and is an agonist of both EphA4 and Epha2. The Fc variant may have the same immunoreactivity for more than one Eph receptor or alternatively, the Fc variant may immunoreact more strongly with one Eph receptor versus another. It is specifically contemplated that Fc variants of the invention may be bispecific antibodies. It is also contemplated that an Fc variant of the invention may bind to a common epitope shared by more then one Eph receptor.

The present invention also encompasses Fc variants with modified binding affinity to one or more Fc ligand (e.g., FcγRs, C1q) and altered ADCC and/or CDC activity that immunospecifically bind to at least one Eph receptor conjugated or fused to a moiety (e.g., therapeutic agent or drug).

The present invention also encompasses the use of Fc variants with modified binding affinity to one or more Fc ligand (e.g., FcγRs, C1q) and altered ADCC and/or CDC activity that immunospecifically bind to at least one Eph receptor for the prevention, management, treatment or amelioration of Eph receptor-mediated (and/or ephrin-mediated) and/or associated diseases and disorders or one or more symptoms thereof, including but not limited to cancer, inflammatory and autoimmune diseases either alone or in combination with other therapies. The invention also encompasses the use of Fc variants with modified binding affinity to one or more Fc ligand (e.g., FcγRs, C1q) and altered ADCC and/or CDC activity that immunospecifically bind to at least one Eph receptor conjugated or fused to a moiety (e.g., therapeutic agent or drug) for preventing, managing, treating or ameliorating Eph receptor-mediated and/or associated diseases and disorders or one or more symptoms thereof, including but not limited to cancer, inflammatory and autoimmune diseases either alone or in combination with other therapies.

The invention further encompasses treatment protocols that enhance the prophylactic or therapeutic effect of Fc variants with altered binding affinity to to one or more Fc ligand (e.g., FcγRs, C1q) and altered ADCC and/or CDC activity that immunospecifically bind to at least one Eph receptor.

The invention provides methods for the identification and/or generation of antibodies that immunospecifically bind to at least one Eph receptor. In addition, the invention provides methods for the screening and identification of antibodies that bind to at least one Eph receptor and are either antagonists or agonists of at least one Eph receptor including but not limited to assays that monitor Eph receptor activity (e.g., cell adhesion, angiogenesis, tumor cell growth and tumor progression) and/or plasma concentration. Further, the invention provides for a method to manipulate both the ADCC and or CDC activity as well as the binding affinities for FcγR and/or C1q of antibodies identified using such screening methods. The antibodies identified and manipulated utilizing such methods can be used for the prevention, treatment, management or amelioration of Eph receptor-mediated diseases and disorders or one or more symptoms thereof, including but not limited to cancer, inflammatory and autoimmune diseases either alone or in combination with other therapies.

The present invention provides kits comprising one or more Fc variants with modified binding affinity to one or more Fc ligand (e.g., FcγRs, C1q) and altered ADCC and/or CDC function that immunospecifically bind to at least one Eph receptor conjugated or fused to a detectable agent, therapeutic agent or drug, in one or more containers, for use in the prevention, treatment, management, amelioration, detection, monitoring or diagnosis of Eph receptor-mediated and/or associated diseases and disorders including but not limited to cancer, inflammatory and autoimmune diseases.

5. BRIEF DESCRIPTION OF THE FIGURES

FIG. 1. The nucleotide and deduced amino acid sequence of the variable region of the antibody Vitaxin®, (A) heavy chain variable region (SEQ ID NO: 1 and SEQ ID NO: 3, respectively) (B) light chain variable region (SEQ ID NO: 2 and SEQ ID NO: 4, respectively). The CDRs are underlined.

FIG. 2. The nucleotide and deduced amino acid sequence of the variable region of the anti-EphA2 antibody 12G3H11 (abbreviated "12G3") (A) heavy chain variable region (SEQ ID NO: 62 and SEQ ID NO: 64, respectively) (B) light chain variable region (SEQ ID NO: 63 and SEQ ID NO: 65, respectively). The CDRs are underlined.

FIG. 3. The nucleotide and deduced amino acid sequence of the variable region of the anti-EphA2 antibody 3F2 (A) heavy chain variable region (SEQ ID NO: 66 and SEQ ID NO: 68, respectively) (B) light chain variable region (SEQ ID NO: 67 and SEQ ID NO: 69, respectively). The CDRs are underlined.

FIG. 4. Map of the expression plasmid used for the production of full length IgGs. SmaI/BsiWI restriction sites used to clone the light chain variable region, XbaI/ApaI restriction sites used to clone variable region of heavy chain and ApaI/NotI restriction sites were used to replace the constant region of the heavy chain.

FIG. 5. Screening of Vitaxin Fc variant clones by characterizing their relative binding to FcγRIIIA compared to parental scFv-Fc as determined by ELISA. Numerous clones were seen to have improved binding.

Figure 6:
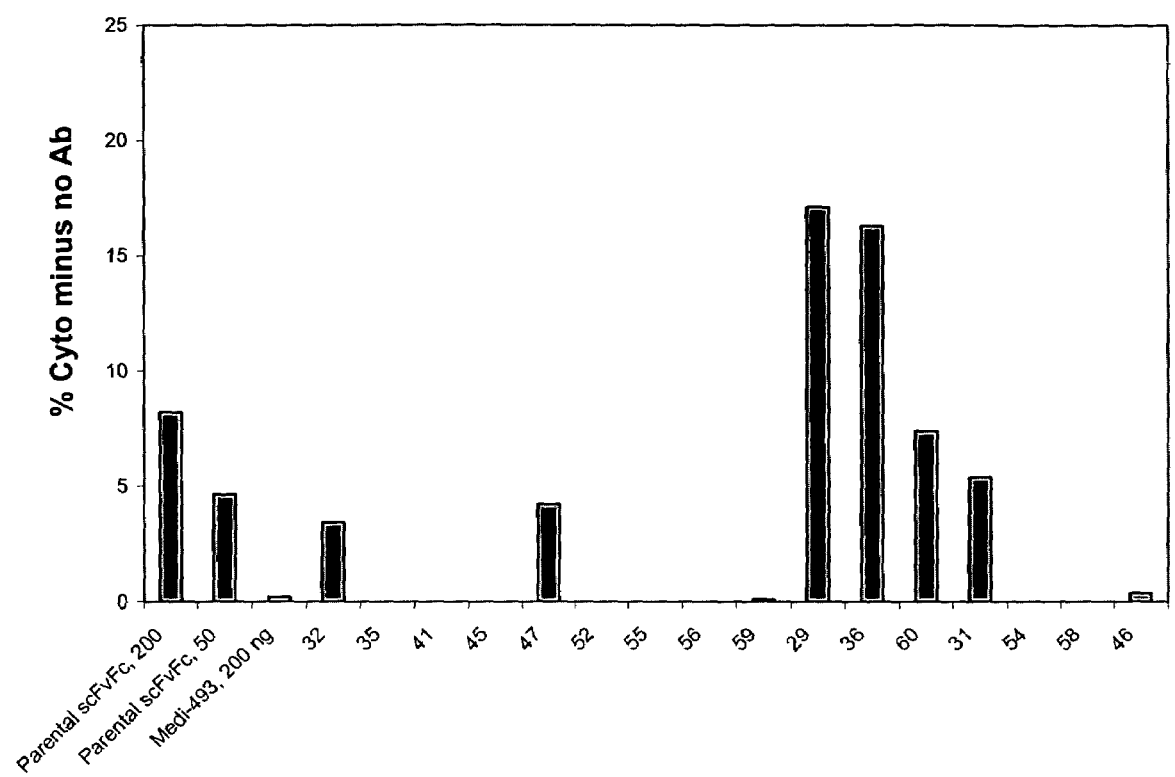

FIG. 6. Relative ADCC activity of several Vitaxin Fc variant clones against M21 cells as determined by a cell-based assay. Several Fc variants, including I332E, showed improved ADCC activity relative to the parental scFv-Fc.

Figure 7:
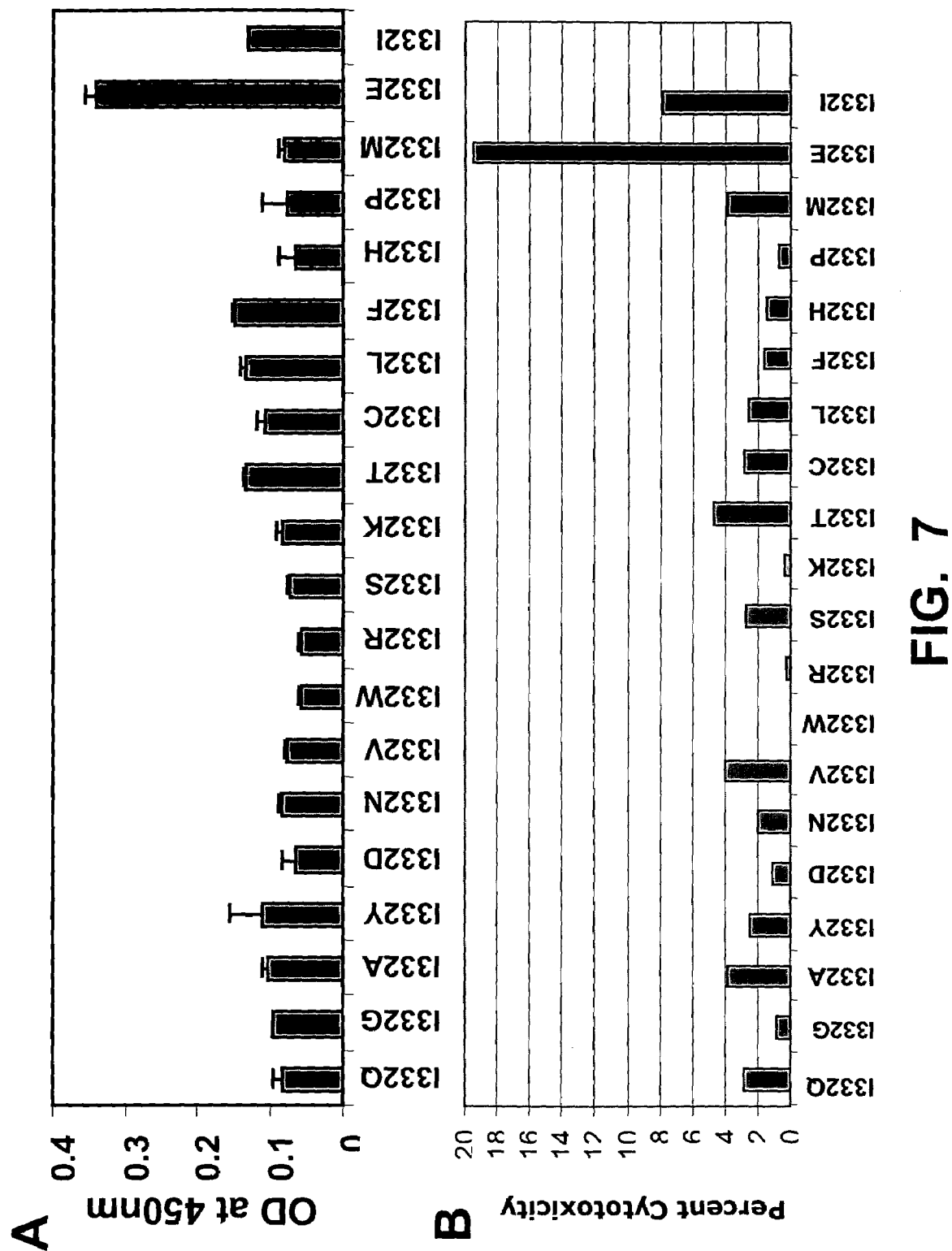

FIG. 7. All 20 amino acids were substituted at position 332 of Vitaxin. The relative binding affinities of each position 332 Fc variant to FcγRIIIA was determined by ELISA (panel A). The relative ADCC activity of each position 332 Fc variant was determined by a cell-based assay (panel B). The I322E Fc variant was seen to provide the greatest improvement in both binding and in ADCC activity.

FIG. 8. Binding of Vitaxin® and the I332E (Vitaxin-1M) Fc variant to FcγRIIIA (A) and FcγRIIB (B) as determined by ELISA. The binding of Vitaxin-1M Fc variant to Fc FcγRIIIA is improved while the binding to FcγRIIB appears unchanged.

Figure 9:
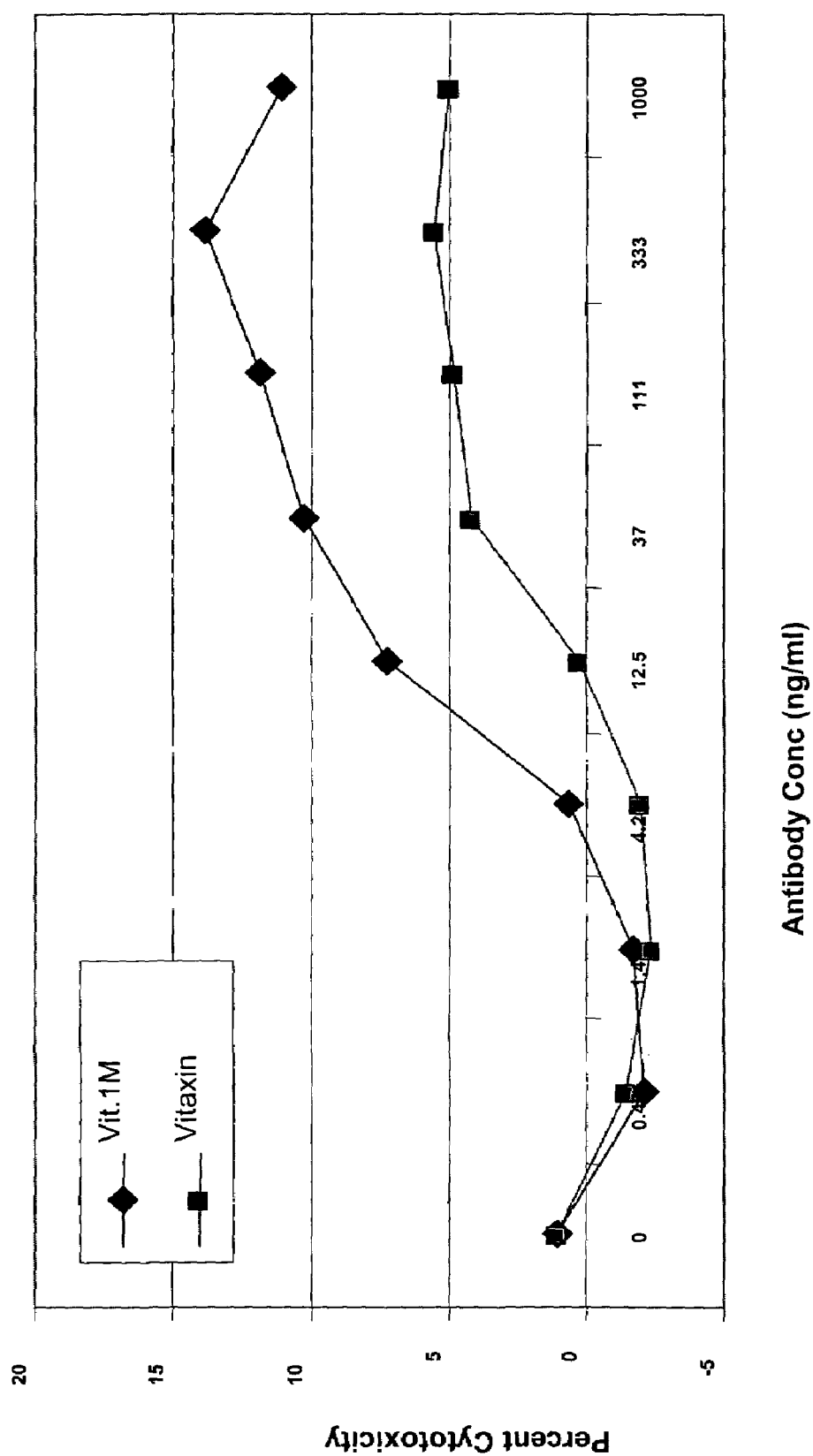

FIG. 9. Cell-based ADCC assay of Vitaxin® and the I332E (Vitaxin-1M) Fc variant using 50:1 ratio of effector to target cells at a variety of antibody concentrations from 0.4 to 1000 ng/ml. The I332E Fc variant shows higher ADCC activity over a wide range of antibody concentrations.

Figure 10:
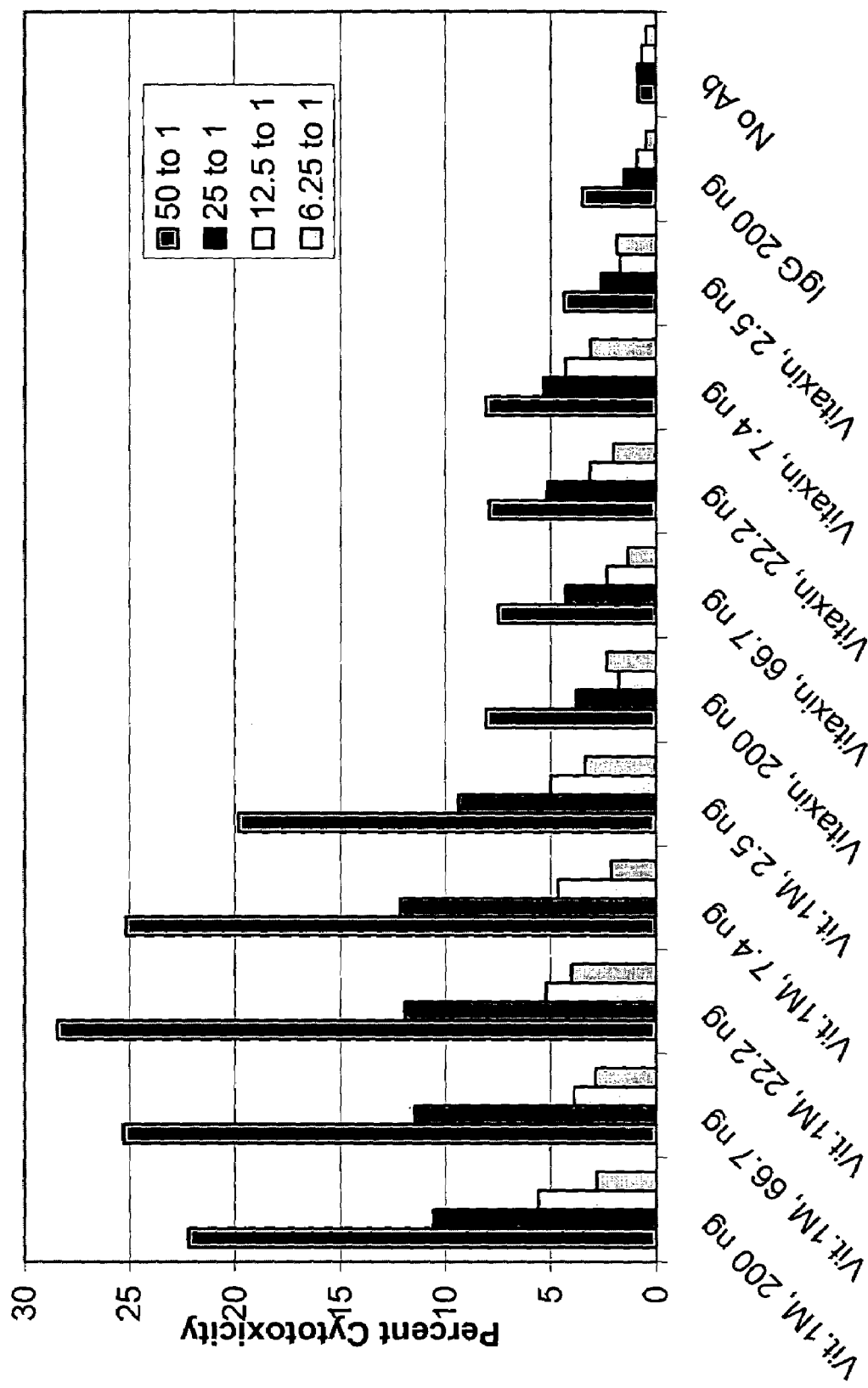

FIG. 10. Cell-based ADCC assay of Vitaxin® and the I332E (Vitaxin-1M) Fc variant using different ratios of effector to target cells and different amounts of antibody ranging from 2.5 ng to 200 ng per well. The I332E Fc variant shows higher ADCC activity over a wide range of antibody concentrations at all E:T ratios.

Figure 11:
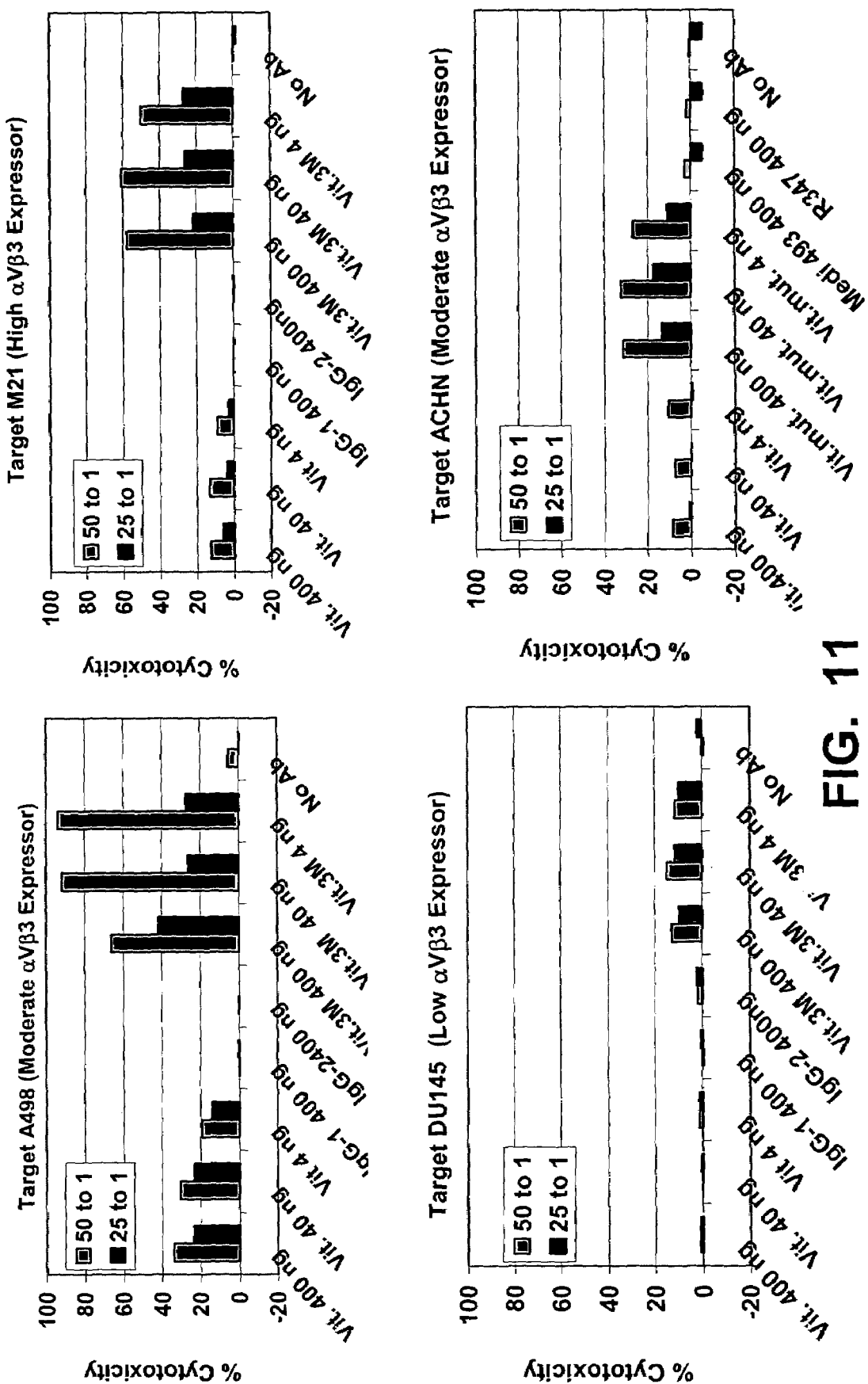

FIG. 11. Cell-based ADCC assay of Vitaxin® and the Vitaxin S239D/A330L/I332E (Vitaxin-3M) Fc variant against several target cell lines expressing different levels of Integrin αVβ3, A498 (moderate), DU145 (low), M21 (high) and ACHN (moderate), using two different E:T ratios and antibody amounts ranging from 4 ng to 400 ng per well. In all cases the S239D/A330L/I332E (Vitaxin-3M) Vitaxin Fc variant shows higher ADCC activity.

Figure 12:
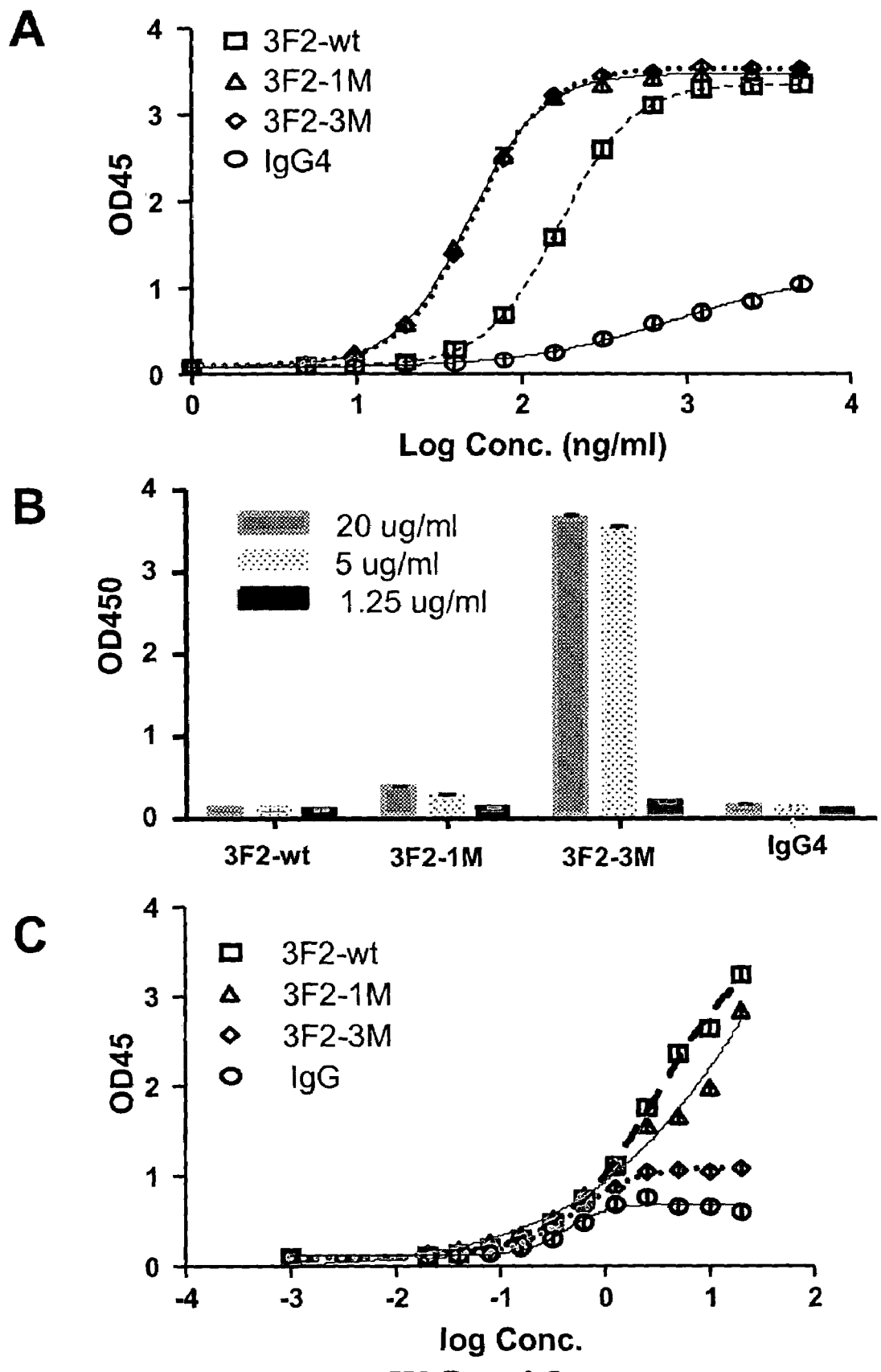

FIG. 12. ELISA analysis of the wild type anti-EphA2 antibody 3F2 and the 3F2 I332E (3F2-1M) and 3F2 S239D/A330L/I332E (3F2-3M) Fc variants binding to FcγRIIIA tetramer (panel A), FcγRIIIA monomer (panel B) and C1q (panel C). Both the 3F2-1M and 3F2-3M Fc variants bind better to FcγRIIIA monomers and tetramers, although the 3F2-3M Fc variant binds the monomer significantly better then either the wild type antibody or 3F2-1M Fc variant. In contrast both the 3F2-1M and 3F2-3M Fc variants did not bind C1q to the same degree as the wild type antibody with the 3M Fc variant showing the largest decrease in binding.

Figure 13:
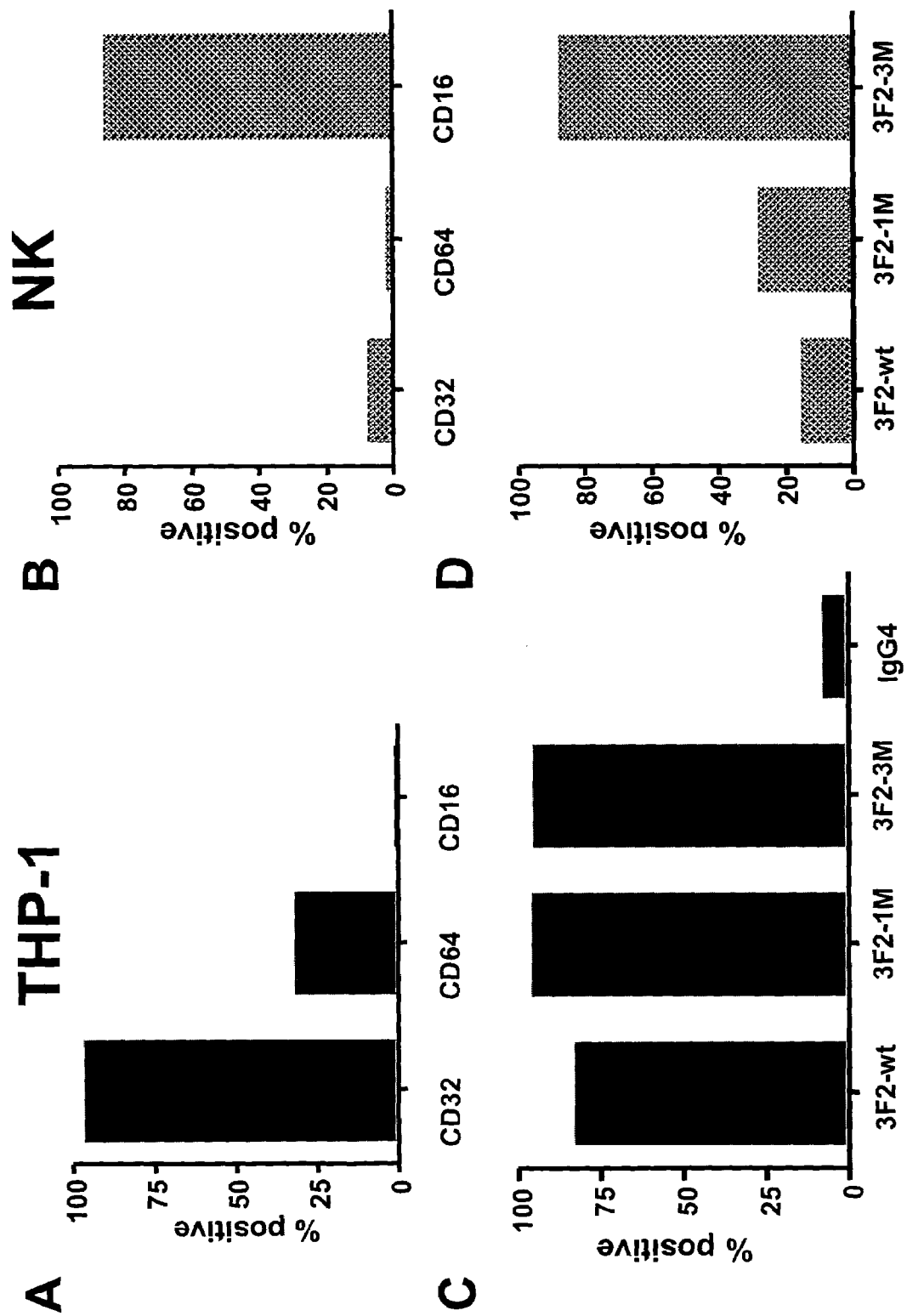

FIG. 13. FACS analysis of anti-EphA2 antibody 3F2-WT, 3F2-1M and 3F2-3M binding to cells via Fc-domain interactions. THP-1 and NK cells were stained with antibodies to FcγRI, FcγRII and FcγRIII (also commonly referred to CD64, CD32 and CD16, respectively). THP-1 cells have high levels of CD32 on their cell surface, moderate levels of CD64 and very low levels of CD16 (panel A). NK cells however show the opposite profile, high levels of CD16 and low levels of CD32 and CD64 (panel B). All three versions of 3F2 (wt, 1M and 3M) bound to a similar degree to THP-1 cells (panel C). However, the variants were seen to bind to a greater extent to NK cells, with the 3F2-3M Fc variant showing the largest increase in binding (panel D).

FIG. 14. Cell-based ADCC assay of 12G3H11 (anti-EphA2 antibody) and its I332E Fc variant using 50:1 ratio of effector to A549 target cells (panel A) and a similar study using two different E:T ratios from (panel B). In both studies the amount of antibody ranged from 4 ng to 400 ng per well. The I332E Fc variant shows higher ADCC activity over a wide range of antibody concentrations at all E:T ratios.

Figure 15:
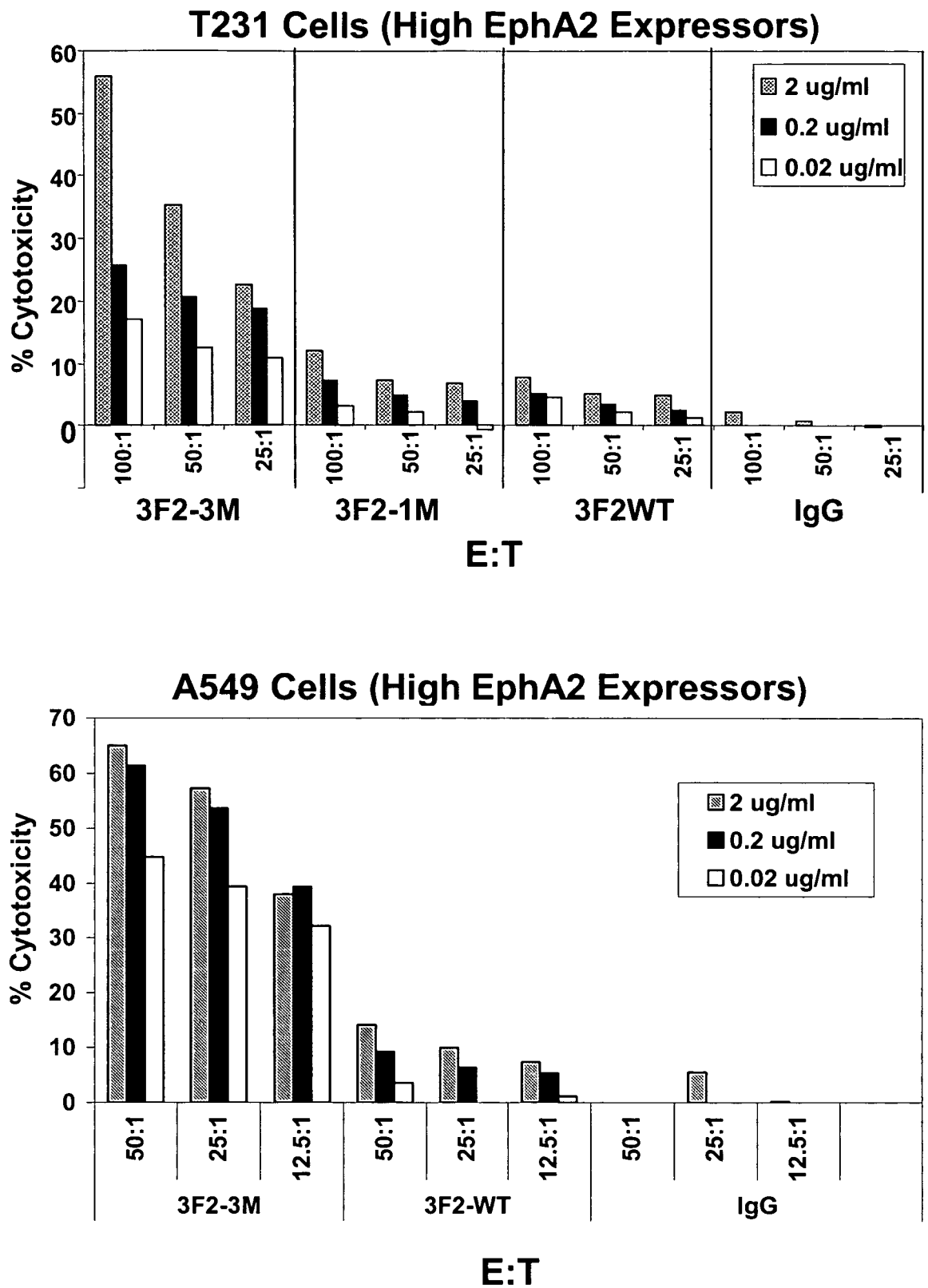

FIG. 15. Cell-based ADCC assay of anti-EphA2 antibody 3F2 and the 3F2-1M and 3F2-3M Fc variants to target cells expressing high (T231, A549) levels of EphA2. In each assay the antibody concentration ranged from 0.02 ug/ml to 2 µg/ml. E:T ratios varied from 12.5:1 to 100:1 depending on the assay. The 3F2-3M Fc variant was seen to have the highest ADCC activity against all cell types. Although the 3F2-1M Fc variant showed higher ADCC activity against more cell types than the 3F2 wild type, it was generally not as active as the 3F2-3M Fc variant.

FIG. 16. Cell-based ADCC assay of anti-EphA2 antibody 3F2-WT, 3F2-1M and 3F2-3M Fc variants to target cells expressing high (Hey8) and moderate (SKOV3) levels of EphA2. The antibody concentration and E:T ratios are the same as for FIG. 15. The 3F2-3M Fc variant was seen to have the highest ADCC activity against all cell types. Although the 3F2-1M Fc variant showed higher ADCC activity against most cell types than the 3F-WT, it was generally not as active as the 3F2-3M Fc variant.

FIG. 17. Cell-based ADCC assay of anti-EphA2 antibody 3F2, 3F2-1M and 3F2-3M Fc variants to target cells expressing low (A498, SKMEL28) levels of EphA2. The SKMEL28 cells express Integrin αVβ5 as were also used as target cells for the Vitaxin and Vitaxin-3M antibodies. The antibody concentration and E:T ratios are the same as for FIG. 15. None of the 3F2 antibodies were seen to have activity against SKMEL28 cells. Although both Vitaxin and the Vitaxin-3M antibodies had activity, the Vitaxin-3M Fc variant was significantly more active.

Figure 18A:
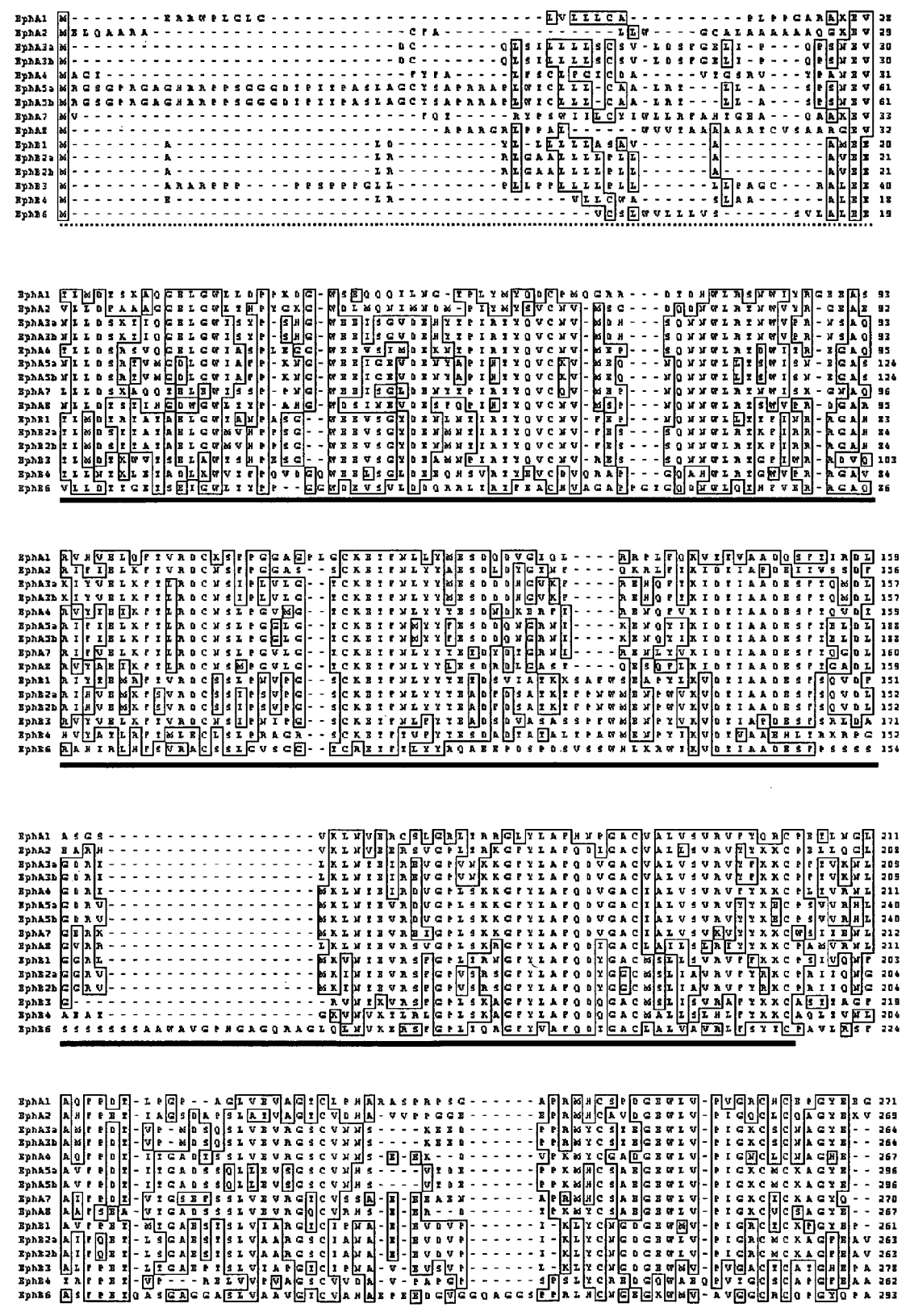
Figure 18B:
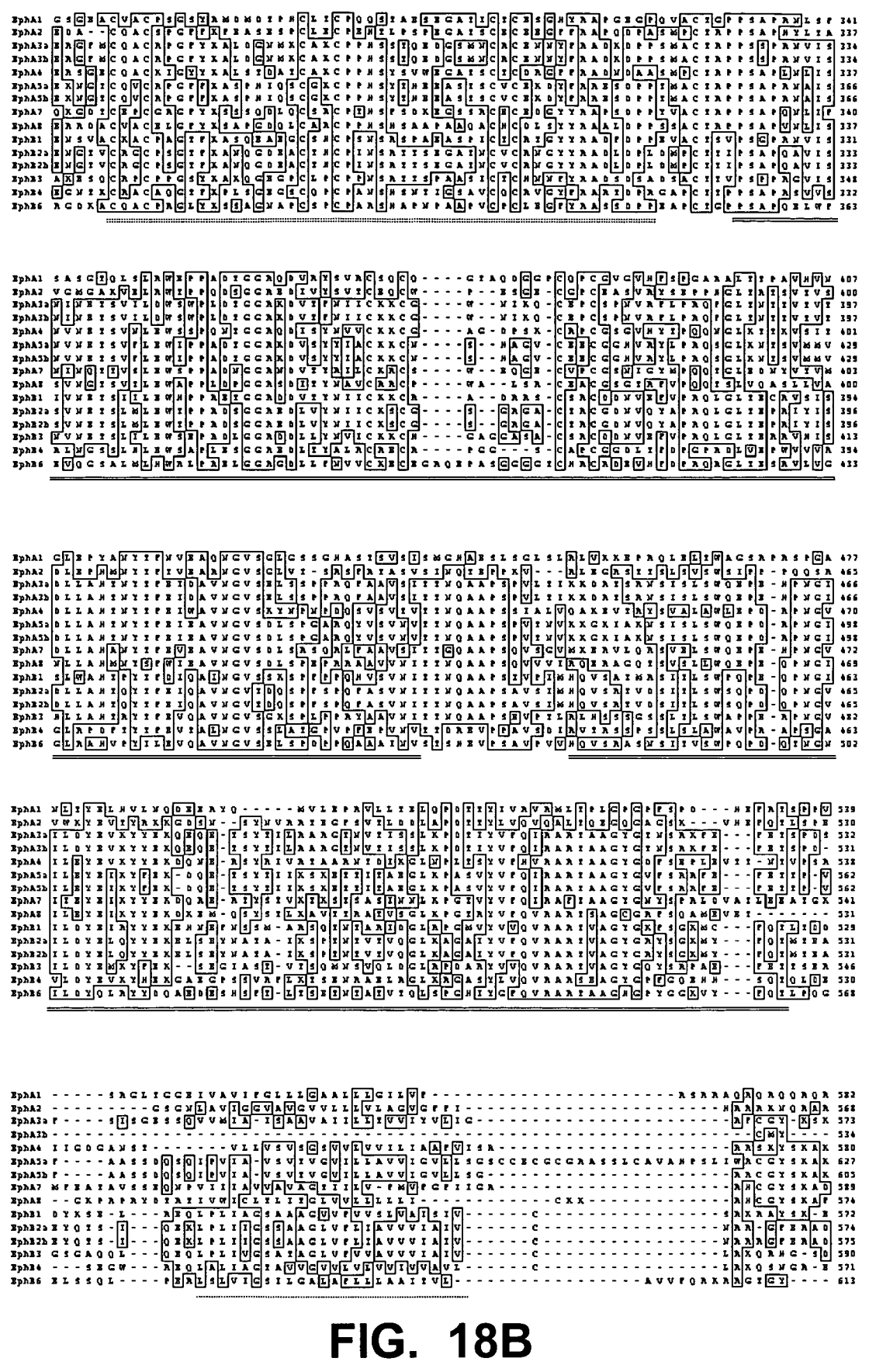
Figure 18C:
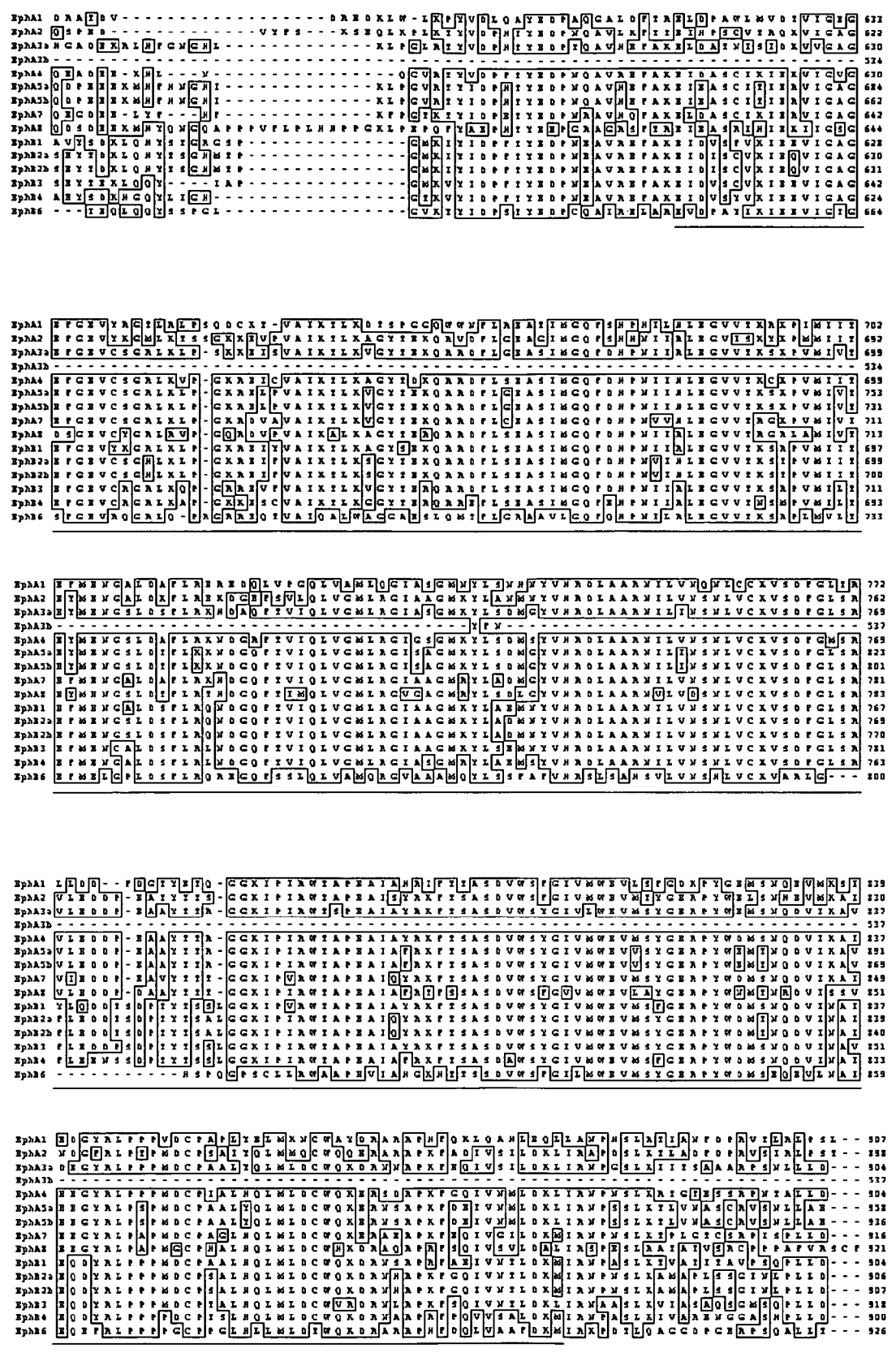
Figure 18D:
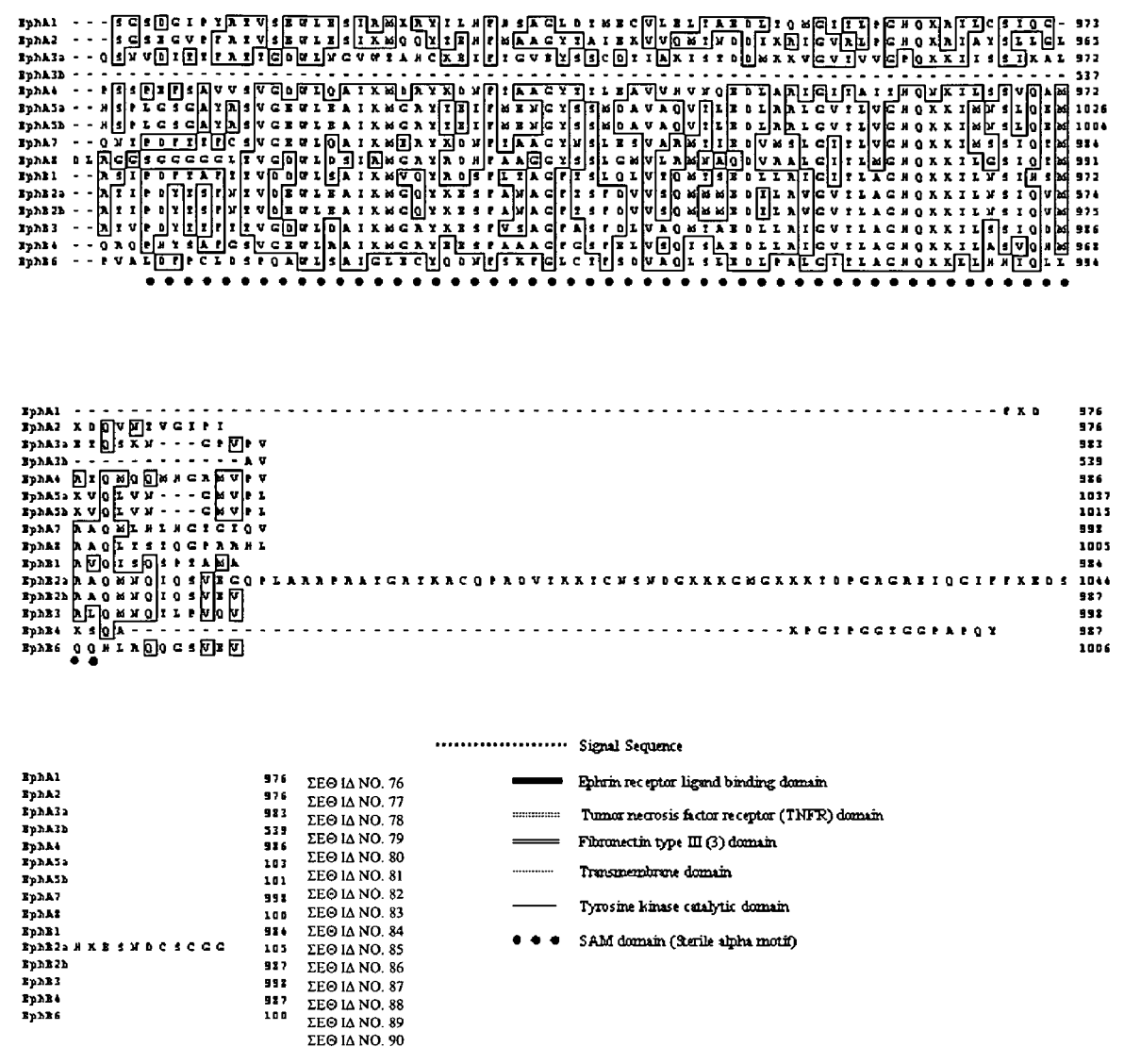

FIG. 18A-D. Alignment of the currently known human Eph family of receptors. The following protein motifs are underlined as described in the key: signal sequence; ephrin receptor ligand binding domain; fibronectin type III domain; transmembrane domain; tyrosine kinase catalytic domain; SAM domain.

Figure 19:
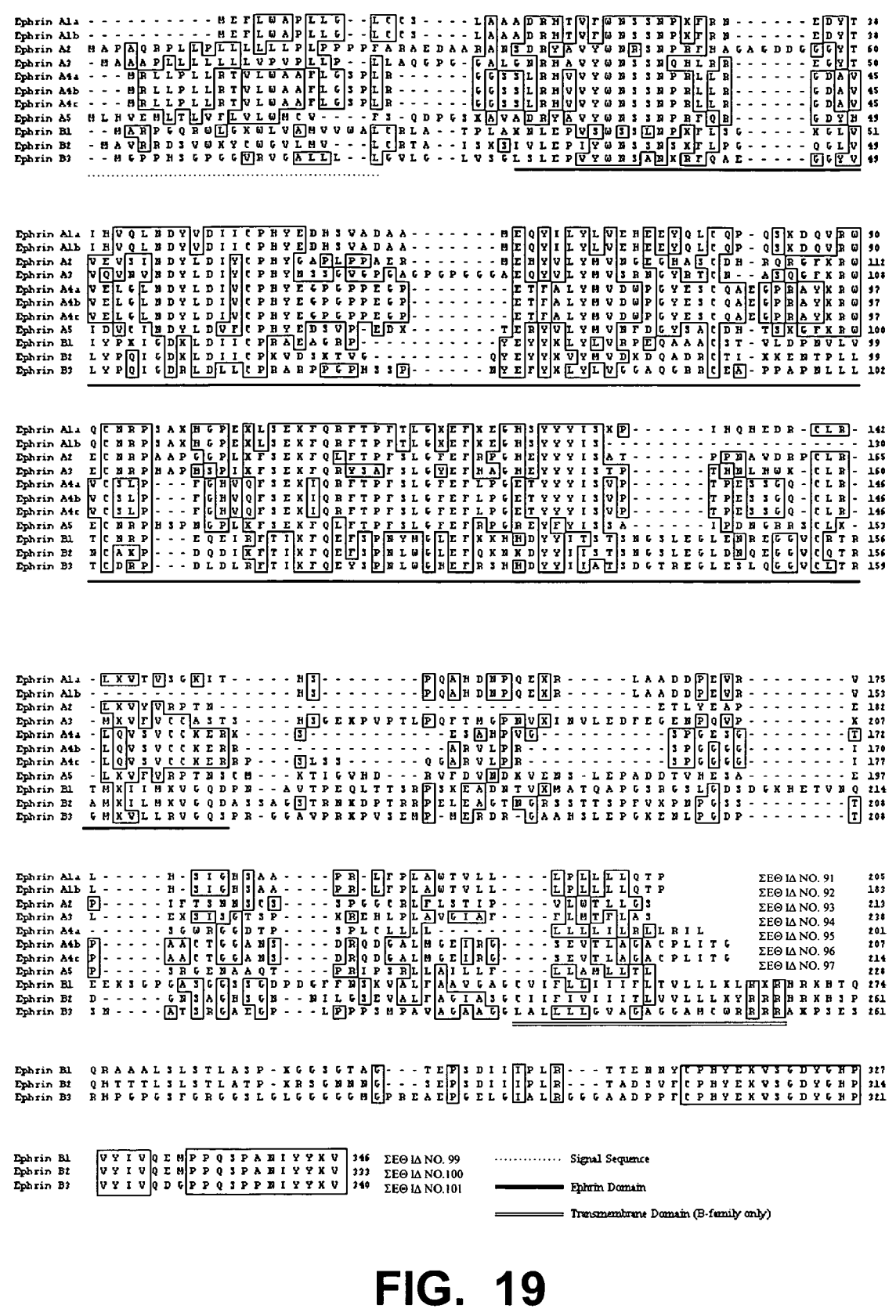

FIG. 19. Alignment of the currently known human Ephrin family of Eph receptor ligands. The following protein motifs are underlined as described in the key: signal sequence; Ephrin domain; transmembrane domain (B-family only).

6. DETAILED DESCRIPTION OF THE INVENTION

The present invention provides certain amino acids residues in the Fc region of an IgG antibody that correlate with high effector function. Further, the invention provides high effector function residues in the Fc region of an antibody which exhibit high binding affinity for the Fc receptor, FcγRIIIA. In further embodiments, the invention encompasses the introduction of at least one of the high effector amino acid residues of the invention that does not result in a concomitant increase in binding the FcγRIIB receptor. In another embodiment, the invention encompasses the introduction of at least one of the high effector amino acid residues of the invention that results in a concomitant decrease in binding the FcγRIIB receptor and/or C1q. In still another embodiment, the introduction of at least one of the high effector amino acid residues of the invention that results in a concomitant increase in binding to both the FcγRIIIA and FcγRIIB receptors. In a preferred embodiment, the ratio of FcγRIIIA/FcγRIIB equilibrium dissociation constants ($K_D$), is decreased. Furthermore, the presence of at least one of the high effector amino acid residue of the invention results in antibodies with an enhanced antibody dependent cell-mediated cytotoxicity (ADCC) activity. Accordingly, the invention provides Fc variants that exhibit altered effector function (e.g., ADCC, CDC, etc.) and/or altered binding affinity for at least one Fc ligand (e.g., FcγRIIIA, FcγRIIB, C1q, etc.) relative to an antibody (or other Fc-domain containing polypeptide) having the same amino acid sequence as the molecule of the invention but not comprising the novel amino acids residues of the invention (referred to herein as a "comparable molecule") such as an antibody comprising an unmodified Fc region containing naturally occurring amino acid residues at the corresponding position in the Fc domain. In particular, the present invention provides Fc variants comprising a variable region, or fragment thereof, that immunospecifically binds to at least one Eph receptor and a Fc region that further comprises at least one high effector function amino acid residue.

The present invention further provides Fc variants of antibodies that immunospecifically bind to at least one Eph receptor, said Fc variants comprising an Fc region in which at least one amino acid residue has been substituted. The present invention also relates to Fc variants with altered binding affinity to their FcγRs compared to that of a comparable molecule (e.g., an antibody having an original unmodified Fc region). In one embodiment, the Fc variants have higher binding affinity to activating FcγRs (e.g., FcγRIIIA). In a specific embodiment, the Fc variants of the invention have equilibrium dissociation constants ($K_D$) that are decreased relative to a comparable molecule. In another embodiment the Fc variants have higher binding affinity to activating FcγRs and unchanged or lower binding affinity to inhibitory FcγRs (e.g., FcγRIIB). In a further embodiment, are Fc variants which have a ratio of FcγRIIIA/FcγRIIB equilibrium dissociation constants ($K_D$) that are decreased relative to a comparable molecule. In yet a further embodiment, the Fc variants of the invention also exhibit increased ADCC activity when compared to a comparable molecule (e.g., an antibody having an original unmodified Fc region) in addition to the above changes in FcγR affinities. In another embodiment, the Fc variants of the invention are variants of an antibody that immunospecifically binds to at least one Eph receptor (e.g., EphA1, A2, A3a, A3b, A4, A5a, A5b, A6, A7, A8, B 1, B2a, B2b, B3, B4 and B6). In a specific embodiment, the Fc variants of the invention immunospecifically bind least one Eph receptor and are antagonists of at least one Eph receptor. In another specific embodiment, the Fc variants of the invention immunospecifically bind least one Eph receptor and are agonists of at least one Eph receptor.

The antibodies of the present invention may be produced "de novo" by combining a variable domain, or fragment thereof, that immunospecifically binds at least one Eph receptor with an Fc domain comprising one or more of the high effector function residues disclosed herein, or may be produced by modifying an Fc domain-containing antibody that binds an at least one Eph receptor by introducing one or more high effector function and/or other modulatory amino acid residues into the Fc domain.

The present invention also relates to novel Fc variants with a higher binding affinity to inhibitory FcγRs and a lower binding affinity to activating FcγRs (e.g., FcγRIIIA) reative to a comparable molecule (e.g., an antibody having an original unmodified Fc region). In one embodiment, said Fc variants will also exhibit a reduced ability to mediate ADCC activity compared to a comparable molecule (e.g., an antibody having an original unmodified Fc region). In another embodiment, the Fc variants of the invention are variants of an antibody that immunospecifically binds to at least one Eph receptor. In a specific embodiment, the Fc variants of the invention with a higher binding affinity to inhibitory FcγRs and a lower binding affinity to activating FcγRs immunospecifically bind least one Eph receptor and are Antagonists of at least one Eph receptor. In another specific embodiment, the Fc variants of the invention with a higher binding affinity to inhibitory FcγRs and a lower binding affinity to activating FcγRs immunospecifically bind least one Eph receptor and are Eph receptor agonists.

In addition, the present invention further provides novel Fc variants with altered binding to C1q relative to a comparable molecule (e.g., an antibody having an original unmodified Fc region). Specifically, the Fc variants of the invention may exhibit a higher binding affinity for C1q and increased CDC activity. Alternatively, the Fc variants of the invention may exhibit a lower binding affinity for C1q and reduced CDC activity. In other situations, the Fc variants of the invention with altered binding to C1q exhibit CDC activity that is unchanged relative to a comparable molecule. It is specifically contemplated that Fc variants with alterations in C1q binding and CDC activity may also exhibit alterations in binding to one or more FcγRs and/or ADCC activity. In one embodiment, the Fc variants of the invention are variants of an antibody that immunospecifically binds to at least one Eph receptor. In a specific embodiment, the Fc variants of the invention altered binding to C1q immunospecifically bind at least one Eph receptor and are antagonists of at least one Eph receptor.

In a further specific embodiment, the Fc variants of the invention altered binding to C1q immunospecifically bind at least one Eph receptor and are agonists of at least one Eph receptor.

The Fc variants of the invention may be useful to prevent, treat, or manage metastasis of tumors or the inhibition of other functions mediated or influenced by an Eph receptor, including but not limited to cell proliferation, cell attachment, cell migration, granulation tissue development, tumor growth, tumor cell invasion and/or inflammation. Although not intending to be bound by any mechanism of action, Fc variants of the invention that immunospecifically bind to at least one Eph receptor may function through a variety of mechanisms including but not limited to, targeting a cell aberrantly expressing an Eph receptor for destruction, or acting as an agonist or antagonist of one or more Eph receptor activity. Also encompassed by the invention are Fc variants that inhibit or stimulate the functional activity of at least one Eph receptor resulting in the inhibition of Eph receptor-mediated pathologies. Agonistic antibodies of EphA2 and EphA4 have been described in PCT Publication Nos. WO 04/014292, WO 03/094859 and U.S. patent application Ser. No. 10/863,729, all of which are incorporated by reference herein in their entireties.

In other embodiments, the Fc variants of the invention that immunospecifically bind an Eph receptor are used to treat, prevent and/or manage a disease or disorder associated with cell hyperproliferation, such as but not limited to cancer, asthma, chronic obstructive pulmonary disease, inflammatory diseases of the bowel, intestine, stomach, and other vital organs, restenosis (smooth muscle and/or endothelial), Crohn's disease, psoriasis, and other non-metastatic diseases. In one embodiment, the hyperproliferative cells are epithelial. In another embodiment, the hyperproliferative cells overexpress EphA4. In a further embodiment, some EphA4 is not bound to ligand, either as a result of decreased cell-cell contacts, altered subcellular localization, or increases in amount of EphA4 relative to EphA4-ligand. In yet a further embodiment, the hyperproliferative cells overexpress EphA2. In another embodiment, some EphA2 is not bound to ligand, either as a result of decreased cell-cell contacts, altered subcellular localization, or increases in amount of EphA2 relative to EphA2-ligand.

As used herein, the terms "antibody" and "antibodies" refer to monoclonal antibodies, multispecific antibodies, human antibodies, humanized antibodies, camelised antibodies, chimeric antibodies, single-chain Fvs (scFv), disulfide-linked Fvs (sdFv), Fab fragments, F(ab') fragments, and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site, these fragments may or may not be fused to another immunoglobulin domain including but not limited to, an Fc region or fragment thereof. As outlined herein, the terms "antibody" and "antibodies" specifically include the Fc variants described herein, full length antibodies and variant Fc-Fusions comprising Fc regions, or fragments thereof, comprising at least one novel amino acid residue described herein fused to an immunologically active fragment of an immunoglobulin or to other proteins as described herein. Such variant Fc fusions include but are not limited to, scFv-Fc fusions, variable region (e.g., VL and VH)-Fc fusions, scFv-scFv-Fc fusions. Immunoglobulin molecules can be of any type (e.g., IgG, IgE, IgM, IgD, IgA and IgY), class (e.g., IgG1, IgG2, IgG3, IgG4, IgA1 and IgA2) or subclass.

As used herein, the term "Eph receptor(s)" encompasses a family of polypeptides comprising proteins that are defined by a certain degree of homology to the known Eph receptor tyrosine kinases (RTKs). Eph receptors include, but are not limited to EphA1 (also known as ephrin type-A receptor 1, erythropoietin-producing hepatoma amplified sequence and exemplified by GenBank Acc. No. NP_005223.2), EphA2 (also known as epithelial cell receptor protein tyrosine kinase and exemplified by GenBank Acc. No. NP_004422.2), EphA3 (also known as human embryo kinase 1, eph-like tyrosine kinase 1, TYRO4 protein tyrosine kinase and exemplified by GenBank Acc. Nos. NP_005224.2 and NP_872585.1, isoforms 3a and 3b respectively), EphA4 (also known as ephrin type-A receptor 4, TYRO1 protein tyrosine kinase, tyrosine-protein kinase receptor SEK, receptor protein-tyrosine kinase HEK8 and exemplified by GenBank Acc. No. NP_004429.1), EphA5 (also known as Eph homology kinase-1, ephrin type-A receptor 5, receptor protein-tyrosine kinase HEK7, tyrosine-protein kinase receptor EHK-1 and exemplified by GenBank Acc. Nos. NP_004430.2 and NP_872272 isoforms 5a and 5b respectively), EphA6 (exemplified by GenBank Acc. No. XP_114973.4), EphA7 (also known as Eph homology kinase-3, ephrin type-A receptor 7, receptor protein-tyrosine kinase HEK11, tyrosine-protein kinase receptor EHK-3 and exemplified by GenBank Acc. No. NP_004431.1), EphA8 (also known as tyrosylprotein kinase, protein-tyrosine kinase, hydroxyaryl-protein kinase, ephrin type-A receptor 8 precursor, eph- and elk-related tyrosine kinase, tyrosine-protein kinase receptor eek and exemplified by GenBank Acc. No. NP_065387.1), EphB1 (also known as eph tyrosine kinase 2 and exemplified by GenBank Acc. No. NP_004432.1), EphB2 (also known as eph tyrosine kinase 3, elk-related tyrosine kinase, developmentally-regulated eph-related tyrosine kinase and exemplified by GenBank Acc. Nos. NP_059145.1 and NP_004433.2 isoforms 2a and 2b respectively), EphB3 (also known as human embryo kinase 2, EPH-like tyrosine kinase-2 and exemplified by GenBank Acc. No. NP_004434.2), EphB4 (also known as hepatoma transmembrane kinase and exemplified by GenBank Acc. No. NP_004435.3) and B6 (exemplified by GenBank Acc. No. NM_004445.1). An alignment of several Eph receptor polypeptides contemplated by the present invention is shown in FIG. 18.

As used herein, the term "immunospecifically binds to an Eph receptor" and analogous terms refer to peptides, polypeptides, proteins, fusion proteins and antibodies or fragments thereof that specifically bind to at least one Eph receptor or a fragment thereof. A peptide, polypeptide, protein, or antibody that immunospecifically binds to at least one Eph receptor or a fragment thereof may bind to other peptides, polypeptides, or proteins with lower affinity as determined by, e.g., immunoassays, BIAcore, or other assays known in the art. Antibodies or fragments that immunospecifically bind to at least one Eph receptor or a fragment thereof may be cross-reactive with related antigens. Preferably, antibodies or fragments that immunospecifically bind to at least one Eph receptor or a fragment thereof preferentially bind to at least one Eph receptor over other antigens. However, the present invention specifically encompasses antibodies with multiple specificities (e.g., an antibody with specificity for two or more discrete antigens (reviewed in Cao et al., 2003, Adv Drug Deliv Rev 55:171; Hudson et al., 2003, Nat Med 1:129)) in the definition of an antibody that "immunospecifically binds to an Eph receptor." For example, bispecific antibodies contain two different binding specificities fused together. In the simplest case a bispecific antibody would bind to two adjacent epitopes on a single target antigen, such an antibody would not cross-react with other antigens (as described supra). Alternatively, bispecific antibodies can bind to two different antigens. Such an antibody immunospecifically binds to two different molecules, but not to other unrelated molecules. Another class of multispecific antibodies may recognize a shared subunit of multi-subunit complexes in the context of one or more specific complexes. In addition, an antibody that immunospecifically binds an Eph receptor may cross-react with related Eph receptors or RTKs.

Antibodies or fragments that immunospecifically bind to an Eph receptor or a fragment thereof can be identified, for example, by immunoassays, BIAcore, or other techniques known to those of skill in the art. An antibody or fragment thereof binds specifically to an Eph receptor or a fragment thereof when it binds to an Eph receptor or a fragment thereof with higher affinity than to any cross-reactive antigen as determined using experimental techniques, such as radioimmunoassays (RIA) and enzyme-linked immunosorbent assays (ELISAs). See, e.g., Paul, ed., 1989, Fundamental Immunology Second Edition, Raven Press, New York at pages 332-336 for a discussion regarding antibody specificity.

Without wishing to be bound by any particular theory, the amino acid substitutions of the invention alter the affinity of an antibody for its FcγRs and/or the complement protein C1q by modulating one or more of the factors that regulate protein-protein interactions (e.g., receptor-ligand and antibody-antigen interactions). Such factors include but are not limited to, factors affecting protein folding or three dimensional configuration such as hydrogen bonds, hydrophobic interactions, ionic interactions, Von der Waals forces and/or disulfide bonds as well as factors affecting allosteric interactions, solubility and covalent modifications.

Without wishing to be bound by any particular theory, the amino acid substitutions of the invention modulate the ADCC and/or CDC activity of an antibody by altering one more of the factors that influence downstream effector function including but not limited to, the affinity of the antibody for its FcγRs and/or to C1q, ability to mediate cytotoxic effector and/or complement cascade functions, protein stability, antibody half life and recruitment of effector cells and/or molecules.

It will be understood that Fc region (also referred to herein as "Fc" and "Fc polypeptide") as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. Note: Polymorphisms have been observed at a number of Fc positions, including but not limited to Kabat 270, 272, 312, 315, 356, and 358, and thus slight differences between the presented sequence and sequences in the prior art may exist.

It will be understood that the complementarity determining regions (CDRs) residue numbers referred to herein are those of Kabat et al. (1991, NIH Publication 91-3242, National Technical Information Service, Springfield, Va.). Specifically, residues 24-34 (CDR1), 50-56 (CDR2) and 89-97 (CDR3) in the light chain variable domain and 31-35 (CDR1), 50-65 (CDR2) and 95-102 (CDR3) in the heavy chain variable domain. Note that CDRs vary considerably from antibody to antibody (and by definition will not exhibit homology with the Kabat consensus sequences). Maximal alignment of framework residues frequently requires the insertion of "spacer" residues in the numbering system, to be used for the Fv region. It will be understood that the CDRs referred to herein are those of Kabat et al. supra. In addition, the identity of certain individual residues at any given Kabat site number may vary from antibody chain to antibody chain due to interspecies or allelic divergence.

In one embodiment, Fc variants of the invention will have at least one amino acid substitution of the Fc region wherein said antibody variant has a modified binding affinity for its FcγRs and/or for C1q relative to a comparable molecule (e.g., the original antibody without said substitution).

In a specific embodiment, Fc variants comprise an Fc region comprising at least one high effector function amino acid reside selected from the group consisting of: 234E, 235R, 235A, 235W, 235P, 235V, 235Y, 236E, 239D, 265L, 269S, 269G, 298I, 298T, 298F, 327N, 327G, 327W, 328S, 328V, 329H, 329Q, 330K, 330V, 330G, 330Y, 330T, 330L, 330I, 330R, 330C, 332E, 332H, 332S, 332W, 332F, 332D, and 332Y, wherein the numbering system is that of the EU index as set forth in Kabat. Contemplated high effector function amino acid residues of the invention are also set forth in Table 1.

In another embodiment, the Fc variants comprise an Fc region comprising at least 2, or at least 3, or at least 4, or at least 5, or at least 6, or at least 10, or at least 20, or at least 30, or at least 40, or at least 50, or at least 60, or at least 70, or at least 80, or at least 90, or at least 100, or at least 200 high effector function amino acid residues.

In another specific embodiment, Fc variants of the invention comprise an Fc region comprising at least one high effector function amino acid residue selected from the group consisting of: 239D, 330K, 330V, 330G, 330Y, 330T, 330L, 330I, 330R, 330C, 332E, 332H, 332S, 332W, 332F, 332D, and 332Y, wherein the numbering system is that of the EU index as set forth in Kabat.

In still another specific embodiment, Fc variants of the invention comprise an Fc region comprising at least one high effector function amino acid residue selected from the group consisting of: 239D, 330L and 332E. In one embodiment, Fc variants of the invention comprise an Fc region comprising at least the high effector function amino acid residue 332E. In a specific embodiment, Fc variants of the invention comprise an Fc region comprising the high effector function amino acid residues 239D, 330L and 332E.

In a specific embodiment, Fc variants will have one or more amino acid substitutions at positions selected from the group consisting of: 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 239, 242, 246, 250, 251, 257, 259, 260, 261, 265, 269, 273, 274, 275, 277, 281, 282, 284, 287, 291, 298, 300, 302, 304, 306, 308, 310, 314, 316, 318, 319, 321, 323, 327, 328, 329, 330, 332 and 336, of the Fc region wherein the numbering of the residues in the Fc region is that of the EU index as set forth in Kabat.

In another specific embodiment, the Fc variants comprise at least one substitution selected from the group consisting of: L234E, L235R, L235A, L235W, L235P, L235V, L235Y, G236E, S239D, D265L, E269S, E269C; S298I, S298T, S298F, A327N, A327G, A327W, L328S, L328V, P329H, P329Q, A330K, A330V, A330G, A330Y, A330T, A330L, A330I, A330R, A330C, I332E, I332H, I332S, I332W, I332F, I332D, and I332Y, wherein the numbering system is that of the EU index as set forth in Kabat. Specific amino acid substitutions of the invention are also set forth in Table 1.

In another embodiment, the Fc variants comprise at least at least 2, or at least 3, or at least 4, or at least 5, or at least 6, or at least 10, or at least 20, or at least 30, or at least 40, or at least 50, or at least 60, or at least 70, or at least 80, or at least 90, or at least 100, or at least 200 amino acid substitutions of the Fc region.

TABLE 1

Preferred Amino Acid Residues with High Effector Function (HEF)

| Position[a] | Amino Acid[b] | HEF Residue(s)[c] |
|---|---|---|
| 234 | L | E |
| 235 | L | R, A, W, P, V, Y |
| 236 | G | E |
| 239 | S | D |
| 265 | D | L |
| 269 | E | S, G |
| 298 | S | I, T, F |
| 327 | A | N, G, W |
| 328 | L | S, V |
| 329 | P | H, Q |
| 330 | A | K, V, G, Y, T, L, I, R, C |
| 332 | I | E, H, S, W, F, Y, D |

[a]heavy chain position number and amino acid residue
[b]amino acid residue present in naturally occurring antibody
[c]residues that can be engineered into corresponding position to generate an Fc region with high effector function.

In one embodiment, the Fc variants comprise at least one substitution selected from the group consisting of S239D, A330L and I332E. In another embodiment, the Fc variants comprise at least each of the following substitutions, S239D, A330L and I332E. In a further embodiment, the Fc variants of the invention have at least the high effector amino acid 332E.

It is specifically contemplated that conservative amino acid substitutions may be made for said amino acid substitutions in the Fc of the antibody of interest, described supra (see Table 1). It is well known in the art that "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 2.

TABLE 2

Families of Conservative Amino Acid Substitutions

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |

TABLE 2-continued

Families of Conservative Amino Acid Substitutions

| Family | Amino Acids |
|---|---|
| aromatic | Trp, Tyr, Phe, His |

The term "conservative amino acid substitution" also refers to the use of amino acid analogs or variants. Guidance concerning how to make phenotypically silent amino acid substitutions is provided in Bowie et al., "Deciphering the Message in Protein Sequences: Tolerance to Amino Acid Substitutions," (1990, Science 247:1306-1310).

In another embodiment, the Fc variants have at least the high effector amino acid 332D.

One skilled in the art will understand that that the Fc variants of the invention may have altered FcγR and/or C1q binding properties (examples of binding properties include but are not limited to, binding specificity, equilibrium dissociation constant ($K_D$), dissociation and association rates (Koff and Kon respectively), binding affinity and/or avidity) and that certain alterations are more or less desirable. It is well known in the art that the equilibrium dissociation constant ($K_D$) is defined as $k_{off}/k_{on}$. It is generally understood that a binding molecule (e.g., and antibody) with a low $K_D$ is preferable to a binding molecule (e.g., and antibody) with a high $K_D$. However, in some instances the value of the $k_{on}$ or $k_{off}$ may be more relevant than the value of the $K_D$. One skilled in the art can determine which kinetic parameter is most important for a given antibody application. For example a modification that enhances Fc binding to one or more positive regulators (e.g., FcγRIIIA) while leaving unchanged or even reducing Fc binding to the negative regulator FcγRIIB would be more preferable for enhancing ADCC activity. Alternatively, a modification that reduced binding to one or more positive regulator and/or enhanced binding to FcγRIIB would be preferable for reducing ADCC activity. Accordingly, the ratio of binding affinities (e.g., equilibrium dissociation constants ($K_D$)) can indicate if the ADCC activity of an Fc variant is enhanced or decreased. For example a decrease in the ratio of FcγRIIIA/FcγRIIB equilibrium dissociation constants ($K_D$), will correlate with improved ADCC activity, while an increase in the ratio will correlate with a decrease in ADCC activity. Additionally, modifications that enhanced binding to C1q would be preferable for enhancing CDC activity while modification that reduced binding to C1q would be preferable for reducing or eliminating CDC activity.

The binding affinities and properties of an Fc domain for its ligand, may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA; see Example 3 or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In one embodiment, the Fc variants of the invention bind FcγRIIIA with increased affinity relative to a comparable molecule. In another embodiment, the Fc variants of the invention bind FcγRIIIA with increased affinity and bind FcγRIIB with a binding affinity that is unchanged when relative to a comparable molecule. In still another embodiment, the Fc variants of the invention bind FcγRIIIA with increased affinity and bind FcγRIIB with a decreased affinity relative to a comparable molecule. In yet another embodiment, the Fc variants of the invention have a ratio of FcγRIIIA/FcγRIIB equilibrium dissociation constants ($K_D$) that is decreased relative to a comparable molecule.

In a preferred embodiment, the Fc variants of the invention bind FcγRIIIA with increased affinity and bind FcγRIIB with a decreased affinity when relative to a comparable molecule and immunospecifically bind an Eph receptor.

In one embodiment, said Fc variants bind with increased affinity to FcγRIIIA. In another embodiment said Fc variants have affinity for FcγRIIIA that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In a further embodiment said Fc variants have affinity for FcγRIIIA that is at least about 2 fold, or at least about 3 fold, or at least about 5 fold, or at least about 7 fold, or a least about 10 fold, or at least about 20 fold, or at least about 30 fold, or at least about 40 fold, or at least about 50 fold, or at least about 60 fold, or at least about 70 fold, or at least about 80 fold, or at least about 90 fold, or at least about 100 fold, or at least about 200 fold greater than that of a comparable molecule.

In another embodiment, an Fc variant of the invention has an equilibrium dissociation constant ($K_D$) that is decreased between about 2 fold and about 10 fold, or between about 5 fold and about 50 fold, or between about 25 fold and about 250 fold, or between about 100 fold and about 500 fold, or between about 250 fold and about 1000 fold relative to a comparable molecule. In a further embodiment, an Fc variant of the invention has an equilibrium dissociation constant ($K_D$) that is decreased between 2 fold and 10 fold, or between 5 fold and 50 fold, or between 25 fold and 250 fold, or between 100 fold and 500 fold, or between 250 fold and 1000 fold relative to a comparable molecule. In a specific embodiment, said Fc variants have an equilibrium dissociation constants ($K_D$) for FcγRIIIA that is reduced by at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold, or at least 400 fold, or at least 600 fold, relative to a comparable molecule. In a further specific embodiment, said Fc variants have an equilibrium dissociation constants ($K_D$) for FcγRIIIA that is reduced by at least about 2 fold, or at least about 3 fold, or at least about 5 fold, or at least about 7 fold, or a least about 10 fold, or at least about 20 fold, or at least about 30 fold, or at least about 40 fold, or at least about 50 fold, or at least about 60 fold, or at least about 70 fold, or at least about 80 fold, or at least about 90 fold, or at least about 100 fold, or at least about 200 fold, or at least about 400 fold, or at least about 600 fold, relative to a comparable molecule.

In one embodiment, said Fc variant binds to FcγRIIB with an affinity that is unchanged or reduced. In another embodiment said Fc variants have affinity for FcγRIIB that is unchanged or reduced by at least 1 fold, or by at least 3 fold, or by at least 5 fold or by at least 10 fold or by at least 20 fold, or by at least 50 fold relative to a comparable molecule. In a further embodiment said Fc variants have affinity for FcγRIIB that is unchanged or reduced by at least about 1 fold, or by at least about 3 fold, or by at least about 5 fold or by at least about 10 fold or by at least about 20 fold, or by at least about 50 fold relative to a comparable molecule.

In another embodiment, said Fc variants have an equilibrium dissociation constants ($K_D$) for FcγRIIB that is unchanged or increased by at least at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold relative to a comparable molecule. In a further embodiment, said Fc variants have an equilibrium dissociation constants ($K_D$) for FcγRIIB that is unchanged or increased by at least at least about 2 fold, or at least about 3 fold, or at least about 5 fold, or at least about 7 fold, or a least about 10 fold, or at least about 20 fold, or at least about 30 fold, or at least about 40 fold, or at least about 50 fold, or at least about 60 fold, or at least about 70 fold, or at least about 80 fold, or at least about 90 fold, or at least about 100 fold, or at least about 200 fold relative to a comparable molecule.

In another embodiment, the Fc variants of the invention bind FcγRIIIA with decreased affinity and bind FcγRIIB with increased affinity when compared to the original antibodies without the substituted Fc. In one embodiment, said Fc variants have affinity for FcγRIIIA that is reduced by at least 1 fold, or by at least 3 fold, or by at least 5 fold or by at least 10 or by at least 20 fold, or by at least 50 fold when compared to that of the original antibody without the substituted Fc. In another embodiment, said Fc variants have affinity for FcγRIIIA that is reduced by at least about 1 fold, or by at least about 3 fold, or by at least about 5 fold or by at least about 10 or by at least about 20 fold, or by at least about 50 fold when compared to that of the original antibody without the substituted Fc. In a further embodiment, said Fc variants have affinity for FcγRIIB that is at least 2 fold, or at least 3 fold, or at least 5 fold, or at least 7 fold, or a least 10 fold, or at least 20 fold, or at least 50 fold or at least 100 fold, greater than that of a comparable molecule. In yet a further embodiment, said Fc variants have affinity for FcγRIIB that is at least about 2 fold, or at least about 3 fold, or at least about 5 fold, or at least about 7 fold, or a least about 10 fold, or at least about 20 fold, or at least about 50 fold or at least about 100 fold, greater than that of a comparable molecule.

In still another embodiment, the Fc variants have an equilibrium dissociation constants ($K_D$) for FcγRIIIA that are increased by at least 1 fold, or by at least 3 fold, or by at least 5 fold or by at least 10 fold or by at least 20 fold, or by at least 50 fold when compared to that of the original antibody without the substituted Fc. In a further embodiment, the Fc variants have an equilibrium dissociation constants ($K_D$) for FcγRIIIA that are increased by at least about 1 fold, or by at least about 3 fold, or by at least about 5 fold or by at least about 10 fold or by at least about 20 fold, or by at least about 50 fold when compared to that of the original antibody without the substituted Fc. In another embodiment said Fc variants have equilibrium dissociation constants ($K_D$) for FcγRIIB that are decreased at least 2 fold, or at least 3 fold, or at least 5 fold, or at least 7 fold, or a least 10 fold, or at least 20 fold, or at least 50 fold or at least 100 fold, relative to a comparable molecule. In a further embodiment said Fc variants have equilibrium dissociation constants ($K_D$) for FcγRIIB that are decreased at least about 2 fold, or at least about 3 fold, or at least about 5 fold, or at least about 7 fold, or a least about 10 fold, or at least about 20 fold, or at least about 50 fold or at least about 100 fold, relative to a comparable molecule.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement.

The ability of any particular antibody to mediate lysis of the target cell by ADCC can be assayed. To assess ADCC activity an antibody of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985, 79:277; Bruggemann et al., 1987, J Exp Med 166:1351; Wilkinson et al., 2001, J Immunol Methods 258:183; Patel et al., 1995 J Immunol Methods 184:29 (each of which is incorporated by reference) and herein (see example 3). Alternatively, or additionally, ADCC activity of the antibody of interest may be assessed in vivo, e.g., in a animal model such as that disclosed in Clynes et al., 1998, PNAS USA 95:652 (incorporated by reference).

In one embodiment, the Fc variants of the invention are also characterized by in vitro functional assays for determining one or more FcγR mediator effector cell functions (See Example 3). In another embodiment, the molecules of the invention have similar binding properties and effector cell functions in in vivo models (such as those described and disclosed herein) as those in in vitro based assays. However, the present invention does not exclude molecules of the invention that do not exhibit the desired phenotype in in vitro based assays but do exhibit the desired phenotype in vivo.

The present invention further provides Fc variants with enhanced ADCC function. In one embodiment, the Fc variants of the invention have increased ADCC activity. In one embodiment said Fc variants have ADCC activity that is at least 2 fold, or at least 3 fold, or at least 5 fold or at least 10 fold or at least 50 fold or at least 100 fold greater than that of a comparable molecule. In another embodiment said Fc variants have ADCC activity that is at least about 2 fold, or at least about 3 fold, or at least about 5 fold or at least about 10 fold or at least about 50 fold or at least about 100 fold greater than that of a comparable molecule. In a specific embodiment, Fc variants of the invention bind FcγRIIIA with increased affinity, bind FcγRIIB with decreased affinity and have enhanced ADCC activity relative to a comparable molecule.

In a further embodiment, the Fc variants of the invention have enhanced ADCC activity and immunospecifically bind to at least one Eph receptor. In another embodiment are Fc variants of the invention have enhanced ADCC activity and have a ratio of FcγRIIIA/FcγRIIB equilibrium dissociation constants ($K_D$) that is decreased relative to a comparable molecule and immunospecifically bind to at least one Eph receptor. In still another embodiment, the Fc variants of the invention have enhanced ADCC activity, bind activating FcγRs (e.g., FcγRIIIA) with higher affinity and bind inhibitory FcγRs (e.g., FcγRIIB) with unchanged or lower affinity and immunospecifically bind to at least one Eph receptor.

The present invention also provides Fc variants with reduced ADCC function. In one embodiment, the Fc variants of the invention have reduced ADCC activity. In another embodiment, said Fc variants have ADCC activity that is at least 2 fold, or at least 3 fold, or at least 5 fold or at least 10 fold or at least 50 fold or at least 100 fold less than that of a comparable molecule. In a further embodiment, said Fc variants have ADCC activity that is at least about 2 fold, or at least about 3 fold, or at least about 5 fold or at least about 10 fold or at least about 50 fold or at least about 100 fold less than that of a comparable molecule. In a specific embodiment, Fc variants of the invention bind FcγRIIIA with decreased affinity, bind FcγRIIB with increased affinity and have reduced ADCC activity.

In one embodiment, the Fc variants of the invention have reduced ADCC activity and immunospecifically bind to at least one Eph receptor. In another embodiment, the antibody variants of the invention have reduced ADCC activity, bind activating FcγRs (e.g., FcγRIIIA) with lower affinity, bind inhibitory FcγRs (e.g., FcγRIIB) with higher affinity and immunospecifically bind to at least one Eph receptor.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, J. Immunol. Methods, 202:163, may be performed.

The present invention further provides Fc variants with enhanced CDC function. In one embodiment, the Fc variants of the invention have increased CDC activity. In another embodiment, said Fc variants have CDC activity that is at least 2 fold, or at least 3 fold, or at least 5 fold or at least 10 fold or at least 50 fold or at least 100 fold greater than that of a comparable molecule. In a further embodiment, said Fc variants have CDC activity that is at least about 2 fold, or at least about 3 fold, or at least about 5 fold or at least about 10 fold or at least about 50 fold or at least about 100 fold greater than that of a comparable molecule. In another embodiment, an Fc variant of the invention binds C1q with an affinity that is at least 2 fold, or at least 3 fold, or at least 5 fold, or at least 7 fold, or a least 10 fold, or at least 20 fold, or at least 50 fold or at least 100 fold, greater than that of a comparable molecule. In a further embodiment, an Fc variant of the invention binds C1q with an affinity that is at least about 2 fold, or at least about 3 fold, or at least about 5 fold, or at least about 7 fold, or a least about 10 fold, or at least about 20 fold, or at least about 50 fold or at least about 100 fold, greater than that of a comparable molecule. In a specific embodiment, Fc variants of the invention bind C1q with increased affinity; have enhanced CDC activity and immunospecifically bind to at least one Eph receptor.

The present invention also provides Fc variants with reduced CDC function. In one embodiment, the Fc variants of the invention have reduced CDC activity. In another embodiment, said Fc variants have CDC activity that is at least 2 fold, or at least 3 fold, or at least 5 fold or at least 10 fold or at least 50 fold or at least 100 fold less than that of a comparable molecule. In a further embodiment, said Fc variants have CDC activity that is at least about 2 fold, or at least about 3 fold, or at least about 5 fold or at least about 10 fold or at least about 50 fold or at least about 100 fold less than that of a comparable molecule. In another embodiment, an Fc variant of the invention binds C1q with an affinity that is reduced by at least 1 fold, or by at least 3 fold, or by at least 5 fold or by at least 10 or by at least 20 fold, or by at least 50 fold relative to a comparable molecule. In another embodiment, an Fc variant of the invention binds C1q with an affinity that is reduced by at least about 1 fold, or by at least about 3 fold, or by at least about 5 fold or by at least about 10 or by at least about 20 fold, or by at least about 50 fold relative to a comparable molecule. In a specific embodiment, Fc variants of the invention bind to at least one Eph receptor, binds C1q with decreased affinity have reduced CDC activity and immunospecifically bind to at least one Eph receptor It is also specifically contemplated that the Fc variants of the invention may contain inter alia one or more additional amino acid residue substitutions, mutations and/or modifications which result in an antibody with preferred characteristics including but not limited to: increased serum half life, increase binding affinity, reduced immunogenicity, increased production, altered Fc ligand binding, enhanced or reduced ADCC or CDC activity, altered glycosylation and/or disulfide bonds and modified binding specificity (for examples see infra). The invention encompasses combining an Fc variant of the invention with other Fc modifications to provide additive, synergistic, or novel properties in antibodies or Fc fusions. In one embodiment, the other Fc modifications enhance the phenotype of the Fc variant with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In one embodiment, the Fc variants of the present invention may be combined with other known Fc variants such as those disclosed in Ghetie et al., 1997, *Nat Biotech.* 15:637-40; Duncan et al, 1988, *Nature* 332:563-564; Lund et al., 1991, *J. Immunol* 147:2657-2662; Lund et al, 1992, *Mol Immunol* 29:53-59; Alegre et al, 1994, *Transplantation* 57:1537-1543; Hutchins et al., 1995, *Proc Natl. Acad Sci USA* 92:11980-11984; Jefferis et al, 1995, *Immunol Lett.* 44:111-117; Lund et al., 1995, *Faseb J* 9:115-119; Jefferis et al, 1996, *Immunol Lett* 54:101-104; Lund et al, 1996, *J Immunol* 157:4963-4969; Armour et al., 1999, *Eur J Immunol* 29:2613-2624; Idusogie et al, 2000, *J Immunol* 164:4178-4184; Reddy et al, 2000, *J Immunol* 164:1925-1933; Xu et al., 2000, *Cell Immunol* 200:16-26; Idusogie et al, 2001, *J Immunol* 166:2571-2575; Shields et al., 2001, *J Biol Chem* 276:6591-6604; Jefferis et al, 2002, *Immunol Lett* 82:57-65; Presta et al., 2002, *Biochem Soc Trans* 30:487-490); U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; U.S. patent application Ser. Nos. 10/370,749 and PCT Publications WO 94/2935; WO 99/58572; WO 00/42072; WO 02/060919, WO 04/029207, each of which is incorporated herein by reference in its entirety.

In some embodiments, the Fc variants of the present invention comprises one or more engineered glycoforms, i.e., a carbohydrate composition that is covalently attached to a molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, *Nat. Biotechnol* 17:176-180; Davies et al., 20017 *Biotechnol Bioeng* 74:288-294; Shields et al, 2002, *J Biol Chem* 277:26733-26740; Shinkawa et al., 2003, *J Biol Chem* 278: 3466-3473) U.S. Pat. No. 6,602,684; U.S. Ser. No. 10/277, 370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland); each of which is incorporated herein by reference in its entirety. See, e.g., WO 00061739; EA01229125; US 20030115614; Okazaki et al., 2004, *JMB,* 336: 1239-49 each of which is incorporated herein by reference in its entirety. Additional methods are described in section 6.2 entitled "Antibodies of the Invention" below.

The receptor tyrosine kinases (RTKs) are transmembrane molecules which transduce signals from the extracellular environment into the cytoplasm. The Eph family of RTKs is the largest subfamily of RTKs. This group is distinguished by a cysteine-rich region and two fibronectin type III repeats in the extracellular domain. The Eph receptors are activated by a second family of cell surface-anchored proteins, the ephrins. Members of both the Eph tyrosine kinases and the ephrin ligands mediate signaling after receptor-ligand interaction (Bruckner et al., 1997, Science 275:1640; Holland et al., 1996, Nature 383:722). This bi-directional signaling are known to affect processes involving cellular interaction, like cell adhesion, cell migration and tissue border formation (Boyd et al., 2001 Sci STKE RE20; Schmucher et al., 2001, Cell 105:7014; Kullander et al., 2002 Nat. Rev. Mol. Cell Biol. 3:475). More recently, the Eph receptors have been linked to the development and progression of cancers. As cell surface molecules the Eph receptors are readily accessible target molecules for antibody directed therapies. In one embodiment, the Fc variants of the invention are variants of an antibody that immunospecifically binds to at least one Eph receptor. Eph receptors to which the Fc variant of the invention immunospecifically binds to include but are not limited to EphA1, EphA2, EphA3a, EphA3b, EphA4, EphA5a, EphA5b, EphA6, EphA7, EphA8, EphB1, EphB2a, EphB2b, EphB3, EphB4 and EphB6.

The skilled artisan will appreciate that an Eph receptor of the invention is a molecule that exhibits a substantial degree of homology to known Eph receptors (see, e.g., supra), such that it has been or can be classified as an Eph receptor family molecule based upon, its amino acid sequence. Pairwise comparisons of the known human Eph receptors were performed using the MegaAlign program (DNASTAR) with the Clustal W algorithm (Thompson et al., 1994 Nucleic Acids Res 22:4673-80). The results (FIG. 18) show that there are multiple regions each protein that share a high degree of similarity among the Eph receptor family members. It is specifically contemplated that one skilled in the art could generate antibodies to regions of an Eph receptor that would allow for cross reactivity of said antibody between family members or a more restricted specificity such that said antibody immunospecifically bound only one family member with high affinity. To identify potential immunogenic peptides for use in generating antibodies that could be either protein specific or would bind with one or more Eph receptors, the antigenic index of each protein can be examined using the Protean program (DNASTAR) with the Jameson-Wolf algorithm. The regions with the highest antigenic indices among all members of the Eph receptor family can be identified and those regions which are highly conserved among one or more family members and would be excellent candidates for raising an antibody which recognizes more then one family member. While the use of less conserved regions would likely generate an antibody specific for one Eph receptor family member.

In one embodiment, the Fc variants of the invention preferentially bind to an Eph receptor present on a tumor cell and do not bind to an Eph receptor present on a non-tumor cell. In another embodiment, the Fc variants of the invention do not stain normal tissues including but not limited to, brain, lung, pancreas, liver, prostate, heart, ovary, skin, kidney, intestine and stomach. Antibody binding and specific staining patterns can be readily determined by immunological labeling methods well known in the art including but not limited to, immunohistochemistry and Fluorescence Activated Cell Scanning/Sorting (FACS). Specific methods and protocols are found in Polak and Van Noorden (1997) *Introduction to Immunocytochemistry,* second edition, Springer Verlag, N.Y. and in Haugland (2004) *Handbook of Fluorescent Probes and Research Chemicals,* ninth edition, a combined handbook and catalogue Published by Molecular Probes, Inc., Eugene, Oreg. among others.

In another embodiment, the Fc variants of the invention are variants of antibodies that immunospecifically bind EphA2 and/or EphA4, their derivatives, analogs and epitope-binding fragments thereof, such as but not limited to, those disclosed herein and in PCT Publication Nos. WO 04/014292, WO 03/094859 and U.S. patent application Ser. No. 10/863,729, each of which is incorporated herein by reference in its entirety and any of the antibodies listed in Table 4. In a specific embodiment, the Fc variants of the invention are antibodies that immunospecifically bind EphA2 and/or EphA4 which comprise all or a portion of the variable region (e.g., one or more CDR) from 12G3H11, and/or 3F2 and/or any of the antibodies listed in Table 4.

The present invention further encompasses the use of Fc variants of the invention that have a high binding affinity for at least on Eph receptor. In a specific embodiment, an Fc variant of the invention that immunospecifically binds to at least one Eph receptor has an association rate constant or $k_{on}$ rate (Fc variant (Ab)+antigen $(Ag) \overset{k_{on}}{\leftarrow}$ Ab-Ag) of at least $10^5 M^{-1}s^{-1}$, at least $5\times10^5 M^{-1}s^{-1}$, at least $10^6 M^{-1}s^{-1}$, at least $5\times10^6 M^{-1}s^{-1}$, at least $10^7 M^{-1}s^{-1}$, at least $5\times10^7 M^{-1}s^{-1}$, or at least $10^8 M^{-1}s^{-1}$. In a further specific embodiment, an Fc variant of the invention that immunospecifically binds to at least one Eph receptor has an association rate constant or $k_{on}$ rate (Fc variant (Ab)+antigen $(Ag) \overset{k_{on}}{\leftarrow}$ Ab-Ag) of at least about $10^5 M^{-1}s^{-1}$, at least about $5\times10^5 M^{-1}s^{-1}$, at least about $10^6 M^{-1}s^{-1}$, at least about $5\times10^6 M^{-1}s^{-1}$, at least about $10^7 M^{-1}s^{-1}$, at least about $5\times10^7 M^{-1}s^{-1}$, or at least about $10^8 M^{-1}s^{-1}$. In another embodiment, an Fc variant that immunospecifically binds to at least one Eph receptor has a $k_{on}$ of at least $2\times10^5 M^{-1}s^{-1}$, at least $5\times10^5 M^{-1}s^{-1}$, at least $10^6 M^{-1}s^{-1}$, at least $5\times10^6 M^{-1}s^{-1}$, at least $10^7 M^{-1}s^{-1}$, at least $5\times10^7 M^{-1}s^{-1}$, or at least $10^8 M^{-1}s^{-1}$. In a further embodiment, an Fc variant that immunospecifically binds to at least one Eph receptor has a $k_{on}$ of at least about $2\times10^5 M^{-1}s^{-1}$, at least about $5\times10^5 M^{-1}s^{-1}$, at least about $10^6 M^{-1}s^{-1}$, at least about $5\times10^6 M^{-1}s^{-1}$, at least about $10^7 M^{-1}s^{-1}$, at least about $5\times10^7 M^{-1}s^{-1}$, or at least about $10^8 M^{-1}s^{-1}$.

In another embodiment, an Fc variant of the invention that immunospecifically binds to least on Eph receptor has a $k_{off}$ rate (Fc variant (Ab)+antigen $(Ag) \overset{k_{off}}{\leftarrow}$ Ab-Ag) of less than $10^{-1}s^{-1}$, less than $5\times10^{-1}s^{-1}$, less than $10^{-2}s^{-1}$, less than $5\times10^{-2}s^{-1}$, less than $10^{-3}s^{-1}$, less than $5\times10^{-3}s^{-1}$, less than $10^{-4}s^{-1}$, less than $5\times10^{-4}s^{-1}$, less than $10^{-5}s^{-1}$, less than $5\times10^{-5}s^{-1}$, less than $10^{-6}s^{-1}$, less than $5\times10^{-6}s^{-1}$, less than $10^{-7}s^{-1}$, less than $5\times10^{-7}s^{-1}$, less than $10^{-8}s^{-1}$, less than $5\times10^{-8}s^{-1}$, less than $10^{-9}s^{-1}$, or less than $5\times10^{-9}s^{-1}$, or less than $10^{-10-1}s^{-1}$. In still another embodiment, an Fc variant of the invention that immunospecifically binds to least on Eph receptor has a $k_{off}$ rate (Fc variant (Ab)+antigen (Ag) $k_{off}\leftarrow$Ab-Ag) of less than about $10^{-1}s^{-1}$, less than about $5\times10^{-1}s^{-1}$, less than about $10^{-2}s^{-1}$, less than about $5\times10^{-2}s^{-1}$, less than about $10^{-3}s^{-1}$, less than about $5\times10^{-3}s^{-1}$, less than about $10^{-4}s^{-1}$, less than about $5\times10^{-4}s^{-1}$, less than about $10^{-5}s^{-1}$, less than about $5\times10^{-5}s^{-1}$, less than about $10^{-6}s^{-1}$, less than about $5\times10^{-6}s^{-1}$, less than about $10^{-7}s^{-1}$, less than about $5\times10^{-7}s^{-1}$, less than about $10^{-8}s^{-1}$, less than about $5\times10^{-8}s^{-1}$, less than about $10^{-9}s^{-1}$, less than about $5\times10^{-9}s^{-1}$, or less than about $10^{-10-1}s^{-1}$. In a further embodiment, an Fc variant that immunospecifically binds to least on Eph receptor has a $k_{off}$ of less than $5\times10^{-4}s^{-1}$, less than $10^{-5}s^{-1}$, less than $5\times10^{-5}s^{-1}$, less than $10^{-6}s^{-1}$, less than $5\times10^{-6}s^{-1}$, less than $10^{-7}s^{-1}$, less than $5\times10^{-7}s^{-1}$, less than $10^{-8}s^{-1}$, less than $5\times10^{-8}s^{-1}$, less than $10^{-9}s^{-1}$, less than $5\times10^{-9}s^{-1}$, or less than $10^{-10}s^{-1}$. In another embodiment, an Fc variant that immunospecifically binds to least on Eph receptor has a $k_{off}$ of less than about $5\times10^{-4}s^{-1}$, less than about $10^{-5}s^{-1}$, less than about $5\times10^{-5}s^{-1}$, less than about $10^{-6}s^{-1}$, less than about $5\times10^{-6}s^{-1}$, less than about $10^{-7}s^{-1}$, less than about $5\times10^{-7}s^{-1}$, less than about $10^{-8}s^{-1}$, less than about $5\times10^{-8}s^{-1}$, less than about $10^{-9}s^{-1}$, less than about $5\times10^{-9}s^{-1}$, or less than about $10^{-10}s^{-1}$.

In another embodiment, an Fc variant of the invention that immunospecifically binds to least on Eph receptor has an affinity constant or $K_a$ ($k_{on}/k_{off}$) of at least $10^2M^{-1}$, at least $5\times10^2M^{-1}$, at least $10^3M^{-1}$, at least $5\times10^3M^{-1}$, at least $10^4M^{-1}$, at least $5\times10^4M^{-1}$, at least $10^5M^{-1}$, at least $5\times10^5M^{-1}$, at least $10^6M^{-1}$, at least $5\times10^6M^{-1}$, at least $10^7M^{-1}$, at least $5\times10^7M^{-1}$, at least $10^8M^{-1}$, at least $5\times10^8M^{-1}$, at least $10^9M^{-1}$, at least $5\times10^9M^{-1}$, at least $10^{10}M^{-1}$, at least $5\times10^1M^{-1}$, at least $10^{11}M^{-1}$, at least $5\times10^{11}M^{-1}$, at least $10^{12}M^{-1}$, at least $5\times10^{12}M$, at least $10^{13}M^{-1}$, at least $5\times10^{13}M^{-1}$, at least $10^{14}M^{-1}$, at least $5\times10^{14}M^{-1}$, at least $10^{15}M^{-1}$, or at least $5\times10^{15}M^{-1}$. In a further embodiment, an Fc variant of the invention that immunospecifically binds to least on Eph receptor has an affinity constant or $K_a$ ($k_{on}/k_{off}$) of at least about $10^2M^{-1}$, at least about $5\times10^2M^{-1}$, at least about $10^3M^{-1}$, at least about $5\times10^3M^{-1}$, at least about $10^4M^{-1}$, at least about $5\times10^4M^{-1}$, at least about $10^5M^{-1}$, at least about $5\times10^5M^{-1}$, at least about $10^6M^{-1}$, at least about $5\times10^6M^{-1}$, at least about $10^7M^{-1}$, at least about $5\times10^7M^{-1}$, at least about $10^8M^{-1}$, at least about $5\times10^8M^{-1}$, at least about $10^9M^{-1}$, at least about $5\times10^9M^{-1}$, at least about $10^{10}M^{-1}$, at least about $5\times10^1M^{-1}$, at least about $10^{11}M^{-1}$, at least about $5\times10^{11}M^{-1}$, at least about $10^{12}M^{-1}$, at least about $5\times10^{12}M$, at least about $10^{13}M^{-1}$, at least about $5\times10^{13}M^{-1}$, at least about $10^{14}M^{-1}$, at least about $5\times10^{14}M^{-1}$, at least about $10^{15}M^{-1}$, or at least about $5\times10^{15}M^{-1}$.

In yet another embodiment, an Fc variant that immunospecifically binds to least on Eph receptor has a dissociation constant or $K_d$ ($k_{off}/k_{on}$) of less than $10^{-2}M$, less than $5\times10^{-2}M$, less than $10^{-3}M$, less than $5\times10^{-3}M$, less than $10^{-4}M$, less than $5\times10^{-4}M$, less than $10^{-5}M$, less than $5\times10^{-5}M$, less than $10^{-6}M$, less than $5\times10^{-6}M$, less than $10^{-9}M$, less than $5\times10^{-7}M$, less than $10^{-8}M$, less than $5\times10^{-8}M$, less than $10^{-9}M$, less than $5\times10^{-9}M$, less than $10^{-10}M$, less than $5\times10^{-10}M$, less than $10^{-11}M$, less than $5\times10^{-11}M$, less than $10^{-12}M$, less than $5\times10^{-12}M$, less than $10^{-13}M$, less than $5\times10^{-13}M$, less than $10^{-14}M$, less than $5\times10^{-14}M$, less than $10^{-15}M$, or less than $5\times10^{-15}M$. In a further embodiment, an Fc variant that immunospecifically binds to least on Eph receptor has a dissociation constant or $K_d$ ($k_{off}/k_{on}$) of less than about $10^{-2}M$, less than about $5\times10^{-2}M$, less than about $10^{-3}M$, less than about $5\times10^{-3}M$, less than about $10^{-4}M$, less than about $5\times10^{-4}M$, less than about $10^{-5}M$, less than about $5\times10^{-5}M$, less than about $10^{-6}M$, less than about $5\times10^{-6}M$, less than about $10^{-7}M$, less than about $5\times10^{-7}M$, less than about $10^{-8}M$, less than about $5\times10^{-8}M$, less than about $10^{-9}M$, less than about $5\times10^{-9}M$, less than about $10^{-10}M$, less than about $5\times10^{-10}M$, less than about $10^{-11}M$, less than about $5\times10^{-11}M$, less than about $10^{-12}M$, less than about $5\times10^{-12}M$, less than about $10^{-13}M$, less than about $5\times10^{-13}M$, less than about $10^{-14}M$, less than about $5\times10^{-14}M$, less than about $10^{-15}M$, or less than about $5\times10^{-15}M$.

Other RTK molecules contemplated as targets for Fc variants include Anaplastic Lymphoma Kinase (ALK), an orphan RTK. ALK was originally identified as a fusion protein with nucleophosmin (npm/ALK) due to a t(2;5) translocation (Morris et al., 1994) this fusion results in constitutive activation of the intracellular ALK kinase and was shown to induce anaplastic lymphoma. The full-length ALK receptor has been shown to be highly expressed in the developing nervous system and down-regulated postnatally (Iwahara et al., 1997). It was recently discovered that ALK is a cell receptor for pleiotrophin (PTN) in humans and that this tyrosine kinase receptor is over expressed in human glioblastoma and is rate-limiting for the growth of a xenograft model of glioblastoma. (U.S. patent publication No. 2002/034768). In one embodiment, the Fc variants of the invention immunospecifically bind to ALK (e.g., Genbank Acc. No.:Q9UM73). In a specific embodiment, variants of the invention immunospecifically bind to the extracellular domain of ALK. In another embodiment, the Fc variants of the invention immunospecifically bind to PTN (e.g., Genbank Acc. No. NP_002816). In a specific embodiment, the Fc variants of the invention block the binding of PTN to ALK.

6.1 Fc Variants that Immunospecifically Bind to an Eph Receptor

As discussed above, the invention encompasses Fc variants comprising a variable region that immunospecifically binds to at least one Eph receptor and a Fc region that further comprises at least one high effector function amino acid residue (e.g., 239D, 330L, 332E wherein the numbering of the residues is that of the EU index as set forth in Kabat). The invention further encompasses Fc variants that immunospecifically bind to at least one Eph receptor, have altered ADCC and/or CDC activity and modified binding affinities for one or more Fc ligand (e.g., FcγRs, C1q) relative to a comparable molecule. The invention specifically encompasses Fc variants derived from anti-Eph receptor antibodies or fragments thereof including, but not limited to, Eph099B-102.147 (ATCC access No. PTA-4572), Eph099B-208.261 (ATCC access No. PTA-4573), Eph099B-210.248 (ATCC access No. PTA-4574), Eph099B-233.152 (ATCC access No. PTA-5194), (PCT Publication No. WO 03/094859 which is incorporated herein by reference in its entirety); EA2 (ATCC access No. PTA-4380), EA3, EA4, EA5 (ATCC access No. PTA-4381), (PCT Publication No. WO 04/014292 which is incorporated herein by reference in its entirety); LX-13 and scFv EA44 (ATCC access No. PTA-6044), (U.S. patent application Ser. No. 10/863,729 which is incorporated herein by reference in its entirety), and 12G3H11 (infra) and analogs, derivatives, or fragments thereof. It is specifically contemplated that the Fc variants of the invention may comprise all or a portion of the variable region (e.g., one or more CDR) from 12G3H11 (see Table 3) and/or any of the antibodies listed in Table 4.

In one embodiment, the Fc variant is an Fc variant of 12G3H11, a humanized agonistic monoclonal antibody that binds EphA2. The DNA and deduced amino acid sequence of the variable region of the heavy and light chains of 12G3H11 are shown in FIGS. 2A and 2B respectively. The amino acid sequences for the heavy chain variable region and light chain variable region are provided herein as SEQ ID NO: 64 and SEQ ID NO: 65, respectively (FIGS. 2A and 2B). The nucleotide sequence for the heavy chain variable and light chain variable region are provided herein as SEQ ID NO: 62 and SEQ ID NO: 63, respectively (FIGS. 2A and 2B). In another embodiment, Fc variant of the present invention binds to the same epitope as 12G3H11 or competes with 12G3H11 for binding to EphA2. In an alternative embodiment, the Fc variant of the invention that immuno-specifically binds to an Eph receptor is not an Fc variant of 12G3H11.

In one embodiment, the Fc variant is an Fc variant of 3F2, a humanized agonistic monoclonal antibody that binds EphA2. The DNA and deduced amino acid sequence of the variable region of the heavy and light chains of 3F2 are shown in FIGS. 3A and 3B respectively. The amino acid sequences for the heavy chain variable region and light chain variable region are provided herein as SEQ ID NO: 68 and SEQ ID NO: 69, respectively (FIGS. 3A and 3B). The nucleotide sequence for the heavy chain variable and light chain variable region are provided herein as SEQ ID NO: 66 and SEQ ID NO: 67, respectively (FIGS. 3A and 3B). In another embodiment, Fc variant of the present invention binds to the same epitope as 3F2 or competes with 3F2 for binding to EphA2. In an alternative embodiment, the Fc variant of the invention that immuno-specifically binds to an Eph receptor is not an Fc variant of 3F2.

In a specific embodiment, an Fc of the invention is generated by combining a antigen binding domain (e.g., variable region) or fragment thereof of an antibody or fragment thereof that immunospecifically binds an Eph receptor (examples supra) with an Fc region comprising at least one high effector function amino acid residue. Methods for generating such a recombinant antibody are well know to one skilled in the art and are further described infra.

In one embodiment, the Fc variant of the invention preferentially binds EphA2 over other Eph receptors. In another embodiment, the Fc variant of the invention preferentially binds EphA4 over other Eph receptors. In still another embodiment, the Fc variant of the invention immunoreacts with one or more Eph receptor complex (e.g., an Eph receptor-Ephrin ligand complex). In still another embodiment, an Fc variant of the invention immunospecifically binds more then one Eph receptor. Combinations of Eph receptors bound by an Fc variant that immunospecifically binds more then one Eph receptor are represented by the following formulas, EphA(x)+EphB(y); EphA(x)+EphA(x); EphB(y)+EphB(y); wherein (x) is 1, 2, 3, 3a, 3b, 4, 5, 5a, 5b, 6, 7 or 8 and (y) is 1, 2, 2a, 2b, 3, 4, 5 or 6. In a specific embodiment, an Fc variant that specifically immunoreacts with more then one Eph receptor binds to, e.g., EphA2+EphA4, or EphA2+EphA3, or EphA2+EphB4, or EphA4+EphA3, or EphA4+EphB4. It is specifically contemplated that an Fc variant that immunospecifically binds more then one Eph receptor is a bispecific antibody. It is further contemplated that an Fc variant that immunospecifically binds more then one Eph receptor is an antibody that binds a common epitope between two or more Eph receptors. It is further contemplated that an Fc variant that immunospecifically binds more then one Eph receptor is an antibody that cross-reacts with one or more Eph receptors. In addition, the Fc variant of the invention may have the same immunoreactivity for more then one Eph receptor (e.g., EphA2 and EphA4) or alternatively, the Fc variant may immunoreact more strongly with one Eph receptor then with another.

The present invention encompasses Fc variants that immunospecifically bind to EphA2, said antibodies comprising a variable heavy ("VH") domain having an amino acid sequence of the VH domain of 12G3H11, Eph099B-102.147, Eph099B-208.261, Eph099B-210.248, Eph099B-233.152, EA2, EA3, EA4, or EA5. The present invention also encompasses Fc variants that immunospecifically bind to EphA2, said antibodies comprising a variable light ("VL") domain having an amino acid sequence of the VL domain of 12G3H11, Eph099B-102.147, Eph099B-208.261, Eph099B-210.248, Eph099B-233.152, EA2, EA3, EA4, or EA5. The invention further encompasses Fc variants that immunospecifically bind to EphA2, said antibodies comprising a VH domain disclosed herein combined with a VL domain disclosed herein, or other VL domain. The present invention further encompasses Fc variants Fc variants that immunospecifically bind to EphA2, said Fc variants comprising a VL domain disclosed herein combined with a VH domain disclosed herein, or other VH domain.

The present invention encompasses Fc variants that immunospecifically bind to EphA4, said antibodies comprising a variable heavy ("VH") domain having an amino acid sequence of the VH domain of LX-13 or scFv EA44. The present invention also encompasses Fc variants that immunospecifically bind to EphA4, said antibodies comprising a variable light ("VL") domain having an amino acid sequence of the VL domain of LX-13 or scFv EA44. The invention further encompasses Fc variants that immunospecifically bind to EphA4, said antibodies comprising a VH domain disclosed herein combined with a VL domain disclosed herein, or other VL domain. The present invention further encompasses Fc variants Fc variants that immunospecifically bind to EphA4, said Fc variants comprising a VL domain disclosed herein combined with a VH domain disclosed herein, or other VH domain.

The present invention encompasses Fc variants that immunospecifically bind to an Eph receptor, said antibodies comprising a VH CDR having an amino acid sequence of any one of the VH CDRs listed in Table 3 infra. The present invention also encompasses Fc variants that immunospecifically bind to an Eph receptor, said antibodies comprising a VL CDR having an amino acid sequence of any one of the VL CDRs listed in Table 3 infra. The present invention also encompasses Fc variants that immunospecifically bind to an Eph receptor, said Fc variants comprising one or more VH CDRs and one or more VL CDRs listed in Table 3. The present invention further encompasses Fc variants that immunospecifically binds to an Eph receptor, Fc variants comprising any combination of some or all of the VH CDRs and VL CDRs listed in Table 3 infra.

TABLE 3

CDR Sequences Of 12G3H11 and 3F2

| CDR | Sequence | SEQ ID NO: |
|---|---|---|
| 12G3H11 VH1 | DYSMN | 5 |
| 12G3H11 VH2 | FIRNKANDYTTEYADSVKG | 6 |
| 12G3H11 VH3 | YPRHHAMDS | 7 |
| 12G3H11 VL1 | RASQSISNNLH | 8 |

TABLE 3-continued

CDR Sequences Of 12G3H11 and 3F2

| CDR | Sequence | SEQ ID NO: |
|---|---|---|
| 12G3H11 VL2 | YAFQSIS | 9 |
| 12G3H11 VL3 | QQANSWPLT | 10 |
| 3F2 VH1 | DYSMN | 70 |
| 3F2 VH2 | FIRNKANAYTTEYSASVKG | 71 |
| 3F2 VH3 | YPRYHAMDS | 72 |
| 3F2 VL1 | RASQSISNNLH | 73 |
| 3F2 VL2 | YGFQSIS | 74 |
| 3F2 VL3 | QQANSWPLT | 75 |

TABLE 4 anti-Eph receptor antibodies

| Antibody/ Hybridoma | EphR | ATCC No. | Date of deposit | Patent App. No. |
|---|---|---|---|---|
| Eph099B-102.147 | EphA2 | PTA-4572 | Aug. 7, 2002 | WO 03/094859 |
| Eph099B208.261 | EphA2 | PTA-4573 | Aug. 7, 2002 | WO 03/094859 |
| Eph099B-210.248 | EphA2 | PTA-4574 | Aug. 7, 2002 | WO 03/094859 |
| Eph099B-233.152 | EphA2 | PTA-5194 | May 12, 2003 | WO 03/094859 |
| EA2 | EphA2 | PTA-4380 | May 22, 2002 | WO 04/014292 |
| EA5 | EphA2 | PTA-4381 | May 22, 2002 | WO 04/014292 |
| EA44 | EphA4 | PTA-6044 | Jun. 4, 2004 | 10/863,729 |

The present invention also encompasses Fc variants that compete with 12G3H11, Eph099B-102.147, Eph099B-208.261, Eph099B-210.248, Eph099B-233.152, EA2, EA3, EA4, EA5, LX-13 or scFv EA44 or an antigen-binding fragment thereof for binding to an Eph receptor. Competition assays, which can be used to identify such antibodies, are well known to one skilled in the art. In a particular embodiment, 1 µg/ml of an antibody of the invention prevents 75%, 80%, 85% or 90% of ORIGEN TAG labeled 12G3H11, Eph099B-102.147, Eph099B-208.261, Eph099B-210.248, Eph099B-233.152, EA2, EA3, EA4, EA5, LX-13 or scFv EA44 from binding to biotin-labeled Eph receptor as measured by well-known ORIGEN analysis.

The present invention also provides Fc variants that comprise a framework region known to those of skill in the art. In one embodiment, the fragment region of an antibody of the invention or fragment thereof is human or humanized.

The present invention encompasses Fc variants comprising the amino acid sequence of 12G3H11, 3F2, Eph099B-102.147, Eph099B-208.261, Eph099B-210.248, Eph099B-233.152, EA2, EA3, EA4, EA5, LX-13 or scFv EA44 with mutations (e.g., one or more amino acid substitutions) in the framework or variable regions in addition to any other substitutions or changes (e.g., Fc substitution(s) as described supra). In one embodiment, mutations in these antibodies maintain or enhance the avidity and/or affinity of the antibodies for the Eph receptor to which they immunospecifically bind. Standard techniques known to those skilled in the art (e.g., immunoassays) can be used to assay the affinity of an antibody for a particular antigen.

The present invention encompasses the use of a nucleic acid molecule(s), generally isolated, encoding an Fc variant that immunospecifically binds to an Eph receptor. In a specific embodiment, an isolated nucleic acid molecule encodes an Fc variant that immunospecifically binds to an Eph receptor, said Fc variant having the amino acid sequence of 12G3H11, Eph099B-102.147, Eph099B-208.261, Eph099B-210.248, Eph099B-233.152 EA2, EA3, EA4, EA5, LX-13 or scFv EA44 containing one or more Fc substitution (e.g. supra). In another embodiment, an isolated nucleic acid molecule encodes an Fc variant that immunospecifically binds to and Eph receptor, said Fc variant comprising a VH domain having the amino acid sequence of the VH domain of 12G3H11, Eph099B-102.147, Eph099B-208.261, Eph099B-210.248, Eph099B-233.152, EA2, EA3, EA4, EA5, LX-13 scFv EA44. In another embodiment, an isolated nucleic acid molecule encodes an Fc variant that immunospecifically binds to an Eph receptor, said antibody comprising a VL domain having the amino acid sequence of the VL domain of 12G3H11, Eph099B-102.147, Eph099B-208.261, Eph099B-210.248, Eph099B-233.152, EA2, EA3, EA4, EA5, LX-13 scFv EA44.

The invention encompasses the use of an isolated nucleic acid molecule encoding an Fc variant that immunospecifically binds to an Eph receptor, said Fc variant comprising a VH CDR having the amino acid sequence of any of the VH CDRs listed in Table 3 and/or derived from the heavy chain of any of the antibodies listed in Table 4. In particular, the invention encompasses the use of an isolated nucleic acid molecule encoding an Fc variant that immunospecifically binds to an Eph receptor, said antibody comprising one, two, or more VH CDRs having the amino acid sequence of any of the VH CDRs listed in Tables 3 and/or derived from the heavy chain of any of the antibodies listed in Table 4.

The present invention encompasses the use of an isolated nucleic acid molecule encoding an Fc variant that immunospecifically binds to an Eph receptor, said Fc variant comprising a VL CDR having an amino acid sequence of any of the VL CDRs listed in Table 3, and/or derived from the light chain of any of the antibodies listed in Table 4. In particular, the invention encompasses the use of an isolated nucleic acid molecule encoding an Fc variant that immunospecifically binds to an Eph receptor, said antibody comprising one, two or more VL CDRs having the amino acid sequence of any of the VL CDRs listed in Table 3 and/or derived from the light chain of any of the antibodies listed in Table 4.

The present invention encompasses the use of Fc variants that immunospecifically bind to an Eph receptor, Fc variants comprising derivatives of the VH domains, VH CDRs, VL domains, or VL CDRs described herein that immunospecifically bind to an Eph receptor. Standard techniques known to those of skill in the art can be used to introduce mutations (e.g., additions, deletions, and/or substitutions) in the nucleotide sequence encoding an antibody of the invention, including, for example, site-directed mutagenesis and PCR-mediated mutagenesis are routinely used to generate amino acid substitutions. In one embodiment, the VH and/or VL CDRs derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions in the relative to the original VH and/or VL CDRs. In another embodiment, the VH and/or VL CDRs derivatives have conservative amino acid substitutions (e.g. supra) are made at one or more predicted non-essential amino acid residues (i.e., amino acid residues which are not critical for the antibody to immunospecifically bind to an Eph receptor). Alternatively, mutations can be introduced randomly along all or part of the VH and/or VL CDR coding sequence, such as by saturation mutagenesis, and the resultant mutants can be screened for biological activity to identify mutants that retain activity. Following mutagenesis, the encoded antibody can be expressed and the activity of the antibody can be determined.

The present invention encompasses Fc variants of 12G3H11, Eph099B-102.147, Eph099B-208.261, Eph099B-210.248, Eph099B-233.152, EA2, EA3, EA4, EA5, LX-13 or scFv EA44 with one or more additional amino acid residue substitutions in the variable light (VL) domain and/or variable heavy (VH) domain. The present invention also encompasses Fc variants of 12G3H11, Eph099B-102.147, Eph099B-208.261, Eph099B-210.248, Eph099B-233.152, EA2, EA3, EA4, EA5, LX-13 or scFv EA44 with one or more additional amino acid residue substitutions in one or more VL CDRs and/or one or more VH CDRs. The antibody generated by introducing substitutions in the VH domain, VH CDRs, VL domain and/or VL CDRs of an Fc variant of 12G3H11, Eph099B-102.147, Eph099B-208.261, Eph099B-210.248, Eph099B-233.152, EA2, EA3, EA4, EA5, LX-13 or scFv EA4 can be tested in vitro and in vivo, for example, for its ability to bind to an Eph receptor and/or Fc□Rs (by, e.g., immunoassays including, but not limited to ELISAs and BIAcore), or for its ability to mediate ADCC, prevent, treat, manage or ameliorate cancer or one or more symptoms thereof.

The present invention also encompasses the use of Fc variants that immunospecifically bind to at least one Eph receptor or a fragment thereof, said Fc variants comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of 12G3H11 (i.e., SEQ ID NO: 64 and/or SEQ ID NO: 65), 3F2 (i.e., SEQ ID NO: 68 and/or SEQ ID NO: 69), Eph099B-102.147, Eph099B-208.261, Eph099B-210.248, Eph099B-233.152, EA2, EA3, EA4, EA5, LX-13 or scFv EA44. The present invention also encompasses the use of Fc variants that immunospecifically bind to at least one Eph receptor or a fragment thereof, said Fc variants comprising an amino acid sequence of a variable heavy chain and/or variable light chain that is at least about 45%, at least about 50%, at least about 55%, at least about 60%, at least about 65%, at least about 70%, at least about 75%, at least about 80%, at least about 85%, at least about 90%, at least about 95%, or at least about 99% identical to the amino acid sequence of the variable heavy chain and/or light chain of 12G3H11 (i.e., SEQ ID NO: 64 and/or SEQ ID NO: 65), 3F2 (i.e., SEQ ID NO: 68 and/or SEQ ID NO: 69), Eph099B-102.147, Eph099B-208.261, Eph099B-210.248, Eph099B-233.152, EA2, EA3, EA4, EA5, LX-13 or scFv EA44. The present invention further encompasses the use of Fc variants that immunospecifically bind to at least one Eph receptor or a fragment thereof, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of 12G3H11, Eph099B-102.147, Eph099B-208.261, Eph099B-210.248, Eph099B-233.152, EA2, EA3, EA4, EA5, LX-13 or scFv EA44. The present invention further encompasses the use of Fc variants that immunospecifically bind to at least one Eph receptor or a fragment thereof, said antibodies or antibody fragments comprising an amino acid sequence of one or more CDRs that is at least about 45%, at least about 50%, at least about 55%, at least about 60%, at least about 65%, at least about 70%, at least about 75%, at least about 80%, at least about 85%, at least about 90%, at least about 95%, or at least about 99% identical to the amino acid sequence of one or more CDRs of 12G3H11, Eph099B-102.147, Eph099B-208.261, Eph099B-210.248, Eph099B-233.152, EA2, EA3, EA4, EA5, LX-13 or scFv EA44. The determination of percent identity of two amino acid sequences can be determined by any method known to one skilled in the art, including BLAST protein searches.

The present invention also encompasses the use of Fc variants that immunospecifically bind to at least one Eph receptor or fragments thereof, where said Fc variants are encoded by a nucleotide sequence that hybridizes to the nucleotide sequence of 12G3H11 (i.e., SEQ ID NO: 62 and/or SEQ ID NO: 63), 3F2 (i.e., SEQ ID NO: 66 and/or SEQ ID NO: 67), Eph099B-102.147, Eph099B-208.261, Eph099B-210.248, Eph099B-233.152, EA2, EA3, EA4, EA5, LX-13 or scFv EA44 under stringent conditions. In another preferred embodiment, the invention encompasses Fc variants that immunospecifically bind to an Eph receptor or a fragment thereof, said Fc variants comprising one or more CDRs encoded by a nucleotide sequence that hybridizes under stringent conditions to the nucleotide sequence of one or more CDRs of 12G3H11, Eph099B-102.147, Eph099B-208.261, Eph099B-210.248, Eph099B-233.152, EA2, EA3, EA4, EA5, LX-13 or scFv EA44. Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

Set forth below, is a more detailed description of the antibodies encompassed within the various aspects of the invention.

6.2 Antibodies of the Invention

Fc variants of the invention may include, but are not limited to, synthetic antibodies, monoclonal antibodies, oligoclonal antibodies recombinantly produced antibodies, intrabodies, multispecific antibodies, bispecific antibodies, human antibodies, humanized antibodies, chimeric antibodies, synthetic antibodies, single-chain FvFcs (scFvFc), single-chain Fvs (scFv), and anti-idiotypic (anti-Id) antibodies. In particular, antibodies used in the methods of the present invention include immunoglobulin molecules and immunologically active portions of immunoglobulin molecules. The antibodies of the invention can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule.

Fc variants of the invention may be from any animal origin including birds and mammals (e.g., human, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes.

Antibodies like all polypeptides have an Isoelectric Point (pI), which is generally defined as the pH at which a polypeptide carries no net charge. It is known in the art that protein solubility is typically lowest when the pH of the solution is equal to the isoelectric point (pI) of the protein. It is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI. The pI of a protein may be determined by a variety of methods including but not limited to, isoelectric focusing and various computer algorithms (see for example Bjellqvist et al., 1993, *Electrophoresis* 14:1023). In one embodiment, the pI of the Fc variants of the invention is between is higher then about 6.5, about 7.0, about 7.5, about 8.0, about 8.5, or about 9.0. In another embodiment, the pI of the Fc variants of the invention is between is higher then 6.5, 7.0, 7.5, 8.0, 8.5, or 9.0. In one embodiment, substitutions resulting in alterations in the pI of the Fc variant of the invention will not significantly diminish its binding affinity for an Eph receptor. It is specifically contemplated that the substitution(s) of the Fc region that result in altered binding to FcγR (described supra) may also result in a change in the pI. In a preferred embodiment, substitution(s) of the Fc region are specifically chosen to effect both the desired alteration in FcγR binding and any desired change in pI. As used herein the pI value is defined as the pI of the predominant charge form. The pI of a protein may be determined by a variety of methods including but not limited to, isoelectric focusing and various computer algorithms (see, e.g., Bjellqvist et al., 1993, *Electrophoresis* 14:1023).

The Tm of the Fab domain of an antibody, can be a good indicator of the thermal stability of an antibody and may further provide an indication of the shelf-life. A lower Tm indicates more aggregation/less stability, whereas a higher Tm indicates less aggregation/more stability. Thus, antibodies having higher Tm are preferable. In one embodiment, the Fab domain of an Fc variant has a Tm value higher than at least 50° C., 55° C., 60° C., 65° C., 70° C., 75° C., 80° C., 85° C., 90° C., 95° C., 100° C., 105° C., 110° C., 115° C. or 120° C. In another embodiment, the Fab domain of an Fc variant has a Tm value higher than at least about 50° C., about 55° C., about 60° C., about 65° C., about 70° C., about 75° C., about 80° C., about 85° C., about 90° C., about 95° C., about 100° C., about 105° C., about 110° C., about 115° C. or about 120° C. Thermal melting temperatures (Tm) of a protein domain (e.g., a Fab domain) can be measured using any standard method known in the art, for example, by differential scanning calorimetry (see, e.g., Vermeer et al., 2000, *Biophys. J.* 78:394-404; Vermeer et al., 2000, *Biophys. J.* 79: 2150-2154).

Fc variants of the invention may be monospecific, bispecific, trispecific or have greater multispecificity. Multispecific antibodies may immunospecifically bind to different epitopes of desired target molecule or may immunospecifically bind to both the target molecule as well as a heterologous epitope, such as a heterologous polypeptide or solid support material. See, e.g., International Publication Nos. WO 94/04690; WO 93/17715; WO 92/08802; WO 91/00360; and WO 92/05793; Tutt, et al., 1991, *J. Immunol.* 147:60-69; U.S. Pat. Nos. 4,474,893, 4,714,681, 4,925,648, 5,573,920, and 5,601,819; and Kostelny et al., 1992, *J. Immunol.* 148:1547; each of which is incorporated herein by reference in their entireties). In one embodiment, one of the binding specificities is for an Eph receptor, the other one is for any other antigen (i.e., another Eph receptor, an Ephrin, a signaling or effector molecule).

Multispecific antibodies have binding specificities for at least two different antigens. While such molecules normally will only bind two antigens (i.e. bispecific antibodies, BsAbs), antibodies with additional specificities such as trispecific antibodies are encompassed by the instant invention. Examples of BsAbs include without limitation those with one arm directed against a Integrin $α_vβ_3$ and the other arm directed against any other antigen. Methods for making bispecific antibodies are known in the art. Traditional production of full-length bispecific antibodies is based on the coexpression of two immunoglobulin heavy chain-light chain pairs, where the two chains have different specificities (Millstein et al., 1983, *Nature*, 305:537-539 which is incorporated herein by reference in its entirety). Because of the random assortment of immunoglobulin heavy and light chains, these hybridomas (quadromas) produce a potential mixture of different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., 1991, *EMBO J.*, 10:3655-3659. A more directed approach is the generation of a Di-diabody a tetravalent bispecific antibody. Methods for producing a Di-diabody are known in the art (see e.g., Lu et al., 2003, J Immunol Methods 279:219-32; Marvin et al., 2005, Acta Pharmacolical Sinica 26:649).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. In one embodiment, the first heavy-chain constant region (CH1) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm (e.g., an Eph receptor), and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 (incorporated herein by reference in its entirety). For further details of generating bispecific antibodies see, for example, Suresh et al., 1986, *Methods in Enzymology*, 121:210 (incorporated herein by reference in its entirety). According to another approach described in WO96/27011 (incorporated herein by reference in its entirety), a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089) The above references are each incorporated herein by reference in their entireties. Heteroconjugate antibodies may be made using any convenient cross-linking methods. Suitable cross-linking agents are well known in the art, and are disclosed in U.S. Pat. No. 4,676,980, along with a number of cross-linking techniques. Each of the above references is incorporated herein by reference in its entirety.

Antibodies with more than two valencies incorporating at least one hinge modification of the invention are contemplated. For example, trispecific antibodies can be prepared. See, e.g., Tutt et al. J. Immunol. 147: 60 (1991), which is incorporated herein by reference.

The Fc variants of the invention encompass single domain antibodies, including camelized single domain antibodies (see e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231: 25; International Publication Nos. WO 94/04678 and WO 94/25591; U.S. Pat. No. 6,005,079; which are incorporated herein by reference in their entireties).

Other antibodies specifically contemplated are "oligoclonal" antibodies. As used herein, the term "oligoclonal" antibodies" refers to a predetermined mixture of distinct monoclonal antibodies. See, e.g., PCT publication WO 95/20401; U.S. Pat. Nos. 5,789,208 and 6,335,163 which are incorporated by reference herein. Preferably oligoclonal antibodies consist of a predetermined mixture of antibodies against one or more epitopes are generated in a single cell. More preferably oligoclonal antibodies comprise a plurality of heavy chains capable of pairing with a common light chain to generate antibodies with multiple specificities (e.g., PCT publication WO 04/009618 which is incorporated by reference herein). Oligoclonal antibodies are particularly useful when it is desired to target multiple epitopes on a single target molecule (e.g., Integrin $\alpha_v\beta_3$). Those skilled in the art will know or can determine what type of antibody or mixture of antibodies is applicable for an intended purpose and desired need.

In one embodiment, antibodies of the present invention also encompass Fc variants that have half-lives (e.g., serum half-lives) in a mammal, preferably a human, of greater than 5 days, greater than 10 days, greater than 15 days, preferably greater than about 20 days, greater than about 25 days, greater than 30 days, greater than 35 days, greater than 40 days, greater than 45 days, greater than 2 months, greater than 3 months, greater than 4 months, or greater than 5 months. In another embodiment, antibodies of the present invention also encompass Fc variants that have half-lives (e.g., serum half-lives) in a mammal, preferably a human, of greater than about 5 days, greater than about 10 days, greater than about 15 days, preferably greater than about 20 days, greater than about 25 days, greater than about 30 days, greater than about 35 days, greater than about 40 days, greater than about 45 days, greater than about 2 months, greater than about 3 months, greater than about 4 months, or greater than about 5 months. The increased half-lives of the antibodies of the present invention in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S. patent Publication No. 2003/0190311, each of which are incorporated herein by reference in their entireties).

In one embodiment, the Fc variants of the invention may be chemically modified (e.g., one or more chemical moieties can be attached to the antibody) or be modified to alter its glycosylation, again to alter one or more functional properties of the antibody.

In still another embodiment, the glycosylation of the Fc variants of the invention is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861, each of which is incorporated herein by reference in its entirety.

Additionally or alternatively, an Fc variant can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277: 26733-26740; Umana et al. (1999) *Nat. Biotech.* 17:176-1, as well as, European Patent No: EP 1,176,195; PCT Publications WO 03/035835; WO 99/54342, each of which is incorporated herein by reference in its entirety.

In still another embodiment, the glycosylation of an Fc variant of the invention is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861, each of which is incorporated herein by reference in its entirety.

Additionally or alternatively, an Fc variant can be made that has an altered type of glycosylation, such as a hypofucosylated Fc variant having reduced amounts of fucosyl residues or an Fc variant having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342, each of which is incorporated herein by reference in its entirety.

6.3 Antibody Conjugates and Derivatives

Fc variants of the invention include derivatives that are modified (i.e., by the covalent attachment of any type of molecule to the antibody such that covalent attachment). For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Further, antibodies can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. EP 413, 622, all of which are incorporated herein by reference. The present invention encompasses the use of antibodies or fragments thereof conjugated or fused to one or more moieties, including but not limited to, peptides, polypeptides, proteins, fusion proteins, nucleic acid molecules, small molecules, mimetic agents, synthetic drugs, inorganic molecules, and organic molecules.

In one embodiment, the present invention encompasses the use of antibodies or fragments thereof recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In another embodiment, the present invention encompasses the use of antibodies or fragments thereof recombinantly fused or chemically conjugated (including both covalent and non-covalent conjugations) to a heterologous protein or polypeptide (or fragment thereof, preferably to a polypeptide of at least about 10, at least about 20, at least about 30, at least about 40, at least about 50, at least about 60, at least about 70, at least about 80, at least about 90 or at least about 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452, which are incorporated by reference in their entireties.

The present invention further includes formulations comprising heterologous proteins, peptides or polypeptides fused or conjugated to antibody fragments. For example, the heterologous polypeptides may be fused or conjugated to a Fab fragment, Fd fragment, Fv fragment, F(ab)2 fragment, a VH domain, a VL domain, a VH CDR, a VL CDR, or fragment thereof. Methods for fusing or conjugating polypeptides to antibody portions are well known in the art. See, e.g., U.S. Pat. Nos. 5,336,603, 5,622,929, 5,359,046, 5,349,053, 5,447, 851, and 5,112,946; European Pat. Nos. EP 307,434 and EP 367,166; International publication Nos. WO 96/04388 and WO 91/06570; Ashkenazi et al., 1991, Proc. Natl. Acad. Sci. USA 88: 10535-10539; Zheng et al., 1995, J. Immunol. 154: 5590-5600; and Vil et al., 1992, Proc. Natl. Acad. Sci. USA 89:11337-11341 (said references incorporated by reference in their entireties).

Additional fusion proteins, e.g., of antibodies that immunospecifically bind an Eph receptor (e.g., supra), may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834, 252; and 5,837,458, and Patten et al., 1997, Curr. Opinion Biotechnol. 8:724-33; Harayama, 1998, Trends Biotechnol. 16(2): 76-82; Hansson, et al., 1999, J. Mol. Biol. 287:265-76; and Lorenzo and Blasco, 1998, Biotechniques 24(2): 308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions immunospecifically bind to an Eph receptor may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexahistidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

In other embodiments, Fc variants of the present invention or analogs or derivatives thereof are conjugated to a diagnostic or detectable agent. Such antibodies can be useful for monitoring or prognosing the development or progression of a cancer as part of a clinical testing procedure, such as determining the efficacy of a particular therapy. Such diagnosis and detection can be accomplished by coupling the antibody to detectable substances including, but not limited to various enzymes, such as but not limited to horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($131I$, $125I$, $123I$, $121I$,), carbon ($14C$), sulfur ($35S$), tritium ($3H$), indium ($115In$, $113In$, $112In$, $111In$,), and technetium ($99Tc$), thallium ($201Ti$), gallium ($68Ga$, $67Ga$), palladium ($103Pd$), molybdenum ($99Mo$), xenon ($133Xe$), fluorine ($18F$), $153Sm$, $177Lu$, $159Gd$, $149Pm$, $140La$, $175Yb$, $166Ho$, $90Y$, $47Sc$, $186Re$, $188Re$, $142Pr$, $105Rh$, $97Ru$, $68Ge$, $57Co$, $65Zn$, $85Sr$, $32P$, $153Gd$, $169Yb$, $51Cr$, $54Mn$, $75Se$, $113Sn$, and $117Tin$; positron emitting metals using various positron emission tomographies, noradioactive paramagnetic metal ions, and molecules that are radiolabelled or conjugated to specific radioisotopes.

The present invention further encompasses uses of Fc variants of the invention or fragments thereof conjugated to a therapeutic agent.

An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publications WO 03/075957; which is incorporated herein by reference in its entirety.

Further, an antibody or fragment thereof may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, Onconase (or another cytotoxic RNase), pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, an antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943; each incorporated by reference in their entireties.

Techniques for conjugating therapeutic moieties to antibodies are well known. Moieties can be conjugated to antibodies by any method known in the art, including, but not limited to aldehyde/Schiff linkage, sulphydryl linkage, acid-labile linkage, cis-aconityl linkage, hydrazone linkage, enzymatically degradable linkage (see generally Garnett, 2002, Adv Drug Deliv Rev 53:171). Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119; each incorporated by reference in their entireties.

Methods for fusing or conjugating antibodies to polypeptide moieties are known in the art. See, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337; each incorporated by reference in their entireties. The fusion of an antibody to a moiety does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171, each of which is incorporated herein by reference in its entirety.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The therapeutic moiety or drug conjugated to an antibody or fragment thereof that immunospecifically binds to an Eph receptor should be chosen to achieve the desired prophylactic or therapeutic effect(s) for a particular disorder in a subject. A clinician or other medical personnel should consider the following when deciding on which therapeutic moiety or drug to conjugate to an antibody or fragment thereof that immunospecifically binds to an Eph receptor: the nature of the disease, the severity of the disease, and the condition of the subject.

6.4 Methods of Generating Antibodies

The Fc variants of the invention can be produced by any method known in the art for the synthesis of antibodies, in particular, by chemical synthesis or by recombinant expression techniques.

Polyclonal antibodies to an Eph receptor can be produced by various procedures well known in the art. For example, an Eph receptor or immunogenic fragments thereof can be administered to various host animals including, but not limited to, rabbits, mice, rats, etc. to induce the production of sera containing polyclonal antibodies specific for an Eph receptor. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with an Eph receptor or a domain thereof (e.g., the extracellular domain) and once an immune response is detected, e.g., antibodies specific for an Eph receptor are detected in the mouse serum, the mouse spleen is harvested and splenocytes isolated. The splenocytes are then fused by well known techniques to any suitable myeloma cells, for example cells from cell line SP20 available from the ATCC. Additionally, a RIMMS (repetitive immunization, multiple sites) technique can be used to immunize an animal (Kilpatrick et al., 1997, Hybridoma 16:381-9, incorporated herein by reference in its entirety). Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, monoclonal antibodies can be generated by culturing a hybridoma cell secreting an antibody, wherein the hybridoma is generated by fusing splenocytes isolated from a mouse immunized with an Eph receptor or immunogenic fragments thereof, with myeloma cells and then screening the hybridomas resulting from the fusion for hybridoma clones that secrete an antibody able to bind an Eph receptor.

The Fc variants of the invention contain novel amino acid residues in their Fc regions. Fc variants can be generated by numerous methods well known to one skilled in the art. Non-limiting examples include, isolating antibody coding regions (e.g., from hybridoma) and making one or more desired substitutions in the Fc, region of the isolated antibody coding region. Alternatively, the variable regions may be subcloned into a vector encoding an Fc region comprising one or more high effector function amino acid residues. Additional methods and details are provided below.

Antibody fragments that recognize specific an Eph receptor epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles that carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in $E. coli$ and the $E. coli$ is infected with helper phage. Phage used in these methods are typically filamentous phage including fd and M13 and the VH and VL domains are usually recombinantly fused to either the phage gene III or gene VIII. Phage expressing an antigen binding domain that binds to the an Eph receptor epitope of interest can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, BioTechniques 12(6): 864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma constant, and the PCR amplified VL domains can be cloned into vectors expressing a VL constant region, e.g., human kappa or lamba constant regions. In one embodiment, the constant region is an Fc region containing at least one high effector function amino acid. In another embodiment, the vectors for expressing the VH or VL domains comprise a promoter, a secretion signal, a cloning site for both the variable and constant domains, as well as a selection marker such as neomycin. The VH and VL domains may also be cloned into one vector expressing the desired constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,311,415, which are incorporated herein by reference in their entirety.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and PCT Publication Nos. WO 98/46645, WO 98/50433, WO 98/24893, WO98/16654, WO 96/34096, WO 96/33735, and WO 91/10741; each of which is incorporated herein by reference in its entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')2, Fabc, Fv) in which all or substantially all of the CDR regions correspond to those of a non-human immunoglobulin (i.e., donor antibody) and all or substantially all of the framework regions are those of a human immunoglobulin consensus sequence. In one embodiment, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG.sub.1. Where such cytotoxic activity is not desirable, the constant domain may be of the IgG.sub.2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. In one embodiment, at least 75% of the humanized antibody residues will correspond to those of the parental framework region (FR) and CDR sequences. In another embodiment at least 90% of the humanized antibody residues will correspond to those of the parental framework region (FR) and CDR sequences. In a further embodiment, greater than 95% of the humanized antibody residues will correspond to those of the parental framework region (FR) and CDR sequences. In yet another embodiment, at least about 75% of the humanized antibody residues will correspond to those of the parental framework region (FR) and CDR sequences. In a further embodiment at least about 90% of the humanized antibody residues will correspond to those of the parental framework region (FR) and CDR sequences. In yet a further embodiment, greater than about 95% of the humanized antibody residues will correspond to those of the parental framework region (FR) and CDR sequences. Humanized antibody can be produced using variety of techniques known in the art, including but not limited to, CDR-grafting (European Pat. No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5): 489-498; Studnicka et al., 1994, Protein Engineering 7(6): 805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119-25 (2002), Caldas et al., Protein Eng. 13(5): 353-60 (2000), Morea et al., Methods 20(3): 267-79 (2000), Baca et al., J. Biol. Chem. 272(16): 10678-84 (1997), Roguska et al., Protein Eng. 9(10): 895-904 (1996), Couto et al., Cancer Res. 55 (23 Supp): 5973s-5977s (1995), Couto et al., Cancer Res. 55(8): 1717-22 (1995), Sandhu J S, Gene 150(2): 409-10 (1994), and Pedersen et al., J. Mol. Biol. 235(3): 959-73 (1994). Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., an Eph receptor or immunogenic fragments thereof. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.), Genpharm (San Jose, Calif.) and Medarex (Princeton, N.J.) can be engaged to provide human antibodies directed against a selected antigen using technology similar to that described above.

Further, the antibodies of the invention can, in turn, be utilized to generate anti-idiotype antibodies that "mimic" an Eph receptor using techniques well known to those skilled in the art. (See, e.g., Greenspan & Bona, 1989, FASEB J. 7(5): 437-444; and Nissinoff, 1991, J. Immunol. 147(8): 2429-2438). For example, antibodies of the invention which bind to and competitively inhibit the binding of an Eph receptor (as determined by assays well known in the art and disclosed infra) to its ligands can be used to generate anti-idiotypes that "mimic" an Eph receptor binding domains and, as a consequence, bind to and neutralize an Eph receptor and/or its ligands. Such neutralizing anti-idiotypes or Fab fragments of such anti-idiotypes can be used in therapeutic regimens to neutralize an Eph receptor. The invention provides methods employing the use of polynucleotides comprising a nucleotide sequence encoding an antibody of the invention or a fragment thereof.

In a preferred embodiment, the nucleotide sequence encoding an antibody that immunospecifically binds an Eph receptor is obtained and used to generate the Fc variants of the invention. The nucleotide sequence can be obtained from sequencing hybridoma clone DNA. If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+RNA, isolated from any tissue or cells expressing the antibody, such as hybridoma cells selected to express an antibody) by PCR amplification using synthetic primers that hybridize to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, Or example, the techniques described in Current Protocols in Molecular Biology, F. M. Ausubel et al., ed., John Wiley & Sons (Chichester, England, 1998); Molecular Cloning: A Laboratory Manual, 3nd Edition, J. Sambrook et al., ed., Cold Spring Harbor Laboratory Press (Cold Spring Harbor, N.Y., 2001); Antibodies: A Laboratory Manual, E. Harlow and D. Lane, ed., Cold Spring Harbor Laboratory Press (Cold Spring Harbor, N.Y., 1988); and Using Antibodies: A Laboratory Manual, E. Harlow and D. Lane, ed., Cold Spring Harbor Laboratory (Cold Spring Harbor, N.Y., 1999) which are incorporated by reference herein in their entireties), to generate antibodies having a different amino acid sequence by, for example, introducing deletions, and/or insertions into desired regions of the antibodies.

In a preferred embodiment, one or more substitutions are made within the Fc region (e.g. supra) of an antibody able to immunospecifically bind an Eph receptor. In one embodiment, the amino acid substitutions modify binding to one or more Fc ligands (e.g., FcγRs, C1q) and alter ADCC and/or CDC activity.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). In one embodiment, the polynucleotide generated by the combination of the framework regions and CDRs encodes an antibody that immunospecifically binds to an Eph receptor. In another embodiment, as discussed supra, one or more amino acid substitutions may be made within the framework regions, and, in yet another embodiment, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

6.5 Polypeptides and Fusion Proteins that Bind to an Eph Receptor

The present invention encompasses polypeptides and fusion proteins that immunospecifically bind to an Eph receptor.

In a one embodiment, a polypeptide or a fusion protein that immuno-specifically binds to an Eph receptor inhibits or reduces the interaction between an Eph receptor and its ligands by about 25%, 30%, 35%, 45%, 50%, 55%, 60%, 65%, 70%, 75%, 80%, 85%, 90%, 95%, or 98% in an in vivo or in vitro assay described herein or well-known to one of skill in the art. In this context "about" means plus or minus 0.1% to 2.5%. In alternative embodiment, a polypeptide or a fusion protein that immunospecifically binds to an Eph receptor does not significantly inhibit the interaction between an Eph receptor and its ligands in an in vivo or in vitro assay described herein or well-known to one of skill in the art.

In a one embodiment, a polypeptide or a fusion protein that immuno-specifically binds to an Eph receptor comprises an Eph receptor ligand or a fragment thereof which immunospecifically binds to an Eph receptor fused to an Fc domain. It is specifically contemplated that the Fc domain of said fusion protein comprises at least one high effector function amino acid and/or substitution as described supra. In a preferred embodiment, said Fc domain is that of an Fc variant of the present invention, the Fc domain of an Fc variant is hereafter referred to as a variant Fc domain. Examples of an Eph receptor ligand include, but are not limited to, GPI-membrane anchored ligands of the Ephrin-A subclass (e.g., A1, A2, A3, A4, A5) and transmembrane domain-membrane anchored ligands of the Ephrin-B subclass (e.g., B1, B2, B3). An alignment of preferred Ephrin molecules of the present invention is shown in FIG. 19.

In another embodiment, a polypeptide or a fusion protein that immunospecifically binds to an Eph receptor comprises a bioactive molecule fused to a variant Fc domain of the present invention. In accordance with these embodiments, the bioactive molecule immunospecifically binds to an Eph receptor. Bioactive molecules that immunospecifically bind to an Eph receptor include, but are not limited to, peptides, polypeptides, proteins, small molecules, mimetic agents, synthetic drugs, inorganic molecules, and organic molecules. In one embodiment, a bioactive molecule that immunospecifically binds to an Eph receptor is a polypeptide comprising at least 5, at least 10, at least 20, at least 30, at least 40, at least 50, at least 60, at least 70, at least 80, at least 90 or at least 100 contiguous amino acid residues, and is heterologous to the amino acid sequence of the variant Fc domain of the invention. In another embodiment, a bioactive molecule that immunospecifically binds to an Eph receptor is a polypeptide comprising at least about 5, at least about 10, at least about 20, at least about 30, at least about 40, at least about 50, at least about 60, at least about 70, at least about 80, at least about 90 or at least about 100 contiguous amino acid residues, and is heterologous to the amino acid sequence of the variant Fc domain of the invention.

In another embodiment, a peptide, a polypeptide or a fusion protein that immunospecifically binds to an Eph receptor comprises a polypeptide having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of an Eph receptor ligand (e.g., Ephrin-A and/or -B subclass, see FIG. 19) or a fragment thereof fused to a variant Fc domain of the present invention. In a further embodiment, a peptide, a polypeptide or a fusion protein that immunospecifically binds to an Eph receptor comprises a polypeptide having an amino acid sequence that is at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% identical to the amino acid sequence of an Eph receptor ligand (e.g., Ephrin-A and/or -B subclass, see FIG. 19) or a fragment thereof fused to a variant Fc domain of the present invention.

The present invention provides polypeptides or fusion proteins that immunospecifically bind to an Eph receptor comprising a variant Fc domain of the present invention fused to a polypeptide encoded by a nucleic acid molecule that hybridizes to the nucleotide sequence encoding an Eph receptor ligand (e.g., Ephrin-A and/or -B subclass, see FIG. 19), or a fragment thereof.

In a specific embodiment, a polypeptide or a fusion protein that immunospecifically binds to an Eph receptor comprises a variant Fc domain of the present invention fused to a polypeptide encoded by a nucleic acid molecule that hybridizes to the nucleotide sequence encoding an Eph receptor ligand (e.g., Ephrin-A and/or -B subclass, see FIG. 19) or a fragment thereof under stringent conditions, e.g., hybridization to filter-bound DNA in 6× sodium chloride/sodium citrate (SSC) at about 45° C. followed by one or more washes in 0.2×SSC/ 0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

The present invention also encompasses polypeptides and fusion proteins that immunospecifically bind to an Eph receptor comprising of a variant Fc domain, fused to marker sequences, such as but not limited to, a peptide, to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

The present invention further encompasses polypeptides and fusion proteins that immunospecifically bind to an Eph receptor fused to a variant Fc further conjugated to a therapeutic moiety. A polypeptide or a fusion protein that immunospecifically binds to an Eph receptor may be conjugated to a therapeutic moiety such as a cytotoxin, e.g., a cytostatic or cytocidal agent, an agent which has a potential therapeutic benefit, or a radioactive metal ion, e.g., alpha-emitters. A cytotoxin or cytotoxic agent includes any agent that is detrimental to cells. Examples of a therapeutic moieties and cytotoxin or cytotoxic agents are listed supra (see section 6.3 entitled "Antibody Conjugates And Derivatives")

Polypeptides, proteins and fusion proteins can be produced by standard recombinant DNA techniques or by protein synthetic techniques, e.g., by use of a peptide synthesizer. For example, a nucleic acid molecule encoding a peptide, polypeptide, protein or a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al., eds., John Wiley & Sons, 1992). Moreover, a nucleic acid encoding a bioactive molecule can be cloned into an expression vector containing the variant Fc domain or a fragment thereof such that the bioactive molecule is linked in-frame to the variant Fc domain or variant Fc domain fragment.

Methods for fusing or conjugating polypeptides to the constant regions of antibodies are known in the art. See, e.g., U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; International Publication Nos. WO 91/06570, WO 96/04388, WO 96/22024, WO 97/34631, and WO 99/04813; Ashkenazi et al., 1991, Proc. Natl. Acad. Sci. USA 88: 10535-10539; Traunecker et al., 1988, Nature, 331:84-86; Zheng et al., 1995, J. Immunol. 154:5590-5600; and Vil et al., 1992, Proc. Natl. Acad. Sci. USA 89:11337-11341, which are incorporated herein by reference in their entireties.

The nucleotide sequences encoding a bioactive molecule and an Fc domain or fragment thereof may be obtained from any information available to those of skill in the art (i.e., from GenBank, the literature, or by routine cloning). The nucleotide sequences encoding Eph receptor ligands may be obtained from any available information, e.g., from GenBank, the literature or by routine cloning. See, e.g., FIG. 3. The nucleotide sequence coding for a polypeptide a fusion protein can be inserted into an appropriate expression vector, i.e., a vector that contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

6.6 Recombinant Expression of Antibodies and Fusion Proteins

Recombinant expression of an Fc variant or fusion protein comprising a variant Fc domain (referred to herein as an "variant Fc fusion protein", or "variant Fc fusion"), derivative, analog or fragment thereof, (e.g., a heavy or light chain of an antibody of the invention or a portion thereof or a single chain antibody of the invention), requires construction of an expression vector containing a polynucleotide that encodes the antibody, or fusion protein. Once a polynucleotide encoding an antibody molecule or a heavy or light chain of an antibody, or fusion protein of the invention has been obtained, the vector for the production of the antibody or fusion protein molecule may be produced by recombinant DNA technology using techniques well known in the art. Thus, methods for preparing a protein by expressing a polynucleotide containing an antibody or fusion protein encoding nucleotide sequence are described herein. Methods that are well known to those skilled in the art can be used to construct expression vectors containing antibody or fusion protein coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an Fc variant or variant Fc fusion of the invention, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody, or a polypeptide for generating a variant Fc fusion may be cloned into such a vector for expression of the full length antibody chain (e.g. heavy or light chain), or complete variant Fc fusion protein.

The expression vector is transferred to a host cell by conventional techniques and the transfected cells are then cultured by conventional techniques to produce an Fc variant or variant Fc fusion protein of the invention. Thus, the invention includes host cells containing a polynucleotide encoding an Fc variant or variant Fc fusion protein of the invention or fragments thereof, or a heavy or light chain thereof, or portion thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody or fusion protein molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody or fusion protein molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody or fusion protein coding sequences; yeast (e.g., *Saccharomyces Pichia*) transformed with recombinant yeast expression vectors containing antibody or fusion protein coding sequences; insect cell systems infected with recombinant virus expression vectors (e.g., baculovirus) containing antibody or fusion protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody or fusion protein coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In one embodiment, bacterial cells such as *Escherichia coli*, and in another embodiment, eukaryotic cells, especially for the expression of whole recombinant antibody or fusion protein molecules, are used for the expression of a recombinant antibody or fusion protein molecules. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding antibodies or fusion protein that bind to an Eph receptor is regulated by a constitutive promoter, inducible promoter or tissue specific promoter.

In bacterial systems, a number of expression vectors may be advantageously selected depending upon the use intended for the antibody or fusion protein molecule being expressed. For example, when a large quantity of such a protein is to be produced, for the generation of pharmaceutical compositions of an antibody or fusion protein molecule, vectors that direct the expression of high levels of fusion protein products that are readily purified may be desirable. Such vectors include, but are not limited to, the *E. coli* expression vector pUR278 (Ruther et al., 1983, EMBO 12:1791), in which the antibody or fusion protein coding sequence may be ligated individually into the vector in frame with the lac Z coding region so that a lac Z-fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody or fusion protein coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody or fusion protein coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody or fusion protein molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

The expression of an antibody or a fusion protein may be controlled by any promoter or enhancer element known in the art. Promoters which may be used to control the expression of the gene encoding an antibody or fusion protein include, but are not limited to, the SV40 early promoter region (Bernoist and Chambon, 1981, Nature 290:304-310), the promoter contained in the 3' long terminal repeat of *Rous sarcoma* virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Omitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

Expression vectors containing inserts of a gene encoding an antibody or fusion protein can be identified by three general approaches: (a) nucleic acid hybridization, (b) presence or absence of "marker" gene functions, and (c) expression of inserted sequences. In the first approach, the presence of a gene encoding a peptide, polypeptide, protein or a fusion protein in an expression vector can be detected by nucleic acid hybridization using probes comprising sequences that are homologous to an inserted gene encoding the peptide, polypeptide, protein or the fusion protein, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding an antibody or fusion protein in the vector. For example, if the nucleotide sequence encoding the antibody or fusion protein is inserted within the marker gene sequence of the vector, recombinants containing the gene encoding the antibody or fusion protein insert can be identified by the absence of the marker gene function. In the third approach, recombinant expression vectors can be identified by assaying the gene product (e.g., antibody or fusion protein) expressed by the recombinant. Such assays can be based, for example, on the physical or functional properties of the fusion protein in in vitro assay systems, e.g., binding with anti-bioactive molecule antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product may be used. Such mammalian host cells include, but are not limited to, CHO, VERY, BHK, Hela, COS, MDCK, 293, 3T3, WI38, NS0, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N-SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In vitro Cell. Dev. Biol. 28A: 609-614), IMR-32 human neuroblastoma (Cancer Res., 1970, 30: 2110-2118), 1321N1 human astrocytoma (Proc. Natl Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant proteins, stable expression is often preferred. For example, cell lines which stably express an antibody or fusion protein may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express an Fc variant or variant Fc fusion protein that specifically binds to an Eph receptor. Such engineered cell lines may be particularly useful in screening and evaluation of compounds that affect the activity of a polypeptide or a fusion protein that immunospecifically binds to an Eph receptor.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Once a peptide, polypeptide, protein or a fusion protein of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

The expression levels of an antibody or fusion protein molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an antibody or fusion protein is amplifiable, increase in the level of inhibitor present in culture of host cell will increase the number of copies of the marker gene. Since the amplified region is associated with the antibody gene, production of the antibody or fusion protein will also increase (Crouse et al., 1983, Mol. Cell. Biol. 3:257).

The host cell may be co-transfected with two expression vectors of the invention. For example, the first vector encoding a heavy chain derived polypeptide and the second vector encoding a light chain derived polypeptide. The two vectors may contain identical selectable markers, which enable equal expression of heavy and light chain polypeptides. Alternatively, a single vector may be used which encodes, and is capable of expressing, a fusion protein or both heavy and light chain polypeptides. The coding sequences for the fusion protein or heavy and light chains may comprise cDNA or genomic DNA.

6.7 Antagonists of an Eph Receptor

The invention specifically encompasses Fc variants, or variant Fc fusions, of the invention that are antagonists of at least one Eph receptor. The terms "antagonist" and "antagonists" when used herein refers to a to any protein, polypeptide, peptide, peptidomimetic, glycoprotein, antibody, antibody fragment, carbohydrate, nucleic acid, organic molecule, inorganic molecule, large molecule, or small molecule that blocks, inhibits, reduces or neutralizes the function, activity and/or expression of a target molecule, such as an Eph receptor. In various embodiments, an antagonist reduces the function, activity and/or expression of another molecule by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS). More specifically, an antagonist of at least one Eph receptor inhibits, reduces or neutralizes the function, activity and/or expression of at least one Eph receptor or inhibits or reduces at least one Eph receptor-mediated pathology.

Antagonists may act by interfering with the binding of a receptor to a ligand and vice versa, by incapacitating or killing cells which have been activated by a ligand, and/or by interfering with receptor or ligand activation (e.g. tyrosine kinase activation) or signal transduction after ligand binding to a cellular receptor. The antagonist may completely block receptor-ligand interactions or may substantially reduce such interactions. All such points of intervention by an antagonist shall be considered equivalent for purposes of this invention. Thus, included within the scope of the invention are antagonists (e.g. Fc variants and/or variant Fc fusion proteins (infra)) that bind to Eph receptor, Eph ligand or a complex of an Eph receptor and Eph ligand; soluble Eph receptor or soluble Eph ligand fused to a variant Fc region of the invention, as well as synthetic or native sequence peptides which bind to Eph receptor or Eph ligand fused to a variant Fc region of the invention. In addition, an Eph receptor "antagonist" herein includes, but is not limited to antibodies that antagonize at least one Eph receptor and also inhibit cancer cell phenotype (e.g., colony formation in soft agar or tubular network formation in a three-dimensional basement membrane or extracellular matrix preparation). An Eph receptor antagonist may or may not preferentially bind an Eph epitope that is exposed in a cancer cell relative to a non-cancer cell and may or may not have a low $K_{off}$ rate.

The invention also provides methods for screening for antagonists of an Eph receptor. Said screening methods include but are not limited to assays that monitor Eph receptor activity (e.g., phosphorylation of the Eph receptor, degradation of the Eph receptor protein and downstream Eph receptor mediated signaling events), ligand binding and/or plasma concentration. These and additional methods are further described infra (see section 6.9 entitled "Biological Assays") and in PCT Publication Nos. WO 03/094859, WO 04/014292, WO 04/069264, WO 04/028551, WO 03/004057, U.S. Pat. No. 5,795,734 and U.S. patent application Ser. Nos. 10/863, 729, 10/770,543; each of which is incorporated herein by reference in their entireties. In addition, the invention provides for a method to manipulate both the ADCC activity and the binding affinities for FcγR of antibodies identified using such screening methods.

The Fc of antibodies identified from such screening methods can be substituted as described supra to alter ADCC and/or CDC activity and to modify binding affinities for one or more Fc ligand (e.g., FcγRs, C1q).). Other antagonistic binding molecules (e.g., Eph receptor ligands and variants thereof) identified from such screening methods can be fused to a variant Fc domain of the invention. It is further contemplated that the Fc variants of the newly identified Eph receptor antagonistic antibodies and variant Fc fusions of the newly identified Eph receptor antagonists are useful for the prevention, management and treatment of Eph receptor—mediated and/or associated diseases and disorders, including but not limited to inflammatory diseases, autoimmune diseases, bone metabolism related disorders, angiogenic related disorders, disorders related to aberrant expression and/or activity of an Eph receptor, and cancer. Such Fc variants and/or variant Fc fusions can be used in the methods and formulations of the present invention.

6.8 Antibody Agonists of an Eph Receptor

An "agonist" herein refers to any protein, polypeptide, peptide, peptidomimetic, glycoprotein, antibody, antibody fragment, carbohydrate, nucleic acid, organic molecule, inorganic molecule, large molecule, or small molecule which is capable of activating one or more of the biological activities of a target molecule, such as an Eph receptor. In various embodiments, an agonist activates the function, activity and/or expression of another molecule by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS). In further various embodiments, an agonist activates the function, activity and/or expression of another molecule by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or at least about 99% relative to a control such as phosphate buffered saline (PBS). More specifically, an agonist of at least one Eph receptor activates the function, activity and/or expression of at least one Eph receptor. It is specifically contemplated that the action of agonizing at least one Eph receptor will result in the inhibition or reduction in at least one Eph receptor-mediated pathology.

Agonists may, for example, act by activating a target molecule and/or mediating signal transduction. Included within the scope of the invention are Fc variants and/or variant Fc fusion proteins (infra) that bind to and activate the Eph receptor, Eph ligand or a complex of an Eph receptor and Eph ligand; soluble Eph receptor or soluble Eph ligand fused to a variant Fc region of the invention which activate the Eph receptor, as well as synthetic or native sequence peptides, Eph receptor or Eph ligand fused to a variant Fc region of the invention that bind to and activate the Eph receptor, Eph ligand or a complex of Eph receptor and Eph ligand.

In addition, an Eph receptor "agonist" herein includes, but is not limited to antibodies that agonize at least one Eph receptor and also inhibit cancer cell phenotype (e.g., colony formation in soft agar or tubular network formation in a three-dimensional basement membrane or extracellular matrix preparation). An Eph receptor agonist may or may not preferentially bind an Eph epitope that is exposed in a cancer cell relative to a non-cancer cell and may or may not have a low $K_{off}$ rate.

Thus, in one embodiment, the Eph antibodies (and Fc variants thereof) of the invention agonize Eph receptor (e.g., Epha2 and/or Epha4) signaling and increase phosphorylation of an Eph receptor and/or the Eph-associated polypeptides.

The invention also provides methods for screening for antibody agonists of an Eph receptor. Said screening methods include but are not limited to assays that monitor Eph receptor activity (e.g., phosphorylation of the Eph receptor, degradation of the Eph receptor protein and downstream Eph receptor mediated signaling events), ligand binding and/or plasma concentration. These and additional methods are further described infra (see section 6.9 entitled "Biological Assays") and in PCT Publication Nos. WO 03/094859, WO 04/014292, WO 04/069264, WO 04/028551, WO 03/004057, U.S. Pat. No. 5,795,734 and U.S. patent application Ser. Nos. 10/863,729, 10/770,543; each of which is incorporated herein by reference in their entireties. In addition, the present invention provides for a method to manipulate both the ADCC activity and the binding affinities for FcγR of antibodies identified using such screening methods.

The Fc of antibodies identified from such screening methods can be substituted as described supra to alter ADCC and/or CDC activity and to modify binding affinities for one or more Fc ligand (e.g., FcγRs, C1q). Other agonistic binding molecules (e.g., Eph receptor ligands and variants thereof) identified from such screening methods can be fused to a variant Fc domain of the invention. It is further contemplated that the Fc variants of the newly identified Eph receptor agonistic antibodies and variant Fc fusions of the newly identified Eph receptor agonists are useful for the prevention, management and treatment of Eph receptor—mediated and/or associated diseases and disorders, including but not limited to inflammatory diseases, autoimmune diseases, bone metabolism related disorders, angiogenic related disorders, disorders related to aberrant expression and/or activity of an Eph receptor, and cancer. Such Fc variants and/or variant Fc fusions can be used in the methods and formulations of the present invention.

6.9 Biological Assays

The antagonistic and/or agonistic effect of one or more Fc variant, or variant Fc fusion protein of the invention on an Eph receptor activity can be determined by any method known in the art. Methods include but are not limited to those described infra and in PCT publications WO 04/014292, WO 03/094859, WO 04/069264, WO 04/028551, WO 03/004057, WO 03/040304, U.S. Pat. No. 5,795,734 and U.S. patent application Ser. Nos. 10/770,543, and 10/863,729; each of which are incorporated herein by reference in their entireties. For example, the blockage of an Eph receptor activity and/or the plasma concentration of an Eph receptor can be assayed by any technique known in the art that measures the activity and/or expression of an Eph receptor, including but not limited to, Western blot, Northern blot, RNase protection assays, enzymatic activity assays, in situ hybridization, immunohistochemistry, and immunocytochemistry. More specifically, the activity of an Fc variant or variant Fc fusion protein can be determined by measuring binding to an Eph receptor and its cross-reactivity to other Eph receptors, inhibition or stimulation of Eph receptor phosphorylation, Eph receptor degradation, Eph receptor ligand (e.g., Ephrin) binding.

The binding specificity, affinity and functional activity of an Fc variant, or variant Fc fusion protein of the invention can be characterized in various in vitro binding and cell adhesion assays known in the art, including but not limited to, ELISA, Western Blot analysis, cell surface staining, inhibition of ligand-receptor interactions, flow cytometric analysis and those disclosed in International Publication Nos. WO 04/014292, WO 03/094859, WO 04/069264, WO 04/028551, WO 03/004057, WO 03/040304, WO 00/78815, WO 02/070007 and WO 03/075957, U.S. Pat. Nos. 5,795,734, 6,248,326 and 6,472,403 and U.S. patent application Ser. Nos. 10/770,543, and 10/863,729, Pecheur et al., 2002, FASEB J. 16(10): 1266-1268; Almed et al., The Journal of Histochemistry & Cytochemistry 50:1371-1379 (2002), all of which are incorporated herein by reference. For example, the binding affinity, specificity and the off-rate of an Fc variant and/or variant Fc fusion protein can be determined by a competitive binding assay with the parental anti-Eph receptor antibody, by measuring the inhibitory activity of an Fc variant, or variant Fc fusion protein of the invention on an Eph receptor binding to Ephrin. One example of a competitive binding assay is a radioimmunoassay comprising the incubation of labeled Eph receptor (e.g., 3H or 125I) with the Fc variant of interest in the presence of increasing amounts of unlabeled Eph receptor, and the detection of the monoclonal antibody bound to the labeled Eph receptor. The affinity of an Fc variant for an Eph receptor and the binding off-rates can be determined from the data by scatchard plot analysis. Competition with a second antibody can also be determined using radioimmunoassays. In this case, an Eph receptor is incubated with an Fc variant conjugated to a labeled compound (e.g., 3H or 125I) in the presence of increasing amounts of a second unlabeled monoclonal antibody.

The kinetic parameters of an Fc variant, or variant Fc fusion protein may also be determined using any surface plasmon resonance (SPR) based assays known in the art. For a review of SPR-based technology see Mullet et al., 2000, Methods 22: 77-91; Dong et al., 2002, Review in *Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entirety.

The binding specificity of an Fc variant, or variant Fc fusion protein of the invention to an Eph receptor can be assessed by any method known in the art including but not limited to, measuring binding to an Eph receptor and its crossreactivity to other Eph receptors. In addition, binding affinity and specificity can be determined by a competitive binding assay with the parental anti-Eph receptor antibody against an Eph receptor or by measuring the inhibitory activity of an Fc variant, or variant Fc fusion protein of the invention on Eph receptor binding to its ligand, Ephrin.

The inhibitory, antagonistic and/or agonistic activity of an Fc variant, or variant Fc fusion protein of the invention can be tested by numerous assays known to one skilled in the art including but not limited to, phosphorylation assays (Koolpe et al., 2002, J Biol Chem 277:46974 and Gu et al., 2001, Mol Cell Biol 21:4579), cell adhesion (Lawrenson et al., 2002, J Cell Sci 115:1059 and Davy et al., 2000, EMBO 19:5396), endothelial cell migration assays such as the transwell cell migration assay (Choi et al., 1994, J Vascular Sur 19:125-134 and Leavesly et al., 1993, J Cell Biol 121:163-170) and cell rounding assays (Miao et al., 2000, Nature Cell. Bio. 2:62) signal transduction assays (Sharfe et al., 2002, Eur J Immunol 32:3745; Zou et al., 1999, PNAS U.S.A. 96:13813) (all of which are incorporated herein by reference in their entirety). The ability of an Fc variant, or variant Fc fusion protein of the invention to inhibit a cancer cell phenotype can be determined by in vitro assays including, but not limited to, colony formation in soft agar, tubular network formation in a three-dimensional basement membrane or extracellular matrix preparation such as MATRIGEL™.

Phosphorylation/degradation assays can be performed as described in U.S. Pat. No. 5,766,863 and PCT Publication Nos. WO 03/094859, WO 04/014292, and WO 04/069264 (all of which are incorporated herein by reference in their entirety). Briefly, cells are incubated in the presence of an Fc variant and/or variant Fc fusion protein or control molecule for at least 15 minutes at 37° C. Cell lysates are then immunoprecipitated with an appropriate anti-Eph antibody (e.g., anti-Eph receptor antibodies are available from commercial sources including Santa Cruz Biotechnology, Inc; Santa Cruz Calif.) resolved by SDS-PAGE, and subjected to western blot analysis with a cocktail of the anti-phosphotyrosine antibodies 4G10 (Upstate Biotechnology; Lake Placid N.Y.) and PY20 (BD Transduction Laboratories; Franklin Lakes, N.J.). Increased Eph receptor phosphorylation following treatment with Fc variant and/or variant Fc fusion protein, indicates that the Fc variant and/or variant Fc fusion protein agonize the Eph receptor and likely promote auto-phosphorylation, while a decrease in phosphorylation is consistent with antagonistic activity of an Fc variant and/or variant Fc fusion protein. Western blot Western blot analyses and immunoprecipitations are performed as described previously (Zantek et al., 1999, Cell Growth Diff. 10:629, which is incorporated by reference in its entirety). Briefly, detergent extracts of cell monolayers are extracted in Tris-buffered saline containing 1% Triton X-100 (Sigma, St. Louis, Mo.). After measuring protein concentrations (BioRad, Hercules, Calif.), 1.5 mg of cell lysate is immunoprecipitated, resolved by SDS-PAGE and transferred to nitrocellulose (PROTRAN™, Schleicher and Schuell, Keene, N.H.). Antibody binding is detected by enhanced chemiluminescence (Pierce, Rockford, Ill.) and autoradiography (Kodak X-OMAT; Rochester, N.Y.).

Cell adhesion and cell rounding assays can also be performed as described in Miao, et al. (Nature Cell Biol. 2:62, 2000), which is incorporated by reference herein in its entirety. To study cell adhesion, briefly, cells are plated in triplicate onto 96-well plates previously coated with various ECM proteins or poly-L-lysine. Cells are plated at a density of $1 \times 10^5$ cells per well in the presence or absence of an Fc variant and/or variant Fc fusion protein and allowed to adhere for 30 minutes at 37° C. Non-adherent cells are washed from the wells, and adherent cells are fixed, stained, and quantified by measuring absorbance on an enzyme-linked immunosorbent assay (ELISA) reader. Cells treated with an Fc variant and/or variant Fc fusion protein show decreases in attachment to ECM protein-treated wells relative to control cells allowed to adhere in the absence of and Fc variant or variant Fc fusion protein of the invention.

For cell rounding assays, briefly, cells are plated onto ECM protein coated six-well dishes, or ECM protein-coated coverslips in 24-well dishes. Cells are allowed to adhere for 48 hours, then treated with media with or without an Fc variant and/or variant Fc fusion protein for 10 minutes. Plates or coverslips are washed, fixed and stained and visualized by microscopy. Cells treated with an Fc variant and/or variant Fc fusion protein show cell rounding relative to cells treated with media lacking an Fc variant and/or variant Fc fusion protein, indicating decreased attachment to the ECM matrix.

The ability of the antibodies of the invention to inhibit cancer cell formation in soft agar may be assayed (such assays may be carried out, e.g., as described in Zelinski et al., 2001, Cancer Res. 61:2301, incorporated by reference herein in its entirety). Briefly, cells are suspended in soft agar for 7 days at 37° C. in the presence of an Fc variant and/or variant Fc fusion protein or control solution (PBS). Following incubation with an Fc variant and/or variant Fc fusion protein or PBS, cells are washed and incubated with either an anti-Fc variant and/or anti-variant Fc fusion protein secondary monoclonal antibody (secondary mab) or PBS. Colony formation is scored microscopically. Clusters containing at least three cells are scored as a positive.

Tumor cell behavior within a three-dimensional microenvironment, such as MATRIGEL™, can reliably predict the differentiation state and aggressiveness of breast epithelial cells. Monolayer cultures of benign (MCF-10A) or malignant (MDA-MB-231) breast epithelial cells are incubated on MATRIGEL™ in the presence of an Fc variant and/or variant Fc fusion protein or control solution (PBS). The behavior of cells on MATRIGEL™ is analyzed as described in Zelinski et al. (2001, Cancer Res. 61:2301). Briefly, tissue culture dishes are coated with MATRIGEL™ (Collaborative Biomedical Products, Bedford, Mass.) at 37° C. before adding $1 \times 10^5$ MDA-MB-231 or MCF-10A cells previously incubated on ice for 1 hour with the Fc variant and/or variant Fc fusion protein or control solution (PBS). Cells are incubated on MATRIGEL™ for 24 hours at 37° C., and cell behavior is assessed using an Olympus IX-70 inverted light microscope. All images are recorded onto 35 mm film (T-Max-400. Kodak, Rochester, N.Y.).

Additional examples of in vitro assays, e.g., Western blotting analysis, flow cytometric analysis, cell adhesion assay to cortical bone and extracellular matrix proteins, cell migration assay, cell invasion assay, and cell proliferation assay, can be found in Pecheur et al., 2002, FASEB J. 16(10): 1266-1268, of which the entire text is incorporated herein by reference.

The anti-cancer activity of an Fc variant, or variant Fc fusion protein of the invention can be determined by using various experimental animal models for the study of cancer such as the scid mouse model or transgenic mice where a mouse Eph receptor is replaced with the human Eph receptor, nude mice with human xenografts, animal models such as hamsters, rabbits, etc. known in the art and described in Relevance of Tumor Models for Anticancer Drug Development (1999, eds. Fiebig and Burger); Contributions to Oncology (1999, Karger); The Nude Mouse in Oncology Research (1991, eds. Boven and Winograd); and Anticancer Drug Development Guide (1997 ed. Teicher), herein incorporated by reference in their entireties. For example the ability of the Fc variants an/or variant Fc fusion proteins of the invention to inhibit tumor cancer growth in vivo can be assayed as follows, MDA-MB-231 breast cancer cells are implanted subcutaneously into athymic mice. After the tumors have grown to an average volume of 100 mm3, mice are administered an Fc variant an/or variant Fc fusion protein or PBS control intraperitoneally twice a week for 3 weeks. Tumor growth is assessed and expressed as a ratio of the tumor volume divided by initial tumor volume (100 mm3). Tumor growth is allowed to proceed until tumor volume reaches 1000 mm3. Survival of the mice is assessed by scoring the percent of mice living each day post treatment. Similarly, animal models of colon cancer can be generated by passaging colon cancer cells in animals, e.g., nude mice, leading to the appearance of tumors in these animals. An orthotopic transplant model of human colon cancer in nude mice has been described, for example, by Wang et al., 1994, Cancer Research, 54: 4726 and Too et al., 1995, Cancer Research, 55: 681. This model is based on the so-called "METAMOUS5'" sold by AntiCancer, Inc., (San Diego, Calif.).

Various animal models known in the art that are relevant to a targeted disease or disorder, e.g., inflammatory diseases, autoimmune diseases, diseases or disorders associated with aberrant bone metabolism and/or aberrant angiogenesis, cancers, disorders associated with aberrant Eph receptor expression and/or activity can be used, including but not limited to, growth factor or tumor-induced angiogenesis in the chick chorioallantoic membrane (CAM) (see, e.g., Ausprunk et al. (1980) *Am. J. Pathol.*, 79:597-618; Ossonski et al. (1975) *Cancer Res.*, 40:2300-2309; Brooks et al. (1994) *Science*, 264:569-571 and Brooks et al., (1994), *Cell*, 79:1157-1164), V×2 carcinoma cells in rabbits (see, e.g., Voelkel et al., (1975) *Metabolism* 24:973-86), tumors induced in BALB/c nu/nu mice and SCID mice with subcutaneously implanted human bone fragments (SCID-human-bone model). Additional examples of tumor models can be found in Teicher et al., Tumor Models in Cancer Research, (Humana Press, Totowa, N.J., 2001).

The protocols and formualations of the invention are preferably tested in vitro, and then in vivo, for the desired therapeutic or prophylactic activity, prior to use in humans. For example, in vitro assays which can be used to determine whether administration of a specific therapeutic protocol formulation or combination therapy of the invention is indicated, include in vitro cell culture assays in which a patient tissue sample is grown in culture, and exposed to or otherwise contacted with a formulation of the invention, and the effect of such a formulation upon the tissue sample is observed. The tissue sample can be obtained by biopsy from the patient. This test allows the identification of the therapeutically most effective prophylactic or therapeutic agent(s) for each individual patient. In various specific embodiments, in vitro assays can be carried out with representative cells of cell types involved in an autoimmune disorder, an inflammatory disorder, a disorder associated with aberrant expression and/or activity of at least one Eph receptor, to determine if a formulation of the invention has a desired effect upon such cell types. A lower level of proliferation or survival of the contacted cells indicates that the composition of the invention is effective to treat the condition in the patient. Alternatively, instead of culturing cells from a patient, a formulation of the invention may be screened using cells of a tumor or malignant cell line, osteoclasts, endothelial cells or an endothelial cell line. Many assays standard in the art can be used to assess such survival and/or growth; for example, cell proliferation can be assayed by measuring 3H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

Prophylactic or therapeutic agents can be tested in suitable animal model systems prior to testing in humans, including but not limited to in rats, mice, chicken, cows, monkeys, rabbits, hamsters, etc.

The principle animal models for known in the art and widely used are known and described in the art as described above.

Further, any assays known to those skilled in the art can be used to evaluate the prophylactic and/or therapeutic utility of the combinatorial therapies disclosed herein for treatment or prevention of cancer.

6.10 Prophylactic and Therapeutic Uses

As discussed above, agents that immunospecifically bind an Eph receptor can be utilized for the inhibition of angiogenesis or the inhibition of other functions mediated or influenced by an Eph receptor, including but not limited to cell proliferation, cell attachment, cell migration, granulation tissue development, and/or inflammation. Accordingly, the present invention relates to the use of agents that immunospecifically bind and preferably modulate the activity of at least one Eph receptor for the prevention, management, treatment or amelioration of cancer or one or more symptoms thereof and/or the inhibition of angiogenesis.

Angiogenesis, also called neovascularization, is the process where new blood vessels form from pre-existing vessels within a tissue. As described above, Eph receptors are believed to play a role in this process this process. There are a variety of pathological conditions that require new blood vessel formation or tissue angiogenesis and inhibition of this process inhibits the pathological condition. As such, pathological conditions that require angiogenesis for growth or maintenance may be considered to be Eph receptor-mediated diseases. The extent of treatment, or reduction in severity, of these diseases will therefore depend on the extent of inhibition of angiogenesis. These Eph receptor-mediated diseases include, for example, inflammatory disorders such as immune and non-immune inflammation, thrombosis, acute ischemic stroke, chronic articular rheumatism, psoriasis, disorders associated with inappropriate or inopportune invasion of vessels such as diabetic retinopathy, neovascular glaucoma and capillary proliferation in atherosclerotic plaques as well as cancer disorders.

Such cancer disorders can include, for example, solid tumors, tumor metastasis, angiofibromas, angiosarcomas, retrolental, fibroplasia, hemangiomas, Kaposi's sarcoma, carcinomas, carcinosarcomas, and other cancers which require neovascularization to support tumor growth. Additional diseases which are considered angiogenic include psoriasis and rheumatoid arthritis as well as retinal diseases such as macular degeneration.

Further examples of such cancers include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and ciliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoid-cystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

Accordingly, the present invention relates to the use of agents that immunospecifically bind and preferably modulate at least one Eph receptor activity for the prevention, management, treatment or amelioration of cancer, solid tumor metastasis, as well as, inflammatory diseases such as rheumatoid arthritis and psoriasis or one or more symptoms thereof and/or the inhibition of angiogenesis or conditions associated therewith In one embodiment, the methods and formulations of the invention are used for inhibiting angiogenesis. In a specific embodiment, the methods and formulations of the invention are used for inhibiting angiogenesis in a solid tumor. In another embodiment, the methods and formulations of the invention are used for inhibiting angiogenesis in an inflamed, angiogenic tissue including but not limited to retinal tissues and joint tissues.

Further, the present invention provides Fc variants that immunospecifically bind and preferably inhibit an Eph receptor which are useful for therapeutic purposes, more specifically, for the treatment, prevention, management or amelioration of cancer. Specific examples of cancers that can be prevented, managed, treated or ameliorated in accordance with the invention include, but are not limited to, cancer of the head, neck, eye, mouth, throat, esophagus, chest, bone, lung, colon, rectum, colorectal or other gastrointestinal tract organs, stomach, spleen, renal, skeletal muscle, subcutaneous tissue, metastatic melanoma, endometrial, prostate, breast, ovaries, testicles or other reproductive organs, skin, thyroid, blood, lymph nodes, kidney, liver, pancreas, and brain or central nervous system.

In a specific embodiment, the methods and formulations of the invention are used for the prevention, management, treatment or amelioration of a primary or secondary cancer that expresses an Eph receptor. In another embodiment, the methods and formulations of the invention are used for the prevention, management, treatment or amelioration of a primary or secondary cancer that does not express an Eph receptor. In a preferred embodiment, the methods and formulations are used for the prevention, management, treatment or amelioration of a cancer that has the potential to metastasize or has metastasized to other tissues or organs (e.g., bone). In another preferred embodiment, the methods and formulations of the invention are used for the prevention, management, treatment or amelioration of lung cancer, prostate cancer, ovarian cancer, melanoma, bone cancer or breast cancer. Methods using agents that immunospecifically inhibit an Eph receptor include but are not limited to those disclosed in PCT publications WO 03/094859 and WO 04/014292 and U.S. application Ser. No. 10/863,729, each of which is herein incorporated by reference in its entirety.

The invention provides methods for screening for antibody and other antagonists and agonists of an Eph receptor. Further, the invention provides for a method to manipulate the ADCC and/or CDC activity and the binding affinities for one or more Fc ligand (e.g., FcγR, C1q) of the antibodies and/or other antagonists or agonists identified using such screening methods. The Eph receptor antagonists and agonists identified and manipulated utilizing such methods can be used for the prevention, treatment, management or amelioration of Eph receptor-mediated and/or associated diseases and disorders or one or more symptoms thereof, including but not limited to cancer, inflammatory and autoimmune diseases either alone or in combination with other therapies.

The invention also provides variant Fc fusion proteins that immunospecifically bind to an Eph receptor. Said variant Fc fusion proteins can be used for the prevention, treatment, management or amelioration of Eph receptor-mediated and/or associated diseases and disorders or one or more symptoms thereof, including but not limited to cancer, inflammatory and autoimmune diseases either alone or in combination with other therapies.

In a specific embodiment, Fc variants and/or Fc variant fusion proteins of the invention that immunospecifically bind to an Eph receptor are used for the prevention, management, treatment or amelioration of cancer or one or more symptoms thereof. In a preferred embodiment, Fc variant antibodies and/or Fc variant fusion proteins of the invention used for the prevention, management, treatment or amelioration of cancer or one or more symptoms thereof are antagonists of an Eph receptor.

The invention also encompasses the use of Fc variants and/or variant Fc fusion proteins with modified binding affinity to one or more Fc ligand (e.g., FcγRs, C1q) and altered ADCC and/or CDC activity that immunospecifically bind to an Eph receptor conjugated or fused to a moiety (e.g., therapeutic agent or drug) for prevention, treatment, management or amelioration of Integrin $\alpha_v\beta_3$-mediated diseases and disorders or one or more symptoms thereof, including but not limited to cancer, inflammatory and autoimmune diseases. The invention further encompasses treatment protocols that enhance the prophylactic or therapeutic effect of said Fc variants and/or variant Fc fusion proteins.

The invention provides methods for preventing, managing, treating or ameliorating cancer that has the potential to metastasize or has metastasized to an organ or tissue (e.g., bone) or one or more symptoms thereof, said methods comprising administering to a subject in need thereof one or more doses of a prophylactically or therapeutically amount of one or more Fc variants and/or variant Fc fusion protein of the invention.

The invention provides methods for preventing, managing, treating or ameliorating cancer or one or more symptoms thereof, said methods comprising administering to a subject in need thereof one or more doses of a prophylactically or therapeutically effective amount of one or more Fc variants and/or variant Fc fusion protein with modified binding affinity to one or more Fc ligand (e.g., FcγRs, C1q) and altered ADCC and/or CDC activity fused or conjugated to a moiety (e.g., a therapeutic agent or drug). Examples of a moiety that an Fc variant can be fused or conjugated to include, but are not limited to those disclosed in PCT publication WO 2003/075957 which is herein incorporated by reference in its entirety. Examples of Fc variants and variant Fc fusion proteins with modified binding affinity to one or more Fc ligand (e.g., FcγRs, C1q) and altered ADCC and/or CDC activity include, but are not limited to, those variants disclosed supra.

The present invention encompasses protocols for the prevention, management, treatment or amelioration of Ep receptor-mediated diseases and disorders or one or more symptoms thereof, including but not limited to, cancer, inflammatory and autoimmune diseases or one or more symptoms thereof in which one or more Fc variants and/or variant Fc fusion protein with modified binding affinity to one or more Fc ligand (e.g., FcγRs, C1q) and altered ADCC and/or CDC activity that immunospecifically binds to an Eph receptor is used in combination with the administration of a dosage of a prophylactically or therapeutically effective amount of one or more other therapies other than an Fc variant and/or variant fusion protein. The invention is based, in part, on the recognition that the Fc variants and/or variant fusion proteins of the invention potentiate and synergize with, enhance the effectiveness of, improve the tolerance of, and/or reduce the side effects caused by, other therapies, including current standard and experimental chemotherapies. The combination therapies of the invention have additive potency, an additive therapeutic effect or a synergistic effect. The combination therapies of the invention enable lower dosages of the therapy (e.g., prophylactic or therapeutic agents) utilized in conjunction with Fc variants and/or variant Fc fusion proteins for the prevention, management, treatment or amelioration of Eph receptor-mediated diseases and disorders or one or more symptoms thereof, including but not limited to, cancer, inflammatory and autoimmune diseases and/or less frequent administration of such prophylactic or therapeutic agents to a subject with an Eph receptor-mediated diseases (e.g., cancer) to improve the quality of life of said subject and/or to achieve a prophylactic or therapeutic effect. Further, the combination therapies of the invention reduce or avoid unwanted or adverse side effects associated with the administration of current single agent therapies and/or existing combination therapies for diseases, such as cancer, which in turn improves patient compliance with the treatment protocol.

In one embodiment, the invention provides methods for preventing, managing, treating or ameliorating an Eph receptor-mediated disease (e.g., cancer) or one or more symptoms thereof, said methods comprising administering to a subject in need thereof a dose of a prophylactically or therapeutically effective amount of an Fc variant and/or variant Fc fusion protein in combination with the administration of an Integrin antagonist, a standard or experimental chemotherapy, a hormonal therapy, a biological therapy/immunotherapy and/or a radiation therapy. In another embodiment, the invention provides methods for preventing, managing, treating or ameliorating an Eph receptor-mediated disease (e.g., cancer) or one or more symptoms thereof, said methods comprising administering to a subject in need thereof a dose of a prophylactically or therapeutically effective amount of an Fc variant and/or variant Fc fusion protein in combination with surgery, alone or in further combination with the administration of an Eph receptor antagonist and/or Eph receptor agonist, a standard or experimental chemotherapy, a hormonal therapy, a biological therapy/immunotherapy and/or a radiation therapy. In accordance with these embodiments, the Fc variant and/or variant Fc fusion protein utilized to prevent, manage, treat or ameliorate an Eph receptor-mediated disease (e.g., cancer) or one or more symptoms thereof may or may not be conjugated or fused to a moiety (e.g., therapeutic agent or drug) and said Fc variants and/or variant Fc fusion proteins are agonists or antagonists that immunospecifically bind to an Eph receptor.

Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices and nucleotide sequences encoding biologically active proteins, polypeptides or peptides), antibodies, synthetic or natural inorganic molecules, mimetic agents, and synthetic or natural organic molecules. Any agent which is known to be useful, or which has been used or is currently being used for the prevention, treatment or amelioration of Eph receptor-mediated disease or disorder including but not limited to cancer, inflammatory and autoimmune diseases or symptom associated therewith can be used in combination with an Fc variant and/or variant Fc fusion in accordance with the invention described herein.

Exemplary agents to be used in the combination therapies described supra include but are not limited to Integrin antagonists (e.g., RGD peptides and disintegrins), standard or experimental chemotherapy agents (e.g., doxorubicin, epirubicin, cyclophosphamide, 5-fluorouracil, taxanes such as docetaxel and paclitaxel, leucovorin, levamisole, irinotecan, estramustine, etoposide, vinblastine, dacarbazine, nitrosoureas such as carmustine and lomustine, vinca alkaloids, platinum compounds, cisplatin, mitomycin, vinorelbine, gemcitabine, carboplatin, hexamethylmelamine and/or topotecan), immunomodulatory agents (e.g., cytokines, antibodies, interleukins and hemapoietic factors), biological therapies/immunotherapies (e.g., tamoxifen, LHRH agonists, non-steroidal antiandrogens, steroidal antiandrogens, estrogens, aminoglutethimide, hydrocortisone, flutamide withdrawal, progesterone, ketoconazole, prednisone, interferon-alpha, interferon-beta, interferon-gamma, interleukin-2, tumor necrosis factor-alpha, and melphalan), anti-inflammatory agents (e.g., non-steroidal anti-inflammatory drugs (NSAIDs), steroidal anti-inflammatory drugs, beta-agonists, anticholingeric agents, and methyl xanthines), analgesics (e.g., NSAIDs, salicylates, acetominophen, narcotics, and non-narcotic and anxiolytic combinations). Additional agents and therapies and their dosages, routes of administration and recommended usage are known in the art and have been described in such literature as the *Physician's Desk Reference* ($57^{th}$ ed., 2003). Additional agents and other combination therapies are described in PCT applications WO 02/070007; WO 04/066956 WO 03/075741; and WO 03/075957 each of which are incorporated herein in their entireties.

Further exemplary agents to be used in the combination therapies described supra include but are not limited to Examples of anti-cancer agents that can be used in the various embodiments of the invention, including pharmaceutical compositions and dosage forms and kits of the invention, include, but are not limited to: acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decarbazine, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin 2 (including recombinant interleukin 2, or rIL2), interferon alpha 2a, interferon alpha 2b, interferon alpha n1, interferon alpha n3, interferon beta I a, interferon gamma I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nitrosoureas, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride. Other anti cancer drugs include, but are not limited to: 20 epi 1,25 dihydroxyvitamin D3, 5 ethynyluracil, abiraterone, aclarubicin, acylfulvene, adecypenol, adozelesin, aldesleukin, ALL TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti dorsalizing morphogenetic protein 1, antiandrogens, antiestrogens, antineoplaston, aphidicolin glycinate, apoptosis gene modulators, apoptosis regulators, apurinic acid, ara CDP DL PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL 2, capecitabine, carboxamide amino triazole, carboxyamidotriazole, CaRest M3, CARN 700, cartilage derived inhibitor, carzelesin, casein kinase inhibitors (ICOS), castanospermine, cecropin B, cetrorelix, chloroquinoxaline sulfonamide, cicaprost, cis porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro 5 azacytidine, dihydrotaxol, dioxamycin, diphenyl spiromustine, docetaxel, docosanol, dolasetron, doxifluridine, droloxifene, dronabinol, duocarmycin SA, ebselen, ecomustine, edelfosine, edrecolomab, eflornithine, elemene, emitefur, epirubicin, episteride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin like growth factor 1 receptor inhibitor, interferon agonists, interferons, interleukins, iobenguane, iododoxorubicin, ipomeanol, iroplact, irsogladine, isobengazole, isohomohalicondrin B, itasetron, jasplakinolide, kahalalide F, lamellarin N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor I based therapy, mustard anticancer agent, mycaperoxide B, mycobacterial cell wall extract, myriaporone, N acetyldinaline, N substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6 benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum triamine complex, porfimer sodium, porfiromycin, prednisone, propyl bis acridone, prostaglandin J2, proteasome inhibitors, protein A based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras GAP inhibitor, retelliptine demethylated, rhenium Re 186 etidronate, rhizoxin, ribozymes, RII retinamide, rogletimide, rohitukine, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, taxol, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thioguanine, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, and zinostatin stimalamer. Additional anti-cancer drugs are 5-fluorouracil and leucovorin.

The methods and formulations of the invention are useful in preventing, managing, treating or ameliorating cancers, including, but not limited to, cancer of the head, neck, eye, mouth, throat, esophagus, chest, bone, lung, colon, rectum, colorectal or other gastrointestinal tract organs, stomach, spleen, renal, skeletal muscle, subcutaneous tissue, metastatic melanoma, endometrial, prostate, breast, ovaries, testicles or other reproductive organs, skin, thyroid, blood, lymph nodes, kidney, liver, pancreas, and brain or central nervous system. In a specific embodiment, the methods and formulations of the invention are used for the prevention, management, treatment or amelioration of a primary or secondary cancer that expresses an Eph receptor. In another embodiment, the methods and formulations of the invention are used for the prevention, management, treatment or amelioration of a primary or secondary cancer that does not express an Eph receptor.

The methods and formulations of the invention are useful not only in untreated cancer patients but are also useful in the management or treatment of cancer patients partially or completely refractory to current standard and experimental cancer therapies, including, but not limited to, chemotherapies, hormonal therapies, biological therapies, radiation therapies, and/or surgery.

6.11 Formulations and Administration

As described above, the present invention relates to the use of agents that immunospecifically bind and preferably inhibit one or more Eph receptor activity for the prevention, management, treatment or amelioration of an Eph receptor-mediated disease (e.g., cancer) or one or more symptoms thereof and/or the inhibition of angiogenesis. Accordingly, the present invention provides formulations (e.g., a pharmaceutical composition) comprising one or more Fc variants and/or variant Fc fusion protein with modified binding affinity to one or more Fc ligand (e.g., FcγRs, C1q) and altered ADCC and/or CDC activity that immunospecifically bind to an Eph receptor (also referred to herein as "formulation(s) of the invention" or simply "formulation(s)"). In a specific embodiment, said Fc variants and/or Fc variant fusions are antagonists of one or more Eph receptor. In another specific embodiment, said Fc variants and/or Fc variant fusions are agonists of one or more Eph receptor.

In one embodiment, formulations (e.g., a pharmaceutical composition) comprising one or more Fc variants and/or Fc variant fusions are liquid formulations (referred to herein as "liquid formulation(s)" which are specifically encompassed by the more generic terms "formulation(s) of the invention" and "formulation(s)"). In a specific embodiment, the liquid formulations are substantially free of surfactant and/or inorganic salts. In another specific embodiment, the liquid formulations have a pH ranging from about 5.0 to about 7.0, about 5.5 to about 6.5, about 5.8 to about 6.2, and about 6.0. In a further specific embodiment, the liquid formulations have a pH ranging from 5.0 to 7.0, 5.5 to about 6.5, 5.8 to 6.2, and 6.0. In yet another specific embodiment, the liquid formulations comprise histidine at a concentration ranging from about 1 mM to about 100 mM, from about 5 mM to about 50 mM, about 10 mM to about 25 mM. In still another specific embodiment, the liquid formulations comprise histidine at a concentration ranging from 1 mM to 100 mM, from 5 mM to 50 mM, 10 mM to 25 mM.

In a preferred embodiment, the liquid formulations have a concentration of one or more Fc variants and/or Fc variant fusions is about 50 mg/ml, about 75 mg/ml, about 100 mg/ml, about 125 mg/ml, about 150 mg/ml, about 175 mg/ml, about 200 mg/ml, about 225 mg/ml, about 250 mg/ml, about 275 mg/ml, or about 300 mg/ml. In one embodiment, the liquid formulations should exhibit one or more of the following characteristics, stability, low to undetectable levels of antibody fragmentation and/or aggregation, very little to no loss of the biological activities of the antibodies or antibody fragments during manufacture, preparation, transportation, and storage. In other embodiments the liquid formulations lose less than 50%, less than 30%, less than 20%, less than 10% or even less than 5% or 1% of the antibody activity within 1 year storage under suitable conditions at or about 4° C. In yet other embodiments the liquid formulations lose less than about 50%, less than about 30%, less than about 20%, less than about 10% or even less than about 5% or about 1% of the antibody activity within 1 year storage under suitable conditions at or about 4° C. The activity of an antibody can be determined by a suitable antigen-binding or effector function assay for the respective antibody. In yet another preferred embodiment, the liquid formulations are of low visoscity and turbidity. In a particular embodiment, the liquid formulations have a viscosity of less than 10.00 cP or about 10.00 cP at any temperature in the range of 1° C. to 26° C. or about between about 1° C. to about 26° C. Viscosity can be determined by numerous method well known in the art. For example, the viscosity of a polypeptide solution can be measured using a ViscoLab 4000 Viscometer System (Cambridge Applied Systems) equipped with a ViscoLab Piston (SN:7497, 0.3055", 1-20 cP) and S6S Reference Standard (Koehler Instrument Company, Inc.) and connected to a water bath to regulate the temperature of the samples being analyzed. The sample is loaded into the chamber at a desired starting temperature (e.g., 2° C.) and the piston lowered into the sample. After sample was equilibrated to the temperature of the chamber, measurement is initiated. The temperature is increased at a desired rate to the desired final temperature (e.g., $\geq 25°$ C.). And the viscosity over time is recorded.

It is contemplated that the liquid formulations may further comprise one or more excipients such as a saccharide, an amino acid (e.g. arginine, lysine, and methionine) and a polyol. Additional descriptions and methods of preparing and analyzed liquid formulations can be found, for example, in PCT publications WO 03/106644; WO 04/066957; WO 04/091658 each of which is herein incorporated by reference in its entirety.

In one embodiment the formulations (e.g., liquid formulations) of the invention are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)). When therapeutic proteins are administered in amounts of several hundred or thousand milligrams per kilogram body weight, as can be the case with monoclonal antibodies, it is advantageous to remove even trace amounts of endotoxin. In one embodiment, endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg. In another embodiment, endotoxin and pyrogen levels in the composition are less then about 10 EU/mg, or less then about 5 EU/mg, or less then about 1 EU/mg, or less then about 0.1 EU/mg, or less then about 0.01 EU/mg, or less then about 0.001 EU/mg.

It will be apparent to one skilled in the art that a formulation comprising one or more Fc variants and/or Fc variant fusions to be administered to a subject (e.g., a human) in need thereof should be formulated in a pharmaceutically-acceptable excipient. Examples of formulations, pharmaceutical compositions in particular, of the invention include but are not limited to those disclosed in PCT publications WO 02/070007; WO 04/066957 and WO 03/075957 each of which is herein incorporated by reference in its entirety. Briefly, the excipient that is included with the Fc variants and/or variant Fc fusion protein of the present invention in these formulations (e.g., liquid formulations) can be selected based on the expected route of administration of the composition in therapeutic applications. The route of administration of the composition depends on the condition to be treated. For example, intravenous injection may be preferred for treatment of a systemic disorder such as a lymphatic cancer or a tumor which has metastasized. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the Fc variants and/or variant Fc fusion of the present invention in these formulations in milliliters (mL) to be administered. There may be no downward adjustment to "ideal" weight. In such a situation, an appropriate dose may be calculated by the following formula:

Dose (mL)=[patient weight (kg)×dose level (mg/kg)/ drug concentration (mg/mL)]

Depending on the condition, the formulations can be administered orally, parenterally, intramuscularly, intranasally, vaginally, rectally, lingually, sublingually, buccally, intrabuccally, intravenously, cutaneously, subcutaneously and/or transdermally to the patient.

Accordingly, formulations designed for oral, parenteral, intramuscular, intranasal, vaginal, rectal, lingual, sublingual, buccal, intrabuccal, intravenous, cutaneous, subcutaneous and/or transdermal administration can be made without undue experimentation by means well known in the art, for example, with an inert diluent or with an edible carrier. The formulations may be enclosed in gelatin capsules or compressed into tablets. For the purpose of oral therapeutic administration, the formulations of the present invention may be incorporated with excipients and used in the form of tablets, troches, capsules, elixirs, suspensions, syrups, wafers, chewing gums, and the like.

Tablets, pills, capsules, troches and the like may also contain binders, recipients, disintegrating agent, lubricants, sweetening agents, and/or flavoring agents. Some examples of binders include microcrystalline cellulose, gum tragacanth and gelatin. Examples of excipients include starch and lactose. Some examples of disintegrating agents include alginic acid, cornstarch, and the like. Examples of lubricants include magnesium stearate and potassium stearate. An example of a glidant is colloidal silicon dioxide. Some examples of sweetening agents include sucrose, saccharin, and the like. Examples of flavoring agents include peppermint, methyl salicylate, orange flavoring, and the like. Materials used in preparing these various formulations should be pharmaceutically pure and non-toxic in the amounts used.

The pharmaceutical formulations of the present invention can be administered parenterally, such as, for example, by intravenous, intramuscular, intrathecal and/or subcutaneous injection. Parenteral administration can be accomplished by incorporating the formulations of the present invention into a solution or suspension. Such solutions or suspensions may also include sterile diluents, such as water for injection, saline solution, fixed oils, polyethylene glycols, glycerine, propylene glycol and/or other synthetic solvents. Parenteral formulations may also include antibacterial agents, such as, for example, benzyl alcohol and/or methyl parabens, antioxidants, such as, for example, ascorbic acid and/or sodium bisulfite, and chelating agents, such as EDTA. Buffers, such as acetates, citrates and phosphates, and agents for the adjustment of tonicity, such as sodium chloride and dextrose, may also be added. The parenteral preparation can be enclosed in ampules, disposable syringes and/or multiple dose vials made of glass or plastic. Rectal administration includes administering the formulation into the rectum and/or large intestine. This can be accomplished using suppositories and/or enemas. Suppository formulations can be made by methods known in the art. Transdermal administration includes percutaneous absorption of the formulation through the skin. Transdermal formulations include patches, ointments, creams, gels, salves, and the like. The formulations of the present invention can be administered nasally to a patient. As used herein, nasally administering or nasal administration includes administering the formulations to the mucous membranes of the nasal passage and/or nasal cavity of the patient.

In further embodiments, the formulations (e.g., liquid formulations) are administered to the mammal by subcutaneous (i.e., beneath the skin) administration. For such purposes, the formulations may be injected using a syringe. However, other devices for administration of the formulations are available such as injection devices (e.g. the Inject-ease_ and Genject_devices), injector pens (such as the GenPen™); auto-injector devices, needleless devices (e.g., MediJector and BioJector); and subcutaneous patch delivery systems.

In another aspect of the invention there is provided a slow release formulations. In a specific embodiment, a slow release formulation comprises a liquid formulation. Slow release formulations may be formulated from a number of agents including, but not limited to, polymeric nano or microparticles and gels (e.g., a hyaluronic acid gel). Besides convenience, slow release formulations offer other advantages for delivery of protein drugs including protecting the protein (e.g., Fc variant and/or variant Fc fusion) over an extended period from degradation or elimination, and the ability to deliver the protein locally to a particular site or body compartment thereby lowering overall systemic exposure.

The present invention, for example, also contemplates injectable depot formulations in which the protein (e.g., Fc variant and/or variant Fc fusion) is embedded in a biodegradable polymeric matrix. Polymers that may be used include, but are not limited to, the homo- and co-polymers of lactic and glycolic acid (PLGA). PLGA degrades by hydrolysis to ultimately give the acid monomers and is chemically unreactive under the conditions used to prepare, for example, microspheres and thus does not modify the protein. After subcutaneous or intramuscular injection, the protein is released by a combination of diffusion and polymer degradation. By using polymers of different composition and molecular weight, the hydrolysis rate can be varied thereby allowing release to last from days to months. In a further aspect the present invention provides a nasal spray formulation. In a specific embodiment, a nasal spray formulation comprises the liquid formulation of the present invention.

The formulations of the invention may be used in accordance with the methods of the invention for the prevention, management, treatment or amelioration of cancer, inflammatory and autoimmune diseases or one or more symptoms thereof. In one embodiment, the formulations of the invention are sterile and in suitable form for a particular method of administration to a subject with cancer, inflammatory and autoimmune diseases, in particular an Eph receptor-mediated disease.

The invention provides methods for preventing, managing, treating or ameliorating cancer, inflammatory and autoimmune diseases (in particular an Eph receptor-mediated disease) or one or more symptoms thereof, said method comprising: (a) administering to a subject in need thereof a dose of a prophylactically or therapeutically effective amount of a formulation comprising one or more Fc variants and/or variant Fc fusion proteins, that immunospecifically bind to an Eph receptor and (b) administering one or more subsequent doses of said Fc variants an/or variant Fc fusion proteins, to maintain a plasma concentration of the said Fc variants an/or variant Fc fusion proteins at a desirable level (e.g., about 0.1 to about 100 µg/ml), which continuously binds to an Eph receptor. In a specific embodiment, the plasma concentration of the said Fc variants an/or variant Fc fusion proteins is maintained at 10 µg/ml, 15 µg/ml, 20 µg/ml, 25 µg/ml, 30 µg/ml, 35 µg/ml, 40 µg/ml, 45 µg/ml or 50 µg/ml. In a specific embodiment, said effective amount of Fc variant and/or variant Fc fusion protein to be administered is between at least 1 mg/kg and 100 mg/kg per dose. In another specific embodiment, said effective amount of Fc variant and/or variant Fc fusion to be administered is between at least 1 mg/kg and 20 mg/kg per dose. In another specific embodiment, said effective amount of Fc variant and/or variant Fc fusion protein to be administered is between at least 4 mg/kg and 10 mg/kg per dose. In yet another specific embodiment, said effective amount of Fc variant and/or variant Fc fusion protein to be administered is between 50 mg and 250 mg per dose. In still another specific embodiment, said effective amount of Fc variant and/or variant Fc fusion protein to be administered is between 100 mg and 200 mg per dose.

The present invention provides kits comprising one or more Fc variants and/or variant Fc fusions with modified binding affinity to one or more Fc ligand (e.g., FcγRs, C1q) and altered ADCC and/or CDC activity that immunospecifically bind to an Eph receptor conjugated or fused to a detectable agent, therapeutic agent or drug, in one or more containers, for use in the prevention, treatment, management, amelioration, detection, monitoring or diagnosis of cancer, inflammatory and autoimmune diseases, in particular an Eph receptor-mediated disease.

The invention also provides kits comprising one or more Fc variants and/or variant Fc fusions with modified binding affinity to one or more Fc ligand (e.g., FcγRs, C1q) and altered ADCC and/or CDC activity that immunospecifically bind to an Eph receptor in a first vial and one or more prophylactic or therapeutic agents, other than Fc variants that immunospecifically bind to an Eph receptor, in a second vial for use in the prevention, treatment, management, amelioration, detection, monitoring or diagnosis of cancer, inflammatory and autoimmune diseases, in particular an Eph receptor-mediated disease. The invention also provides kits comprising one or more Fc variants and/or variant Fc fusions with modified binding affinity to one or more Fc ligand (e.g., FcγRs, C1q) and altered ADCC and/or CDC activity that immunospecifically bind to an Eph receptor conjugated or fused to a therapeutic agent or drug in a first vial and one or more prophylactic or therapeutic agents, other than an Fc variant an/or variant Fc fusion protein that immunospecifically binds an Eph receptor, in a second vial for use in the prevention, treatment, management, amelioration, detection, monitoring or diagnosis of cancer, inflammatory and autoimmune diseases, in particular an Eph receptor-mediated disease. The kits may further comprise packaging materials and/or instructions.

7. EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

7.1 Example 1

Construction and Expression of Novel Fc Variants of Antibodies

Based on the structural information available for the Fc-FcγRIIIB complex, each of the putative FcγR contact residues of the IgG1 Fc portion was randomly mutated by using degenerated oligonucleotides incorporating all possible single mutations. The contact residues were divided into four regions (RI: $Leu^{234}$, $Leu^{235}$, $Gly^{236}$, $Gly^{237}$, $Pro^{238}$, Ser239; RII: $Asp^{265}$, $Ser^{267}$, $Glu^{269}$; RIII: $Ser^{298}$; and RIV: $Ala^{327}$, $Leu^{328}$, $Pro^{329}$, $Ala^{330}$, and $Ile^{332}$). Primers used for the amplification and library construction are listed in table 5. The IgG1 of antibody Vitaxin™, converted into scFv-Fc format, was used as the model for this study. The DNA and corresponding amino acid sequences of the variable regions of the Vitaxin® heavy and light chains used to generate the scFv-Fc are shown in FIG. 1 (panels A and B, respectively). The scFv-Fc was then harnessed as the template to build three Fc mutant libraries containing single mutations in the Fc region. Library I contains all single mutations in the RI region; library II covers the RII and RIII regions; and library III covers the RIV region. Overlapping PCR approach was used to synthesize entire Fc region containing mutations.

TABLE 5

Primers

| Primer | Sequence | Notes | SEQ ID |
|--------|----------|-------|--------|
| MDAD-1 | CCG TGC CCA GCA CCT GAA NNK CTG GGG GGA CCG TCA GTC | contact Region I | 11 |
| MDAD-2 | CCG TGC CCA GCA CCT GAA CTC NNK GGG GGA CCG TCA GTC TTC | contact Region I | 12 |
| MDAD-3 | CCG TGC CCA GCA CCT GAA CTC CTG NNK GGA CCG TCA GTC TTC CTC | contact Region I | 13 |
| MDAD-4 | CCG TGC CCA GCA CCT GAA CTC CTG GGG NNK CCG TCA GTC TTC CTC TTC | contact Region I | 14 |
| MDAD-5 | CCC TGG CCA GCA CGT GAA CTC GTG GGG GGA NNK TCA GTC TTC CTC TTC CCC | contact Region I | 15 |
| MDAD-6 | CCG TGC CCA GCA CCT GAA CTC CTG GGG GGA CCG NNK GTC TTC CTC TTG CCC CCA | contact Region I | 16 |
| MDAD-7 | GTC ACA TGC GTG GTG GTG NNK GTG AGC CAC GAA GAC CCT | contact Region II | 17 |
| MDAD-8 | GTC ACA TGC GTG GTG GTG GAC GTG NNK CAC GAA GAC CCT GAG GTC | contact Region II | 18 |

TABLE 5-continued

Primers

| Primer | Sequence | Notes | SEQ ID |
|---|---|---|---|
| MDAD-9 | GTC ACA TGC GTG GTG GTG GAC GTG AGC CAC NNK GAC CCT GAG GTC AAG TTC | contact Region II | 19 |
| MDAD-10 | CGG GAG GAG CAG TAC AAC NNK ACG TAC CGT GTG GTC AGC | contact Region III | 20 |
| MDAD-11 | TGC AAG GTC TCC AAC AAA NNK CTC CCA GCC CCC ATC GAG | contact Region IV | 21 |
| MDAD-12 | TGC AAG GTC TCC AAC AAA GCC NNK CCA GCC CCC ATC GAG AAA | contact Region IV | 22 |
| MDAD-13 | TGC AAG GTC TCC AAC AAA GCC CTC NNK GCC CCC ATC GAG AAA ACC | contact Region IV | 23 |
| MDAD-14 | TGC AAG GTC TCC AAC AAA GCC CTC CCA NNK CCC ATC GAG AAA ACC ATC | contact Region IV | 24 |
| MDAD-15 | TGC AAG GTC TCC AAC AAA GCC CTC CCA GCC CCC NNK GAG AAA ACC ATC TCC AAA | contact Region IV | 25 |
| MDAD-16 | ACT CAC ACA TGT CCA CCG TGC CCA GCA CCT GAA | Fc N-terminus | 26 |
| MDAD-17 | CAC CAC CAC GCA TGT GAC | RII primer | 27 |
| MDAD-18 | GTT GTA CTG CTC CTC CCG | RIII primer | 28 |
| MDAD-19 | TTT GTT GGA GAC CTT GCA | RIV primer | 29 |
| MDAD-20 | AAC CTC TAC AAA TGT GGT ATG GCT | Fc C-terminus | 30 |
| A1 | AAG CTT CGG TCC GCC ACC ATG GCA ACT GAA GAT CTC CCA AAG | FcγRIIIA primer | 31 |
| A2 | GTC TGC CGA ACC GCT GCC TGC CAA ACC TTG AGT GAT GGT | FcγRIIIA primer | 32 |
| B1 | AGC TTC GGT CCG CCA CCA TGG CTG TGC TAT CCT TGG CAG CTC CCC CAA | FcγRIIB primer | 33 |
| B2 | GTC TGC CGA ACC GCT GCC CCC CAT CGG TGA AGA GCT GGG AGC | FcγRIIB primer | 34 |
| SA1 | GGC AGC GGT TCG GCA GAC CCC TCC AAG GAC | Streptavidin primer | 35 |
| SA2 | CAG GGC TAG CTT ACT GCT GAA CGG CGT CGA GCG G | Streptavidin primer | 36 |
| EA1 | TCC ACA GGT GTC CAC TCC GGA CTG AAG ATC TCC CCA AAG | FcγRIIIA primer | 37 |
| EA2 | GGG AGA ATT CCG CGG CCG CTT ATT TGT CAT CGT CAT CTT TGT AGT CAT GGT GAT GGT GAT GGT GTG CGC TGC CAA ACT TGA GTG ATG GT | FcγRIIIA primer | 38 |
| EB1 | TCC ACA GGT GTC CAC TCC GCT GTG CTA TTC CTG GCA GCT CCC CCA AAG | FcγRIIB primer | 39 |
| EB2 | GGG AGA ATT CCG CGG CCG CTT ATT TGT CAT CGT CAT CTT TGT AGT CAT GGT GAT GGT GAT GGT GTG CGC CCC ATC GTG AAG AGC TGG AGC | FcγRIIB primer | 40 |
| Oligo 1 | GCC CTC CCA GCC CCC gag GAG AAA ACC ATC TCC | I332E | 41 |
| Oligo 2 | GCC CTC CCA GCC CCC cag GAG AAA ACC ATC TCC | I332Q | 42 |
| Oligo 3 | GCC CTC CCA GCC CCC ggc GAG AAA ACC ATC TCC | I332G | 43 |
| Oligo 4 | GCC CTC CCA GCC CCC gcc GAG AAA ACC ATC TCC | I332A | 44 |
| Oligo 5 | GCC CTC CCA GCC CCC tac GAG AAA ACC ATC TCC | I332Y | 45 |

TABLE 5-continued

Primers

| Primer | Sequence | Notes | SEQ ID |
|---|---|---|---|
| Oligo 6 | GCC CTC CCA GCC CCC gac GAG AAA ACC ATC TCC | I332D | 46 |
| Oligo 7 | GCC CTC CCA GCC CCC aac GAG AAA ACC ATC TCC | I332N | 47 |
| Oligo 8 | GCC CTC CCA GCC CCC gtg GAG AAA ACC ATC TCC | I332V | 48 |
| Oligo 9 | GCC CTC CCA GCC CCC tgg GAG AAA ACC ATC TCC | I332W | 49 |
| Oligo 10 | GGC CTC CGA GCC CCC cgc GAG AAA ACC ATC TCC | I332R | 50 |
| Oligo 11 | GCC CTC CCA GCC CCC agc GAG AAA ACC ATC TCC | I332S | 51 |
| Oligo 12 | GCC CTC CCA GCC CCC aag GAG AAA ACC ATC TCC | I332K | 52 |
| Oligo 13 | GCC CTC CCA GCC CCC atg GAG AAA ACC ATC TCC | I332M | 53 |
| Oligo 14 | GCC CTC CCA GCC CCC acc GAG AAA ACC ATC TCC | I332T | 54 |
| Oligo 15 | GCC CTC CCA GCC CCC tgc GAG AAA ACC ATC TCC | I332C | 55 |
| Oligo 16 | GCC CTC CCA GCC CCC ctg GAG AAA ACC ATC TCC | I332L | 56 |
| Oligo 17 | GCC CTC CCA GCC CCC ttc GAG AAA ACC ATC TCC | I332F | 57 |
| Oligo 18 | GCC CTC CCA GCC CCC cac GAG AAA ACC ATC TCC | I332H | 58 |
| Oligo 19 | CCC CTC CCA CCC CCC cct GAG AAA ACC ATC TCC | I332P | 59 |
| Oligo 20 | CTGGGGGGACCG gac GTCTTCCTCTTC | S239D | 60 |
| Oligo 21 | AAAGCCCTCCCA ctg CCCgagGAGAAA | A330L/I332E | 61 |

7.1.1 Materials and Methods

Construction of Fc Libraries: For constructing Fc library I, primers MDAD-16, equimolar mixture of MAD-2 to -6, and MDAD-20 were used in the PCR reaction. The PCR products were gel purified and digested by restriction enzymes Not I/Pci I, and ligated into the expression vector pMI under the control of the CMV promoter. For constructing Fc library II, two PCR products incorporating RII and RIII mutations were mixed at 3:1 molar ratio for cloning into pMI vector. Primers MDAD-16, MDAD-17, equimolar mixture of MDAD-7 to -9, and MDAD-20 were used to amplify Fc region to incorporate RII mutations, and primers MDAD-16, -18, -10, and -20 were used to amplify Fc region to incorporate RIII mutations. For Fc library III, primers MDAD-16, MDAD-19, equimolar mixture of MDAD-11 to -15, and MDAD-20 were used in the PCR reaction.

Transfection: The plasmids of three Fc libraries (I, II, and III) were linearized by Sal I, ethanol precipitated and resuspended in $H_2O$. 50 µg of each linearized library DNA was individually transfected into $10^7$ NS0 cells by electroporation. After electroporation, the cells were transferred to a tube containing 30 ml of growth medium (Glutamine-free IMDM, 1×GS supplement and 2 mM L-glutamine) and seeded in 96-well plates (50 µl/well) at variable dilutions. The cells were cultured at 37° C. in humid air containing 5% $CO_2$.

Selection of Stable Transfectants: The selection of stably transfected NS0 cells expressing scFv-Fc mutants was started 18-24 hours after transfection by converting to selection medium (same as growth medium but without glutamine). The medium was changed twice a week at one half of the total volume. After 2-3 weeks of incubation, the culture supernatants were collected for screening of antibody expression.

Purification of scFv-Fc Variants: The culture supernatants containing scFv-Fc mutants were purified by using a Protein A spin chromatography kit following manufacturer's protocol (Pierce). The bound scFv-Fc mutants were eluted with 0.1 M citrate buffer and then dialyzed in PBS. All proteins were analyzed by SDS-polyacrylamide gel electrophoresis and were applied to quantitative ELISA using anti-human IgG assay plates (Becton Dickson) or BCA kits (PIERCE) to determine scFv-Fc concentrations.

Antibody Quantitation by ELISA: To determine the expression level of the Fc variants, anti-human IgG-coated microtiter plates (Becton Dickson) were used. The culture supernatants were added to the wells at dilutions of 1:10 and 1:100. After a 1 hour incubation at room temperature, the plates were washed with PBST (PBS+0.1% Tween 20) and incubated at room temperature for an additional hour with anti-human IgG (Pierce) at a 1:60000 dilution. The signals were detected by TME substrate (Pierce) and read by an ELISA reader at 450 nm. Purified parental Vitaxin™ scFv-Fc expressed in a pMI vector was employed as a standard (at serial dilutions of 0.003 µg-10 µg/ml).

7.2 Example 2

Construction and Expression of the Extracellular Domains of FcγRIIIA and FcγRIIB To facilitate the binding studies of the Fc variants to FcγRs the extracellular domains of FcγRIIIA and FcγRIIB were subcloned for expression as strepavidin fusion proteins in *E. coli* and for expression in mammalian cells. The FcγRIIIA prepared for analysis is the low affinity (F158) allotype. Two forms of FcγRIIIA and FcγRIIB were prepared, a "tetramer"

form, generated as as Strepavidin fusion, and a "monomer" form generated as a Flag-tagged.

7.2.1 Materials and Methods

Construction and Bacterial Expression of the Extracellular Domains of FcγRIIIA- and FcγRIIB-Strepavidin Fusion Proteins (Tetramer): Primer pairs SA1/SA2, A1/A2, and B1/B2 (see primer list, Table 5) were used to PCR amplify streptavidin and the extracellular domains of FcγR IIIA and FcγR IIB, respectively. The cDNA library of human bone marrow (Clontech) was used as a template for FcγR IIIA and FcγR IIB amplification, and the genomic DNA of Streptomyces avidinii was used as the template for the amplification of Streptavidin. Overlapping PCR was used to assemble fusion genes of FcγR IIIA-streptavidin and FcγR IIB-strepavidin. The fusion genes were digested by the restriction enzymes Nco I/Nhe I and cloned into the expression vector pET-28a. The fusion proteins were expressed as inclusion bodies and refolded by dialysis to slowly remove urea as described by C. Gao, et al. (1997, PNAS USA 94:11777-82). The refolded fusion proteins were then purified by an immunobiotin column (PIERCE) according to manufacturer's instructions.

Construction and Mammalian Expression of the Extracellular Domains of FcγRIIIA and FcγRIIB (Monomer): The extracellular domains of FcγR IIIA and FcγR IIB were PCR amplified from the cDNA library of human bone marrow (Clontech) with primers EA1/EA2 and EB1/EB2, respectively (see primer list, Table 5). The PCR products were digested by Xba I/Not I and cloned into the mammalian cell expression vector pMI226 under the control of the CMV promoter to generate proteins in which the extracelluar domains of FcγR IIIA and FcγR IIB are tagged with His6-tag followed by FLAG tag at the C-terminal end. The plasmid DNA was transiently transfected into 293H cells by Lipofectamine 2000 Transfection Reagent (Invitrogen). After three collections within 9 days, the proteins were purified by passing the culture supernatant through anti-FLAG M2 agarose columns (Sigma). The FLAG-tagged FcγRIIIA/IIB proteins were eluted from the column and dialyzed against PBS.

7.3 Example 3

Characterization of the Fc Variants

After mutagenesis of the Fc domain (see example 1 supra) Fc variants, in the scFV-Fc fusion format, were screened for enhanced binding to FcγRIIIA tetramer by ELISA as detailed below. The results for several clones are shown in FIG. 5. In addition, the ADCC activity of these clones was determined against M21 cells. The results for several clones are shown in FIG. 6. Based on these studies three substitutions were chosen for further study, S239D, A330L and I332E. These substitutions were introduced into the Fc region of the intact Vitaxin® IgG1 heavy chain and coexpressed with Vitaxin® light chain to produce full length Vitaxin® Fc variant IgG1 molecules. The Vitaxin® Fc variant having the I332E substitution was designated Vitaxin®-1M, the Vitaxin® Fc variant having the S239D, A330L, I332L triple substitution was designated Vitaxin®-3M.

A panel of Vitaxin® Fc variants, in IgG format, was generated in which each of the standard 20 amino acids was substituted at position 332. These variants were characterized. FIG. 7A shows the relative binding to FcγRIIIA of these Fc variants, as determined by ELISA. It can be seen that under these conditions several substitutions showed enhanced binding including I332T, I332L, I332F and most dramatically, I332E. However, as shown in FIG. 7B, only the I332E substitution showed a similar increase in ADCC activity.

Representative binding curves for Vitaxin® and one Fc variant of Vitaxin® (I332E; Vitaxin-1M) to FcγRIIIA and FcγRIIB are shown in FIGS. 8A and 8B respectively. Vitaxin® was prepared from two cell sources, NSO and HEK293 cells, no difference in binding was observed between these two sources of Vitaxin. The Vitaxin® Fc variant was then prepared from HEK293 cells. The Vitaxin® Fc variant showed approximately a 2.5 fold increase in binding affinity to FcγRIIIA (FIG. 8A) with no corresponding change in binding to FcγRIIB as determined by ELISA (FIG. 8B).

The binding of Vitaxin® and the Vitaxin® Fc variants to FcγRIIIA was further analyzed by BIAcore analysis. The binding of Vitaxin® and the Vitaxin® Fc variants were analyzed with the receptor soluble and the antibody immobile (see methods below). The Vitaxin-1M Fc variant was shown to have a roughly 7 fold increase in binding affinity to FcγIIIA as compared to that of the parental wild type Vitaxin antibody. The interaction of the Vitaxin-3M Fc variant to FcγRIIIA was also analyzed by BIAcore and found to have a binding affinity of ~114 nM, nearly 80 time better than that of the parental wild type Vitaxin antibody. The results are summarized in Table 6.

TABLE 6

Binding Constants ($K_D$) of wild type antibodies and Fc variants to FcγRIIIA

| Antibody   | Run # | RUs Immobilized | $K_D$ Isotherm | $K_D$ Scatchard | Fold increase over WT[a] |
|------------|-------|-----------------|----------------|-----------------|--------------------------|
| Vitaxin ®  | 1     | 9608            | 3.47 μM        | 3.26 μM         |                          |
| Vitaxin-1M | 1     | 9331            | 458 nM         | 458 nM          | 6.5                      |
| Vitaxin ®  | 2     | 9434            | 8.9 μM         | 7.6 μM          |                          |
| Vitaxin-1M | 2     | 9383            | 1.28 μM        | 1.22 μM         | 7.0                      |
| Vitaxin-3M | 2     | 8284            | 114 nM         | 113 nM          | 78.0                     |
| 3F2        | 3     | 8568            | 15.6 μM        | 14.2 μM         |                          |
| 3F2-1M     | 3     | 7718            | 1.77 μM        | 1.68 μM         | 8.8                      |
| 3F2-3M     | 3     | 7809            | 158 nM         | 162 nM          | 99                       |

[a]calculated using Isoltherm values

The Vitaxin-1M Fc variant was further characterized in ADCC assays against M21 cells. First, the ratio of target to effector cells was kept constant at 50:1 and the concentration of the two antibodies was varied from 0.4 to 1000 ng/ml (FIG. 9). Next, the concentration of antibody was varied for several different ratios of target to effector cell (6.25:1, 12.5:1, 25:1 and 50:1) (FIG. 10). In both assays the ADCC activity of the Vitaxin-1M Fc (I332E) variant was approximately 3 fold higher than that of the parent Vitaxin® antibody.

The Vitaxin-3M Fc variant was also characterized in ADCC assays against a target cells expressing differing levels of Integrin αVβ3 (FIG. 11). The target cell lines used were M21 (a high expressor), DU145 (a low expressor), A498 and ACHN (moderate expressors). The assays were performed using two different ratios of target to effector cell (50:1 and 25:1) and antibody concentrations ranging from 4 to 400 ng per well. In all cases the ADCC activity of the Vitaxin-3M Fc variant was seen to be higher than wild type Vitaxin®. Vitaxin-3M Fc variant was also shown to have higher ADCC activity compared to the wild type Vitaxin® antibody against SKMEL28 target cells which express Integrin αVβ3 (FIG. 18).

7.3.1 Materials and Methods

ELISA Receptor Binding Assay: Microtiter plates were coated with protein A/G (PIERCE) solution (0.25 μg/ml) and incubated at 4° C. overnight. Any remaining binding sites were blocked with 4% skim milk. Approximately 25 µl per-well of mutant antibody solution was added to each well and incubated for 1 h at 37° C. After washing, FcγRIIIA-strepta-vidin or FcγRIIB-streptavidin fusion protein (in 1% BSA) was added for 1 hour at 37° C., followed by washing and biotin-conjugated HRP for 30 min. Detection was carried out by adding 30 µl of tetramethylbenzidine substrate (Pierce) followed by neutralization with 30 µl of 0.2 M $H_2SO_4$. The absorbance was read at 450 nm Generation of 332 Amino Acid Substitutions: QuikChange® II XL site-directed mutagenesis kit (Strat-agene, San Diego) was used to generate all the amino acid substitutions at position 332 of the gene encoding the heavy chain of wild type Vitaxin® in the plasmid pMI331 (see FIG. 4). Oligos 1 to 19 (see Table 5) were applied to change the Isoleucine to all other 19 different amino acids at the position 332, using Vitaxin as the template. The mutation was further confirmed by DNA sequencing.

The plasmid DNA containing antibody genes was transiently transfected into 293H cells by Lipofectamine 2000 Transfection Reagent (Invitrogen). After three collections within 9 days, the culture supernatants containing antibody were affinity purified by using a pre-packed Protein A column (Amersham Biosciences, now belongs to GE healthcare). The bound antibody were eluted with elution buffer (100 mM Glycine, pH3.2), neutralized by 1M Tris buffer (pH 8.0) and then dialyzed in PBS. All purified antibodies were analyzed by SDS-polyacrylamide gel electrophoresis and were applied to quantitative ELISA using anti-human IgG assay plates (Becton Dickson) or BCA kits (PIERCE) to determine IgG concentrations.

Generation of Vitaxin®-1M and 3M Fc variants: The I332E substitution was generated by site directed mutagenesis (as described above) of the gene encoding the heavy chain of wild type Vitaxin® in the plasmid pMI331 (see FIG. 4). The mutant I332E was designated as Vitaxin 1M. The Vitaxin 3M was further generated by two sequential site directed mutagenesis (as described above), using oligo 20 and 21 (see Table 5) as primers and Vitaxin 1M as template. Expression and purification of the 1M and 3M Vitaxin® Fc variants was the same as described above.

Kinetic Analysis via BIAcore: for Run 1 the interaction of FcγRIIIA with immobilized Vitaxin® and Vitaxin® Fc variant IgGs were monitored by surface plasmon resonance detection using a BIAcore 3000 instrument (Pharmacia Biosensor, Uppsala, Sweden). Vitaxin® and Vitaxin® Fc variant IgGs were coupled to the dextran matrix of a CM5 sensor chip (Pharmacia Biosensor) using an Amine Coupling Kit, as described (Johnsson et al., 1992, *Anal Biochem* 198:268-277), at a surface density of between 7700 and 9400 RUs (see Table 6). FcγRIIIA was serially diluted in 0.01 M HEPES pH 7.4 containing 0.15 M NaCl, 3 mM EDTA and 0.005% P20, at concentrations ranging from 2 μM down to 7.8 nM. Duplicate injections of each concentration were made. All binding experiments were performed at 25° C., and at a flow rate of 10 μL/min. Binding was monitored for 25 min. Following each injection of FcγRIIIA, the IgG surfaces were regenerated with a 30 sec. pulse of 5 mM HCl. FcγRIIIA was also passed over a blank reference cell which is connected, in series, to the IgG-containing flow cells. The steady-state binding curves were also corrected for injection artifacts by subtraction of buffer injections. This doubly-corrected data was then fit to a steady-state isotherm provided by the instrument manufacturer (Pharmacia Biosensor, Uppsala, Sweden) to derive the respective equilibrium binding constants (KD). Separately, a Scatchard plot of the Req data from each IgG surface was constructed to confirm the results of the binding isotherms.

For Run 2 the interaction of The interaction of FcγRIIIA with immobilized Vitaxin® and Vitaxin® Fc variant IgGs were monitored by surface plasmon resonance detection using a BIAcore 3000 instrument (Pharmacia Biosensor, Uppsala, Sweden). Vitaxin® and Vitaxin® Fc variant IgGs were coupled to the dextran matrix of a CM5 sensor chip (Pharmacia Biosensor) using an Amine Coupling Kit, as described (Johnsson et al., 1992, *Anal Biochem* 198:268-277), at a surface density of between approximately 8200 and 9400 RUs (see Table 6). FcγRIIIA was serially diluted in 0.01 M HEPES pH 7.4 containing 0.15 M NaCl, 3 mM EDTA and 0.005% P20, at concentrations ranging from 16 μM down to 7.8 nM. Duplicate injections of each concentration were made. All binding experiments were performed at 25° C., and at a flow rate of 10 μL/min. Binding was monitored for 25 min. Following each injection of FcγRIIIA, the IgG surfaces were regenerated with a 30 sec. pulse of 5 mM HCl. FcγRIIIA was also passed over a blank reference cell which is connected, in series, to the IgG-containing flow cells. The steady-state binding curves were also corrected for injection artifacts by subtraction of buffer injections. This doubly-corrected data was then fit to a steady-state isotherm provided by the instrument manufacturer (Pharmacia Biosensor, Uppsala, Sweden) to derive the respective equilibrium binding constants (KD). Separately, a Scatchard plot of the Req data from each IgG surface was constructed to confirm the results of the binding isotherms.

Antibody-Dependent Cell-Mediated Catotoxicity (ADCC) Assay: Antibody-dependent cell cytotoxicity (ADCC) was assayed in a four-hour non-radioactive lactate dehydrogenase (LDH) release assay (Promega Corporation, Madison, Wis.). Briefly, M21, A549, or H358 target cells were distributed into 96-well U-bottomed plates ($1\times10^4$/50 μl) and pre-incubated with serial dilution of antibodies (50 μl) for 20 min at 37° C. Human effector cells (100 μl) were then added at effector to target ratios of 50:1 and 25:1. Human effector cells were peripheral blood mononuclear cells (PBMC) purified from healthy donors using Lymphocyte Separation Medium (MP Biomedicals, Irvine, Calif.). After a 4-h incubation at 37° C., plates were centrifuged, and cell death was analyzed by measuring the release of LDH into the cell supernatant with a 30-minute coupled enzymatic assay. The percentage of specific lysis was calculated according to the formula: % specific lysis$=100\times(E_x-E_{spon}-T_{spon})/(T_{max}-T_{spon})$ where $E_x$ represents the release from experimental wells, $E_{spon}$ is the spontaneous release of effector cells alone, $T_{spon}$ is spontaneous release of target cells alone, and $T_{max}$ is the maximum release from lysed target cells.

The cell lines used for the ADCC studies included the following: A498 and ACHN renal cell carcinomas with moderate expression of Integrin αVβ3, M21 a melanoma cell line with high Integrin αVβ3 expression, DU145 a prostate cancer cell line with low levels of Integrin αVβ3, SKMEL28 a human melanoma expressing Integrin αVβ3 but little or no human EphA2.

7.4 Example 4

Fc Variants of Antibodies Recognizing Other Epitopes

Given the remarkable improvement in ADCC activity of the Vitaxin® Fc (I332E) variant the (I332E) substitution was made in two other antibodies designated 12G3H11 (abbreviated 12G3) and 3F2, both of which bind the EphA2 tyrosine receptor kinase. The variable regions of 12G3 (FIG. 2A) and 3F2 (FIG. 3A) heavy chain were fused to the wt and variant Fc domains generated above (see sections 7.1 and 7.3). The variable region of the light chain of Vitaxins was replaced with the corresponding light chain variable region (i.e., 12G3 or 3F2, see FIGS. 2B and 3B, resectively) such that an intact 12G3 or 3F2 antibody was encoded by the plasmid (see FIG. 4 for a map of the plasmid encoding Vitaxin®). The antibodies containing the single substitutions were designated 12G3-1M and 3F2-1M, respectively. In addition, the S239D, A330L, I332L triple substitution was generated in 3F2, designated 3F2-3M.

The binding characteristics of the 3F2-wt, 3F2-1M and 3F2-3M Fc variants to several Fc ligands were examined in vitro by ELISA (FIG. 12). Representative binding curves for 3F2 and the Fc variants of 3F2 (3F2-1M and 3F2-3M) to FcγRIIIA tetramers (FIG. 12, top panel), FcγRIIIA monomers (FIG. 12, middle panel) and C1q (FIG. 12, bottom panel). From these data it can be seen that both the 3F2 Fc variants have improved binding to the monomeric and tetrameric forms of FcγRIIIA. In contrast both the 3F2 Fc variants have reduced C1q binding with 3F2-3M having the largest reduction in C1q binding (FIG. 12, bottom panel).

The binding of the 3F2 and the 3F2 Fc variants to FcγRIIIA was further analyzed by BIAcore analysis. The binding of 3F2 and the 3F2 Fc variant was analyzed with the receptor soluble and the antibody immobile (see methods below). The data obtained for 3F2 and the 3F2 Fc variants (Run 3) is similar to that obtained for Vitaxin® and the Vitaxin® Fc variants (Runs 1 & 2) with improvements in binding of about 7 fold and 80 fold for the Vitaxin® 1M and 3M Fc variants, respectively, and about 9 fold and 100 fold for the 3F2-1M and 3M Fc variants, respectively. The small differences between these numbers may reflect subtle differences in glycosylation between antibody produced in 293H cells vs NSO cells (Vitaxin antibodies and 3F2 antibodies, respectively) as the variable domain is generally not thought to affect FcγRIIIA binding. The results are summarized in Table 6.

The binding of 3F2-wt, 3F2-1M and 3F2-3M Fc variants to the surface of cells via Fc ligand interactions was examined. Two cell types were utilized, THP-1 cells and NK cells. To determine which Fc ligands were present on the surface both cell types were stained with antibodies recognizing CD32 (FcγRII); CD64 (FcγRI) or CD16 (FcγIII) and analyzed by FACS. The percent of cell staining positive for each Fc ligand are plotted in FIG. 13. As can be seen in FIG. 14 panel A, THP-1 cells predominantly express CD32 with a small amount of CD64 present on the cell surface. In contrast NK cells express CD16 almost exclusively (FIG. 13, panel B). All three versions of 3F2 (wt, 1M and 3M) bound to a similar degree to THP-1 cells (FIG. 13, panel C). However, the two Fc variants (3F2-1M and 3F2-3M) were seen to bind to a greater extent to NK cells, with the 3F2-3M Fc variant showing the largest increase in binding (FIG. 13, panel D).

The ADCC activity of all the variants was examined. Shown in FIGS. 14A and 14B are ADCC assays performed using the 12G3H11-Fc (I332E) variant and the parental 12G3H11 antibody against A549 target cells using effector cells from two donors. The assays were performed using two different ratios of target to effector cell (50:1 and 25:1) and antibody concentrations ranging from 4 to 400 ng per well. Remarkably, a 10 fold increase in ADCC activity is seen for the 12G3H11-Fc (I332E) variant compared to the parent antibody.

FIGS. 15, 16 and 17 are ADCC assays comparing the activity of 3F2-wt and the 3F2 Fc variants against target cells expressing different levels of EphA2. The target cell lines used were T23,1 A549 and Hey8 (high expressors), SKOV3 (a moderate expressor), A498 and SKMEL28 (low expressors). The assays were performed using three different ratios of target to effector cell (between 12.5:1 and 100:1) and antibody concentrations ranging from 0.02 to 2 μg/ml. In all cases the ADCC activity of the 3F2-3M Fc variant was seen to be higher than wild type 3F2. The activity of the 3F2-1M Fc variant was also higher than the 3F2-wt.

7.4.1 Materials and Methods

Generation of 12G3 and 3F2 Fc variants: To generate the 12G3 and 3F2 Fc variants, the DNA sequences encoding the variable region of Vitaxin® 1M or 3M heavy chain (VH) was replaced with the variable region of 12G3 or 3F2 heavy chain to create 12G3-1M, 3F2-1M and 3F2-3M Fc variants using Xba I/Apa I restriction sites (see plasmid map, FIG. 4). The DNA sequences encoding the variable region of Vitaxin® light chain were also replaced with the variable region of 12G3 or 3F2 light chain using SmaI/BsiWI restriction sites (see plasmid map, FIG. 4). The nucleotide sequence of the 12G3 heavy and light chain variable regions are listed as SEQ ID NO.: 62 and 63 respectively. The amino acid sequence of the 12G3 heavy and light chain variable regions are listed as SEQ ID NO.: 64 and 65 respectively. The nucleotide sequence of the 3F2 heavy and light chain variable regions are listed as SEQ ID NO.: 66 and 67 respectively. The amino acid sequence of the 3F2 heavy and light chain variable regions are listed as SEQ ID NO.: 68 and 69 respectively.

The plasmid DNA containing the 12G3 antibody genes was stably transfected into 293H cells by Lipofectamine 2000 Transfection Reagent (Invitrogen). The plasmid DNA containing the 3F2 antibody genes was stably transfected into NSO by electroporation. Antibodies were purified from cell culture supernatants by using a pre-packed Protein A column (Amersham Biosciences, now belongs to GE healthcare). The bound antibody were eluted with elution buffer (100 mM Glycine, pH3.2), neutralized by 1M Tris buffer (pH 8.0) and then dialyzed in PBS. All purified antibodies were analyzed by SDS-polyacrylamide gel electrophoresis and were applied to quantitative ELISA using anti-human IgG assay plates (Becton Dickson) or BCA kits (PIERCE) to determine IgG concentrations.

Kinetic Analysis via BIAcore: for Run 3 the interaction of FcγRIIIA with immobilized Vitaxin® and Vitaxin® Fc variant IgGs were monitored by surface plasmon resonance detection using a BIAcore 3000 instrument (Pharmacia Biosensor, Uppsala, Sweden). Vitaxin® and Vitaxin® Fc variant IgGs were coupled to the dextran matrix of a CM5 sensor chip (Pharmacia Biosensor) using an Amine Coupling Kit, as described (Johnsson et al., 1992, *Anal Biochem* 198:268-277), at a surface density of between approximately 7700 and 9400 RUs (see Table 6). FcγRIIIA was serially diluted in 0.01M HEPES pH 7.4 containing 0.15 M NaCl, 3 mM EDTA and 0.005% P20, at concentrations ranging from 16 μM down to 7.8 nM. Duplicate injections of each concentration were made. All binding experiments were performed at 25° C., and at a flow rate of 10 μL/min. Binding was monitored for 25 min. Following each injection of FcγRIIIA, the IgG surfaces were regenerated with a 30 sec. pulse of 5 mM HCl. FcγRIIIA was also passed over a blank reference cell which is connected, in series, to the IgG-containing flow cells. The steady-state binding curves were also corrected for injection artifacts by subtraction of buffer injections. This doubly-corrected data was then fit to a steady-state isotherm provided by the instrument manufacturer (Pharmacia Biosensor, Uppsala, Sweden) to derive the respective equilibrium binding constants (K$_D$). Separately, a Scatchard plot of the Req data from each IgG surface was constructed to confirm the results of the binding isotherms.

Cell Surface Binding: NK cells were isolated from healthy donor by using NK cell isolation kit from Miltenybiotec (Cat# 130-091-152) THP-1: early passage of THP-1 cells were used. For FACS staining of FcγRs, either THP-1 or human NK cells were resuspended in FACS buffer (1% BSA in PBS, pH 7.2) at 1×10$^6$ cells/ml and 0.5 ml of the cells were transfered into 96 deep well plate, 10 ul of the anti-CD32-PE (Immunotech), anti-CD16-FITC (Pharmingen) or anti-CD64-FITC (PharMingen) was added to the tubes. The samples were incubated at 40 C for 30 min. After incubation the cells were washed with FACS buffer. The samples were analyzed by using Guava EasyCyte For binding of antibody 3F2 to Human NK cell surface (FcγRIIIA), 10 μl of the antibody dilution (10 μg/ml or 1 μg/ml) was added to the cells and incubated at 4° C. for 30 min. The cells were washed with FACS buffer, then stained with goat ant-human IgG(H+L)-FITC(Pierce) for 30 min at 4° C. The cells were washed and analyzed by Guava EasyCyte.

For binding of antibody 3F2 to THP-1 cell surface (FcγRI and FcγRII), 10 μl of the antibody dilution (10 μg/ml or 1 μg/ml) were added to the cells, incubatee at 4° C. for 30 min. The cells were washed with FACS buffer, then stained with goat ant-human IgG(H+L)-FITC(Pierce) for 30 min at 4° C. The cells were washed and analyzed by Guava EasyCyte.

ELISA for FcγRIIIA Tetramer Binding: Microtiter plates were coated with protein A/G (PIERCE) solution (0.25 μg/ml) and incubated at 4° C. overnight. The plates were then washed with PBS/0.1% Tween and any remaining binding sites were blocked with 1% BSA. 50 μl of test antibody at 1:1 dilution (from 5000 ng/ml to 4.9 ng/ml), was added to each well and incubated for 60 min at 37° C. 50 μl of 1:500 dilution of the Fcγ tetramer was added to each well and incubated for 60 min at 37° C. followed by washing. 50 μl of 1:1000 dilution of biotin-conjugated HRP (PIERCE) was added to each well and incubated for 30 min at 37° C. Detection was carried out by adding 30 μl of tetramethylbenzidine (TMB) substrate (Pierce) followed by neutralization with 30 μl of 0.2 M H$_2$SO$_4$. The absorbance was read at 450 nm.

ELISA for FcγRIIIA Monomer Binding: Microtiter plates were coated with 50 μl to test antibody at concentration range from 20 μg/ml to 0.0019 μg/ml and incubated at 4° C. overnight. 50 μl of 10 μg/ml FcγRIIIA-flag protein was added to each well and incubated for 60 min at 37° C. 50 μl of 2.5 μg/ml anti-flag-ME-biotin (Sigma) was added to each well and incubated for 30 min at 37° C. 50 μl of 1:1000 diulation of avidin-conjugated HRP (PIERCE) was added to each well and incubated for 30 min at 37° C. Detection was carried out by adding 30 μl of tetramethylbenzidine (TMB) substrate (Pierce) followed by neutralization with 30 μl of 0.2 M H$_2$SO$_4$. The absorbance was read at 450 nm.

ELISA for C1q Bindinj: Microtiter plates were coated with 50 μl of test antibody at concentration range from 20 μg/ml to 0.0019 μg/ml and incubated at 4° C. overnight. The plate was then blocked with 5% nonfat powdered milk for 60 min at 37° C. 50 μl of 5 μg/ml human C1q complement protein (Quidal, SanDiego) was added to each well and inclubated for 60 min at 37° C. 50 μl of 1:1000 dilution of anti-complement C1q antibody (Biodesign) was added to each well and incubated for 60 min at 37° C. 50 μl of 1:1000 dilution of donkey anti-sheep/goat antibody-conjugated HRP (PIERCE) was added to each well and incubated for 60 min at 37° C. Detection was carried out by adding 30 μl of tetramethylbenzidine (TMB) substrate (Pierce) followed by neutralization with 30 μl of 0.2 M H$_2$SO$_4$. The absorbance was read at 450 nm.

Antibody-Dependent Cell-Mediated Cytotoxicity (ADCC) Assay: Antibody-dependent cell cytotoxicity (ADCC) was assayed as described above in section 7.3.1 using different target cells. The target cell lines used for these assays are A549 a human non-small cell lung adenocarcinoma cell line expressing high levels of human EphA2, T231 a more metastatic variant of MDA-MB-231 human breast adenocarcinoma cell line obtained from collaborator Kathy Miller at Indiana University Medical Center expressing high levels of human EphA2, HeyA8 a human ovarian carcinoma expressing high levels of human EphA2, SKOV3 a human ovarian adenocarcinoma derived from ascites expressing moderate levels of human EphA2, A498 a human renal cell carcinoma expressing low levels of human EphA2, SKMEL28 a human melanoma expressing Integrin αVβ3 but little or no human EphA2.

Whereas, particular embodiments of the invention have been described above for purposes of description, it will be appreciated by those skilled in the art that numerous variations of the details may be made without departing from the invention as described in the appended claims.

All publications, patents and patent applications mentioned in this specification are herein incorporated by reference into the specification to the same extent as if each individual publication, patent or patent application was specifically and individually indicated to be incorporated herein by reference. In addition, U.S. Provisional Patent Application Nos. 60/601,634, filed, Aug. 16, 2004 and 60/608,852, filed, Sep. 13, 2004, and U.S. patent application entitled "Integrin Antagonists With Enhanced Antibody Dependent Cell-Mediated Cytotoxicity Activity," filed Aug. 15, 2005, are incorporated by reference in their entirety

We claim:

1. An antibody that binds and agonizes at least the Erythropoeitin-Producing human Hepatocellular (Eph) receptor A2, wherein said antibody comprises a heavy chain variable domain which comprises a VH CDR1 having SEQ ID NO:70, a VH CDR2 having SEQ ID NO:71, and a VH CDR3 having SEQ ID NO:72 and a light chain variable domain which comprises a VL CDR1 having SEQ ID NO:73, a VL CDR2 having SEQ ID NO:74, and a VL CDR3 having SEQ ID NO:75.

2. The antibody of claim 1, wherein said antibody comprises an IgG1 Fc region, wherein the Fc region comprises the high effector function amino acid residues 239D, 330L and 332E, as numbered by the EU index as set forth in Kabat, said antibody has an increased binding affinity for FcγRIIIA as compared to the same antibody not comprising the high effector function amino acid residues and wherein said increased affinity for FcγRIIIA results in an enhanced ADCC activity.

3. The antibody of claim 1, wherein said antibody is humanized, CDR-grafted, or chimeric.

4. The antibody of claim 1, wherein said antibody is conjugated to a detectable agent, therapeutic agent or drug.

5. A formulation comprising the antibody of claim 1 in a pharmaceutically-acceptable excipient.

6. The antibody of claim 1, wherein said antibody comprises a variable heavy chain and a variable light chain, wherein said heavy chain has a sequence comprising SEQ ID NO:68, and wherein said light chain has a sequence comprising SEQ ID NO:69.

7. The antibody of claim 6, wherein said antibody comprises an IgG1 Fc region, wherein the Fc region comprises the high effector function amino acid residues 239D, 330L and 332L, as numbered by the EU index as set forth in Kabat, said antibody has an increased binding affinity for FcγRIIIA as compared to the same antibody not comprising the high effector function amino acid residues and wherein said increased affinity for FcγRIIIA results in an enhanced ADCC activity.

8. The antibody of claim 7, wherein said antibody is conjugated to a detectable agent, therapeutic agent or drug.

9. A formulation comprising the antibody of claim 7 in a pharmaceutically-acceptable excipient.

10. The antibody of claim 2, wherein said antibody is humanized, CDR-grafted, or chimeric.

11. The antibody of claim 2, wherein said antibody is conjugated to a detectable agent, therapeutic agent or drug.

12. A formulation comprising the antibody of claim 2 in a pharmaceutically acceptable excipient.

13. The antibody of claim 6, wherein said antibody is conjugated to a detectable agent, therapeutic agent or drug.

14. A formulation comprising of the antibody of claim 6 in a pharmaceutically-acceptable excipient.

* * * * *